United States Patent
Dyka et al.

(10) Patent No.: US 12,188,041 B2
(45) Date of Patent: Jan. 7, 2025

(54) CODON OPTIMIZED OTOFERLIN AAV DUAL VECTOR GENE THERAPY

(71) Applicant: University of Florida Research Foundation, Incorporated, Gainesville, FL (US)

(72) Inventors: Frank M. Dyka, Gainesville, FL (US); William W. Hauswirth, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 912 days.

(21) Appl. No.: 17/290,082

(22) PCT Filed: Nov. 1, 2019

(86) PCT No.: PCT/US2019/059549
§ 371 (c)(1),
(2) Date: Apr. 29, 2021

(87) PCT Pub. No.: WO2020/093018
PCT Pub. Date: May 7, 2020

(65) Prior Publication Data
US 2021/0395778 A1 Dec. 23, 2021

Related U.S. Application Data

(60) Provisional application No. 62/754,458, filed on Nov. 1, 2018.

(51) Int. Cl.
| | |
|---|---|
| *C12N 15/86* | (2006.01) |
| *C07K 14/47* | (2006.01) |
| *C12N 7/00* | (2006.01) |
| *A61K 38/00* | (2006.01) |
| *A61K 48/00* | (2006.01) |

(52) U.S. Cl.
CPC .............. *C12N 15/86* (2013.01); *C07K 14/47* (2013.01); *C12N 7/00* (2013.01); *A61K 38/00* (2013.01); *A61K 48/00* (2013.01); *C12N 2750/14132* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 8,298,818 B2 | 10/2012 | Boye et al. | |
| 10,214,572 B2 | 2/2019 | Boye et al. | |
| 11,178,145 B2 * | 11/2021 | Chang | H04L 63/0807 |
| 11,325,956 B2 | 5/2022 | Boye et al. | |
| 11,525,139 B2 * | 12/2022 | Simons | A61K 38/1709 |
| 11,807,867 B2 * | 11/2023 | Simons | A61K 35/761 |
| 2007/0161110 A1 | 7/2007 | Iida et al. | |
| 2010/0003218 A1 | 1/2010 | Duan et al. | |
| 2010/0266551 A1 | 10/2010 | Richard et al. | |
| 2012/0003190 A1 | 1/2012 | Yamoah et al. | |
| 2012/0087862 A1 | 4/2012 | Hood et al. | |
| 2013/0210895 A1 | 8/2013 | Boye et al. | |
| 2014/0249208 A1 | 9/2014 | Bancel et al. | |
| 2014/0256802 A1 | 9/2014 | Boye et al. | |
| 2016/0022836 A1 | 1/2016 | Banfi et al. | |
| 2016/0076054 A1 * | 3/2016 | Auricchio | C12N 15/86 |
| | | | 435/320.1 |
| 2018/0015172 A1 | 1/2018 | Muzyczka et al. | |
| 2019/0002916 A1 | 1/2019 | Kalatzis et al. | |
| 2019/0153050 A1 | 5/2019 | Boye et al. | |
| 2019/0309326 A1 | 10/2019 | Maclaren et al. | |
| 2020/0157573 A1 | 5/2020 | Boye et al. | |
| 2021/0130421 A1 | 5/2021 | Boye et al. | |
| 2023/0149565 A1 | 5/2023 | Boye et al. | |
| 2024/0011039 A1 | 1/2024 | Simons et al. | |

FOREIGN PATENT DOCUMENTS

| | | | |
|---|---|---|---|
| CA | 3034527 A1 | 3/2018 | |
| CN | 110225975 A | 9/2019 | |
| JP | 2016-516424 A | 6/2016 | |
| JP | 7240675 B2 | 3/2023 | |
| KR | 10-2007-0004636 A | 1/2007 | |
| WO | WO-0170972 A2 * | 9/2001 | ............. C07K 14/47 |
| WO | WO 2008/088895 A2 | 7/2008 | |
| WO | WO 2013/075008 A1 | 5/2013 | |
| WO | WO 2014/140051 A1 | 9/2014 | |
| WO | WO 2014/170480 A1 | 10/2014 | |

(Continued)

OTHER PUBLICATIONS

Geleoc, et al. (2014)"Sound Strategies for Hearing Restoration", Science, 344: Article 1241062-1, 8 pages long. (Year: 2014).*

(Continued)

*Primary Examiner* — Robert M Kelly
(74) *Attorney, Agent, or Firm* — Wolf, Greenfield & Sacks, P.C.

(57) ABSTRACT

Provided herein are methods and compositions for expressing Otoferlin, e.g., utilizing adeno-associated viral (AAV) particles. Further provided herein are compositions of AAV particles comprising one or more polynucleotides encoding Otoferlin are codon optimized for expression in human cells. Such methods and compositions may be useful for treatment of diseases and disorders such as Deafness, Autosomal Recessive 9 (DFNB9). Also provided are kits comprising such compositions.

7 Claims, 51 Drawing Sheets

Specification includes a Sequence Listing.

(56) References Cited

FOREIGN PATENT DOCUMENTS

| WO | WO-2016131981 A1 * | 8/2016 | ........... A61K 35/761 |
|---|---|---|---|
| WO | WO 2016/139321 A1 | 9/2016 | |
| WO | WO 2017/049252 A1 | 3/2017 | |
| WO | WO 2017/216560 A1 | 12/2017 | |
| WO | WO 2018/039375 A1 | 3/2018 | |
| WO | WO 2018/162748 A1 | 9/2018 | |
| WO | WO 2018/204734 A1 | 11/2018 | |
| WO | WO 2019/183641 A1 | 9/2019 | |

OTHER PUBLICATIONS

Trapani, et al. (2014) "Effective delivery of large genes to the retina by dual AAV vectors", EMBO Mol. Med., 6(2): 194-211. (Year: 2014).*

International Search Report and Written Opinion for International Application No. PCT/US2012/065645 mailed Mar. 29, 2013.

International Preliminary Report on Patentability for International Application No. PCT/US2012/065645 mailed May 30, 2014.

Extended European Search Report for European Application No. EP 21781660.2 mailed on Apr. 9, 2024.

Invitation to Pay Additional Fees for International Application No. PCT/US2021/025281 mailed Jun. 29, 2021.

International Search Report and Written Opinion for International Application No. PCT/US2021/025281 mailed Sep. 10, 2021.

International Preliminary Report on Patentability for International Application No. PCT/US2021/025281 mailed Oct. 13, 2022.

[No Author Listed] OTOF sequence comparison of Yasunaga SEQ ID No. 70 with present SEQ ID No. 5 (dated Apr. 12, 2024), from U.S. Appl. No. 17/290,082 Office Action, Apr. 18, 2024, 5 pages.

[No Author Listed], NCBI Accession No. NM_001632.5. *Homo sapiens* alkaline phosphatase, placental (ALPP), mRNA. https://www.ncbi.nlm.nih.gov/nuccore/1531243738?sat=47&satkey=4899452. Dec. 7, 2018. 4 pages.

[No Author Listed], NCBI Accession No. NP_000251. unconventional myosin-VIIa isoform 1 [*Homo sapiens*]. Aug. 14, 2022. 5 pages.

[No Author Listed], NCBI Accession No. NP_001274418. OTOF otoferlin [ *Homo sapiens* (human) ]. Nov. 17, 2023. 3 pages.

[No Author Listed], NCBI Accession No. U39226.1. Human myosin VIIA (USH1B) mRNA, complete cds. Jul. 11, 1996. 5 pages.

Akil et al., Restoration of hearing in the VGLUT3 knockout mouse using virally mediated gene therapy. Neuron. Jul. 26, 2012;75(2):283-93. doi: 10.1016/j.neuron.2012.05.019.

Al-Hussaini et al., Mature retinal pigment epithelium cells are retained in the cell cycle and proliferate in vivo. Mol Vis. 2008; 14:1784-91. Epub Oct. 6, 2008.

Allocca et al., Serotype-dependent packaging of large genes in adeno-associated viral vectors results in effective gene delivery in mice. J Clin Invest. May 1, 2008; 118(5): 1955-1964. Published online Apr. 15, 2008. doi: 10.1172/JCI34316.

Avraham, What's hot about otoferlin. EMBO J. Dec. 1, 2016;35(23):2502-2504. doi: 10.15252/embj.201695881. Epub Nov. 7, 2016.

Calabro, Exploring MYO&A function in novel mouse models and improving AAV-Dual Vector gene therapy for Usher Syndrome 1B. PHD dissertation. University of Florida. pp. 1-138 (Year: 2019).

Chen et al., Molecular cloning and domain structure of human myosin-VIIa, the gene product defective in Usher syndrome 1B. Genomics. Sep. 15, 1996;36(3):440-8. doi: 10.1006/geno.1996.0489.

Daya et al., Gene therapy using adeno-associated virus vectors. Clin Microbiol Rev. Oct. 2008;21(4):583-93. doi: 10.1128/CMR.00008-08.

Dong et al., Characterization of genome integrity for oversized recombinant AAV vector. Mol Ther. Jan. 2010;18(1):87-92. doi: 10.1038/mt.2009.258. Epub Nov. 10, 2009.

Duan et al., Circular intermediates of recombinant adeno-associated virus have defined structural characteristics responsible for long-term episomal persistence in muscle tissue. J Virol. Nov. 1998;72(11):8568-77.

Duan et al., Expanding AAV packaging capacity with trans-splicing or overlapping vectors: a quantitative comparison. Mol Ther. Oct. 2001;4(4):383-91.

Gao et al., The Dystrophin Complex: Structure, Function, and Implications for Therapy. Compr Physiol. Jul. 1, 2015;5(3):1223-39. doi: 10.1002/cphy.c140048. Author Manuscript, 33 pages.

Geleoc et al., Sound strategies for hearing restoration. Science. May 9, 2014;344(6184):1241062. doi: 10.1126/science.1241062.

Ghosh et al., A hybrid vector system expands adeno-associated viral vector packaging capacity in a transgene-independent manner. Mol Ther. Jan. 2008;16(1):124-30. doi: 10.1038/sj.mt.6300322. Epub Nov. 6, 2007.

Hashimoto et al., Lentiviral gene replacement therapy of retinas in a mouse model for Usher syndrome type 1B. Gene Therapy. 2007:14;584-594.

Hirsch et al., Delivering Transgenic DNA Exceeding the Carrying Capacity of AAV Vectors. Methods Mol Biol. 2016;1382:21-39. doi: 10.1007/978-1-4939-3271-9_2. Author Manuscript, 20 pages.

Jacobson et al., Usher syndromes due to MYO7A, PCDH15, USH2A or GPR98 mutations share retinal disease mechanism. Hum Mol Genet. Aug. 1, 2008;17(15):2405-15. doi: 10.1093/hmg/ddn140. Epub May 7, 2008.

Lai et al., Evidence for the Failure of Adeno-associated Virus Serotype 5 to Package a Viral Genome ≥8.2 kb. Mol Ther. 2010; 18 1, 75-79. doi:10.1038/mt.2009.256.

Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.

Lopes et al., Retinal gene therapy with a large MYO7A cDNA using adeno-associated virus. Gene Ther. Aug. 2013;20(8):824-33. doi: 10.1038/gt.2013.3. Epub Jan. 24, 2013. Author Manuscript, 21 pages.

Lostal et al., Full-length dystrophin reconstitution with adeno-associated viral vectors. Hum Gene Ther. Jun. 2014:25(6):552-62. doi: 10.1089/hum.2013.210. Epub Mar. 31, 2014.

Majewski et al., GT repeats are associated with recombination on human chromosome 22. Genome Res. Aug. 2000; 10(8):1108-14. doi: 10.1101/gr.10.8.1108.

McClements et al., A fragmented adeno-associated viral dual vector strategy for treatment of diseases caused by mutations in large genes leads to expression of hybrid transcripts. J Genet Syndr Gene Ther. Nov. 14, 2016;7(5):311. doi: 10.4172/2157-7412.1000311. Author Manuscript, 16 pages.

Petrs-Silva et al., Novel properties of tyrosine-mutant AAV2 vectors in the mouse retina. Mol Ther. Feb. 2011;19(2):293-301. doi: 10.1038/mt.2010.234. Epub Nov. 2, 2010.

Pryadkina et al., A comparison of AAV strategies distinguishes overlapping vectors for efficient systemic delivery of the 6.2 kb Dysferlin coding sequence. Mol Ther Methods Clin Dev. Mar. 25, 2015;2:15009. doi: 10.1038/mtm.2015.9.

Trapani et al., Effective delivery of large genes to the retina by dual AAV vectors. EMBO Mol Med. Feb. 2014;6(2):194-211. doi: 10.1002/emmm.201302948. Epub Dec. 15, 2013.

Weil et al., Human myosin VIIA responsible for the Usher 1B syndrome: a predicted membrane-associated motor protein expressed in developing sensory epithelia. Proc Natl Acad Sci U S A. Apr. 1, 1996;93(8):3232-7. doi: 10.1073/pnas.93.8.3232.

Wu et al., Effect of genome size on AAV vector packaging. Mol Ther. Jan. 2010;18(1):80-6. doi: 10.1038/mt.2009.255. Epub Nov. 10, 2009.

Yan et al., Inverted terminal repeat sequences are important for intermolecular recombination and circularization of adeno-associated virus genomes. J Virol. Jan. 2005;79(1):364-79.

Yan et al., Recombinant AAV-mediated gene delivery using dual vector heterodimerization. Methods Enzymol. 2002;346:334-57. doi: 10.1016/s0076-6879(02)46065-x.

(56) References Cited

OTHER PUBLICATIONS

Yasunaga et al., OTOF encodes multiple long and short isoforms: genetic evidence that the long ones underlie recessive deafness DFNB9. Am J Hum Genet. Sep. 2000;67(3):591-600. doi: 10.1086/303049. Epub Jul. 19, 2000.

Extended European Search Report for European Application No. EP 18793935.0 mailed on Feb. 22, 2021.

International Search Report and Written Opinion mailed Jul. 30, 2018 for Application No. PCT/US2018/031009.

International Preliminary Report on Patentability mailed Nov. 14, 2019 for Application No. PCT/US2018/031009.

International Search Report and Written Opinion for Application No. PCT/US2019/059549, mailed Feb. 20, 2020.

International Preliminary Report on Patentability for Application No. PCT/US2019/059549, mailed May 14, 2021.

Akil et al., Dual AAV-mediated gene therapy restores hearing in a DFNB9 mouse model. Proc Natl Acad Sci U S A. Mar. 5, 2019;116(10):4496-4501. doi: 10.1073/pnas.1817537116. Epub Feb. 19, 2019.

Alemi et al., Progress Report: AOS Research Grant: Restoration of Hearing in the Otoferlin Knockout Mouse using Viral Gene Therapy. 145th Annual Meeting. American Otological Society, Inc. Apr. 21-22, 2012; p. 68. Available online at: https://www.americanotologicalsociety.org/assets/2012.pdf.

Al-Moyed et al., A dual-AAV approach restores fast exocytosis and partially rescues auditory function in deaf otoferlin knock-out mice. EMBO Mol Med. Jan. 2019;11(1):e9396. doi: 10.15252/emmm.201809396.

Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.

Ghosh et al., Efficient transgene reconstitution with hybrid dual AAV vectors carrying the minimized bridging sequences. Hum Gene Ther. Jan. 2011;22(1):77-83. doi: 10.1089/hum.2010.122. Epub Dec. 12, 2010.

\* cited by examiner pTR22-smCBA-otoferlinNT-APSD-APhead

| Nucleotide positions | Abbreviation | Description |
|---|---|---|
| 20-162 | TR: | inverted terminal repeat sequence of AAV2 |
| 186-440 | CBA promoter: | -CMVie enhancer |
| 441-835 | | -chicken b-actin promoter |
| 836-1130 | | -Exon1 and chimeric intron |
| 1153-3600 | Otoferlin NT: | Otoferlin coding sequence 5' part |
| 3601-3684 | APSD: | Splice Donor |
| 3691-3977 | APhead: | homologous sequence for recombination |
| 4017-4159 | TR: | inverted terminal repeat sequence of AAV2 |
| | ColE2: | replication origin for E. coli |
| | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTCGGTACCCTAGTTATTAATAGTAATCAATTACGGGGTCATTAGT
TCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAAC
GCCAATAGGGACTTTCCATTGACGTCAATGGGTGGACTATTTACGGTAAACTGCCCACT
TGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTGCT
TCACTCTCCCCATCTCCCCCCCCTCCCCACCCCCAATTTTGTATTTATTTATTTTTTAATT
ATTTTGTGCAGCGATGGGGGCGGGGGGGGGGGGGGGCGCGCGCCAGGCGGGGCG
GGGCGGGGCGAGGGGCGGGGCGGGGCGAGGCGGAGAGGTGCGGCGGCAGCCAATC
AGAGCGGCGCGCTCCGAAAGTTTCCTTTTATGGCGAGGCGGCGGCGGCGGCGGCCCT
ATAAAAAGCGAAGCGCGCGGCGGGCGGGAGTCGCTGCGACGCTGCCTTCGCCCCGT
GCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGT
TTAATGACGGCTTGTTTCTTTTCTGTGGCTGCGTGAAAGCCTTGAGGGGCTCCGGGAG
CTAGAGCCTCTGCTAACCATGTTCATGCCTTCTTCTTTTTCCTACAGCTCCTGGGCAAC
GTGCTGGTTATTGTGCTGTCTCATCATTTTGGCAAAGAATTCTAGCGGCCGCCACCATG
GCCCTGATTGTTCACCTCAAGACTGTCTCAGAGCTCCGAGGCAAAGGTGACCGGATTG
CCAAAGTCACTTTCCGAGGGCAGTCTTTCTACTCCCGGGTCCTGGAGAACTGCGAGGG
TGTGGCTGACTTTGATGAGACGTTCCGGTGCCAGTGGCCAGCAGCATCGACCGGAAT
GAAGTGTTGGAGATTCAGATTTTCAACTACAGCAAAGTCTTCAGCAACAAGCTGATAGG
GACCTTCTGCATGGTGCTGCAGAAAGTGGTGGAGGAGAATCGGGTAGAGGTGACCGA
CACGCTGATGGATGACAGCAATGCTATCATCAAGACCAGCCTGAGCATGGAGGTCCGG
TATCAGGCCACAGATGGCACTGTGGGCCCCTGGGATGATGGAGACTTCCTGGGAGAT
GAATCCCTCCAGGAGGAGAAGGACAGCCAGGAGACAGATGGGCTGCTACCTGGTTCC
CGACCCAGCACCCGGATATCTGGCGAGAAGAGCTTTCGCAGCAAAGGCAGAGAGAAG
ACCAAGGGAGGCAGAGATGGCGAGCACAAAGCGGGAAGGAGTGTGTTCTCGGCCATG
AAACTCGGCAAAACTCGGTCCCACAAAGAGGAGCCCCAAAGACAAGATGAGCCAGCAG
TGCTGGAGATGGAGGACCTGGACCACCTAGCCATTCAGCTGGGGATGGGCTGGATC
CTGACTCCGTGTCTCTAGCCTCGGTCACCGCTCTCACCAGCAATGTCTCCAACAAACG
GTCTAAGCCAGATATTAAGATGGAGCCCAGTGCTGGAAGGCCCATGGATTACCAGGTC
AGCATCACAGTGATTGAGGCTCGGCAGCTGGTGGGCTTGAACATGGACCCTGTGGTGT
```

FIG. 3A

```
GTGTGGAGGTGGGTGATGACAAGAAATACACGTCAATGAAGGAGTCCACAAACTGCCC
TTACTACAACGAGTACTTTGTCTTCGACTTCCATGTCTCTCCTGATGTCATGTTTGACAA
GATCATCAAGATCTCGGTTATCCATTCTAAGAACCTGCTTCGGAGCGGCACCCTGGTG
GGTTCCTTCAAAATGGATGTGGGGACTGTGTATTCCCAGCCTGAACACCAGTTCCATCA
CAAATGGGCCATCCTGTCAGACCCCGATGACATCTCTGCTGGGTTGAAGGGTTATGTA
AAGTGTGATGTCGCTGTGGTGGGCAAGGGAGACAACATCAAGACACCCCACAAGGCCA
ACGAGACGGATGAGGACGACATTGAAGGGAACTTGCTGCTCCCCGAGGGCGTGCCCC
CCGAACGGCAGTGGGCACGGTTCTATGTGAAAATTTACCGAGCAGAGGGACTGCCCC
GGATGAACACAAGCCTCATGGCCAACGTGAAGAAGGCGTTCATCGGTGAGAACAAGGA
CCTCGTCGACCCCTATGTGCAAGTCTTCTTTGCTGGACAAAAGGGCAAAACATCAGTGC
AGAAGAGCAGCTATGAGCCGCTATGGAATGAGCAGGTCGTCTTCACAGACTTGTTCCC
CCCACTCTGCAAACGCATGAAGGTGCAGATCCGGGACTCTGACAAGGTCAATGATGTG
GCCATCGGCACCCACTTCATCGACCTGCGCAAGATTTCCAACGATGGAGACAAAGGCT
TCCTGCCTACCCTCGGTCCAGCCTGGGTGAACATGTACGGCTCCACGCGCAACTACAC
ACTGCTGGACGAGCACCAGGACTTGAATGAAGGCCTGGGGGAGGGTGTGTCCTTCCG
GGCCCGCCTCATGTTGGGACTAGCTGTGGAGATCCTGGACACCTCCAACCCAGAGCTC
ACCAGCTCCACGGAGGTGCAGGTGGAGCAGGCCACGCCTGTCTCGGAGAGCTGCACA
GGGAGAATGGAAGAATTTTTTCTATTTGGAGCCTTCTTGGAAGCCTCAATGATTGACCG
GAAAAATGGGGACAAGCCAATTACCTTTGAGGTGACCATAGGAAACTACGGCAATGAA
GTCGATGGTATGTCCCGGCCCCTGAGGCCTCGGCCCCGGAAAGAGCCTGGGGATGAA
GAAGAGGTAGACCTGATTCAGAACTCCAGTGACGATGAAGGTGACGAAGCCGGGGAC
CTGGCCTCGGTGTCCTCCACCCCACCTATGCGGCCCCAGATCACGGACAGGAACTATT
TCCACCTGCCCTACCTGGAGCGCAAGCCCTGCATCTATATCAAGAGCTGGTGGCCTGA
CCAGAGGCGGCGCCTCTACAATGCCAACATCATGGATCACATTGCTGACAAGCTGGAA
GAAGGCCTGAATGATGTACAGGAGATGATCAAAACGGAGAAGTCCTACCCGGAGCGCC
GCCTGCGGGGTGTGCTAGAGGAACTCAGCTGTGGCTGCCACCGCTTCCTCTCCCTCTC
GGACAAGGACCAGGGCCGCTCGTCCCGCACCAGGCTGGATCGAGAGCGTCTTAAGTC
CTGTATGAGGGAGTTGGTAAGTATCAAGGTTACAAGACAGGTTTAAGGAGACCAATAGA
AACTGGGCTTGTCGAGACAGAGAAGACTCTTGCGTTTCTGAGCTAGCCCCCGGGTGCG
CGGCGTCGGTGGTGCCGGCGGGGGCGCCAGGTCGCAGGCGGTGTAGGGCTCCAG
GCAGGCGGCGAAGGCCATGACGTGCGCTATGAAGGTCTGCTCCTGCACGCCGTGAAC
CAGGTGCGCCTGCGGGCCGCGCGCGAACACCGCCACGTCCTCGCCTGCGTGGGTCT
CTTCGTCCAGGGGCACTGCTGACTGCTGCCGATACTCGGGGCTCCCGCTCTCGCTCTC
GGTAACATCCGGCCGGGCGCCGTCCTTGAGCACATAGCCTGGACCGTTTCGTCGACT
GTTAATTAAGCATGCTGGGGAGAGATCTAGGAACCCCTAGTGATGGAGTTGGCCACTC
CCTCTCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTGGC
CAACCCCCCCCCCCCCCCCCTGCAGCCCTGCATTAATGAATCGGCCAACGCGCGGG
GAGAGGCGGTTTGCGTATTGGGCGCTCTTCCGCTTCCTCGCTCACTGACTCGCTGCGC
TCGGTCGTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCAATGCT
CACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTGATCTTTTC
TACGGGTCTGACGCTCAGTGGAACGAAAACTCACGTTAAGGGATTTTGGTCATGAGA
```

FIG. 3A (continued)

```
TTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTA
TCTCAGCGATCTGTCTATTTCGTTCATCCATAGTTGCCTGACTCCCCGTCGTGTAGATAA
CTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATC
AAGGCGAGTTACATGATCCCCATGTTGTGCAAAAAAGCGGTTAGCTCCTTCGGTCCTC
CGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCA
ACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGT
TCTTCGGGGCGAAAACTCTCAAGGATCTTACCGCTGTTGAGATCCAGTTCGATGTAACC
CACTCGTGCACCCAACTGATCTTCAGCATCTTTTACTTTCACCAGCGTTTCTGGGTGAG
CAAAAACAGGAAGGCAAAATGCCGCAAAAAAGGGAATAAGGGCGACACGGAAATGTTG
AATACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTT
CCCCGAAAAGTGCCACCTGACGTCAAGAAACCATTATTATCATGACATTAACCTATAAA
AATAGGCGTATCACGAGGCCCTTTCGTCTCGCGCGTTTCGGTGATGACGGTGAAAACC
TCTGACACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGCTGGCTT
AACTATGCGGCATCAGAGCAGATTGTACTGAGAGTGCACCATATGCGGTGTGAAATAC
CGCACAGATGCGTAAGGAGAAAATACCGCATCAGGAAATTGTAAACGTTAATATTTTGT
TAAAATTCGCGTTAAATTTTTGTTAAATCAGCTCATTTTTTAACCAATAGGCCGAAATCGG
CAAAATCCCTTATAAATCAAAAGAATAGACCGAGATAGGGTTGAGTGTTGTTCCAGTTTG
GAACAAGAGTCCACTATTAAAGAACGTGGACTCCAACGTCAAAGGGCGAAAAACCGTC
TATCAGGGCGATGGCCCACTACGTGAACCATCACCCTAATCAAGTTTTTTGGGGTCGAG
GTGCCGTAAAGCACTAAATCGGAACCCTAAAGGGAGCCCCCGATTTAGAGCTTGACGG
GGAAAGCCGGCGAACGTGGCGAGAAAGGAAGGGAAGAAAGCGAAAGGAGCGGGCGC
TAGGGCGCTGGCAAGTGTAGCGGTCACGCTGCGCGTAACCACCACACCCGCCGCGCT
TAATGCGCCGCTACAGGGCGCGTCGCGCCATTCGCCATTCAGGCTACGCAACTGTTGG
GAAGGGCGATCGGTGCGGGCCTCTTCGCTATTACGCCAGGCTGC
(SEQ ID NO: 1)
```

FIG. 3A (continued)

pTR22-APhead-APSA-otoferlinCT

| Nucleotide positions | Abbreviation: | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4095 | Otoferlin CT: | Otoferlin coding sequence 3' part |
| 4133-4354 | bGH PolyA: | bovine growth hormone polyadenylation signal |
| 4421-4563 | TR: | inverted terminal repeat sequence of AAV2 |
|  | ColE2: | replication origin for E. coli |
|  | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCGGGTGCGCGGCGTCGG
TGGTGCCGGCGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAGAGC
ATGGGACAGCAGGCCAAGAGCCTGAGGGCTCAGGTGAAGCGGCACACTGTTCGGGAC
AAGCTGAGGTCATGCCAGAACTTTCTGCAGAAGCTACGCTTCCTGGCGGATGAGCCCC
AGCACAGCATTCCTGATGTGTTCATTTGGATGATGAGCAACAACAAACGTATCGCCTAT
GCCCGCGTGCCTTCCAAAGACCTGCTCTTCTCCATCGTGGAGGAGGAACTGGGCAAG
GACTGCGCCAAAGTCAAGACCCTCTTCCTGAAGCTGCCAGGGAAGAGGGGCTTCGGC
TCGGCAGGCTGGACAGTACAGGCCAAGCTGGAGCTCTACCTGTGGCTGGGCCTCAGC
AAGCAGCGAAAGGACTTCCTGTGTGGTCTGCCCTGTGGCTTCGAGGAGGTCAAGGCA
GCCCAAGGCCTGGGCCTGCATTCCTTTCCGCCCATCAGCCTAGTCTACACCAAGAAGC
AAGCCTTCCAGCTCCGAGCACACATGTATCAGGCCCGAAGCCTCTTTGCTGCTGACAG
CAGTGGGCTCTCTGATCCCTTTTGCCCGTGTCTTCTTCATCAACCAGAGCCAATGCACTG
AGGTTCTAAACGAGACACTGTGTCCCACCTGGGACCAGATGCTGGTATTTGACAACCT
GGAGCTGTACGGTGAAGCTCACGAGTTACGAGATGATCCCCCATCATTGTCATTGAAA
TCTACGACCAGGACAGCATGGGCAAAGCCGACTTCATGGGCCGGACCTTCGCCAAGC
CCCTGGTGAAGATGGCAGATGAAGCATACTGCCCACCTCGCTTCCCGCCGCAGCTTGA
GTACTACCAGATCTACCGAGGCAGTGCCACTGCCGGAGACCTACTGGCTGCCTTCGAG
CTGCTGCAGATTGGGCCATCAGGGAAGGCTGACCTGCCACCCATCAATGGCCCAGTG
GACATGGACAGAGGGCCCATCATGCCTGTGCCCGTGGGAATCCGGCCAGTGCTCAGC
AAGTACCGAGTGGAGGTGCTGTTCTGGGGCCTGAGGGACCTAAAGAGGGTGAACCTG
GCCCAGGTGGACCGACCACGGGTGGACATCGAGTGTGCAGGAAAGGGGGTACAATCC
TCCCTGATTCACAATTATAAGAAGAACCCCAACTTCAACACGCTGGTCAAGTGGTTTGA
AGTGGACCTCCCGGAGAATGAGCTCCTGCACCCACCCTTGAACATCCGAGTGGTAGAT
TGCCGGGCCTTTGGACGATACACCCTGGTGGGTTCCACGCAGTCAGCTCACTGAGG
CGCTTCATCTACCGACCTCCAGACCGCTCAGCCCCAACTGGAACACCACAGGGGAG
GTTGTAGTAAGCATGGAGCCTGAGGAGCCAGTTAAGAAGCTGGAGACCATGGTGAAAC
TGGATGCCGACTTCTGATGCTGTGGTCAAGGTGGATGTGGCTGAAGATGAGAAGGAAAG
GAAGAAGAAGAAAAAGAAAGGCCCGTCAGAGGAGCCAGAGGAGGAAGAGCCCGATGA
GAGCATGCTGGATTGGTGGTCCAAGTACTTCGCCTCCATCGACACAATGAAGGAGCAA
CTTCGACAACATGAGACCTCTGGAACTGACTTGGAAGAGAAGGAAGAGATGGAAAGCG
CTGAGGGCCTGAAGGGACCAATGAAGAGCAAGGAGAAGTCCAGAGCTGCAAAGGAGG
```

FIG. 3B

```
AGAAAAAGAAGAAAAACCAGAGCCCTGGCCCTGGCCAGGGATCGGAGGCTCCTGAGA
AGAAGAAAGCCAAGATCGATGAGCTTAAGGTGTACCCCAAGGAGCTGGAATCGGAGTT
TGACAGCTTTGAGGACTGGCTGCACACCTTCAACCTGTTGAGGGGCAAGACGGGAGAT
GATGAGGATGGCTCCACAGAGGAGGAGCGCATAGTAGGCCGATTCAAGGGCTCCCTC
TGTGTGTACAAAGTGCCACTCCCAGAAGATGTATCTCGAGAAGCTGGCTATGATCCCAC
CTATGGAATGTTCCAGGGCATCCCAAGCAATGACCCCATCAATGTGCTGGTCCGAATCT
ATGTGGTCCGGGCCACAGACCTGCACCCGGCCGACATCAATGGCAAAGCTGACCCCT
ATATTGCCATCAAGTTAGGCAAGACCGACATCCGAGACAAGGAGAACTACATCTCCAAG
CAGCTCAACCCTGTGTTTGGGAAGTCCTTTGACATTGAGGCCTCCTTCCCCATGGAGTC
CATGTTGACAGTGGCCGTGTACGACTGGGATCTGGTGGGCACTGATGACCTCATCGGA
GAAACCAAGATTGACCTGGAAAACCGCTTCTACAGCAAGCATCGCGCCACCTGCGGCA
TCGCACAGACCTATTCCATACATGGCTACAATATCTGGAGGGACCCCATGAAGCCCAG
CCAGATCCTGACACGCCTCTGTAAAGAGGGCAAAGTGGACGGCCCCACTTTGGTCCC
CATGGGAGAGTGAGGGTTGCCAACCGTGTCTTCACGGGGCCTTCAGAAATAGAGGATG
AGAATGGTCAGAGGAAGCCCACAGATGAGCACGTGGCACTGTCTGCTCTGAGACACTG
GGAGGACATCCCCGGGTGGGCTGCCGCCTTGTGCCGGAACACGTGGAGACCAGGC
CGCTGCTCAACCCTGACAAGCCAGGCATTGAGCAGGGCCGCCTGGAGCTGTGGGTGG
ACATGTTCCCCATGGACATGCCAGCCCTGGGACACCTCTGGATATATCCCCCAGGAA
ACCCAAGAAGTACGAGCTGCGGGTCATCGTGTGGAACACAGACGAGGTGGTCCTGGA
AGACGATGATTTCTTCACGGGAGAGAAGTCCAGTGACATTTTTGTGAGGGGGTGGCTG
AAGGGCCAGCAGGAGGACAAACAGGACACAGATGTCCACTATCACTCCCTCACGGGG
GAGGGCAACTTCAACTGGAGATACCTCTTCCCCTTCGACTACCTAGCGGCCGAAGAGA
AGATCGTTATGTCCAAAAAGGAGTCTATGTTCTCCTGGGATGAGACGGAGTACAAGATC
CCTGCGCGGCTCACCCTGCAGATCTGGGACGCTGACCACTTCTCGGCTGACGACTTCC
TGGGGGCTATCGAGCTGGACCTGAACCGGTTCCCGAGGGGCGCTAAGACAGCCAAGC
AGTGCACCATGGAGATGGCCACCGGGGAGGTGGACGTACCCCTGGTTTCCATCTTTAA
ACAGAAACGTGTCAAAGGCTGGTGGCCCCTCCTGGCCCGCAATGAGAATGATGAGTTT
GAGCTCACAGGCAAAGTGGAGGCGGAGCTACACCTACTCACGGCAGAGGAGGCAGAG
AAGAACCCTGTGGGCCTGGCTCGCAATGAACCTGATCCCCTAGAAAAACCCAACCGGC
CTGACACGGCATTCGTCTGGTTCCTGAACCCACTCAAATCTATCAAGTACCTCATCTGC
ACCCGGTACAAGTGGCTGATCATCAAGATCGTGCTGGCGCTGCTGGGGCTGCTCATGC
TGGCCCTCTTCCTTTACAGCCTCCCAGGCTACATGGTCAAGAAGCTCCTAGGGGCCTG
AGCGGCCGCGGTACCAAGGGCGAATTCTGCAGTCGACTAGAGCTCGCTGATCAGCCT
CGACTGTGCCTTCTAGTTGCCAGCCATCTGTTGTTTGCCCCTCCCCCGTGCCTTCCTTG
ACCCTGGAAGGTGCCACTCCCACTGTCCTTTCCTAATAAAATGAGGAAATTGCATCGCA
TTGTCTGAGTAGGTGTCATTCTATTCTGGGGGGTGGGGTGGGGCAGGACAGCAAGGG
GGAGGATTGGGAAGACAATAGCAGGCATGCTGGGGAGAGATCTGAGGACTAGTCCGT
CGACTGTTAATTAAGCATGCTGGGGAGAGATCTAGGAACCCCTAGTGATGGAGTTGGC
CACTCCCTCTCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAG
TGGCCAACCCCCCCCCCCCCCCCCCTGCAGCCCTGCATTAATGAATCGGCCAACGCG
CGGGGAGAGGCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTC
AATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAGTTACCTTCG
```

FIG. 3B (continued)

```
GAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTGAGG
CACCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCGC
GAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTTAGCTCCTTC
GGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGG
AAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATTG
TCTCATGAGCGGATACATATTTGAATGTATTTAGAAAAATAAACAAATAGGGGTTCCGCG
CACATTTCCCCGAAAAGTGCCACCTGACGTCTAAGAAACCATTATTATCATGACATTAAC
CTATAAAAATAGGCGTATCACGAGGCCCTTTCGTCTCGCGCGTTTCGGTGATGACGGT
GAAAACCTCTGACACATGCAGCTCCCGGAGACGGTCACAGCTTGTCTGTAAGCGGATG
CCGGGAGCAGACAAGCCCGTCAGGGCGCGTCAGCGGGTGTTGGCGGGTGTCGGGGC
TGGCTTAACTATGCGGCATCAGAGCAGATTGTACTGAGAGTGCACCATATGCGGTGTG
AAATACCGCACAGATGCGTAAGGAGAAAATACCGCATCAGGAAATTGTAAACGTTAATA
TTTTGTTAAAATTCGCGTTAAATTTTGTTAAATCAGCTCATTTTTTAACCAATAGGCCGA
AATCGGCAAAATCCCTTATAAATCAAAAGAATAGACCGAGATAGGGTTGAGTGTTGTTC
CAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGG
GTCGAGGTGCCGTAAAGCACTAAATCGGAACCCTAAAGGGAGCCCCCGATTTAGAGCT
TGACGGGGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCACACCCGC
CGCGCTTAATGCGCCGCTACAGGGCGCGTCGCGCCATTCGCCATTCAGGCTACGCAA
CTGTTGGGAAGGGCGATCGGTGCGGGCCTCTTCGCTATTACGCCAGGCTGC
(SEQ ID NO: 2)
```

FIG. 3B (continued)

pTR22-smCBA-otoferlinNT Hs var 1+5-APSD-APhead

| Nucleotide positions | Abbreviation | Description |
|---|---|---|
| 20-162 | TR: | inverted terminal repeat sequence of AAV2 |
| 186-551 | CBA promoter: | -CMVie enhancer |
| 553-835 | | -chicken b-actin promoter |
| 836-1130 | | -Exon1 and chimeric intron |
| 1153-3558 | Otoferlin NT: | Otoferlin coding sequence 5' part |
| 3559-3642 | APSD: | Splice Donor |
| 3649-3935 | APhead: | homologous sequence for recombination |
| 3975-4117 | TR: | inverted terminal repeat sequence of AAV2 |
| 4565-4790 | ColE1: | replication origin for E. coli |
| 5040-6040 | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTCGGTACCCTAGTTATTAATAGTAATCAATTACGGGGTCATTAGT
TCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAAC
GCCAATAGGGACTTTCCATTGACGTCAATGGGTGGACTATTTACGGTAAACTGCCCACT
TGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTGCT
TCACTCTCCCCATCTCCCCCCCCTCCCCACCCCCAATTTTGTATTTATTTATTTTTTAATT
ATTTTGTGCAGCGATGGGGGCGGGGGGGGGGGGGGCGCGCGCCAGGCGGGGCG
GGGCGGGGCGAGGGGCGGGGCGGGGCGAGGCGGAGAGGTGCGGCGGCAGCCAATC
AGAGCGGCGCGCTCCGAAAGTTTCCTTTTATGGCGAGGCGGCGGCGGCGGCGGCCCT
ATAAAAAGCGAAGCGCGCGGCGGGCGGGAGTCGCTGCGACGCTGCCTTCGCCCCGT
GCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGT
TTAATGACGGCTTGTTTCTTTTCTGTGGCTGCGTGAAAGCCTTGAGGGGCTCCGGGAG
CTAGAGCCTCTGCTAACCATGTTCATGCCTTCTTCTTTTTCCTACAGCTCCTGGGCAAC
GTGCTGGTTATTGTGCTGTCTCATCATTTTGGCAAAGAATTCTAGCGGCCGCCACCATG
GCCTTGCTCATCCACCTCAAGACAGTCTCGGAGCTGCGGGGCAGGGGCGACCGGATC
GCCAAAGTGACTTTCCGAGGGCAATCCTTCTACTCTCGGGTCCTGGAGAACTGTGAGG
ATGTGGCTGACTTTGATGAGACATTTCGGTGGCCGGTGGCCAGCAGCATCGACAGAAA
TGAGATGCTGGAGATTCAGGTTTTCAACTACAGCAAAGTCTTCAGCAACAAGCTCATCG
GGACCTTCCGCATGGTGCTGCAGAAGGTGGTAGAGGAGAGCCATGTGGAGGTGACTG
ACACGCTGATTGATGACAACAATGCTATCATCAAGACCAGCCTGTGCGTGGAGGTCCG
GTATCAGGCCACTGACGGCACAGTGGGCTCCTGGGACGATGGGGACTTCCTGGGAGA
TGAGTCTCTTCAAGAGGAAGAGAAGGACAGCCAAGAGACGGATGGACTGCTCCCAGG
CTCCCGGCCCAGCTCCCGGCCCCAGGAGAGAAGAGCTTCCGGAGAGCCGGGAGGA
GCGTGTTCTCCGCCATGAAGCTCGGCAAAAACCGGTCTCACAAGGAGGAGCCCCAAAG
ACCAGATGAACCGGCGGTGCTGGAGATGAAGACCTTGACCATCTGGCCATTCGGCTA
GGAGATGGACTGGATCCCGACTCGGTGTCTCTAGCCTCAGTCACAGCTCTCACCACTA
ATGTCTCCAACAAGCGATCTAAGCCAGACATTAAGATGGAGCCAAGTGCTGGGCGGCC
CATGGATTACCAGGTCAGCATCACGGTGATCGAGGCCCGGCAGCTGGTGGGCTTGAA
CATGGACCCTGTGGTGTGCGTGGAGGTGGGTGACGACAAGAAGTACACATCCATGAAG
GAGTCCACTAACTGCCCCTATTACAACGAGTACTTCGTCTTCGACTTCCATGTCTCTCC
GGATGTCATGTTTGACAAGATCATCAAGATTTCGGTGATTCACTCCAAGAACCTGCTGC
GCAGTGGCACCCTGGTGGGCTCCTTCAAAATGGACGTGGGAACCGTGTACTCGCAGC
CAGAGCACCAGTTCCATCACAAGTGGGCCATCCTGTCTGACCCCGATGACATCTCCTC
```

FIG. 13

```
GGGGCTGAAGGGCTACGTGAAGTGTGACGTTGCCGTGGTGGGCAAAGGGGACAACAT
CAAGACGCCCACAAGGCCAATGAGACCGACGAAGATGACATTGAGGGGAACTTGCTG
CTCCCCGAGGGGGTGCCCCCCGAACGCCAGTGGGCCCGGTTCTATGTGAAAATTTAC
CGAGCAGAGGGGCTGCCCCGTATGAACACAAGCCTCATGGCCAATGTAAAGAAGGCTT
TCATCGGTGAAAACAAGGACCTCGTGGACCCCTACGTGCAAGTCTTCTTTGCTGGCCA
GAAGGGCAAGACTTCAGTGCAGAAGAGCAGCTATGAGCCCCTGTGGAATGAGCAGGT
CGTCTTTACAGACCTCTTCCCCCACTCTGCAAACGCATGAAGGTGCAGATCCGAGACT
CGGACAAGGTCAACGACGTGGCCATCGGCACCCACTTCATTGACCTGCGCAAGATTTC
TAATGACGGAGACAAAGGCTTCCTGCCCACACTGGGCCCAGCCTGGGTGAACATGTAC
GGCTCCACACGTAACTACACGCTGCTGGATGAGCATCAGGACCTGAACGAGGGCCTG
GGGGAGGGTGTGTCCTTCCGGGCCCGGCTCCTGCTGGGCCTGGCTGTGGAGATCGTA
GACACCTCCAACCCTGAGCTCACCAGCTCCACAGAGGTGCAGGTGGAGCAGGCCACG
CCCATCTCGGAGAGCTGTGCAGGTAAAATGGAAGAATTCTTTCTCTTTGGAGCCTTCCT
GGAGGCCTCAATGATCGACCGGAGAAACGGAGACAAGCCCATCACCTTTGAGGTCACC
ATAGGCAACTATGGGAACGAAGTTGATGGCCTGTCCCGGCCCAGCGGCCTCGGCCC
CGGAAGGAGCCGGGGGATGAGGAAGAAGTAGACCTGATTCAGAACGCAAGTGATGAC
GAGGCCGGTGATGCCGGGGACCTGGCCTCAGTCTCCTCCACTCCACCAATGCGGCCC
CAGGTCACCGACAGGAACTACTTCCATCTGCCCTACCTGGAGCGAAAGCCCTGCATCT
ACATCAAGAGCTGGTGGCCGGACCAGCGCCGCCGCCTCTACAATGCCAACATCATGGA
CCACATTGCCGACAAGCTGGAAGAAGGCCTGAACGACATACAGGAGATGATCAAAACG
GAGAAGTCCTACCCTGAGCGTCGCCTGCGGGCGTCCTGGAGGAGCTGAGCTGTGGC
TGCTGCCGCTTCCTCTCCCTCGCTGACAAGGACCAGGGCCACTCATCCCGCACCAGGC
TTGACCGGGAGCGCCTCAAGTCCTGCATGAGGGAGCTGGTAAGTATCAAGGTTACAAG
ACAGGTTTAAGGAGACCAATAGAAACTGGGCTTGTCGAGACAGAGAAGACTCTTGCGT
TTCTGAGCTAGCCCCCGGGTGCGCGGCGTCGGTGGTGCCGGCGGGGGGCGCCAGGT
CGCAGGCGGTGTAGGGCTCCAGGCAGGCGGCGAAGGCCATGACGTGCGCTATGAAG
GTCTGCTCCTGCACGCCGTGAACCAGGTGCGCCTGCGGGCCGCGCGCGAACACCGC
CACGTCCTCGCCTGCGTGGGTCTCTTCGTCCAGGGGCACTGCTGACTGCTGCCGATAC
TCGGGGCTCCCGCTCTCGCTCTCGGTAACATCCGGCCGGCGCCGTCCTTGAGCACA
TAGCCTGGACCGTTTCGTCGACTGTTAATTAAGCATGCTGGGGAGAGATCTAGGAACC
CCTAGTGATGGAGTTGGCCACTCCCTCTCTGCGCGCTCGCTCGCTCACTGAGGCCGCC
CGGGCAAAGCCCGGGCGTCGGGCGACCTTTGGTCGCCCGGCCTCAGTGAGCGAGCG
AGCGCGCAGAGAGGGAGTGGCCAACCCCCCCCCCCCCCCCCCTGCAGCCCTGCATTA
ATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAG
CAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAAT
TAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCAG
TGCTGCAATGATACCGCGAGACCCACGCTCACCGGCTCCAGATTTATCAGCAATAAAC
```

FIG. 13 (continued)

```
CAGCCAGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGAACTT
TAAAAGTGCTCATCATTGGAAAACGTTCTTCGGGGCGAAAACTCTCAAGGATCTTACCG
CTGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTTCAATATTATTGA
AGCATTTATCAGGGTTATTGTCTCATGAGCGGATACATATTTGAATGTATTTAGAAAAAT
AAACAAATAGGGGTTCCGCGCACATTTCCCCGAAAAGTGCCACCTGACGTCTAAGAAA
CCATTATTATCATGACATTAACCTATAAAAATAGGCGTATCACGAGGCCCTTTCGTCTCG
CGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGG
TGTTGGCGGGTGTCGGGGCTGGCTTAACTATGCGGCATCAGAGCAGATTGTACTGAGA
GTGCACCATATGCGGTGTGAAATACCGCACAGATGCGTAAGGAGAAAATACCGCATCA
GGAAATTGTAAACGTTAATATTTTGTTAAAATTCGCGTTAAATTTTGTTAAATCAGCTCA
TTTTTTAACCAATAGGCCGAAATCGGCAAAATCCCTTATAAATCAAAAGAATAGACCGAG
ATAGGGTTGAGTGTTGTTCCAGTTTGGAACAAGAGTCCACTATTAAAGAACGTGGACTC
CAACGTCAAAGGGCGAAAAACCGTCTATCAGGGCGATGGCCCACTACGTGAACCATCA
CCCTAATCAAGTTTTTTGGGGTCGAGGTGCCGTAAAGCACTAAATCGGAACCCTAAAGG
GAGCCCCCGATTTAGAGCTTGACGGGGAAAGCCGGCGAACGTGGCGAGAAAGGAAGG
GAAGAAAGCGAAAGGAGCGGGCGCTAGGGCGCTGGCAAGTGTAGCGGTCACGCTGC
GCGTAACCACCACACCCGCCGCGCTTAATGCGCCGCTACAGGGCGCGTCGCGCCATT
CGCCATTCAGGCTACGCAACTGTTGGGAAGGGCGATCGGTGCGGGCCTCTTCGCTATT
ACGCCAGGCTGC
(SEQ ID NO: 14)
```

FIG. 13 (continued)

pTR22-APhead-APSA-otoferlinCT Hs var 1

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4152 | Otoferlin CT: | Otoferlin coding sequence 3' part |
| 4195-4416 | bGH PolyA: | bovine growth hormone polyadenylation signal |
| 4483-4625 | TR: | inverted terminal repeat sequence of AAV2 |
| 5073-5298 | ColE1: | replication origin for E. coli |
| 5548-6548 | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCGGGTGCGCGGCGTCGG
TGGTGCCGGCGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAAAAC
ATGGGGCAGCAGGCCAGGATGCTGCGGGCCCAGGTGAAGCGGCACACGGTGCGGGA
CAAGCTGAGGCTGTGCCAGAACTTCCTGCAGAAGCTGCGCTTCCTGGCGGACGAGCC
CCAGCACAGCATTCCCGACATCTTCATCTGGATGATGAGCAACAACAAGCGTGTCGCC
TATGCCCGTGTGCCCTCCAAGGACCTGCTCTTTCTCCATCGTGGAGGAGGAGACTGGCA
AGGACTGCGCCAAGGTCAAGACGCTCTTCCTTAAGCTGCCAGGGAAGCGGGGCTTCG
GCTCGGCAGGCTGGACAGTGCAGGCCAAGGTGGAGCTGTACCTGTGGCTGGGCCTCA
GCAAACAGCGCAAGGAGTTCCTGTGCGGCCTGCCCTGTGGCTTCCAGGAGGTCAAGG
CAGCCCAGGGCCTGGGCCTGCATGCCTTCCCACCCGTCAGCCTGGTCTACACCAAGA
AGCAGGCGTTCCAGCTCCGAGCGCACATGTACCAGGCCCGCAGCCTCTTTGCCGCCG
ACAGCAGCGGACTCTCAGACCCCTTTGCCCGCGTCTTCTTCACAATCAGAGTCAGTGC
ACAGAGGTGCTGAATGAGACCCTGTGTCCCACCTGGGACCAGATGCTGGTGTTCGACA
ACCTGGAGCTCTATGGTGAAGCTCATGAGCTGAGGGACGATCCGCCCATCATTGTCAT
TGAAATCTATGACCAGGATTCCATGGGCAAAGCTGACTTCATGGGCCGTGACCTTCGC
CAAACCCCTGGTGAAGATGGCAGACGAGGCGTACTGCCCACCCCGCTTCCCACCTCA
GCTCGAGTACTACCAGATCTACCGTGGCAACGCCACAGCTGGAGACCTGCTGGCGGC
CTTCGAGCTGCTGCAGATTGGACCAGCAGGGAAGGCTGACCTGCCCCCATCAATGG
CCCGGTGGACGTGGACCGAGGTCCCATCATGCCCGTGCCCATGGGCATCCGGCCCGT
GCTCAGCAAGTACCGAGTGGAGGTGCTGTTCTGGGGCCTACGGGACCTAAAGCGGGT
GAACCTGGCCCAGGTGGACCGGCCACGGGTGGACATCGAGTGTGCAGGGAAGGGGG
TGCAGTCGTCCCTGATCCACAATTATAAGAAGAACCCCAACTTCAACACCCTCGTCAAG
TGGTTTGAAGTGGACCTCCCAGAGAACGAGCTGCTGCACCCGCCCTTGAACATCCGTG
TGGTGGACTGCCGGGCCTTCGGTCGCTACACACTGGTGGGCTCCATGCCGTCAGCT
CCCTGCCGACGCTTCATCTACCGGCCCCAGACCGCTCGGCCCCAGCTGGAACACCA
CGGTCAGGCTTCTCCGGCGCTGCCGTGTGCTGTGCAATGGGGGCTCCTCCTCTCACTC
CACAGGGGAGGTTGTGGTGACTATGGAGCCAGAGGTACCCATCAAGAAACTGGAGAC
CATGGTGAAGCTGGACGCGACTTCTGAAGCTGTTGTCAAGGTGGATGTGGCTGAGGAG
GAGAAGGAGAAGAAGAAGAAGAAGAAGGGCACTGCGGAGGAGCCAGAGGAGGAGGA
GCCAGACGAGAGCATGCTGGACTGGTGGTCCAAGTACTTTGCCTCCATTGACACCATG
AAGGAGCAACTTCGACAACAAGAGCCCTCTGGAATTGACTTGGAGGAGAAGGAGGAAG
TGGACAATACCGAGGGCCTGAAGGGGTCAATGAAGGGCAAGGAGAAGGCAAGGGCTG
CCAAAGAGGAGAAGAAGAAGAAAACTCAGAGCTCTGGCTCTGGCCAGGGGTCCGAGG
```

FIG. 14

```
CCCCCGAGAAGAAGAAACCCAAGATTGATGAGCTTAAGGTATACCCCAAAGAGCTGGA
GTCCGAGTTTGATAACTTTGAGGACTGGCTGCACACTTTCAACTTGCTTCGGGGCAAGA
CCGGGGATGATGAGGATGGCTCCACCGAGGAGGAGCGCATTGTGGGACGCTTCAAGG
GCTCCCTCTGCGTGTACAAAGTGCCACTCCCAGAGGACGTGTCCCGGGAAGCCGGCT
ACGACTCCACCTACGGCATGTTCCAGGGCATCCCGAGCAATGACCCCATCAATGTGCT
GGTCCGAGTCTATGTGGTCCGGGCCACGGACCTGCACCCTGCTGACATCAACGGCAA
AGCTGACCCCTACATCGCCATCCGGCTAGGCAAGACTGACATCCGCGACAAGGAGAAC
TACATCTCCAAGCAGCTCAACCCTGTCTTTGGGAAGTCCTTTGACATCGAGGCCTCCTT
CCCCATGGAATCCATGCTGACGGTGGCTGTGTATGACTGGGACCTGGTGGGCACTGAT
GACCTCATTGGGGAAACCAAGATCGACCTGGAGAACCGCTTCTACAGCAAGCACCGCG
CCACCTGCGGCATCGCCCAGACCTACTCCACACATGGCTACAATATCTGGCGGGACCC
CATGAAGCCCAGCCAGATCCTGACCCGCCTCTGCAAAGACGGCAAAGTGGACGGCCC
CCACTTTGGGCCCCCTGGGAGAGTGAAGGTGGCCAACCGCGTCTTCACTGGGCCCTC
TGAGATTGAGGACGAGAACGGTCAGAGGAAGCCCACAGACGAGCATGTGGCGCTGTT
GGCCCTGAGGCACTGGGAGGACATCCCCCGCGCAGGCTGCCGCCTGGTGCCAGAGC
ATGTGGAGACGAGGCCGCTGCTCAACCCCGACAAGCCGGGCATCGAGCAGGGCCGC
CTGGAGCTGTGGGTGGACATGTTCCCCATGGACATGCCAGCCCCTGGGACGCCTCTG
GACATCTCACCTCGGAAGCCCAAGAAGTACGAGCTGCGGGTCATCATCTGGAACACAG
ATGAGGTGGTCTTGGAGGACGACGACTTCTTCACAGGGGAGAAGTCCAGTGACATCTT
CGTGAGGGGGTGGCTGAAGGGCCAGCAGGAGGACAAGCAGGACACAGACGTCCACTA
CCACTCCCTCACTGGCGAGGGCAACTTCAACTGGCGCTACCTGTTCCCCTTCGACTAC
CTGGCGGCGGAGGAGAAGATCGTCATCTCCAAGAAGGAGTCCATGTTCTCCTGGGAC
GAGACCGAGTACAAGATCCCCGCGCGGCTCACCCTGCAGATCTGGGATGCGGACCAC
TTCTCCGCTGACGACTTCCTGGGGCCATCGAGCTGGACCTGAACCGGTTCCCGCGG
GGCGCAAAGACAGCCAAGCAGTGCACCATGGAGATGGCCACCGGGGAGGTGGACGT
GCCCCTCGTGTCCATCTTCAAGCAAAAGCGCGTCAAAGGCTGGTGGCCCCTCCTGGCC
CGCAATGAGAACGATGAGTTTGAGCTCACGGGCAAGGTGGAGGCTGAGCTGCATTTAC
TGACAGCAGAGGAGGCAGAGAAGAACCCAGTGGGCCTGGCCCGCAATGAACCTGACC
CCCTAGAGAAACCCAACCGGCCCGACACGAGCTTCATCTGGTTCCTGAACCCTCTCAA
GTCGGCTCGCTACTTCTTGTGGCACACGTATCGCTGGCTGCTCCTCAAACTGTTGCTG
CTCCTGCTGCTGCTCCTCCTCCTCGCCCTGTTCCTCTACTCTGTGCCTGGCTACCTGGT
CAAGAAAATCCTCGGGGCCTGAACGGCCGCTATGCTAGCTTGGTACCAAGGGCGGATC
CTGCATAGAGCTCGCTGATCAGCCTCGACTGTGCCTTCTAGTTGCCAGCCATCTGTTGT
TTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGG
GGAGAGATCTGAGGACTAGTCCGTCGACTGTTAATTAAGCATGCTGGGGAGAGATCTA
GGAACCCCTAGTGATGGAGTTGGCCACTCCCTCTCTGCGCGCTCGCTCGCTCACTGAG
GCCGCCCGGGCAAAGCCCGGGCGTCGGGCGACCTTTGGTCGCCCGGCCTCAGTGAG
CGAGCGAGCGCGCAGAGAGGGAGTGGCCAACCCCCCCCCCCCCCCCTGCAGCCC
TGCATTAATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTC
CCTTCGGGAAGCGTGGCGCTTTCTCAATGCTCACGCTGTAGGTATCTCAGTTCGGTGT
AGGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTG
CGCTCTGCTGAAGCCAGTTACCTTCGGAAAAAGAGTTGGTAGCTCTTGATCCGGCAAA
CAAACC
```

FIG. 14 (continued)

```
ACCGCTGGTAGCGGTGGTTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATA
AACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTT
GCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCA
GTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTGACGTCTAAGA
AACCATTATTATCATGACATTAACCTATAAAAATAGGCGTATCACGAGGCCCTTTCGTCT
CGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCG
GGTGTTGGCGGGTGTCGGGGCTGGCTTAACTATGCGGCATCAGAGCAGATTGTACTGA
GAGTGCACCATATGCGGTGTGAAATACCGCACAGATGCGTAAGGAGAAAATACCGCAT
CAGGAAATTGTAAACGTTAATATTTTGTTAAAATTCGCGTTAAATTTTTGTTAAATCAGCT
CATTTTTTAACCAATAGGCCGAAATCGGCAAAATCCCTTATAAATCAAAAGAATAGACCG
AGATAGGGTTGAGTGTTGTTCCAGTTTGGAACAAGAGTCCACTATTAAAGAACGTGGAC
TCCAACGTCAAAGGGCGAAAAACCGTCTATCAGGGCGATGGCCCACTACGTGAACCAT
CACCCTAATCAAGTTTTTTGGGGTCGAGGTGCCGTAAAGCACTAAATCGGAACCCTAAA
GGGAGCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCACGCT
GCGCGTAACCACCACACCCGCCGCGCTTAATGCGCCGCTACAGGGCGCGTCGCGCCA
TTCGCCATTCAGGCTACGCAACTGTTGGGAAGGGCGATCGGTGCGGGCCTCTTCGCTA
TTACGCCAGGCTGC
```
(SEQ ID NO: 15)

FIG. 14 (continued)

pTR22-APhead-APSA-otoferlinCT Hs var 5

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4152 | Otoferlin CT: | Otoferlin coding sequence 3' part |
| 4195-4416 | bGH PolyA: | bovine growth hormone polyadenylation signal |
| 4478-4620 | TR: | inverted terminal repeat sequence of AAV2 |
| 5073-5298 | ColE1: | replication origin for E. coli |
| 5548-6548 | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCGGGTGCGCGGCGTCGG
TGGTGCCGGCGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAAAAC
ATGGGGCAGCAGGCCAGGATGCTGCGGGCCCAGGTGAAGCGGCACACGGTGCGGGA
CAAGCTGAGGCTGTGCCAGAACTTCCTGCAGAAGCTGCGCTTCCTGGCGGACGAGCC
CCAGCACAGCATTCCCGACATCTTCATCTGGATGATGAGCAACAACAAGCGTGTCGCC
TATGCCCGTGTGCCCTCCAAGGACCTGCTCTTCTCCATCGTGGAGGAGGAGACTGGCA
AGGACTGCGCCAAGGTCAAGACGCTCTTCCTTAAGCTGCCAGGGAAGCGGGGCTTCG
GCTCGGCAGGCTGGACAGTGCAGGCCAAGGTGGAGCTGTACCTGTGGCTGGGCCTCA
GCAAACAGCGCAAGGAGTTCCTGTGCGGCCTGCCCTGTGGCTTCCAGGAGGTCAAGG
CAGCCCAGGGCCTGGGCCTGCATGCCTTCCCACCCGTCAGCCTGGTCTACACCAAGA
AGCAGGCGTTCCAGCTCCGAGCGCACATGTACCAGGCCCGCAGCCTCTTTGCCGCCG
ACAGCAGCGGACTCTCAGACCCCTTTGCCCGCGTCTTCTTCATCAATCAGAGTCAGTG
CACAGAGGTGCTGAATGAGACCCTGTGTCCCACCTGGGACCAGATGCTGGTGTTCGAC
AACCTGGAGCTCTATGGTGAAGCTCATGAGCTGAGGGACGATCCGCCCATCATTGTCA
TTGAAATCTATGACCAGGATTCCATGGGCAAAGCTGACTTCATGGGCCGGACCTTCGC
CAAACCCCTGGTGAAGATGGCAGACGAGGCGTACTGCCCACCCCGCTTCCCACCCTCA
GCTCGAGTACTACCAGATCTACCGTGGCAACGCCACAGCTGGAGACCTGCTGGCGGC
CTTCAGCTGCTGCAGATTGGACCAGCAGGGAAGGCTGACCTGCCCCCCATCAATGG
CCCGGTGGACGTGGACCGAGGTCCCATCATGCCCGTGCCCATGGGCATCCGGCCCGT
GCTCAGCAAGTACCGAGTGGAGGTGCTGTTCTGGGGCCTACGGGACCTAAAGCGGGT
GAACCTGGCCCAGGTGGACCGGCCACGGGTGGACATCGAGTGTGCAGGGAAGGGGG
TGCAGTCGTCCCTGATCCACAATTATAAGAAGAACCCCAACTTCAACACCCTCGTCAAG
TGGTTTGAAGTGGACCTCCCAGAGAACGAGCTGCTGCACCCGCCCTTGAACATCCGTG
TGGTGGACTGCCGGGCCTTCGGTCGCTACACACTGGTGGGCTCCCATGCCGTCAGCT
CCCTGCGACGCTTCATCTACCGGCCCCAGACCGCTCGGCCCCAGCTGGAACACCA
CGGTCAGGCTTCTCCGGCGCTGCCGTGTGCTGTGCAATGGGGGCTCCTCCTCTCACTC
CACAGGGGAGGTTGTGGTGACTATGAGCCAGAGGTACCCATCAAGAAACTGGAGAC
CATGGTGAAGCTGGACGCGACTTCTGAAGCTGTTGTCAAGGTGGATGTGGCTGAGGAG
GAGAAGGAGAAGAAGAAGAAGAAGGGCACTGCGGAGGAGCCAGAGGAGGAGGA
GCCAGACGAGAGCATGCTGGACTGGTGGTCCAAGTACTTTGCCTCCATTGACACCATG
AAGGAGCAACTTCGACAACAAGAGCCCTCTGGAATTGACTTGGAGGAGAAGGAGGAAG
TGGACAATACCGAGGGCCTGAAGGGGTCAATGAAGGGCAAGGAGAAGGCAAGGGCTG
CCAAAGAGGAGAAGAAGAAGAAAACTCAGAGCTCTGGCTCTGGCCAGGGGTCCGAGG
```

FIG 15

```
CCCCCGAGAAGAAGAAACCCAAGATTGATGAGCTTAAGGTATACCCCAAAGAGCTGGA
GTCCGAGTTTGATAACTTTGAGGACTGGCTGCACACTTTCAACTTGCTTCGGGGCAAGA
CCGGGGATGATGAGGATGGCTCCACCGAGGAGGAGCGCATTGTGGGACGCTTCAAGG
GCTCCCTCTGCGTGTACAAAGTGCCACTCCCAGAGGACGTGTCCCGGGAAGCCGGCT
ACGACTCCACCTACGGCATGTTCCAGGGCATCCCGAGCAATGACCCCATCAATGTGCT
GGTCCGAGTCTATGTGGTCCGGGCCACGGACCTGCACCCTGCTGACATCAACGGCAA
AGCTGACCCCTACATCGCCATCCGGCTAGGCAAGACTGACATCCGCGACAAGGAGAAC
TACATCTCCAAGCAGCTCAACCCTGTCTTTGGAAGTCCTTTGACATCGAGGCCTCCTT
CCCCATGGAATCCATGCTGACGGTGGCTGTGTATGACTGGGACCTGGTGGGCACTGAT
GACCTCATTGGGGAAACCAAGATCGACCTGGAGAACCGCTTCTACAGCAAGCACGCG
CCACCTGCGGCATCGCCCAGACCTACTCCACACATGGCTACAATATCTGGCGGGACCC
CATGAAGCCCAGCCAGATCCTGACCCGCCTCTGCAAAGACGGCAAAGTGGACGGCCC
CCACTTTGGGCCCCCTGGGAGAGTGAAGGTGGCCAACCGCGTCTTCACTGGGCCCTC
TGAGATTGAGGACGAGAACGGTCAGAGGAAGCCCACAGACGAGCATGTGGCGCTGTT
GGCCCTGAGGCACTGGGAGGACATCCCCGCGCAGGCTGCCGCCTGGTGCCAGAGC
ATGTGGAGACGAGGCCGCTGCTCAACCCCGACAAGCCGGGCATCGAGCAGGGCCGC
CTGGAGCTGTGGGTGGACATGTTCCCCATGGACATGCCAGCCCCTGGGACGCCTCTG
GACATCTCACCTCGGAAGCCCAAGAAGTACGAGCTGCGGGTCATCATCTGGAACACAG
ATGAGGTGGTCTTGGAGGACGACGACTTCTTCACAGGGGAGAAGTCCAGTGACATCTT
CGTGAGGGGGTGGCTGAAGGGCCAGCAGGAGGACAAGCAGGACACAGACGTCCACTA
CCACTCCCTCACTGGCGAGGGCAACTTCAACTGGCGCTACCTGTTCCCCTTCGACTAC
CTGGCGGCGGAGGAGAAGATCGTCATCTCCAAGAAGGAGTCCATGTTCTCCTGGGAC
GAGACCGAGTACAAGATCCCCGCGCGGCTCACCCTGCAGATCTGGGATGCGGACCAC
TTCTCCGCTGACGACTTCCTGGGGCCATCGAGCTGGACCTGAACCGGTTCCCGCGG
GGCGCAAAGACAGCCAAGCAGTGCACCATGGAGATGGCCACCGGGGAGGTGGACGT
GCCCCTCGTGTCCATCTTCAAGCAAAAGCGCGTCAAAGGCTGGTGGCCCCTCCTGGCC
CGCAATGAGAACGATGAGTTTGAGCTCACGGGCAAGGTGGAGGCTGAGCTGCATTTAC
TGACAGCAGAGGAGGCAGAGAAGAACCCAGTGGGCCTGGCCCGCAATGAACCTGACC
CCCTAGAGAAACCCAACCGGCCCGACACGGCCTTCGTCTGGTTCCTCAACCCTCTCAA
GTCCATCAAGTACCTCATCTGCACCCGGTACAAGTGGCTCATCATCAAGATCGTGCTGG
CGCTGTTGGGGCTGCTCATGTTGGGCTCTTCCTCTACAGCCTCCCTGGCTACATGGT
CAAAAAGCTCCTTGGGGCATGAACGGCCGCTATGCTAGCTTGGTACCAAGGGCGGATC
CTGCATAGAGCTCGCTGATCAGCCTCGACTGTGCCTTCTAGTTGCCAGCCATCTGTTGT
TTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGT
GGGGTGGGGCAGGACAGCAAGGGGGAGGATTGGGAAGACAATAGCAGGCATGCTGG
GGAGAGATCTGAGGACTAGTCCGTCGACTGTTAATTAAGCATGCTGGGGAGAGATCTA
GGAACCCCTAGTGATGGAGTTGGCCACTCCCTCTCTGCGCGCTCGCTCGCTCACTGAG
GCCGCCCGGGCAAAGCCCGGGCGTCGGGCGACCTTTGGTCGCCCGGCCTCAGTGAG
CGAGCGAGCGCGCAGAGAGGGAGTGGCCAACCCCCCCCCCCCCCCCCTGCAGCCC
TGCATTAATGAATCGGCCAACGCGCGGGAGAGGCGGTTTGCGTATTGGGCGCTCTTC
CGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTC
CCTTCGGGAAGCGTGGCGCTTTCTCAATGCTCACGCTGTAGGTATCTCAGTTCGGTGT
AGGTCGTTCGCTCCAAGCTGGGCTGTGTGCACGAACCCCCGTTCAGCCCGACCGCT
GCGCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTG
CGCTCTGCTGAAGCCAGTTACCTTCGGAAAAAGAGTTGGTAGCTCTTGATCCGGCAAA
CAAACC
```

FIG. 15 (continued)

```
ACCGCTGGTAGCGGTGGTTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATA
AACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTT
GCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCA
GTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTGACGTCTAAGA
AACCATTATTATCATGACATTAACCTATAAAAATAGGCGTATCACGAGGCCCTTTCGTCT
CGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCG
GGTGTTGGCGGGTGTCGGGGCTGGCTTAACTATGCGGCATCAGAGCAGATTGTACTGA
GAGTGCACCATATGCGGTGTGAAATACCGCACAGATGCGTAAGGAGAAAATACCGCAT
CAGGAAATTGTAAACGTTAATATTTTGTTAAAATTCGCGTTAAATTTTTGTTAAATCAGCT
CATTTTTTAACCAATAGGCCGAAATCGGCAAAATCCCTTATAAATCAAAAGAATAGACCG
AGATAGGGTTGAGTGTTGTTCCAGTTTGGAACAAGAGTCCACTATTAAAGAACGTGGAC
TCCAACGTCAAAGGGCGAAAAACCGTCTATCAGGGCGATGGCCCACTACGTGAACCAT
CACCCTAATCAAGTTTTTTGGGGTCGAGGTGCCGTAAAGCACTAAATCGGAACCCTAAA
GGGAGCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCACGCT
GCGCGTAACCACCACACCCGCCGCGCTTAATGCGCCGCTACAGGGCGCGTCGCGCCA
TTCGCCATTCAGGCTACGCAACTGTTGGGAAGGGCGATCGGTGCGGGCCTCTTCGCTA
TTACGCCAGGCTGC
```
(SEQ ID NO: 16)

FIG. 15 (continued)

pTR-APhead-APSA-hOtoferlin V1-CTopt

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4152 | hOtoferlin V1-CTopt | codon-optimized human Otoferlin isoform 1 coding sequence 3' part |
| 4195-4416 | bGH PolyA: | bovine growth hormone polyadenylation signal |
| 4483-4625 | TR: | inverted terminal repeat sequence of AAV2 |
| 5073-5298 | ColE1: | replication origin for E. coli |
| 5548-6548 | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCGGGTGCGCGGCGTCGG
TGGTGCCGGCGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAAAAT
ATGGGACAGCAGGCAAGGATGCTGCGCGCCCAGGTGAAGAGGCACACCGTGAGAGAC
AAGCTGCGGCTGTGCCAGAACTTCCTGCAGAAGCTGCGCTTTCTGGCCGATGAGCCAC
AGCACAGCATCCCCGACATCTTCATCTGGATGATGTCCAACAATAAGAGAGTGGCCTAC
GCCCGGGTGCCCTCTAAGGATCTGCTGTTTAGCATCGTGGAGGAGGAGACAGGCAAG
GACTGTGCCAAGGTGAAGACCCTGTTCCTGAAGCTGCCTGGCAAGAGAGGCTTTGGCA
GCGCCGGATGGACCGTGCAGGCAAAGGTGGAGCTGTATCTGTGGCTGGGCCTGTCTA
AGCAGCGGAAGGAGTTCCTGTGCGGCCTGCCCTGTGGCTTTCAGGAGGTGAAGGCAG
CACAGGGACTGGGACTGCACGCCTTCCCCCCGTGAGCCTGGTGTACACCAAGAAGC
AGGCCTTTCAGCTGAGGGCCCATATGTACCAGGCCAGGTCTCTGTTCGCCGCCGATAG
CTCCGGACTGAGCGACCCTTTTGCCAGGGTGTTCTTTATCAATCAGAGCCAGTGCACA
GAGGTGCTGAACGAGACCCTGTGCCCAACATGGGATCAGATGCTGGTGTTCGACAACC
TGGAGCTGTACGGAGAGGCACACGAGCTGAGGGACGATCCACCCATCATCGTGATCG
AGATCTATGATCAGGACTCCATGGGCAAGGCCGATTTCATGGGCAGGACCTTTGCCAA
GCCCCTGGTGAAGATGGCCGACGAGGCCTACTGCCCTCCAAGATTCCCCCCTCAGCTC
GAGTACTATCAGATCTATAGGGGAAATGCAACCGCCGGAGACCTGCTGGCCGCCTTTG
AGCTGCTGCAGATCGGCCCCGCCGGAAAGGCAGACCTGCCACCCATCAACGGCCCAG
TGGATGTGGACAGAGGCCCCATCATGCCTGTGCCAATGGGCATCAGACCAGTGCTGTC
CAAGTACAGGGTGGAGGTGCTGTTCTGGGGACTGCGCGACCTGAAGAGGGTGAATCT
GGCCCAGGTGGATAGGCCCAGAGTGGACATCGAGTGCGCCGGAAAGGGCGTGCAGT
CTAGCCTGATCCACAACTATAAGAAGAACCCAAATTTCAACACCCTGGTGAAGTGGTTT
GAGGTGGATCTGCCCGAGAATGAGCTGCTGCACCCTCCACTGAACATCCGGGTGGTG
GACTGTAGAGCCTTCGGCAGGTACACCCTGGTGGGCAGCCACGCCGTGAGCAGCCTG
AGGAGGTTCATCTACAGGCCCCCTGACAGGTCCGCCCCTTCTTGGAATACCACAGTGA
GACTGCTGCGGCGCTGCAGGGTGCTGTGCAACGGAGGCAGCTCCTCTCACTCTACCG
GCGAGGTGGTGGTGACAATGGAGCCTGAGGTACCCATCAAGAAGCTGGAGACCATGG
TGAAGCTGGATGCCACAAGCGAGGCAGTGGTGAAGGTGGACGTGGCAGAGGAGGAGA
AGGAGAAGAAGAAGAAGAAGAAGGGAACCGCCGAGGAGCCTGAGGAAGAGGAGCCA
GATGAGAGCATGCTGGACTGGTGGTCCAAGTACTTCGCCTCTATCGACACAATGAAGG
AGCAGCTGAGACAGCAGGAGCCTAGCGGCATCGATCTGGAGGAGAAGGAGGAGGTGG
```

FIG. 17

```
ACAATACCGAGGGCCTGAAGGGCTCCATGAAGGGCAAGGAGAAGGCAAGGGCAGCAA
AGGAAGAGAAGAAGAAGAAGACCCAGAGCAGCGGCTCTGGACAGGGCAGCGAGGCAC
CAGAGAAGAAGAAGCCTAAGATCGATGAGCTGAAGGTGTACCCAAAGGAGCTGGAGTC
CGAGTTCGATAATTTTGAGGACTGGCTGCACACCTTCAACCTGCTGCGCGGCAAGACA
GGCGACGATGAGGACGGCAGCACCGAGGAGGAGAGAATCGTGGGCCGGTTTAAGGG
CTCCCTGTGCGTGTACAAGGTGCCACTGCCTGAGGACGTGAGCAGGGAGGCCGGATA
CGACTCTACCTATGGCATGTTCCAGGGCATCCCCTCTAATGATCCTATCAACGTGCTGG
TGCGCGTGTATGTGGTGAGGGCCACAGATCTGCACCCCGCCGACATCAACGGCAAGG
CCGACCCTTACATCGCCATCCGCCTGGGCAAGACCGATATCAGGGACAAGGAGAATTA
TATCTCCAAGCAGCTGAACCCCGTGTTCGGCAAGTCTTTTTGACATCGAGGCCAGCTTCC
CTATGGAGTCCATGCTGACCGTGGCCGTGTACGATTGGGACCTGGTGGGCACCGACG
ATCTGATCGGCGAGACAAAGATCGATCTGGAGAATCGCTTTTATTCTAAGCACAGGGCA
ACCTGCGGAATCGCACAGACCTACAGCACACACGGCTATAACATCTGGCGCGACCCCA
TGAAGCCTAGCCAGATCCTGACAAGGCTGTGCAAGGATGGCAAGGTGGACGGACCAC
ACTTCGGACCACCCGGCAGAGTGAAGGTGGCCAATCGGGTGTTTACAGGCCCTTCCGA
GATCGAGGATGAGAACGGCCAGCGCAAGCCAACCGACGAGCACGTGGCCCTGCTGGC
CCTGAGGCACTGGAGGATATCCCAAGGGCCGGATGTAGGCTGGTGCCTGAGCACGT
GGAGACCAGACCACTGCTGAATCCAGACAAGCCAGGAATCGAGCAGGGCAGGCTGGA
GCTGTGGGTGGATATGTTCCAATGGACATGCCAGCCCCAGGAACACCCCTGGATATC
TCCCCTAGAAAGCCAAAGAAGTACGAGCTGAGAGTGATCATCTGGAACACAGACGAGG
TGGTGCTGGAGGACGATGACTTCTTTACCGGCGAGAAGTCTAGCGATATCTTTGTGCG
CGGATGGCTGAAGGGACAGCAGGAGGACAAGCAGGATACAGACGTGCACTACCACTC
CCTGACCGGCGAGGGCAATTTCAACTGGAGATACCTGTTCCCTTTTGATTATCTGGCCG
CCGAGGAGAAGATCGTGATCTCTAAGAAGGAGAGCATGTTTTCCTGGGACGAGACAGA
GTATAAGATCCCAGCCAGACTGACCCTGCAGATCTGGGATGCCGACCACTTCAGCGCC
GATGACTTTCTGGGCGCCATCGAGCTGGACCTGAACCGGTTCCCAAGAGGCGCCAAG
ACCGCCAAGCAGTGCACAATGGAGATGGCAACCGGAGAGGTGGACGTGCCTCTGGTG
TCTATCTTCAAGCAGAAGAGGGTGAAGGGCTGGTGGCCACTGCTGGCCAGAAACGAGA
ATGATGAGTTTGAGCTGACAGGCAAGGTGGAGGCAGAGCTGCACCTGCTGACCGCCG
AGGAGGCAGAGAAGAACCCAGTGGGCCTGGCCAGGAATGAGCCCGACCCTCTGGAGA
AGCCAAACAGGCCCGACACCAGCTTCATCTGGTTTCTGAATCCTCTGAAGTCCGCCCG
GTACTTCCTGTGGCACACCTATCGCTGGCTGCTGCTGAAGCTGTTATTACTGTTATTAC
TGCTGCTGCTGCTGGCCCTGTTTCTGTACAGCGTGCCCGGCTATCTGGTGAAGAAGAT
CCTGGGCGCCTGAACGGCCGCTATGCTAGCTTGGTACCAAGGGCGGATCCTGCATAG
AGCTCGCTGATCAGCCTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGGTGGGGTGG
GGCAGGACAGCAAGGGGGAGGATTGGGAAGACAATAGCAGGCATGCTGGGGAGAGAT
CTGAGGACTAGTCCGTCGACTGTAATTAAGCATGCTGGGGAGAGATCTAGGAACCCC
TAGTGATGGAGTTGGCCACTCCCTCTCTGCGCGCTCGCTCGCTCACTGAGGCCGCCC
GGGCAAAGCCCGGGCGTCGGGCGACCTTTGGTCGCCCGGCCTCAGTGAGCGAGCGA
GCGCGCAGAGAGGGAGTGGCCAACCCCCCCCCCCCCCCCCCTGCAGCCCTGCATTAA
TGAATCGGCCAACGCGCGGGAGAGGCGGTTTGCGTATTGGGCGCTCTTCCGCTTCC
TCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTC
CATAGGCTCCGCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAA
GCGTGGCGCTTTCTCAATGCTCACGCTGTAGGTATCTCAGTTCGGTGTAGGTCGTTCG
CTCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAA
```

FIG. 17 (continued)

```
GTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGATCT
CAAGAAGATCCTTTGATCTTTTCTACGGGGTCTGACGCTCAGTGGAACGAAAACTCACG
TTAAGGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCT
GACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGT
CTATTAATTGTTGCCGGGAAGCTAGAGTAAGTAGTTCGCCAGTTAATAGTTTGCGCAAC
GTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACC
GAGTTGCTCTTGCCCGGCGTCAATACGGGATAATACCGCGCCACATAGCAGAACTTTA
AAAGTGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGG
AATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAA
CAAATAGGGGTTCCGCGCACATTTCCCCGAAAAGTGCCACCTGACGTCTAAGAAACCA
TTATTATCATGACATTAACCTATAAAAATAGGCGTATCACGAGGCCCTTTCGTCTCGCGC
GTTTCGGTGATGACGGTGAAAACCTCTGACACATGCAGCTCCCGGAGACGGTCACAGC
TTGTCTGTAAGCGGATGCCGGGAGCAGACAAGCCCGTCAGGGCGCGTCAGCGGGTGT
TGGCGGGTGTCGGGGCTGGCTTAACTATGCGGCATCAGAGCAGATTGTACTGAGAGTG
CACCATATGCGGTGTGAAATACCGCACAGATGCGTAAGGAGAAAATACCGCATCAGGA
AATTGTAAACGTTAATATTTTGTTAAAATTCGCGTTAAATTTTTGTTAAATCAGCTCATTTT
TTAACCAATAGGCCGAAATCGGCAAAATCCCTTATAAATCAAAAGAATAGACCGAGATA
GGGTTGAGTGTTGTTCCAGTTTGGAACAAGAGTCCACTATTAAAGAACGTGGACTCCAA
CGTCAAAGGGCGAAAAACCGTCTATCAGGGCGATGGCCCACTACGTGAACCATCACCC
TAATCAAGTTTTTTGGGGTCGAGGTGCCGTAAAGCACTAAATCGGAACCCTAAAGGGAG
CCCCCGATTTAGAGCTTGACGGGAAAGCCGGCGAACGTGGCGAGAAAGGAAGGGAA
GAAAGCGAAAGGAGCGGGCGCTAGGGCGCTGGCAAGTGTAGCGGTCACGCTGCGCG
TAACCACCACACCCGCCGCGCTTAATGCGCCGCTACAGGGCGCGTCGCGCCATTCGC
CATTCAGGCTACGCAACTGTTGGGAAGGGCGATCGGTGCGGGCCTCTTCGCTATTACG
CCAGGCTGC
(SEQ ID NO: 17)
```

FIG. 17 (continued)

pTR-APhead-APSA-hOtoferlin V5-CTopt

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4152 | hOtoferlin V5-CTopt | codon-optimized human Otoferlin isoform 5 coding sequence 3' part |
| 4195-4416 | bGH PolyA: | bovine growth hormone polyadenylation signal |
| 4483-4625 | TR: | inverted terminal repeat sequence of AAV2 |
| 5073-5298 | ColE1: | replication origin for E. coli |
| 5548-6548 | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCCGGGTGCGCGGCGTCGG
TGGTGCCGGCGGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAAAAT
ATGGGACAGCAGGCAAGGATGCTGCGCGCCCAGGTGAAGAGGCACACCGTGAGAGAC
AAGCTGCGGCTGTGCCAGAACTTCCTGCAGAAGCTGCGCTTTCTGGCCGATGAGCCAC
AGCACAGCATCCCCGACATCTTCATCTGGATGATGTCCAACAATAAGAGAGTGGCCTAC
GCCCGGGTGCCCTCTAAGGATCTGCTGTTTAGCATCGTGGAGGAGGAGACAGGCAAG
GACTGTGCCAAGGTGAAGACCCTGTTCCTGAAGCTGCCTGGCAAGAGAGGCTTTGGCA
GCGCCGGATGGACCGTGCAGGCAAAGGTGGAGCTGTATCTGTGGCTGGGCCTGTCTA
AGCAGCGGAAGGAGTTCCTGTGCGGCCTGCCCTGTGGCTTTCAGGAGGTGAAGGCAG
CACAGGGACTGGGACTGCACGCCTTCCCCCCGTGAGCCTGGTGTACACCAAGAAGC
AGGCCTTTCAGCTGAGGGCCCATATGTACCAGGCCAGGTCTCTGTTCGCCGCCGATAG
CTCCGGACTGAGCGACCCTTTTGCCAGGGTGTTCTTTATCAATCAGAGCCAGTGCACA
GAGGTGCTGAACGAGACCCTGTGCCCAACATGGGATCAGATGCTGGTGTTCGACAACC
TGGAGCTGTACGGAGAGGCACACGAGCTGAGGGACGATCCACCCATCATCGTGATCG
AGATCTATGATCAGGACTCCATGGGCAAGGCCGATTTCATGGGCAGGACCTTTGCCAA
GCCCCTGGTGAAGATGGCCGACGAGGCCTACTGCCCTCCAAGATTCCCCCCTCAGCTC
GAGTACTATCAGATCTATAGGGGAAATGCAACCGCCGGAGACCTGCTGGCCGCCTTTG
AGCTGCTGCAGATCGGCCCCGCCGAAAGGCAGACCTGCCACCCATCAACGGCCCAG
TGGATGTGGACAGAGGCCCCATCATGCCTGTGCCAATGGGCATCAGACCAGTGCTGTC
CAAGTACAGGGTGGAGGTGCTGTTCTGGGGACTGCGCGACCTGAAGAGGGTGAATCT
GGCCCAGGTGGATAGGCCCAGAGTGGACATCGAGTGCGCCGGAAAGGGCGTGCAGT
CTAGCCTGATCCACAACTATAAGAAGAACCCAAATTTCAACACCCTGGTGAAGTGGTTT
GAGGTGGATCTGCCCGAGAATGAGCTGCTGCACCCTCCACTGAACATCCGGGTGGTG
GACTGTAGAGCCTTCGGCAGGTACACCCTGGTGGGCAGCCACGCCGTGAGCAGCCTG
AGGAGGTTCATCTACAGGCCCCCTGACAGGTCCGCCCCTTCTTGGAATACCACAGTGA
GACTGCTGCGGCGCTGCAGGGTGCTGTGCAACGGAGGCAGCTCCTCTCACTCTACCG
GCGAGGTGGTGGTGACAATGGAGCCTGAGGTACCCATCAAGAAGCTGGAGACCATGG
TGAAGCTGGATGCCACAAGCGAGGCAGTGGTGAAGGTGGACGTGGCAGAGGAGGAGA
AGGAGAAGAAGAAGAAGAAGAAGGGAACCGCCGAGGAGCCTGAGGAAGAGGAGCCA
GATGAGAGCATGCTGGACTGGTGGTCCAAGTACTTCGCCTCTATCGACACAATGAAGG
AGCAGCTGAGACAGCAGGAGCCTAGCGGCATCGATCTGGAGGAGAAGGAGGAGGTGG
```

FIG. 18

```
ACAATACCGAGGGCCTGAAGGGCTCCATGAAGGGCAAGGAGAAGGCAAGGGCAGCAA
AGGAAGAGAAGAAGAAGAAGACCCAGAGCAGCGGCTCTGGACAGGGCAGCGAGGCAC
CAGAGAAGAAGAAGCCTAAGATCGATGAGCTGAAGGTGTACCCAAAGGAGCTGGAGTC
CGAGTTCGATAATTTTGAGGACTGGCTGCACACCTTCAACCTGCTGCGCGGCAAGACA
GGCGACGATGAGGACGGCAGCACCGAGGAGGAGAGAATCGTGGGCCGGTTTAAGGG
CTCCCTGTGCGTGTACAAGGTGCCACTGCCTGAGGACGTGAGCAGGGAGGCCGGATA
CGACTCTACCTATGGCATGTTCCAGGGCATCCCCTCTAATGATCCTATCAACGTGCTGG
TGCGCGTGTATGTGGTGAGGGCCACAGATCTGCACCCCGCCGACATCAACGGCAAGG
CCGACCCTTACATCGCCATCCGCCTGGGCAAGACCGATATCAGGGACAAGGAGAATTA
TATCTCCAAGCAGCTGAACCCCGTGTTCGGCAAGTCTTTTGACATCGAGGCCAGCTTCC
CTATGGAGTCCATGCTGACCGTGGCCGTGTACGATTGGGACCTGGTGGGCACCGACG
ATCTGATCGGCGAGACAAAGATCGATCTGGAGAATCGCTTTTATTCTAAGCACAGGGCA
ACCTGCGGAATCGCACAGACCTACAGCACACACGGCTATAACATCTGGCGCGACCCCA
TGAAGCCTAGCCAGATCCTGACAAGGCTGTGCAAGGATGGCAAGGTGGACGGACCAC
ACTTCGGACCACCCGGCAGAGTGAAGGTGGCCAATCGGGTGTTTACAGGCCCTTCCGA
GATCGAGGATGAGAACGGCCAGCGCAAGCCAACCGACGAGCACGTGGCCCTGCTGGC
CCTGAGGCACTGGGAGGATATCCCAAGGGCCGGATGTAGGCTGGTGCCTGAGCACGT
GGAGACCAGACCACTGCTGAATCCAGACAAGCCAGGAATCGAGCAGGGCAGGCTGGA
GCTGTGGGTGGATATGTTCCAATGGACATGCCAGCCCCAGGAACACCCCTGGATATC
TCCCCTAGAAAGCCAAAGAAGTACGAGCTGAGAGTGATCATCTGGAACACAGACGAGG
TGGTGCTGGAGGACGATGACTTCTTTACCGGCGAGAAGTCTAGCGATATCTTTGTGCG
CGGATGGCTGAAGGGACAGCAGGAGGACAAGCAGGATACAGACGTGCACTACCACTC
CCTGACCGGCGAGGGCAATTTCAACTGGAGATACCTGTTCCCTTTTGATTATCTGGCCG
CCGAGGAGAAGATCGTGATCTCTAAGAAGGAGAGCATGTTTTCCTGGGACGAGACAGA
GTATAAGATCCCAGCCAGACTGACCCTGCAGATCTGGGATGCCGACCACTTCAGCGCC
GATGACTTTCTGGGCGCCATCGAGCTGGACCTGAACCGGTTCCCAAGAGGCGCCAAG
ACCGCCAAGCAGTGCACAATGGAGATGGCAACCGGAGAGGTGGACGTGCCTCTGGTG
TCTATCTTCAAGCAGAAGCGGGTGAAGGGATGGTGGCCACTGCTGGCCAGGAACGAG
AATGATGAGTTTGAGCTGACAGGCAAGGTGGAGGCAGAGCTGCACCTGCTGACCGCC
GAGGAGGCAGAGAAGAACCCAGTGGGCCTGGCCAGGAATGAGCCCGACCCTCTGGAG
AAGCCAAACAGGCCCGATACAGCCTTCGTGTGGTTTCTGAATCCTCTGAAGAGCATCAA
GTACCTGATCTGTACCAGGTATAAGTGGCTGATCATCAAGATCGTGCTGGCCCTGCTG
GGACTGCTGATGCTGGGCCTGTTTCTGTACTCCCTGCCCGGCTATATGGTGAAGAAGC
TGCTGGGCGCCTGAACGGCCGCTATGCTAGCTTGGTACCAAGGGCGGATCCTGCATA
GAGCTCGCTGATCAGCCTCGACTGTGCCTTCTAGTTGCCAGCCATCTGTTGTTTGCCCC
TCCCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGCTGGGGAGAG
ATCTGAGGACTAGTCCGTCGACTGTTAATTAAGCATGCTGGGGAGAGATCTAGGAACC
CCTAGTGATGGAGTTGGCCACTCCCTCTCTGCGCGCTCGCTCGCTCACTGAGGCCGCC
CGGGCAAAGCCCGGGCGTCGGGCGACCTTTGGTCGCCCGGCCTCAGTGAGCGAGCG
AGCGCGCAGAGAGGGAGTGGCCAACCCCCCCCCCCCCCCCCTGCAGCCCTGCATTA
ATGAATCGGCCAACGCGCGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAG
```

FIG. 18 (continued)

```
CAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAAT
TAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAG
TGCTGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGAACTT
TAAAAGTGCTCATCATTGGAAAACGTTCTTCGGGGCGAAAACTCTCAAGGATCTTACCG
CTGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTATTGA
AGCATTTATCAGGGTTATTGTCTCATGAGCGGATACATATTTGAATGTATTTAGAAAAAT
AAACAAATAGGGGTTCCGCGCACATTTCCCCGAAAAGTGCCACCTGACGTCTAAGAAA
CCATTATTATCATGACATTAACCTATAAAAATAGGCGTATCACGAGGCCCTTTCGTCTCG
CGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGG
TGTTGGCGGGTGTCGGGGCTGGCTTAACTATGCGGCATCAGAGCAGATTGTACTGAGA
GTGCACCATATGCGGTGTGAAATACCGCACAGATGCGTAAGGAGAAAATACCGCATCA
GGAAATTGTAAACGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAG
ATAGGGTTGAGTGTTGTTCCAGTTTGGAACAAGAGTCCACTATTAAAGAACGTGGACTC
CAACGTCAAAGGGCGAAAAACCGTCTATCAGGGCGATGGCCCACTACGTGAACCATCA
CCCTAATCAAGTTTTTTGGGGTCGAGGTGCCGTAAAGCACTAAATCGGAACCCTAAAGG
GAGCCCCCGATTTAGAGCTTGACGGGGAAAGCCGGCGAACGTGGCGAGAAAGGAAGG
GAAGAAAGCGAAAGGAGCGGGCGCTAGGGCGCTGGCAAGTGTAGCGGTCACGCTGC
GCGTAACCACCACACCCGCCGCGCTTAATGCGCCGCTACAGGGCGCGTCGCGCCATT
CGCCATTCAGGCTACGCAACTGTTGGGAAGGGCGATCGGTGCGGGCCTCTTCGCTATT
ACGCCAGGCTGC
```
(SEQ ID NO:18)

FIG. 18 (continued)

pTR-smCBA-hOtoferlinNT opt-APSD-APhead

| Nucleotide positions | Abbreviation | Description |
|---|---|---|
| 20-162 | TR: | inverted terminal repeat sequence of AAV2 |
| 186-551 | CBA promoter: | -CMVie enhancer |
| 553-835 | | -chicken b-actin promoter |
| 836-1130 | | -Exon1 and chimeric intron |
| 1153-3558 | hOtoferlinNTopt: | codon-optimized human Otoferlin coding sequence 5' part |
| 3559-3642 | APSD: | Splice Donor |
| 3649-3935 | APhead: | homologous sequence for recombination |
| 4975-4117 | TR: | inverted terminal repeat sequence of AAV2 |
| 4565-4790 | ColE1: | replication origin for E. coli |
| 5040-6040 | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTCGGTACCCTAGTTATTAATAGTAATCAATTACGGGGTCATTAGT
TCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAAC
GCCAATAGGGACTTTCCATTGACGTCAATGGGTGGACTATTTACGGTAAACTGCCCACT
TGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTGCT
TCACTCTCCCCATCTCCCCCCCCTCCCCACCCCCAATTTTGTATTTATTTATTTTTTAATT
ATTTTGTGCAGCGATGGGGGCGGGGGGGGGGGGGGCGCGCGCCAGGCGGGGCG
GGGCGGGGCGAGGGGCGGGGCGGGGCGAGGCGGAGAGGTGCGGCGGCAGCCAATC
AGAGCGGCGCGCTCCGAAAGTTTCCTTTTATGGCGAGGCGGCGGCGGCGGCGGCCCT
ATAAAAAGCGAAGCGCGCGGCGGGCGGGAGTCGCTGCGACGCTGCCTTCGCCCCGT
GCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGT
TTAATGACGGCTTGTTTCTTTTCTGTGGCTGCGTGAAAGCCTTGAGGGGCTCCGGGAG
CTAGAGCCTCTGCTAACCATGTTCATGCCTTCTTCTTTTTCCTACAGCTCCTGGGCAAC
GTGCTGGTTATTGTGCTGTCTCATCATTTTGGCAAAGAATTCTAGCGGCCGCCACCATG
GCACTGCTGATCCACCTGAAAACCGTCTCCGAACTGAGAGGCAGAGGGGACAGAATCG
CTAAAGTCACCTTCCGGGGACAGAGCTTTTACAGCAGGGTGCTGGAGAACTGCGAGGA
CGTGGCCGACTTTGACGAGACATTCAGGTGGCCCGTGGCCAGCTCCATCGATCGCAAT
GAGATGCTGGAGATCCAGGTGTTTAACTATAGCAAGGTGTTCTCCAATAAGCTGATCGG
CACCTTCCGGATGGTGCTGCAGAAGGTGGTGGAGGAGTCCCACGTGGAGGTGACCGA
CACACTGATCGACGATAACAATGCCATCATCAAGACATCCCTGTGCGTGGAGGTGCGC
TACCAGGCCACCGATGGCACAGTGGGCTCTTGGGACGATGGCGACTTCCTGGGCGAT
GAGTCCCTGCAGGAGGAGGAGAAGGACTCTCAGGAGACAGATGGCCTGCTGCCTGGC
TCCCGGCCATCTAGCCGCCCCCTGGCGAGAAGTCTTTTAGGAGAGCCGGCAGGTCC
GTGTTCTCTGCCATGAAGCTGGGCAAGAACAGGAGCCACAAGGAGGAGCCTCAGAGG
CCCGACGAGCCAGCCGTGCTGGAGATGGAGGACCTGGATCACCTGGCCATCAGACTG
GGCGATGGCCTGGACCCTGATAGCGTGTCCCTGGCCTCCGTGACCGCCCTGACCACA
AACGTGTCTAATAAGCGGAGCAAGCCAGACATCAAGATGGAGCCATCTGCCGGCAGGC
CCATGGATTACCAGGTGAGCATCACAGTGATCGAGGCCAGACAGCTGGTGGGCCTGAA
CATGGACCCCGTGGTGTGCGTGGAAGTGGGCGACGATAAGAAGTACACCTCCATGAA
GGAGTCTACAAACTGTCCATACTACAACGAGTACTTCGTGTTTGATTTCCACGTGAGCC
CCGACGTGATGTTCGATAAGATCATCAAGATCAGCGTGATCCACTCCAAGAATCTGCTG
CGGTCTGGCACCCTGGTGGGAAGCTTTAAGATGGACGTGGGCACAGTGTACTCTCAGC
```

FIG. 19

```
CTGAGCACCAGTTCCACCACAAGTGGGCCATCCTGAGCGATCCAGACGATATCTCCTC
TGGCCTGAAGGGCTATGTGAAGTGCGACGTGGCAGTGGTGGGCAAGGGCGATAACAT
CAAGACCCCACACAAGGCCAATGAGACAGACGAGGACGATATCGAGGGAAACCTGCT
GCTGCCAGAGGGAGTGCCACCCGAGAGGCAGTGGGCCAGGTTCTACGTGAAGATCTA
TAGGGCAGAGGGCCTGCCTAGGATGAACACCAGCCTGATGGCCAATGTGAAGAAGGC
CTTCATCGGCGAGAACAAGGACCTGGTGGATCCCTACGTGCAGGTGTTCTTTGCCGGC
CAGAAGGGCAAGACCTCCGTGCAGAAGAGCTCCTATGAGCCTCTGTGGAATGAGCAG
GTGGTGTTTACAGACCTGTTCCCTCCACTGTGCAAGAGGATGAAGGTGCAGATCAGAG
ACTCTGATAAGGTGAACGACGTGGCCATCGGCACCCACTTTATCGATCTGAGGAAGAT
CAGCAATGACGGCGATAAGGGCTTCCTGCCCACCCTGGGCCCCGCCTGGGTGAACAT
GTACGGCAGCACCAGAAATTATACACTGCTGGACGAGCACCAGGATCTGAACGAGGGC
CTGGGCGAGGGCGTGAGCTTTAGAGCCAGGCTGCTGCTGGGCCTGGCCGTGGAGATC
GTGGACACCTCCAATCCCGAGCTGACCTCTAGCACAGAGGTGCAGGTGGAGCAGGCC
ACACCTATCTCTGAGAGCTGTGCCGGCAAGATGGAGGAGTTCTTTCTGTTTGGCGCCTT
CCTGGAGGCCTCCATGATCGACCGGCGCAACGGCGATAAGCCTATCACCTTCGAGGT
GACAATCGGCAACTACGGCAATGAGGTGGACGGCCTGTCTCGGCCCCAGCGCCCAAG
GCCCAGAAAGGAGCCTGGCGACGAGGAGGAGGTGGATCTGATCCAGAACGCCAGCGA
CGATGAGGCAGGCGACGCAGGCGATCTGGCCTCCGTGTCCTCTACCCCCCCTATGCG
GCCACAGGTGACAGACCGCAATTACTTTCACCTGCCTTATCTGGAGCGCAAGCCATGC
ATCTACATCAAGTCTTGGTGGCCCGATCAGAGGAGACGGCTGTATAACGCCAATATCAT
GGACCACATCGCCGATAAGCTGGAGGAGGGCCTGAATGACATCCAGGAGATGATCAA
GACCGAGAAGTCCTATCCAGAGCGCAGGCTGAGGGGCGTGCTGGAGGAGCTGAGCTG
TGGCTGCTGTAGATTCCTGTCCCTGGCCGACAAGGATCAGGGGCACTCATCACGGACA
CGGCTGGACCGGGAGCGGCTGAAATCATGTATGCGGGAGCTGGTAAGTATCAAGGTTA
CAAGACAGGTTTAAGGAGACCAATAGAAACTGGGCTTGTCGAGACAGAGAAGACTCTT
GCGTTTCTGAGCTAGCCCCCGGGTGCGCGGCGTCGGTGGTGCCGGCGGGGGGCGCC
AGGTCGCAGGCGGTGTAGGGCTCCAGGCAGGCGGCGAAGGCCATGACGTGCGCTAT
GAAGGTCTGCTCCTGCACGCCGTGAACCAGGTGCGCCTGCGGGCCGCGCGCGAACAC
CGCCACGTCCTCGCCTGCGTGGGTCTCTTCGTCCAGGGGCACTGCTGACTGCTGCCG
ATACTCGGGGCTCCCGCTCTCGCTCTCGGTAACATCCGGCCGGGCGCCGTCCTTGAG
CACATAGCCTGGACCGTTTCGTCGACTGTTAATTAAGCATGCTGGGGAGAGATCTAGG
AACCCCTAGTGATGGAGTTGGCCACTCCCTCTCTGCGCGCTCGCTCGCTCACTGAGGC
CGCCCGGGCAAAGCCCGGGCGTCGGGCGACCTTTGGTCGCCCGGCCTCAGTGAGCG
AGCGAGCGCGCAGAGAGGGAGTGGCCAACCCCCCCCCCCCCCCCCTGCAGCCCTG
CATTAATGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCGGTATCA
GCTCACTCAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCGTTGCTGG
CGTTTTTCCATAGGCTCCGCCCCCTGACGAGCATCACAAAAATCGACGCTCAAGTCA
GAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCC
CTTCGGGAAGCGTGGCGCTTTCTCAATGCTCACGCTGTAGGTATCTCAGTTCGGTGTA
GGTCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGC
GCTCTGCTGAAGCCAGTTACCTTCGGAAAAGAGTTGGTAGCTCTTGATCCGGCAAACA
AACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATCCA
TAGTTGCCTGACTCCCCGTCGTGTAGATAACTACGATACGGGAGGGCTTACCATCTGG
```

FIG. 19 (continued)

```
CCCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTAT
GGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCATGCCATCCGT
AAGATGCTTTTCTGTGACTGGTGAGTACTCAACCAAGTCATTCTGAGAATAGTGTATGC
GGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGCAAA
AAAGGGAATAAGGGCGACACGGAAATGTTGAATACTCATACTCTTCCTTTTTCAATATTA
TTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAG
AAACCATTATTATCATGACATTAACCTATAAAAATAGGCGTATCACGAGGCCCTTTCGTC
TCGCGCGTTTCGGTGATGACGGTGAAAACCTCTGACACATGCAGCTCCCGGAGACGGT
CACAGCTTGTCTGTAAGCGGATGCCGGGAGCAGACAAGCCCGTCAGGGCGCGTCAGC
GGGTGTTGGCGGGTGTCGGGGCTGGCTTAACTATGCGGCATCAGAGCAGATTGTACT
GAGAGTGCACCATATGCGGTGTGAAATACCGCACAGATGCGTAAGGAGAAAATACCGC
ATCAGGAAATTGTAAACGTTAATATTTTGTTAAAATTCGCGTTAAATTTTTGTTAAATCAG
CTCATTTTTTAACCAATAGGCCGAAATCGGCAAAATCCCTTATAAATCAAAAGAATAGAC
CGAGATAGGGTTGAGTGTTGTTCCAGTTTGGAACAAGAGTCCACTATTAAAGAACGTGG
ACTCCAACGTCAAAGGGCGAAAAACCGTCTATCAGGGCGATGGCCCACTACGTGAACC
ATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGG
AAGGGAAGAAAGCGAAAGGAGCGGGCGCTAGGGCGCTGGCAAGTGTAGCGGTCACG
CTGCGCGTAACCACCACACCCGCCGCGCTTAATGCGCCGCTACAGGGCGCGTCGCGC
CATTCGCCATTCAGGCTACGCAACTGTTGGGAAGGGCGATCGGTGCGGGCCTCTTCGC
TATTACGCCAGGCTGC
(SEQ ID NO:19)
```

FIG. 19 (continued)

pTR22-APhead-APSA-hOtoferlinCT.myc

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4149 | hOtoferlinCT: | human Otoferlin coding sequence 3' part |
| 4150-4164 | GGGGS: | GGGGS linker sequence |
| 4162-4197 | myc: | myc tag |
| 4240-4461 | bGH PolyA: | bovine growth hormone polyadenylation signal |
| 4528-4670 | TR: | inverted terminal repeat sequence of AAV2 |
| 5118-5343 | ColE1: | replication origin for E. coli |
| 5593-6593 | Amp r: | beta-lactamase gene = Ampicillin resistance |

AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCCGGGTGCGCGGCGTCGG
TGGTGCCGGCGGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAAAAC
ATGGGGCAGCAGGCCAGGATGCTGCGGGCCCAGGTGAAGCGGCACACGGTGCGGGA
CAAGCTGAGGCTGTGCCAGAACTTCCTGCAGAAGCTGCGCTTCCTGGCGGACGAGCC
CCAGCACAGCATTCCCGACATCTTCATCTGGATGATGAGCAACAACAAGCGTGTCGCC
TATGCCCGTGTGCCCTCCAAGGACCTGCTCTTCTCCATCGTGGAGGAGGAGACTGGCA
AGGACTGCGCCAAGGTCAAGACGCTCTTCCTTAAGCTGCCAGGGAAGCGGGGCTTCG
GCTCGGCAGGCTGGACAGTGCAGGCCAAGGTGGAGCTGTACCTGTGGCTGGGCCTCA
GCAAACAGCGCAAGGAGTTCCTGTGCGGCCTGCCCTGTGGCTTCCAGGAGGTCAAGG
CAGCCCAGGGCCTGGGCCTGCATGCCTTCCCACCCGTCAGCCTGGTCTACACCAAGA
AGCAGGCGTTCCAGCTCCGAGCGCACATGTACCAGGCCCGCAGCCTCTTTGCCGCCG
ACAGCAGCGGACTCTCAGACCCCTTTGCCCGCGTCTTCTTCATCAATCAGAGTCAGTG
CACAGAGGTGCTGAATGAGACCCTGTGTCCCACCTGGGACCAGATGCTGGTGTTCGAC
AACCTGGAGCTCTATGGTGAAGCTCATGAGCTGAGGGACGATCCGCCCATCATTGTCA
TTGAAATCTATGACCAGGATTCCATGGGCAAAGCTGACTTCATGGGCCGGACCTTCGC
CAAACCCCTGGTGAAGATGGCAGACGAGGCGTACTGCCCACCCCGCTTCCCACCTCA
GCTCGAGTACTACCAGATCTACCGTGGCAACGCCACAGCTGGAGACCTGCTGGCGGC
CTTCGAGCTGCTGCAGATTGGACCAGCAGGGAAGGCTGACCTGCCCCCCATCAATGG
CCCGGTGGACGTGGACCGAGGTCCCATCATGCCCGTGCCCATGGGCATCCGGCCCGT
GCTCAGCAAGTACCGAGTGGAGGTGCTGTTCTGGGGCCTACGGGACCTAAAGCGGGT
GAACCTGGCCCAGGTGGACCGGCCACGGGTGGACATCGAGTGTGCAGGGAAGGGGG
TGCAGTCGTCCCTGATCCACAATTATAAGAAGAACCCCAACTTCAACACCCTCGTCAAG
TGGTTTGAAGTGGACCTCCCAGAGAACGAGCTGCTGCACCCGCCCTTGAACATCCGTG
TGGTGGACTGCCGGGCCTTCGGTCGCTACACACTGGTGGGCTCCCATGCCGTCAGCT

FIG. 20

```
CCCTGCGACGCTTCATCTACCGGCCCCCAGACCGCTCGGCCCCCAGCTGGAACACCA
CGGTCAGGCTTCTCCGGCGCTGCCGTGTGCTGTGCAATGGGGCTCCTCCTCTCACTC
CACAGGGGAGGTTGTGGTGACTATGGAGCCAGAGGTACCCATCAAGAAACTGGAGAC
CATGGTGAAGCTGGACGCGACTTCTGAAGCTGTTGTCAAGGTGGATGTGGCTGAGGAG
GAGAAGGAGAAGAAGAAGAAGAAGGGCACTGCGGAGGAGCCAGAGGAGGAGGA
GCCAGACGAGAGCATGCTGGACTGGTGGTCCAAGTACTTTGCCTCCATTGACACCATG
AAGGAGCAACTTCGACAACAAGAGCCCTCTGGAATTGACTTGGAGGAGAAGGAGGAAG
TGGACAATACCGAGGGCCTGAAGGGGTCAATGAAGGGCAAGGAGAAGGCAAGGGCTG
CCAAAGAGGAGAAGAAGAAGAAAACTCAGAGCTCTGGCTCTGGCCAGGGGTCCGAGG
CCCCCGAGAAGAAGAAACCCAAGATTGATGAGCTTAAGGTATACCCCAAAGAGCTGGA
GTCCGAGTTTGATAACTTTGAGGACTGGCTGCACACTTTCAACTTGCTTCGGGGCAAGA
CCGGGGATGATGAGGATGGCTCCACCGAGGAGGAGCGCATTGTGGGACGCTTCAAGG
GCTCCCTCTGCGTGTACAAAGTGCCACTCCCAGAGGACGTGTCCCGGGAAGCCGGCT
ACGACTCCACCTACGGCATGTTCCAGGGCATCCCGAGCAATGACCCCATCAATGTGCT
GGTCCGAGTCTATGTGGTCCGGGCCACGGACCTGCACCCTGCTGACATCAACGGCAA
AGCTGACCCCTACATCGCCATCCGGCTAGGCAAGACTGACATCCGCGACAAGGAGAAC
TACATCTCCAAGCAGCTCAACCCTGTCTTTGGGAAGTCCTTTGACATCGAGGCCTCCTT
CCCCATGGAATCCATGCTGACGGTGGCTGTGTATGACTGGGACCTGGTGGGCACTGAT
GACCTCATTGGGGAAACCAAGATCGACCTGGAGAACCGCTTCTACAGCAAGCACCGCG
CCACCTGCGGCATCGCCCAGACCTACTCCACACATGGCTACAATATCTGGCGGGACCC
CATGAAGCCCAGCCAGATCCTGACCCGCCTCTGCAAAGACGGCAAAGTGGACGGCCC
CCACTTTGGGCCCCCTGGGAGAGTGAAGGTGGCCAACCGCGTCTTCACTGGGCCCTC
TGAGATTGAGGACGAGAACGGTCAGAGGAAGCCCACAGACGAGCATGTGGCGCTGTT
GGCCCTGAGGCACTGGGAGGACATCCCCCGCGCAGGCTGCCGCCTGGTGCCAGAGC
ATGTGGAGACGAGGCCGCTGCTCAACCCCGACAAGCCGGGCATCGAGCAGGGCCGC
CTGGAGCTGTGGGTGGACATGTTCCCCATGGACATGCCAGCCCCTGGGACGCCTCTG
GACATCTCACCTCGGAAGCCCAAGAAGTACGAGCTGCGGGTCATCATCTGGAACACAG
ATGAGGTGGTCTTGGAGGACGACGACTTCTTCACAGGGGAGAAGTCCAGTGACATCTT
CGTGAGGGGGTGGCTGAAGGGCCAGCAGGAGGACAAGCAGGACACAGACGTCCACTA
CCACTCCCTCACTGGCGAGGGCAACTTCAACTGGCGCTACCTGTTCCCCTTCGACTAC
CTGGCGGCGGAGGAGAAGATCGTCATCTCCAAGAAGGAGTCCATGTTCTCCTGGGAC
GAGACCGAGTACAAGATCCCCGCGCGGCTCACCCTGCAGATCTGGGATGCGGACCAC
TTCTCCGCTGACGACTTCCTGGGGGCCATCGAGCTGGACCTGAACCGGTTCCCGCGG
GGCGCAAAGACAGCCAAGCAGTGCACCATGGAGATGGCCACCGGGGAGGTGGACGT
GCCCCTCGTGTCCATCTTCAAGCAAAAGCGCGTCAAAGGCTGGTGGCCCCTCCTGGCC
CGCAATGAGAACGATGAGTTTGAGCTCACGGGCAAGGTGGAGGCTGAGCTGCATTTAC
TGACAGCAGAGGAGGCAGAGAAGAACCCAGTGGGCCTGGCCCGCAATGAACCTGACC
CCCTAGAGAAACCCAACCGGCCCGACACGGCCTTCGTCTGGTTCCTCAACCCTCTCAA
GTCCATCAAGTACCTCATCTGCACCCGGTACAAGTGGCTCATCATCAAGATCGTGCTGG
CGCTGTTGGGGCTGCTCATGTTGGGGCTCTTCCTCTACAGCCTCCCTGGCTACATGGT
CAAAAAGCTCCTTGGGGCAGGAGGTGGCGGATCAGAGCAGAAACTCATCTCTGAAGAG
GATCTGTGAACGGCCGCTATGCTAGCTTGGTACCAAGGGCGGATCCTGCATAGAGCTC
GCTGATCAGCCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAG
```

FIG. 20 (continued)

```
GACAGCAAGGGGGAGGATTGGGAAGACAATAGCAGGCATGCTGGGGAGAGATCTGAG
GACTAGTCCGTCGACTGTTAATTAAGCATGCTGGGGAGAGATCTAGGAACCCCTAGTG
ATGGAGTTGGCCACTCCCTCTCTGCGCGCTCGCTCGCTCACTGAGGCCGCCCGGGCA
AAGCCCGGGCGTCGGGCGACCTTTGGTCGCCCGGCCTCAGTGAGCGAGCGAGCGCG
CAGAGAGGGAGTGGCCAACCCCCCCCCCCCCCCCCTGCAGCCCTGCATTAATGAAT
CGGCCAACGCGCGGGGAGAGGCGGTTTGCGTATTGGGCGCTCTTCCGCTTCCTCGCT
CACTGACTCGCTGCGCTCGGTCGTTCGGCTGCGGCGAGCGGTATCAGCTCACTCAAA
GGCGGTAATACGGTTATCCACAGAATCAGGGGATAACGCAGGAAAGAACATGTGAGCA
AAAGGCCAGCAAAAGGCCAGGAACCGTAAAAAGGCCGCGTTGCTGGCGTTTTTCCATA
GGCTCCGCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAGCG
TGGCGCTTTCTCAATGCTCACGCTGTAGGTATCTCAGTTCGGTGTAGGTCGTTCGCTCC
AAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAGTG
GTGGCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTAAAA
ATGAAGTTTTAAATCAATCTAAAGTATATATGAGTAAACTTGGTCTGACAGTTACCAATG
CTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCT
GCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACG
TTG TTGCCATTGCTACAGGCATCGTGGTGTCACGCTCGTCGTTTGGTATGGCTTCATTC
AGCTCCGGTTCCCAACGATCAAGGCGAGTTACATGATCCCCATGTTGTGCAAAAAAG
CGGTTAGCTCCTTCGGTCCTCCGATCGTTGTCAGAAGTAAGTTGGCCGCAGTGTTATCA
CTCATGGTTATGGCAGCACTGCATAATTCTCTTACTGTCATGCCATCCGTAAGATGCTTT
TCTGTGACTGGTGAGTACTCAACCAAGTCATTCTGAGAATAGTGTATGCGGCGACCGA
GTTGCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTGTT
GAGATCCAGTTCGATGTAACCCACTCGTGCACCCAACTGATCTTCAGCATCTTTTACTTT
CACCAGCGTTTCTGGGTGAGCAAAAACAGGAAGGCAAAATGCCGCAAAAAAGGGAATA
AGGGCGACACGGAAATGTTGAATACTCATACTCTTCCTTTTTCAATATTATTGAAGCATT
TATCAGGGTTATTGTCTCATGAGCGGATACATATTTGAATGTATTTAGAAAAATAAACAA
ATAGGGGTTCCGCGCACATTTCCCCGAAAAGTGCCACCTGACGTCTAAGAAACCATTAT
TATCATGACATTAACCTATAAAAATAGGCGTATCACGAGGCCCTTTCGTCTCGCGCGTT
TCGGTGATGACGGTGAAAACCTCTGACACATGCAGCTCCCGGAGACGGTCACAGCTTG
TCTGTAAGCGGATGCCGGGAGCAGACAAGCCCGTCAGGGCGCGTCAGCGGGTGTTGG
CGGGTGTCGGGGCTGGCTTAACTATGCGGCATCAGAGCAGATTGTACTGAGAGTGCAC
CATATGCGGTGTGAAATACCGCACAGATGCGTAAGGAGAAAATACCGCATCAGGAAATT
GTAAACGTTAATATTTTGTTAAAATTCGCGTTAAATTTTTGTTAAATCAGCTCATTTTTTAA
```

FIG. 20 (continued)

CCAATAGGCCGAAATCGGCAAAATCCCTTATAAATCAAAAGAATAGACCGAGATAGGGT
TGAGTGTTGTTCCAGTTTGGAACAAGAGTCCACTATTAAAGAACGTGGACTCCAACGTC
AAAGGGCGAAAAACCGTCTATCAGGGCGATGGCCCACTACGTGAACCATCACCCTAAT
CAAGTTTTTTGGGGTCGAGGTGCCGTAAAGCACTAAATCGGAACCCTAAAGGGAGCCC
CCGATTTAGAGCTTGACGGGGAAAGCCGGCGAACGTGGCGAGAAAGGAAGGGAAGAA
AGCGAAAGGAGCGGGCGCTAGGGCGCTGGCAAGTGTAGCGGTCACGCTGCGCGTAA
CCACCACACCCGCCGCGCTTAATGCGCCGCTACAGGGCGCGTCGCGCCATTCGCCAT
TCAGGCTACGCAACTGTTGGGAAGGGCGATCGGTGCGGGCCTCTTCGCTATTACGCCA
GGCTGC
(SEQ ID NO: 20)

FIG. 20 (continued)

pTR22-smCBA-myc.hOtoferlinNT-APSD-APhead

| Nucleotide positions | Abbreviation | Description |
|---|---|---|
| 20-162 | TR: | inverted terminal repeat sequence of AAV2 |
| 186-551 | CBA promoter: | -CMVie enhancer |
| 553-835 | | -chicken b-actin promoter |
| 836-1130 | | -Exon1 and chimeric intron |
| 1156-1185 | myc: | myc tag |
| 1186-1200 | GGGGS: | GGGGS linker sequence |
| 1153-3603 | hOtoferlinNT: | human Otoferlin coding sequence 5' part |
| 3604-3687 | APSD: | Splice Donor |
| 3694-3980 | APhead: | homologous sequence for recombination |
| 4020-4162 | TR: | inverted terminal repeat sequence of AAV2 |
| 4610-4835 | ColE2: | replication origin for E. coli |
| 5085-6085 | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTCGGTACCCTAGTTATTAATAGTAATCAATTACGGGGTCATTAGT
TCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAAC
GCCAATAGGGACTTTCCATTGACGTCAATGGGTGGACTATTTACGGTAAACTGCCCACT
TGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTGCT
TCACTCTCCCCATCTCCCCCCCTCCCCACCCCCAATTTTGTATTTATTTATTTTTTAATT
ATTTTGTGCAGCGATGGGGCGGGGGGGGGGGGGGCGCGCGCCAGGCGGGGCG
GGGCGGGGCGAGGGGCGGGCGGGGCGAGGCGGAGAGGTGCGGCGGCAGCCAATC
AGAGCGGCGCGCTCCGAAAGTTTCCTTTTATGGCGAGGCGGCGGCGGCGGCGGCCCT
ATAAAAAGCGAAGCGCGCGGCGGGCGGGAGTCGCTGCGACGCTGCCTTCGCCCCGT
GCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGT
TTAATGACGGCTTGTTTCTTTTCTGTGGCTGCGTGAAAGCCTTGAGGGGCTCCGGGAG
CTAGAGCCTCTGCTAACCATGTTCATGCCTTCTTCTTTTTCCTACAGCTCCTGGGCAAC
GTGCTGGTTATTGTGCTGTCTCATCATTTTGGCAAAGAATTCTAGCGGCCGCCACCATG
GAGCAGAAACTCATCTCTGAAGAGGATCTGGGAGGTGGCGGATCAGCCTTGCTCATCC
ACCTCAAGACAGTCTCGGAGCTGCGGGGCAGGGGCGACCGGATCGCCAAAGTGACTT
TCCGAGGGCAATCCTTCTACTCTCGGGTCCTGGAGAACTGTGAGGATGTGGCTGACTT
TGATGAGACATTTCGGTGGCCGGTGGCCAGCAGCATCGACAGAAATGAGATGCTGGAG
ATTCAGGTTTTCAACTACAGCAAAGTCTTCAGCAACAAGCTCATCGGGACCTTCCGCAT
GGTGCTGCAGAAGGTGGTAGAGGAGAGCCATGTGGAGGTGACTGACACGCTGATTGA
TGACAACAATGCTATCATCAAGACCAGCCTGTGCGTGGAGGTCCGGTATCAGGCCACT
GACGGCACAGTGGGCTCCTGGGACGATGGGGACTTCCTGGGAGATGAGTCTCTTCAA
GAGGAAGAGAAGGACAGCCAAGAGACGGATGGACTGCTCCCAGGCTCCGGCCCAGC
TCCCGGCCCCCAGGAGAGAAGAGCTTCCGGAGAGCCGGGAGGAGCGTGTTCTCCGCC
ATGAAGCTCGGCAAAAACCGGTCTCACAAGGAGGAGCCCCAAAGACCAGATGAACCG
GCGGTGCTGGAGATGGAAGACCTTGACCATCTGGCCATTCGGCTAGGAGATGGACTG
GATCCCGACTCGGTGTCTCTAGCCTCAGTCACAGCTCTCACCACTAATGTCTCCAACAA
GCGATCTAAGCCAGACATTAAGATGGAGCCAAGTGCTGGGCGGCCCATGGATTACCAG
GTCAGCATCACGGTGATCGAGGCCCGGCAGCTGGTGGGCTTGAACATGGACCCTGTG
GTGTGCGTGGAGGTGGGTGACGACAAGAAGTACACATCCATGAAGGAGTCCACTAACT
GCCCCTATTACAACGAGTACTTCGTCTTCGACTTCCATGTCTCTCCGGATGTCATGTTT
```

FIG. 21

```
GACAAGATCATCAAGATTTCGGTGATTCACTCCAAGAACCTGCTGCGCAGTGGCACCCT
GGTGGGCTCCTTCAAAATGGACGTGGGAACCGTGTACTCGCAGCCAGAGCACCAGTTC
CATCACAAGTGGGCCATCCTGTCTGACCCCGATGACATCTCCTCGGGGCTGAAGGGCT
ACGTGAAGTGTGACGTTGCCGTGGTGGGCAAAGGGGACAACATCAAGACGCCCACA
AGGCCAATGAGACCGACGAAGATGACATTGAGGGAACTTGCTGCTCCCCGAGGGGG
TGCCCCCGAACGCAGTGGGCCCGGTTCTATGTGAAAATTTACCGAGCAGAGGGGCT
GCCCCGTATGAACACAAGCCTCATGGCCAATGTAAAGAAGGCTTTCATCGGTGAAAACA
AGGACCTCGTGGACCCCTACGTGCAAGTCTTCTTTGCTGGCCAGAAGGGCAAGACTTC
AGTGCAGAAGAGCAGCTATGAGCCCCTGTGGAATGAGCAGGTCGTCTTTACAGACCTC
TTCCCCCCACTCTGCAAACGCATGAAGGTGCAGATCCGAGACTCGGACAAGGTCAACG
ACGTGGCCATCGGCACCCACTTCATTGACCTGCGCAAGATTTCTAATGACGGAGACAA
AGGCTTCCTGCCCACACTGGGCCCAGCCTGGGTGAACATGTACGGCTCCACACGTAAC
TACACGCTGCTGGATGAGCATCAGGACCTGAACGAGGGCCTGGGGGAGGGTGTGTCC
TTCCGGGCCGGCTCCTGCTGGGCCTGGCTGTGGAGATCGTAGACACCTCCAACCCT
GAGCTCACCAGCTCCACAGAGGTGCAGGTGGAGCAGGCCACGCCCATCTCGGAGAGC
TGTGCAGGTAAAATGGAAGAATTCTTTCTCTTTGGAGCCTTCCTGGAGGCCTCAATGAT
CGACCGGAGAAACGGAGACAAGCCCATCACCTTTGAGGTCACCATAGGCAACTATGGG
AACGAAGTTGATGGCCTGTCCCGGCCCCAGCGGCCTCGGCCCCGGAAGGAGCCGGG
GGATGAGGAAGAAGTAGACCTGATTCAGAACGCAAGTGATGACGAGGCCGGTGATGC
CGGGGACCTGGCCTCAGTCTCCTCCACTCCACCAATGCGGCCCCAGGTCACCGACAG
GAACTACTTCCATCTGCCCTACCTGGAGCGAAAGCCCTGCATCTACATCAAGAGCTGGT
GGCCGGACCAGCGCCGCCGCCTCTACAATGCCAACATCATGGACCACATTGCCGACAA
GCTGGAAGAAGGCCTGAACGACATACAGGAGATGATCAAAACGGAGAAGTCCTACCCT
GAGCGTCGCCTGCGGGGCGTCCTGGAGGAGCTGAGCTGTGGCTGCTGCCGCTTCCTC
TCCCTCGCTGACAAGGACCAGGGCCACTCATCCCGCACCAGGCTTGACCGGGAGCGC
CTCAAGTCCTGCATGAGGGAGCTGGTAAGTATCAAGGTTACAAGACAGGTTTAAGGAG
ACCAATAGAAACTGGGCTTGTCGAGACAGAGAAGACTCTTGCGTTTCTGAGCTAGCCC
CCGGGTGCGCGGCGTCGGTGGTGCCGGCGGGGGCGCCAGGTCGCAGGCGGTGTA
GGGCTCCAGGCAGGCGGCGAAGGCCATGACGTGCGCTATGAAGGTCTGCTCCTGCAC
GCCGTGAACCAGGTGCGCCTGCGGGCCGCGCGCGAACACCGCCACGTCCTCGCCTG
CGTGGGTCTCTTCGTCCAGGGGCACTGCTGACTGCTGCCGATACTCGGGGCTCCCGC
TCTCGCTCTCGGTAACATCCGGCCGGGCGCCGTCCTTGAGCACATAGCCTGGACCGTT
TCGTCGACTGTTAATTAAGCATGCTGGGGAGAGATCTAGGAACCCCTAGTGATGGAGTT
GGCCACTCCCTCTCTGCGCGCTCGCTCGCTCACTGAGGCCGCCCGGGCAAAGCCCGG
GCGTCGGGCGACCTTTGGTCGCCCGGCCTCAGTGAGCGAGCGAGCGCGCAGAGAGG
GAGTGGCCAACCCCCCCCCCCCCCCCCTGCAGCCCTGCATTAATGAATCGGCCAAC
GCGCGGGGAGAGGCGGTTTGCGTATTGGGCGCTCTTCCGCTTCCTCGCTCACTGACT
CGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCA
GCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAG
GACTATAAAGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCGTGGCGCTT
TCTCAAT GCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAAC
AGGATTAGCAGAGCGAGGTATGTAGGCGGTGCTACAGAGTTCTTGAAGTGGTGGCCTA
ACTACGGCTACACTAGAAGGACAGTATTTGGTATCTGCGCTCTGCTGAAGCCAGTTACC
TTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCT
TTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTT
```

FIG. 21 (continued)

```
AAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATA
CCGCGAGACCCACGCTCACCGGCTCCAGATTTATCAGCAATAAACCAGCCAGCCGGAA
GGGCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCCAT
TGCTACAGGCATCGTGGTGTCACGCTCGTCGTTTGGTATGGCTTCATTCAGCTCCGGTT
CCCAACGATCAAGGCGAGTTACATGATCCCCATGTTGTGCAAAAAAGCGGTTAGCTC
CTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTG
GTGAGTACTCAACCAAGTCATTCTGAGAATAGTGTATGCGGCGACCGAGTTGCTCTTGC
CCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTT
CTGGGTGAGCAAAAACAGGAAGGCAAAATGCCGCAAAAAAGGGAATAAGGGCGACAC
GGAAATGTTGAATACTCATACTCTTCCTTTTTCAATATTATTGAAGCATTTATCAGGGTTA
TTGTCTCATGAGCGGATACATATTTGAATGTATTTAGAAAAATAAACAAATAGGGGTTCC
GCGCACATTTCCCCGAAAAGTGCCACCTGACGTCTAAGAAACCATTATTATCATGACAT
TAACCTATAAAAATAGGCGTATCACGAGGCCCTTTCGTCTCGCGCGTTTCGGTGATGAC
GGTGAAAACCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCATATGCGGT
GTGAAATACCGCACAGATGCGTAAGGAGAAAATACCGCATCAGGAAATTGTAAACGTTA
ATATTTTGTTAAAATTCGCGTTAAATTTTTGTTAAATCAGCTCATTTTTTAACCAATAGGC
CGAAATCGGCAAAATCCCTTATAAATCAAAAGAATAGACCGAGATAGGGTTGAGTGTTG
TTCCAGTTTGGAACAAGAGTCCACTATTAAAGAACGTGGACTCCAACGTCAAAGGGCGA
AAAACCGTCTATCAGGGCGATGGCCCACTACGTGAACCATCACCCTAATCAAGTTTTTT
GGGGTCGAGGTGCCGTAAAGCACTAAATCGGAACCCTAAAGGGAGCCCCCGATTTAGA
GCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACC
CGCCGCGCTTAATGCGCCGCTACAGGGCGCGTCGCGCCATTCGCCATTCAGGCTACG
CAACTGTTGGGAAGGGCGATCGGTGCGGGCCTCTTCGCTATTACGCCAGGCTGC
(SEQ ID NO: 21)
```

FIG. 21 (continued)

CODON OPTIMIZED OTOFERLIN AAV DUAL VECTOR GENE THERAPY

CROSS-REFERENCE TO RELATED APPLICATIONS

This application is a national stage filing under 35 U.S.C. § 371 of International Application No. PCT/US2019/059549, filed Nov. 1, 2019, which claims priority to U.S. Provisional Application No. 62/754,458 filed on Nov. 1, 2018, the entire disclosure of each of which is incorporated by reference herein.

FEDERALLY SPONSORED RESEARCH

This invention was made with government support under Grant No. EY021721, EY000331, and DC012118 awarded by the National Institutes of Health. The government has certain rights in the invention.

BACKGROUND OF THE INVENTION

Nonsyndromic deafness is a form of hearing loss that is generally caused by defects or damage to the inner ear and/or middle ear. Mutations in the OTOF gene, which encodes the protein Otoferlin, are thought to cause a type of nonsyndromic deafness called Deafness, Autosomal Recessive 9 (DFNB9). Treatment of DFNB9 and other similar forms of deafness currently involves using cochlear implants for severe or profound hearing loss and hearing aids for milder forms of hearing loss. There remains a need for alternative treatment forms that do not rely on or rely less heavily on electronic devices for restoring hearing.

SUMMARY OF THE INVENTION

Provided herein are compositions and methods for expressing Otoferlin, e.g., in a cell or subject. As described herein, it has been found that delivery of the OTOF cDNA to otof knock-out mice via a dual adeno-associated virus (AAV) system containing different portions of the OTOF cDNA was capable of rescuing hearing in the mice to near wild-type levels.

In some aspects, the disclosure provides a method of increasing expression of Otoferlin in a cell, the method comprising contacting the cell with a first AAV particle comprising a first polynucleotide; and contacting the cell with a second AAV particle comprising a second polynucleotide, wherein the first polynucleotide comprises inverted terminal repeat sequences flanking an expression cassette containing, from 5' to 3': (a) a promoter, (b) a partial coding sequence that encodes an N-terminal portion of an Otoferlin polypeptide, (c) a splice donor site, and (d) a first region of homology containing a sequence that is homologous to a sequence in the second polynucleotide, or a complement thereof, and the second polynucleotide comprises inverted terminal repeat sequences flanking an expression cassette containing, from 5' to 3': (a) a second region of homology containing a sequence that is homologous to a sequence in the first polynucleotide, (b) a splice acceptor site, (c) a partial coding sequence that encodes a C-terminal portion of the Otoferlin polypeptide, and (d) a polyadenylation (pA) signal sequence, or a complement thereof.

In some embodiments, the region of homology in the first and second polynucleotides is between 50 and 500 nucleotides. In some embodiments, the region of homology in the first and second polynucleotides is between 50 and 300 nucleotides. In some embodiments, the region of homology comprises the nucleotide sequence of SEQ ID NO: 3. In some embodiments, the promoter is a chimeric CMV β actin (smcBA) promoter. In some embodiments, the promoter comprises the sequence of SEQ ID NO: 4. In some embodiments, the Otoferlin polypeptide comprises the amino acid sequence of SEQ ID NO: 5 or SEQ ID NO: 6. In some embodiments, the splice donor site comprises the sequence of SEQ ID NO: 7. In some embodiments, the splice acceptor site comprises the sequence of SEQ ID NO: 8. In some embodiments, the inverted terminal repeat sequences are AAV2 inverted terminal repeat sequences. In some embodiments, the first and second AAV particle are AAV2 serotype particles. In some embodiments, the cell is ex vivo. In some embodiments, the cell is in vivo. In some embodiments, the cell is in a mammalian subject. In some embodiments, the subject has Deafness, Autosomal Recessive 9 (DFNB9).

In some embodiments, the first and/or second Otoferlin polynucleotides are codon optimized for expression in human cells. In some embodiments, the first and/or second Otoferlin polynucleotides are tagged with a myc-encoding sequence. In some embodiments, the first and/or second Otoferlin polynucleotides are codon optimized for expression in human cells and tagged with a myc-encoding sequence.

In some aspects, the disclosure provides a composition comprising a first AAV particle comprising a first polynucleotide; and a second AAV particle comprising a second polynucleotide, wherein the first and second polynucleotides are single-stranded. In some embodiments, the first polynucleotide comprises inverted terminal repeat sequences flanking an expression cassette containing, from 5' to 3': (a) a promoter, (b) a partial coding sequence that encodes an N-terminal portion of an Otoferlin polypeptide, (c) a splice donor site, and (d) a first region of homology containing a sequence that is homologous to a sequence in the second polynucleotide, or a complement thereof. In some embodiments, the second polynucleotide comprises inverted terminal repeat sequences flanking an expression cassette containing, from 5' to 3': (a) a second region of homology containing a sequence that is homologous to a sequence in the first polynucleotide. (b) a splice acceptor site, (c) a partial coding sequence that encodes a C-terminal portion of the Otoferlin polypeptide, and (d) a polyadenylation (pA) signal sequence, or a complement thereof.

In some embodiments, the region of homology in the first and second polynucleotides is between 50 and 500 nucleotides. In some embodiments, the region of homology in the first and second polynucleotides is between 50 and 300 nucleotides. In some embodiments, the region of homology comprises the nucleotide sequence of SEQ ID NO: 3. In some embodiments, the promoter is a chimeric CMV β actin (smcBA) promoter. In some embodiments, the promoter comprises the sequence of SEQ ID NO: 4. In some embodiments, the Otoferlin polypeptide comprises the amino acid sequence of SEQ ID NO: 5 or SEQ ID NO: 6. In some embodiments, the splice donor site comprises the sequence of SEQ ID NO: 7. In some embodiments, the splice acceptor site comprises the sequence of SEQ ID NO: 8. In some embodiments, the inverted terminal repeat sequences are AAV2 inverted terminal repeat sequences. In some embodiments, the first and second AAV particle are AAV2 serotype particles. In some embodiments, the composition further comprises a pharmaceutically acceptable carrier.

In yet other aspects, the disclosure provides a kit comprising a composition as described herein or comprising a first AAV particle as described herein and a second AAV particle as described herein.

These and other aspects are described in more detail herein.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIG. 3A shows the annotated sequence of the expression cassette, including the inverted terminal repeats (TR) for the plasmid in FIG. 1A.

FIG. 3B shows the annotated sequence of the expression cassette, including the inverted terminal repeats (TR) for the plasmid in FIG. 1B.

FIG. 6A shows expression of OTOF protein in the mid-turn. FIG. 6B shows expression of OTOF protein in the apex. FIG. 6C shows the difference in OTOF expression in the base, mid-turn and apex in wild-type mice (WT, n=6) and OTOF knock-out mice treated with AAV2-OTOF-NT and AAV2-OTOF-CT (Res. KO NT+CT, n=6). The left bar in each pair of bars is WT and the right bar in each pair of bars is Res. KO NT+CT. FIG. 6D shows RT-PCR data of OTOF mRNA in wild-type (WT), OTOF knock-out mice (KO) and OTOF knock-out mice treated with AAV2-OTOF-NT and AAV2-OTOF-CT (Res. KO).

FIG. 7A is a trace of auditory brainstem response (ABR) patterns induced by auditory stimuli in wild-type mice (WT), OTOF knock-out mice either untreated (KO/KO NT) or treated (Rescued KO) with AAV2-OTOF-NT and AAV2-OTOF-CT. FIG. 7B shows the auditory brainstem response (ABR) threshold in wild-type mice (WT), untreated Otoferlin knock-out mice (KO), Otoferlin knock-out mice treated with AAV2-OTOF-NT and AAV2-OTOF-CT (Res KO NT+CT), and Otoferlin knock-out mice treated with AAV2-OTOF-NT (KO+NT). FIG. 7C shows a time course of hearing recovery in wild-type mice (WT), untreated OTOF knock-out mice (KO), Otoferlin knock-out mice treated with AAV2-OTOF-NT and AAV2-OTOF-CT (Rescued KO NT+CT), and Otoferlin knock-out mice treated with AAV2-OTOF-NT (KONT). FIG. 7D shows the click ABR threshold in wild-type mice (WT), untreated Otoferlin knock-out mice (KO), Otoferlin knock-out mice treated with AAV2-OTOF-NT and AAV2-OTOF-CT (Res. KO (NT+CT)), and Otoferlin knock-out mice treated with AAV2-OTOF-NT (KO+NT).

FIG. 8A shows OTOF protein expression in P12 and older mice treated with AAV2-OTOF-NT and AAV2-OTOF-CT.

FIG. 9A shows ABR threshold values in wild-type mice (WT), OTOF knock-out mice (KO) and OTOF knock-out mice treated with AAV2-OTOF-NT and AAV2-OTOF-CT (Rescued KO). FIG. 9B shows hearing longevity in WT, KO and Rescued KO mice.

FIG. 13 shows the annotated sequence of a human OTOF N-terminal expression cassette, including the inverted terminal repeats (TR) for the plasmid in FIG. 10.

FIG. 14 shows the annotated sequence of a human OTOF C-terminal expression cassette for isoform 1, including the inverted terminal repeats (TR) for the plasmid in FIG. 11.

FIG. 15 shows the annotated sequence of a human OTOF C-terminal expression cassette for isoform 5, including the inverted terminal repeats (TR) for the plasmid in FIG. 12.

FIG. 17 shows the annotated codon-optimized sequence of a human OTOF C-terminal expression cassette for isoform 1, including inverted terminal repeats (TR).

FIG. 18 shows the annotated codon-optimized sequence of a human OTOF C-terminal expression cassette for isoform 5, including the inverted terminal repeats (TR) for the plasmid in FIG. 12.

FIG. 19 shows the annotated codon-optimized sequence of a human OTOF N-terminal expression cassette, including inverted terminal repeats (TR).

FIG. 20 shows the annotated sequence of a myc-tagged human OTOF C-terminal expression cassette, including inverted terminal repeats (TR).

FIG. 21 shows the annotated sequence of a of a myc-tagged human OTOF N-terminal expression cassette, including inverted terminal repeats (TR).

DETAILED DESCRIPTION OF THE INVENTION

Figure 1A:
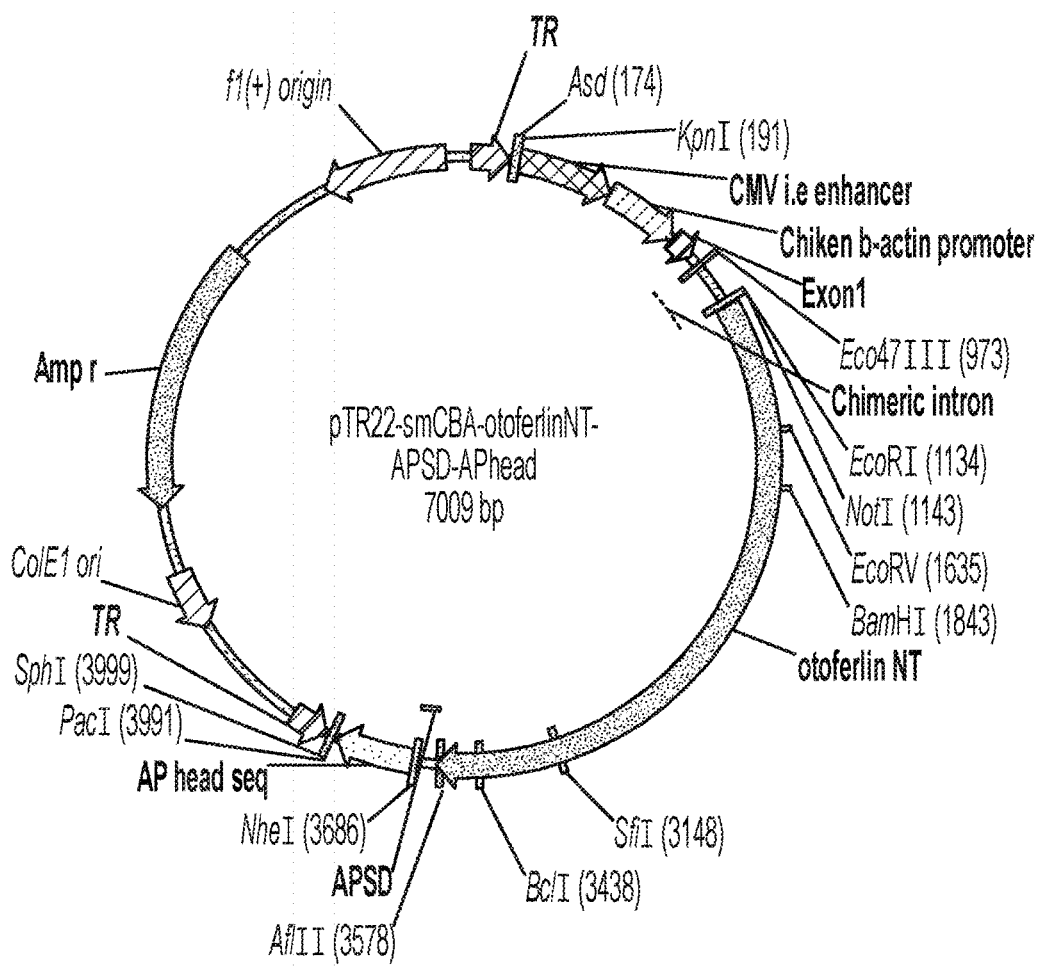
FIG. 1A is a map of a plasmid containing AAV2 inverted terminal repeats (TR) flanking a CMV enhancer, a chicken beta-actin promoter, a 5' section of the mouse Otoferlin cDNA (Otoferlin NT), a splice donor sequence (APSD), and a homologous sequence for recombination (APhead).

This application relates to compositions and methods that restore, at least partially, hearing in a subject (e.g., a human). As described herein, it has been found that hearing can be restored in Otoferlin knock-out mice by treating the mice with two separate AAV particles, one comprising the 5' portion of the OTOF cDNA and one comprising the 3' portion of the OTOF cDNA and each comprising a region of homology (i.e., 100% or partial identity) for promoting homologous recombination between the 5' portion and 3' portion in vivo. This region of homology is flanked by a splice donor sequence on the 5' side within the 5' portion of the OTOF cDNA and a splice acceptor sequence on the 3' side within the 3' portion of the OTOF cDNA. Accordingly, compositions and methods are provided for increasing expression of Otoferlin.

Exemplary Definitions

Unless defined otherwise, all technical and scientific terms used herein have the same meaning as commonly understood by one of ordinary skill in the art to which this invention belongs. Although any methods and compositions similar or equivalent to those described herein may be used in the practice or testing of the present invention, the preferred methods and compositions are described herein. For purposes of the present invention, the following terms are defined below:

As used herein, the terms "nucleic acid" and "polynucleotide" refer to a deoxyribonucleotide or ribonucleotide polymer in either single- or double-stranded form, and unless otherwise limited, encompass known analogs of natural nucleotides that may function in a similar manner as naturally occurring nucleotides.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences may be at least about 80%, preferably at least about 85%, and more preferably about 90% or 95% or higher, as readily determined by one or more of the sequence comparison algorithms well-known to those of ordinary skill in the art, such as e.g., the FASTA program analysis described by Pearson and Lipman (1988).

As used herein, the term "variant" refers to a molecule (e.g. a nucleotide sequence or a peptide sequence) having characteristics that deviate from what occurs in nature, e.g., a "variant" is at least about 80% identical, at least about 90% identical, at least about 95% identical, at least about 96% identical, at least about 97% identical, at least about 98% identical, at least about 99% identical, at least about 99.5% identical, or at least about 99.9% identical to the wild type sequence. Variants of a molecule, e.g. a polynucleotide comprised within an rAAV nucleic acid vector, or the rAAV nucleic acid vector itself, may contain modifications to the nucleotide sequence (e.g., having 1, 2, 3, 4, 5, 6, 7, 8, 9, 10, 10-15, 15-100, 100-250, or more than 250 nucleotide substitutions) relative to the wild type nucleotide sequence, which may arise from point mutations installed into the nucleotide sequence. These modifications include chemical modifications as well as truncations.

Polynucleotides

In some aspects, polynucleotides are provided for delivering portions of coding sequences of an OTOF gene that encode the Otoferlin protein to a cell. In some embodiments, the coding sequences are derived from a human OTOF gene (see, e.g., NCBI Gene ID: 9381 and cDNA sequences NM_001287489.1, NM_004802.3, NM_194248.2, NM_194322.2, and NM_194323.2). In some embodiments, the coding sequences are derived from a mouse OTOF gene (see, e.g., NCBI Gene ID 83762 and cDNA sequences NM_001100395.1, NM_001286421.1, NM_001313767.1, and NM_031875.2). In some embodiments, a first and a second polynucleotide are provided. It is to be understood that "first," "second," "third," and the like are not meant to imply a particular order or importance unless expressly stated otherwise.

In some embodiments, the first polynucleotide comprises inverted terminal repeat sequences flanking an expression cassette containing, from 5' to 3', one or more of (a) a promoter, (b) a partial coding sequence that encodes an N-terminal portion of an Otoferlin polypeptide, (c) a splice donor site, and (d) a first region of homology containing a sequence that is homologous to a sequence in the second polynucleotide, or a complement thereof. In some embodiments, the first polynucleotide comprises at least two, at least three or all four of (a), (b), (c), and (d).

In some embodiments, the second polynucleotide comprises inverted terminal repeat sequences flanking an expression cassette containing, from 5' to 3', one or more of (a) a second region of homology containing a sequence that is homologous to a sequence in the first polynucleotide, (b) a splice acceptor site, (c) a partial coding sequence that encodes a C-terminal portion of the Otoferlin polypeptide, and (d) a polyadenylation (pA) signal sequence, or a complement thereof. In some embodiments, the second polynucleotide comprises at least two, at least three or all four of (a), (b), (c), and (d).

In some embodiments, the first and/or second polynucleotides are codon optimized for expression in particular cells, such as eukaryotic cells. The eukaryotic cells may be those of or derived from a particular organism, such as a mammal, including but not limited to human and mouse. In some embodiments, the first and/or second polynucleotides are codon optimized for expression in human cells. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes may be tailored for improved recombinant protein expression in a given organism based on codon optimization.

Codon usage within mammalian species is very similar, and it can be expected that most genes are already relatively codon optimized. The codon adaptation index (CAI) is a commonly used method to analyze and subsequently improve the codon bias of a given gene. The closer the CAI value is to 1 the better protein expression is expected to be. For the codon-optimized human otoferlin polynucleotide vectors of the present invention, the CAI for human otoferlin cDNA was increased from 0.84 to 0.95. In addition, several restriction endonuclease sites were removed to simplify cloning procedures.

In some embodiments, the first and/or second polynucleotides comprise a sequence encoding an epitope tag (e.g., at the 5' end or the 3' end), such as a myc tag (EQKLISEEDL, SEQ ID NO: 22). An epitope tag such as a myc tag facilitates the distinction between in vivo effects resulting from exogenous otoferlin protein as delivered by a vector and those resulting from endogenous otoferlin as expressed by the inner hair cells of the vestibular organ.

In some embodiments, the first and/or second polynucleotides are codon optimized for expression in particular cells and comprise a sequence encoding an epitope tag (e.g., at the 5' end or the 3' end), such as a myc tag.

The partial coding sequences contained within the polynucleotides described herein may be designed so that, upon delivery of the polynucleotides, the partial coding sequences are joined together, e.g., through homologous recombination, and form a complete coding sequence that encodes an Otoferlin polypeptide.

In some embodiments, the polynucleotides are plasmids (e.g., a circular nucleic acid comprising one or more of an origin of replication, a selectable marker, and a reporter gene). In some embodiments, polynucleotides described herein, such as a plasmid, may also contain marker or reporter genes, e.g., LacZ or a fluorescent protein, and an origin of replication. In some embodiments, the plasmid is transfected into a producer cell that produces AAV particles containing the expression cassettes contained within the plasmids.

In some embodiments, the polynucleotides are nucleic acid vectors such as a recombinant adeno-associated virus (AAV) nucleic acid vectors. Exemplary AAV nucleic acid vectors useful according to the disclosure include single-stranded (ss) and self-complementary (sc) polynucleotides.

In some embodiments, recombinant AAV particles comprise the polynucleotides, such as a single-stranded (ss) or self-complementary (sc) AAV nucleic acid vectors. In some embodiments, the polynucleotides contain expression constructs as described herein and inverted terminal repeat (ITR) sequences (e.g., wild-type ITR sequences or engineered ITR sequences) flanking the expression constructs. In some embodiments, the polynucleotides are encapsidated by viral capsids.

In some aspects, provided herein are AAV nucleic acid vectors comprising a nucleotide sequence that is at least 80%, at least 85%, at least 90%, at least 95%, at least 98%, or at least 99% identical to the sequence as set forth in any one of SEQ ID NOs: 17-21. In some embodiments, the AAV nucleic acid vector comprises a nucleotide sequence comprising the sequence set forth in any one of SEQ ID NOs: 17-21, or a variant thereof.

In some aspects, provided herein are AAV nucleic acid vectors comprising a nucleotide sequence that is at least 80%, at least 85%, at least 90%, at least 95%, at least 98%, or at least 99% identical to the sequence as set forth in SEQ ID NO: 18. In some embodiments, the AAV nucleic acid vector comprises a nucleotide sequence comprising the sequence set forth in SEQ ID NO: 18. In some aspects, the disclosure provides AAV nucleic acid vectors comprising a nucleotide sequence that is at least 80%, at least 85%, at least 90%, at least 95%, at least 98%, or at least 99% identical to the sequence as set forth in SEQ ID NO: 19. In some aspects, the disclosure provides AAV nucleic acid vectors comprising a nucleotide sequence that is at least 80%, at least 85%, at least 90%, at least 95%, at least 98%, or at least 99% identical to the sequence as set forth in SEQ ID NO: 20. In some aspects, the disclosure provides AAV nucleic acid vectors comprising a nucleotide sequence that is at least 80%, at least 85%, at least 90%, at least 95%, at least 98%, or at least 99% identical to the sequence as set forth in SEQ ID NO: 21.

Accordingly, in some embodiments, an AAV particle comprises a viral capsid and a polynucleotide as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively.

In some embodiments, polynucleotides as described herein (e.g., first and second polynucleotides) comprise regions of homology, e.g., to promote homologous recombination between the polynucleotides once delivered to a cell (see, e.g., Ghosh et al. Efficient transgene reconstitution with hybrid dual AAV vectors carrying the minimized bridging sequences. *Hum Gene Ther.* 2011 January; 22(1):77-83). In some embodiments, a first region of homology and a second region of homology have a threshold level of sequence identity with each other in order to promote homologous recombination.

In some embodiments the first region of homology has at least 75%, at least 80%, at least 90%, at least 95%, at least 96%, at least 97%, at least 98%, at least 99% or 100% identity with the second region of homology. Unless otherwise specified, as used herein percent sequence identity and/or similarity of two sequences may be determined using the algorithm of Karlin and Altschul (1990), modified as in Karlin and Altschul (1993). Such an algorithm is incorporated into the NBLAST® and XBLAST® programs of Altschul et al. (1990). BLAST® searches can be performed with the NBLAST® program, score=100, word-length=12, to obtain sequences with the desired percent sequence identity. To obtain gapped alignments for comparison purposes, Gapped BLAST® can be used as described (Altschul et al., 1997). When utilizing BLAST® and Gapped BLAST® programs, the default parameters of the respective programs (NBLAST® and XBLAST®) can be used in accordance with published methods. In some embodiments, each region of homology is independently between 50 and 500, 50 and 400, 50 and 300, 100 and 500, 100 and 400, 100 and 300, 200 and 500, 200 and 400, or 200 and 300 nucleotides. In some embodiments, the regions of homology are identical and each region of homology is between 50 and 500, 50 and 400, 50 and 300, 100 and 500, 100 and 400, 100 and 300, 200 and 500, 200 and 400, or 200 and 300 nucleotides. In some embodiments, the region homology comprises a sequence that is at least 75%, at least 80%, at least 85%, at least 90%, at least 95%, at least 96%, at least 97%, at least 98%, at least 99% or 100% identical with the nucleotide sequence CCCCGGGTGCGCGGCGTCGGTGGTGCCGGCGGGGGGCGCCAGGTCGCAGGCGGTGTAGGGCTCCAGGCAGGCGGCGAAGGCCATGACGTGCGCTATGAAGGTCTGCTCCTGCACGCCGTGAACCAGGTGCGCCTGCGGGCCGCGCGCGAACACCGCCACGTCCTCGCCTGCGTGGGTCTCTTCGTCCAGGGGCACTGCTGACTGCTGCCGATACTCGGGGCTCCCGCTCTCGCTCTCGGTAACATCCGGCCGGGCGCCGTCCTTGAGCACATAGCCTGGACC GTTTC (SEQ ID NO: 3), or a complement thereof.

In some embodiments, polynucleotides described herein may comprise one or more regulatory elements. A person of ordinary skill in the art may select regulatory elements for use in appropriate host cells, for example, mammalian or human host cells. Regulatory elements include, for example, promoters, transcription termination sequences, translation termination sequences, enhancers, and polyadenylation elements. A polynucleotide described herein may comprise a promoter sequence operably linked to a nucleotide sequence encoding a desired polypeptide, such as Otoferlin. Promoters contemplated for use in the subject invention include, but are not limited to, cytomegalovirus (CMV) promoter, SV40 promoter, Rous sarcoma virus (RSV) promoter, chimeric CMV/chicken β actin promoter (CBA) and the truncated form of CBA (smCBA) (see, e.g., Haire et al. 2006 and U.S. Pat. No. 8,298,818, which is specifically incorporated herein in its entirety by express reference thereto). In some embodiments, the promoter is the truncated chimeric CMV β actin (smcBA) promoter. In some embodiments, the promoter comprises a sequence that is at least 75%, at least 80%, at least 85%, at least 90%, at least 95%, at least 96%, at least 97%, at least 98%, at least 99% or 100% identical with the nucleotide sequence GGTACCCTAGTTATTAATAGTAAT-CAATTACGGGGTCATTAGTTCATAGCCCATATATGGAGTTCCGCGTTACATAACT-TACGGTAAATGGCCCGCCTGGCTGACCGCCCAACGACCCCCGCCCATTGACGT-CAATAATGACGTATGTTCCCATAGTAACGC-CAATAGGG ACTTTCCATTGACGTCAATGGGTGGAC-TATTTACGGTAAACTGCCCACTTGGCAGTA CATCAAGTGTATCATATGCCAAGTACGCCCCCTAT-TGACGTCAATGACGGTAAATGG CCCGCCTGGCAT-TATGCCCAGTACATGACCTTATGGGACTTTCC-TACTTGGCAGTAC ATCTACGTATTAGTCATCGCTATTAC-CATGGTCGAGGTGAGCCCCACGTTCTGCTTC ACTCTCCCCATCTCCCCCCCCTCCCCACCCCCAAT-TTTGTATTTATTTATTTTTTAATT ATTTTGTGCAGC-GATGGGGGCGGGGGGGGGGGGGGGGGCGCGCGCCAGGCGGGGCG GGGCGGGGCGAGGGGCGGGGCGGGGCGAGGCG-GAGAGGTGCGGCGGCAGCCAATC AGAGCGGCGCGCTCCGAAAGTTTCCTTT-TATGGCGAGGCGGCGGCGGCGGCCC TATAAAAAGCGAAGCGCGCGGCGGGCG (SEQ ID NO: 4), or a complement thereof.

In some embodiments, polynucleotides as described herein comprise a partial coding sequence that encodes an N-terminal or C-terminal portion of an Otoferlin polypeptide, wherein the partial coding sequences may be spliced or otherwise combined together in vivo in order to encode an Otoferlin polypeptide. In some embodiments, the Otoferlin polypeptide is a human Otoferlin polypeptide. In some embodiments, the Otoferlin polypeptide is a long isoform of a human Otoferlin polypeptide (see, e.g., Yasunaga et al. OTOF Encodes Multiple Long and Short Isoforms: Genetic Evidence That the Long Ones Underlie Recessive Deafness DFNB9. *Am. J. Hum. Genet.* 67:591-600, 2000). In some embodiments, the Otoferlin polypeptide comprises a sequence that is at least 75%, at least 80%, at least 85%, at least 90%, at least 95%, at least 96%, at least 97%, at least 98%, at least 99% or 100% identical with one or both of the following amino acid sequences:

Human OTOF isoform 1-Genbank Number AF183185.1
(SEQ ID NO: 5)
MALLIHLKTVSELRGRGDRIAKVTFRGQSFYSRVLENCEDVADFDETFRWPVASSIDRNE

MLEIQVFNYSKVFSNKLIGTFRMVLQKVVEESHVEVTDTLIDDNNAIIKTSLCVEVRYQA

TDGTVGSWDDGDFLGDESLQEEEKDSQETDGLLPGSRPSSRPPGEKSFRRAGRSVFSAMK

LGKNRSHKEEPQRPDEPAVLEMEDLDHLAIRLGDGLDPDSVSLASVTALTTNVSNKRSKP

DIKMEPSAGRPMDYQVSITVIEARQLVGLNMDPVVCVEVGDDKKYTSMKESTNCPYYNEY

FVFDFHVSPDVMFDKIIKISVIHSKNLLRSGTLVGSFKMDVGTVYSQPEHQFHHKWAILS

DPDDISSGLKGYVKCDVAVVGKGDNIKTPHKANETDEDDIEGNLLLPEGVPPERQWARFY

VKIYRAEGLPRMNTSLMANVKKAFIGENKDLVDPYVQVFFAGQKGKTSVQKSSYEPLWNE

QVVFTDLFPPLCKRMKVQIRDSDKVNDVAIGTHFIDLRKISNDGDKGFLPTLGPAWVNMY

GSTRNYTLLDEHQDLNEGLGEGVSFRARLLLGLAVEIVDTSNPELTSSTEVQVEQATPIS

ESCAGKMEEFFLFGAFLEASMIDRRNGDKPITFEVTIGNYGNEVDGLSRPQRPRPRKEPG

DEEEVDLIQNASDDEAGDAGDLASVSSTPPMRPQVTDRNYFHLPYLERKPCIYIKSWWPD

QRRRLYNANIMDHIADKLEEGLNDIQEMIKTEKSYPERRLRGVLEELSCGCCRFLSLADK

DQGHSSRTRLDRERLKSCMRELENMGQQARMLRAQVKRHTVRDKLRLCQNFLQKLRFLAD

EPQHSIPDIFIWMMSNNKRVAYARVPSKDLLFSIVEEETGKDCAKVKTLFLKLPGKRGFG

SAGWTVQAKVELYLWLGLSKQRKEFLCGLPCGFQEVKAAQGLGLHAFPPVSLVYTKKQAF

QLRAHMYQARSLFAADSSGLSDPFARVFFINQSQCTEVLNETLCPTWDQMLVFDNLELYG

EAHELRDDPPIIVIEIYDQDSMGKADFMGRTFAKPLVKMADEAYCPPRFPPQLEYYQIYR

GNATAGDLLAAFELLQIGPAGKADLPPINGPVDVDRGPIMPVPMGIRPVLSKYRVEVLFW

GLRDLKRVNLAQVDRPRVDIECAGKGVQSSLIHNYKKNPNFNTLVKWFEVDLPENELLHP

PLNIRVVDCRAFGRYTLVGSHAVSSLRRFIYRPPDRSAPSWNTTVRLLRRCRVLCNGGSS

SHSTGEVVVTMEPEVPIKKLETMVKLDATSEAVVKVDVAEEEKEKKKKKKGTAEEPEEEE

PDESMLDWWSKYFASIDTMKEQLRQQEPSGIDLEEKEEVDNTEGLKGSMKGKEKARAAKE

EKKKKTQSSGSGQGSEAPEKKKPKIDELKVYPKELESEFDNFEDWLHTFNLLRGKTGDDE

DGSTEEERIVGRFKGSLCVYKVPLPEDVSREAGYDSTYGMFQGIPSNDPINVLVRVYVVR

ATDLHPADINGKADPYIAIRLGKTDIRDKENYISKQLNPVFGKSFDIEASFPMESMLTVA

VYDWDLVGTDDLIGETKIDLENRFYSKHRATCGIAQTYSTHGYNIWRDPMKPSQILTRLC

KDGKVDGPHFGPPGRVKVANRVFTGPSEIEDENGQRKPTDEHVALLALRHWEDIPRAGCR

LVPEHVETRPLLNPDKPGIEQGRLELWVDMFPMDMPAPGTPLDISPRKPKKYELRVIIWN

TDEVVLEDDDFFTGEKSSDIFVRGWLKGQQEDKQDTDVHYHSLTGEGNFNWRYLFPFDYL

AAEEKIVISKKESMFSWDETEYKIPARLTLQIWDADHFSADDFLGAIELDLNRFPRGAKT

AKQCTMEMATGEVDVPLVSIFKQKRVKGWWPLLARNENDEFELTGKVEAELHLLTAEEAE

KNPVGLARNEPDPLEKPNRPDTSFIWFLNPLKSARYFLWHTYRWLLLKLLLLLLLLLLLA

LFLYSVPGYLVKKILGA

Human OTOF isoform 5-Genbank Number NP_001274418
(SEQ ID NO: 6)
MALLIHLKTVSELRGRGDRIAKVTFRGQSFYSRVLENCEDVADFDETFRWPVASSIDRNE

MLEIQVFNYSKVFSNKLIGTFRMVLQKVVEESHVEVTDTLIDDNNAIIKTSLCVEVRYQA

TDGTVGSWDDGDFLGDESLQEEEKDSQETDGLLPGSRPSSRPPGEKSFRRAGRSVFSAMK

LGKNRSHKEEPQRPDEPAVLEMEDLDHLAIRLGDGLDPDSVSLASVTALTTNVSNKRSKP

DIKMEPSAGRPMDYQVSITVIEARQLVGLNMDPVVCVEVGDDKKYTSMKESTNCPYYNEY

-continued

FVFDFHVSPDVMFDKIIKISVIHSKNLLRSGTLVGSFKMDVGTVYSQPEHQFHHKWAILS

DPDDISSGLKGYVKCDVAVVGKGDNIKTPHKANETDEDDIEGNLLLPEGVPPERQWARFY

VKIYRAEGLPRMNTSLMANVKKAFIGENKDLVDPYVQVFFAGQKGKTSVQKSSYEPLWNE

QVVFTDLFPPLCKRMKVQIRDSDKVNDVAIGTHFIDLRKISNDGDKGFLPTLGPAWVNMY

GSTRNYTLLDEHQDLNEGLGEGVSFRARLLLGLAVEIVDTSNPELTSSTEVQVEQATPIS

ESCAGKMEEFFLFGAFLEASMIDRRNGDKPITFEVTIGNYGNEVDGLSRPQRPRPRKEPG

DEEEVDLIQNASDDEAGDAGDLASVSSTPPMRPQVTDRNYFHLPYLERKPCIYIKSWWPD

QRRRLYNANIMDHIADKLEEGLNDIQEMIKTEKSYPERRLRGVLEELSCGCCRFLSLADK

DQGHSSRTRLDRERLKSCMRELENMGQQARMLRAQVKRHTVRDKLRLCQNFLQKLRFLAD

EPQHSIPDIFIWMMSNNKRVAYARVPSKDLLFSIVEEETGKDCAKVKTLFLKLPGKRGFG

SAGWTVQAKVELYLWLGLSKQRKEFLCGLPCGFQEVKAAQGLGLHAFPPVSLVYTKKQAF

QLRAHMYQARSLFAADSSGLSDPFARVFFINQSQCTEVLNETLCPTWDQMLVFDNLELYG

EAHELRDDPPIIVIEIYDQDSMGKADFMGRTFAKPLVKMADEAYCPPRFPPQLEYYQIYR

GNATAGDLLAAFELLQIGPAGKADLPPINGPVDVDRGPIMPVPMGIRPVLSKYRVEVLFW

GLRDLKRVNLAQVDRPRVDIECAGKGVQSSLIHNYKKNPNFNTLVKWFEVDLPENELLHP

PLNIRVVDCRAFGRYTLVGSHAVSSLRRFIYRPPDRSAPSWNTTVRLLRRCRVLCNGGSS

SHSTGEVVVTMEPEVPIKKLETMVKLDATSEAVVKVDVAEEEKEKKKKKGTAEEPEEEE

PDESMLDWWSKYFASIDTMKEQLRQQEPSGIDLEEKEEVDNTEGLKGSMKGKEKARAAKE

EKKKKTQSSGSGQGSEAPEKKKPKIDELKVYPKELESEFDNFEDWLHTFNLLRGKTGDDE

DGSTEEERIVGRFKGSLCVYKVPLPEDVSREAGYDSTYGMFQGIPSNDPINVLRVYVVR

ATDLHPADINGKADPYIAIRLGKTDIRDKENYISKQLNPVFGKSFDIEASFPMESMLTVA

VYDWDLVGTDDLIGETKIDLENRFYSKHRATCGIAQTYSTHGYNIWRDPMKPSQILTRLC

KDGKVDGPHFGPPGRVKVANRVFTGPSEIEDENGQRKPTDEHVALLALRHWEDIPRAGCR

LVPEHVETRPLLNPDKPGIEQGRLELWVDMFPMDMPAPGTPLDISPRKPKKYELRVIIWN

TDEVVLEDDDFFTGEKSSDIFVRGWLKGQQEDKQDTDVHYHSLTGEGNFNWRYLFPFDYL

AAEEKIVISKKESMFSWDETEYKIPARLTLQIWDADHFSADDFLGAIELDLNRFPRGAKT

AKQCTMEMATGEVDVPLVSIFKQKRVKGWWPLLARNENDEFELTGKVEAELHLLTAEEAE

KNPVGLARNEPDPLEKPNRPDTAFVWFLNPLKSIKYLICTRYKWLIIKIVLALLGLLMLG

LFLYSLPGYMVKKLLGA

In some embodiments, the Otoferlin polypeptide is a mouse Otoferlin polypeptide. In some embodiments, the Otoferlin polypeptide comprises a sequence that is at least 75%, at least 80%, at least 85%, at least 90%, at least 95%, at least 96%, at least 97%, at least 98%, at least 99% or 100% identical with the following amino acid sequence:

```
Mouse OTOF Isoform 1 Genbank Number NP_001093865A
                                    (SEQ ID NO: 9)
MALIVHLKTVSELRGKGDRIAKVTFRGQSFYSRVLENCEGVADF

DETFRWPVASSIDRNEVLEIQIFNYSKVFSNKLIGTFCMVLQKVVEENRVEVIDILMD

DSNAIIKTSLSMEVRYQATDGTVGPWDDGDFLGDESLQEEKDSQEIDGLLPGSRPSTR

ISGEKSFRSKGREKTKGGRDGEHKAGRSVFSAMKLGKIRSHKEEPQRQDEPAVLEMED

LDHLAIQLGDGLDPDSVSLASVTALTSNVSNKRSKPDIKMEPSAGRPMDYQVSITVIE
```

-continued

ARQLVGLNMDPVVCVEVGDDKKYISMKESINCPYYNEYFVFDFHVSPDVMFDKIIKIS

VIHSKNLLRSGILVGSFKMDVGIVYSQPEHQFHHKWAILSDPDDISAGLKGYVKCDVA

VVGKGDNIKTPHKANETDEDDIEGNLLLPEGVPPERQWARFYVKIYRAEGLPRMNTSL

MANVKKAFIGENKDLVDPYVQVFFAGQKGKTSVQKSSYEPLWNEQVVFIDLFPPLCKR

MKVQIRDSDKVNDVAIGTHFIDLRKISNDGDKGFLPTLGPAWVNMYGSTRNYILLDEH

QDLNEGLGEGVSFRARLMLGLAVEILDISNPELTSSTEVQVEQATPVSESCIGRMEEF

FLFGAFLEASMIDRKNGDKPITFEVTIGNYGNEVDGMSRPLRPRPRKEPGDEEEVDLI

QNSSDDEGDEAGDLASVSSIPPMRPQITDRNYFHLPYLERKPCIYIKSWWPDQRRRLY

NANIMDHIADKLEEGLNDVQEMIKTEKSYPERRLRGVLEELSCGCHRFLSLSDKDQGR

SSRTRLDRERLKSCMRELESMGQQAKSLRAQVKRHTVRDKLRSCQNFLQKLRFLADEP

QHSIPDVFIWMMSNNKRIAYARVPSKDLLFSIVEEELGKDCAKVKILFLKLPGKRGFG

SAGWTVQAKLELYLWLGLSKQRKDFLCGLPCGFEEVKAAQGLGLHSFPPISLVYTKKQ

AFQLRAHMYQARSLFAADSSGLSDPFARVFFINQSQCTEVLNETLCPTWDQMLVFDNL

ELYGEAHELRDDPPIIVIEIYDQDSMGKADFMGRTFAKPLVKMADEAYCPPRFPPQLE

YYQIYRGSATAGDLLAAFELLQIGPSGKADLPPINGPVDMDRGPIMPVPVGIRPVLSK

YRVEVLFWGLRDLKRVNLAQVDRPRVDIECAGKGVQSSLIHNYKKNPNENTLVKWFEV

DLPENELLHPPLNIRVVDCRAFGRYTLVGSHAVSSLRRFIYRPPDRSAPNWNITGEVV

VSMEPEEPVKKLETMVKLDATSDAVVKVDVAEDEKERKKKKKKGPSEEPEEEEPDESM

LDWWSKYFASIDTMKEQLRQHETSGIDLEEKEEMESAEGLKGPMKSKEKSRAAKEEKK

KKNQSPGPGQGSEAPEKKKAKIDELKVYPKELESEFDSFEDWLHTFNLLRGKTGDDED

GSTEEERIVGRFKGSLCVYKVPLPEDVSREAGYDPTYGMFQGIPSNDPINVLVRIYVV

RAIDLHPADINGKADPYIAIKLGKIDIRDKENYISKQLNPVFGKSFDIEASFPMESML

TVAVYDWDLVGIDDLIGETKIDLENRFYSKHRATCGIAQTYSIHGYNIWRDPMKPSQI

LTRLCKEGKVDGPHFGPHGRVRVANRVFIGPSEIEDENGQRKPIDEHVALSALRHWED

IPRVGCRLVPEHVETRPLLNPDKPGIEQGRLELWVDMFPMDMPAPGTPLDISPRKPKK

YELRVIVWNIDEVVLEDDDFFIGEKSSDIFVRGWLKGQQEDKQDTDVHYHSLIGEGNF

NWRYLFPFDYLAAEEKIVMSKKESMFSWDETEYKIPARLTLQIWDADHFSADDFLGAI

ELDLNRFPRGAKTAKQCTMEMATGEVDVPLVSIFKQKRVKGWWPLLARNENDEFELTG

KVEAELHLLTAEEAEKNPVGLARNEPDPLEKPNRPDTAFVWFLNPLKSIKYLICTRYK

WLIIKIVLALLGLLMLALFLYSLPGYMVKKLLGA

In some embodiments, polynucleotides described herein comprise a splice donor or splice acceptor site. In some embodiments, the splice donor and/or splice acceptor sites contain splice consensus sequences. In some embodiments, the splice donor and/or splice acceptor sites contain sequences splice consensus sequences derived from alkaline phosphatase. In some embodiments, the splice donor site comprises a sequence that is at least 75%, at least 80%, at least 85%, at least 90%, at least 95%, at least 96%, at least 97%, at least 98%, at least 99% or 100% identical with the nucleotide sequence GTAAGTATCAAGGTTACAAGACAGGTTTAAGGAGAC-CAATAGAAACTGGGCTTGTC GAGACAGAGAA-GACTCTTGCGTTTCTGA (SEQ ID NO: 7), or a complement thereof. In some embodiments, the splice acceptor site comprises a sequence that is at least 75%, at least 80%, at least 85%, at least 90%, at least 95%, at least 96%, at least 97%, at least 98%, at least 99% or 100% identical with the nucleotide sequence TAGGCACCTAT-TGGTCTTACTGACATCCACTTTGCCTTTCTCTC-CACAG (SEQ ID NO: 8), or a complement thereof.

In some embodiments, polynucleotides described herein comprise ITR sequences. The ITR sequences of a polynucleotide described herein may be derived from any AAV serotype (e.g., 1, 2, 3, 4, 5, 6, 7, 8, 9, or 10) or may be derived from more than one serotype. In some embodiments of the polynucleotide provided herein, the ITR sequences are derived from AAV2. ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201© Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference). An exemplary AAV2 ITR sequence for flanking the 5' end of an expression construct comprises the sequence: TTGGC-CACTCCCTCTCTGCGCGCTCGCTCGCTCACT-GAGGCCGGGCGACCAAAGGTC GCCCGACGCCCGGGCTTTGCCCGGGCGGCCTCAGT-GAGCGAGCGAGCGCGCAGAGA GGGAGTGGC-CAACTCCATCACTAGGGGTTC (SEQ ID NO: 10). An exemplary AAV2 ITR sequence for flanking the 3' end of an expression construct comprises the sequence (SEQ ID NO: 11)
ACCCCTAGTGATGGAGTTGGCCACTCCCTCTCTGCGCGCTCGCTCGCTC
ACTGAGGCCGCCCGGGCAAAGCCCGGGCGTCGGGCGACCTTTGGTCGCC
CGGCCTCAGTGAGCGAGCGAGCGCGCAGAGAGGGAGTGGCCAACC.

In some embodiments, polynucleotides described herein may further optionally include one or more transcription termination sequences, one or more translation termination sequences, one or more signal peptide sequences, one or more internal ribosome entry sites (RES), and/or one or more enhancer elements, or any combination thereof. Transcription termination regions may typically be obtained from the 3' untranslated region of a eukaryotic or viral gene sequence. Transcription termination sequences may be positioned downstream of a coding sequence to provide for efficient termination. Signal peptide sequences are amino-terminal peptidic sequences that encode information responsible for the location of an operably-linked polypeptide to one or more post-translational cellular destinations, including, for example, specific organelle compartments, or to the sites of protein synthesis and/or activity, and even to the extracellular environment. In some embodiments, a polynucleotide as described herein comprises a bovine growth hormone polyadenylation signal.

In some embodiments, polynucleotides described herein may be codon optimized for expression in particular cells, such as eukaryotic cells. In some embodiments, the polynucleotides described herein may further optionally include sequences encoding epitope tags, such as myc tags. In some embodiments, the polynucleotides described herein may be codon optimized for expression in particular cells and include sequences encoding epitope tags, such as myc tags.

In some embodiments, the expression constructs contained within the polynucleotides described herein are no more than 5 kilobases, no more than 4 kilobases, or no more than 3 kilobases in size. In some embodiments, the expression construct is between 4 and 5 kilobases in size.

In some embodiments, polynucleotides described herein are contained within one or more recombinant AAV particles (e.g., first and second AAV particles). The AAV particles may be of any AAV serotype (e.g., 1, 2, 3, 4, 5, 6, 7, 8, 9, or 10), including any derivative (including non-naturally occurring variants of a serotype) or pseudotype. Non-limiting examples of derivatives and pseudotypes include AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the first and second AAV particle are AAV2 serotype particles.

Methods of producing AAV particles and polynucleotides are known in the art and commercially available (see, e.g., Zolotukhin et al. Production and purification of serotype 1, 2, and 5 recombinant adeno-associated viral vectors. *Methods* 28 (2002) 158-167; and U.S. Patent Publication Numbers US20070015238 and US20120322861, which are incorporated herein by reference; and plasmids and kits available from ATCC and Cell Biolabs, Inc.). For example, the polynucleotides (e.g., as plasmids) may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the AAV particle may be packaged and subsequently purified.

In some embodiments, the one or more helper plasmids includes a first helper plasmid comprising a rep gene and a cap gene and a second helper plasmid comprising other genes that assist in AAV production, such as a E1a gene, a E1b gene, a E4 gene, a E2a gene, and a VA gene. In some embodiments, the rep gene is a rep gene derived from AAV2. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, *Human Gene Therapy*, Vol. 9, 2745-2760; Kern, A. et al. (2003), Identification of a Heparin-Binding Motif on Adeno-Associated Virus Type 2 Capsids, *Journal of Virology*, Vol. 77, 11072-11081.; Grimm et al. (2003), Helper Virus-Free, Optically Controllable, and Two-Plasmid-Based Production of Adeno-associated Virus Vectors of Serotypes 1 to 6, *Molecular Therapy*, Vol. 7, 839-850; Kronenberg et al. (2005), A Conformational Change in the Adeno-Associated Virus Type 2 Capsid Leads to the Exposure of Hidden VP1 N Termini, *Journal of Virology*, Vol. 79, 5296-5303; and Moullier, P. and Snyder, R. O. (2008), International efforts for recombinant adenoassociated viral vector reference standards, *Molecular Therapy*, Vol. 16, 1185-1188).

An exemplary, non-limiting, AAV particle production method is described next. One or more helper plasmids are produced or obtained, which comprise rep and cap ORFs for the desired AAV serotype and the adenoviral VA, E2A (DBP), and E4 genes under the transcriptional control of their native promoters. HEK293 cells (available from ATCC®) are transfected via $CaPO_4$-mediated transfection, lipids or polymeric molecules such as Polyethylenimine (PEI) with the helper plasmid(s) and a plasmid containing a polynucleotide described herein. Alternatively, in another non-limiting example, Sf9-based producer stable cell lines are infected with a single recombinant baculovirus containing the polynucleotide. As a further non-limiting alternative, in another example HEK293 or BHK cell lines are infected with a HSV containing the polynucleotide and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for AAV particle production. The AAV particles may then be purified using any method known in the art or described herein, e.g., by iodixanol step gradient, CsCl gradient, chromatography, or polyethylene glycol (PEG) precipitation.

The disclosure also contemplates host cells that comprise at least one of the disclosed AAV particles or polynucleotides. Such host cells include mammalian host cells, with human host cells being preferred, and may be either isolated, in cell or tissue culture. In the case of genetically modified animal models (e.g., a mouse), the transformed host cells may be comprised within the body of a non-human animal itself.

Methods and Subjects

In some aspects, methods of increasing expression of Otoferlin in a cell are provided. In some embodiments, the method comprises contacting the cell with a first AAV particle as described herein comprising a first polynucleotide as described herein; and contacting the cell with a second AAV particle as described herein comprising a second polynucleotide as described herein. In some embodiments, the cell is a mammalian cell such as a mouse or human cell. In some embodiments, the cell is ex vivo. In some embodiments, the cell is in vivo. In some embodiments, the cell is a cell of the ear (e.g., the cell of a human ear). In some embodiments, the cell is a cell of the inner ear (e.g., the cell of a human inner ear). In some embodiments, the cell is in a subject (e.g., a mammalian subject such as a human subject).

Other aspects of the disclosure relate to treatment of a disease or condition caused by decreased or absent expression or activity of Otoferlin. In some embodiments, the method comprises administering to a subject a therapeutically effective amount of a first AAV particle as described herein comprising a first polynucleotide as described herein and a therapeutically effective amount of a second AAV particle as described herein comprising a second polynucleotide as described herein. In some embodiments, the subject has a hearing impairment (e.g., deafness). In some embodiments, the subject is a human subject and the subject has Deafness, Autosomal Recessive 9 (DFNB9). In some embodiments, the subject is a human subject having impaired vestibular function or a vestibular disorder (see, e.g., Dulon et al. Otoferlin is Critical for a Highly Sensitive and Linear Calcium Dependent Exocytosis at Vestibular Hair Cell Ribbon Synapses. *J Neurosci.* 2009; 29(34): 10474-10487).

Hearing (or hearing loss, restoration or recovery) in a subject may be evaluated through audiological evaluations, auditory brain stem (ABR) response, a sensory or tactile response in the subject, or any other suitable method known in the art. Hearing may be evaluated through measurement of ABR responses to clicks, tone pips, and/or other sounds, vibrations, noises, or other stimuli. These sounds, vibrations, noises or other stimuli may be provided at one of a number of different frequencies that are audible to the subject, e.g., frequencies of about 4, 8, 16, 32, 64, 128, 256 or 350 kHz. These sounds, vibrations, noises or other stimuli may be provided at one of a number of different volumes, such as 1 decibel (dB), 2 dB, 5 dB, 7.5 dB, 10 dB, 12 dB, 15 dB, 20 dB, or more than 20 dB.

The disclosed methods may provide for complete hearing restoration in a subject (e.g., a human subject). The disclosed methods may provide for partial hearing restoration in a subject. Partial or complete hearing restoration may be evaluated through audiological evaluations, auditory brain stem (ABR) response, a sensory or tactile response in the subject, or any other suitable method. For instance, hearing in a subject (e.g., a human subject) may be restored such that the subject's ABR and/or a sensory or tactile response(s) improve by about 5-25%, about 25-50%, about 50-75%, or about 75-100% relative to baseline, or pre-treatment, levels.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of AAV particles may be an amount of the particles that are capable of transferring an expression construct to a host organ, tissue, or cell. A therapeutically acceptable amount may be an amount that is capable of treating a disease, e.g., DFNB9. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The AAV particles or polynucleotides may be delivered in the form of a composition, such as a composition comprising the active ingredient, such as AAV particles described herein, and a pharmaceutically acceptable carrier as described herein. The AAV particles or polynucleotides may be prepared in a variety of compositions, and may also be formulated in appropriate pharmaceutical vehicles for administration to human or animal subjects. In some embodiments, where first and second AAV particles are utilized, the first and second AAV particles may be contained within the same composition or within different compositions and may be administered together or separately.

In some embodiments, the AAV particles administered to a subject may be provided in a composition having a concentration on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, AAV particles of higher than $10^{13}$ particles/ml are be administered. In some embodiments, the number of AAV particles administered to a subject may be on the order ranging from $10^6$ to $10^{14}$ vector genomes(vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, AAV particles of higher than $10^{13}$ vgs/ml are be administered. The AAV particles may be administered as a single dose, or divided into two or more administrations as may be required to achieve therapy of the particular disease or disorder being treated. In some embodiments, 0.0001 ml to 10 ml are delivered to a subject. In some embodiments, the number of AAV particles administered to a subject may be on the order ranging from $10^6$-$10^{14}$ vg/kg, or any values therebetween, such as for example, about $10^6$, $10^7$, $10^8$, $10^9$, $10^{10}$, $10^{11}$, $10^{12}$, $10^{13}$, or $10^{14}$ vgs/kg. In some embodiments, when a first AAV particle comprising a first polynucleotide as described herein and second AAV particle comprising a second polynucleotide as described herein are administered, the amount administered is the same for both particles. In some embodiments, when a first AAV particle comprising a first polynucleotide as described herein and second AAV particle comprising a second polynucleotide as described herein are administered, the amount administered is different for each particle.

If desired, AAV particles may be administered in combination with other agents or treatments as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The AAV particles may thus be delivered along with various other agents or treatments as required in the particular instance. In some embodiments, AAV particle treatment may be accompanied by use of a hearing aid.

In certain circumstances it will be desirable to deliver the AAV particles in suitably formulated pharmaceutical compositions disclosed herein either subcutaneously, parenterally, intravenously, intramuscularly, intraperitoneally, by oral or nasal inhalation, or by direct injection to one or more cells, tissues, or organs. In some embodiments, the administration is a route suitable for systemic delivery, such as by intravenous injection or infusion. In some embodiments, the administration is to the ear, e.g., via intra-cochlear administration. The pharmaceutical forms of the AAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier may be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subretinal, subcutaneous and intraperitoneal administration. In this connection, a sterile aqueous medium that may be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the AAV particles in the required amount in the appropriate solvent with several of the other ingredients enumerated above, as required, followed by filtered sterilization or another sterilization technique. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of AAV particle or polynucleotide compositions and time of administration of such compositions will be within the purview of the skilled artisan having benefit of the present teachings. It is likely, however, that the administration of therapeutically effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV particle compositions, either over a relatively short, or a relatively prolonged period of time, as may be determined by the medical practitioner overseeing the administration of such compositions.

The composition may include AAV particles, either alone, or in combination with one or more additional active ingredients, which may be obtained from natural or recombinant sources or chemically synthesized.

Toxicity and efficacy of the compositions utilized in methods of the disclosure may be determined by standard pharmaceutical procedures, using either cells in culture or experimental animals to determine the $LD_{50}$ (the dose lethal to 50% of the population). The dose ratio between toxicity and efficacy is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals such as dogs and cats; livestock such as horses, cattle, pigs, sheep, goats, and chickens; and other animals such as mice, rats, guinea pigs, and hamsters.

In some embodiments, the subject has or is suspected of having a disease that may be treated with gene therapy. In some embodiments, the subject has or is suspected of having Deafness, Autosomal Recessive 9 (DFNB9). DFNB9 is an autosomal recessive form of deafness thought to be caused by mutations in the OTOF gene that result in a decrease in expression, functionality, or both, of the Otoferlin protein. Otoferlin protein has been shown to be important for exocytosis at the auditory ribbon synapse (see, e.g., Roux et al. Otoferlin, defective in a human deafness form, is essential for exocytosis at the auditory ribbon synapse. (2006) *Cell* 127(2):277-89). Subjects having DFNB9 can be identified by the skilled physician, e.g., using a combination of electrophysiologic testing of auditory brain stem responses (ABRs) and genetic testing to identify mutations in the OTOF gene (see, e.g., OMIM entries 603681 and 601071). In some embodiments, the subject is a human subject that has one or more of the following nonsense or missense mutations in the OTOF gene: TYR730TER, GLN829TER, PRO1825ALA, PRO50ARG, LEU1011PRO, ILE515THR, ARG1939GLN, or GLY541SER. In some embodiments, the subject is a human subject that has an A-to-G transition at the intron 8/exon 9 junction (IVS8-2A-G) or an G-to-A transition at position +1, the first intronic nucleotide in the splice donor site of exon 5 or a G-C transversion in the donor splice site of intron 39. In some embodiments, the subject is a human subject that has a one base pair deletion (1778G) in exon 16, leading to a stop codon, and a 6141G-A change, resulting in an ARG-to-GLN substitution in exon 48.

Compositions

Other aspects of the disclosure relate to compositions comprising AAV particles or polynucleotides described herein. In some embodiments, AAV particles described herein are added to a composition, e.g., a pharmaceutical composition.

In some aspects, provided herein are one or more compositions comprising an rAAV particle comprising the recombinant AAV nucleic acid vector of any one of SEQ ID NOs: 17-21, or a variant thereof. In some aspects, provided herein are compositions comprising an rAAV particle comprising a recombinant AAV nucleic acid vector having at least 80%, at least 85%, at least 90%, at least 95%, at least 98%, or at least 99% identity to any one of SEQ ID NOs: 17-21.

In some embodiments, the composition comprises a pharmaceutically acceptable carrier. The term "carrier" refers to a diluent, adjuvant, excipient, or vehicle with which the AAV particles are administered. Such pharmaceutical carriers may be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions may also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of AAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22$^{nd}$ edition, Pharmaceutical Press, 2012.

Typically, such compositions may contain at least about 0.1% of the therapeutic agent (e.g., AAV particles) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., AAV particles) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In various aspects, the above-described compositions are useful for restoring, completely or partially, hearing loss in a subject (e.g. a human subject). In some embodiments, a composition described herein may be administered to a subject in need thereof, such as a subject having DFNB9. In some embodiments, a method described herein may comprise administering a composition or multiple compositions comprising AAV particles as described herein to a subject in need thereof. In some embodiments, the subject is a human subject. In some embodiments, the subject has or is suspected of having a disease that may be treated with gene therapy, such as DFNB9. In some embodiments, the subject has been diagnosed with DFNB9.

Kits

Other aspects of the disclosure relate to kits comprising the compositions of AAV particles or polynucleotides as described herein. Kits may include pharmaceutically acceptable carriers and/or diluents. In some embodiments, the disclosed kits include instructions or packaging materials that describe how to administer AAV particles or polynucleotides contained within the kit to a selected cell or recipient. The disclosed kits may comprise one or more containers. Containers of the kits may be of any suitable material, e.g., glass, plastic, metal, etc., and of any suitable size, shape, or configuration. In some embodiments, the kits may include one or more ampoules or syringes that contain AAV particles or polynucleotides in a suitable liquid or solution form.

EXAMPLES

Example 1: Rescue of Hearing in OTOF Knock-Out Mice Using Adeno-Associated Virus Gene Therapy Approach Introduction Otoferlin is the key calcium sensor for neurotransmitter release in the ear (see, e.g., Roux 2006). Otoferlin is mainly expressed in the inner hair cells of the cochlea and only few other cells of the central nervous system (see, e.g., Yasunaga et al. 1999 & 2000). It is a member of the ferlin family of transmembrane proteins which share a common C2 domain also found in synaptotagmin, PKC and PLC.

Mutations in the human OTOF gene, which encodes human Otoferlin, cause a type of nonsyndromic deafness called Deafness, Autosomal Recessive 9 (DFNB9). OTOF knock-out mice have also been shown to have severe hearing loss despite normal inner hair cell development and auditory ribbon synapse formation (see, e.g., Roux et al. (2006) Otoferlin, defective in a human deafness form, is essential for exocytosis at the auditory ribbon synapse. *Cell*, 127:277-289). However, Otof$^{-/-}$ mice lose the auditory brain stem response across all sound frequencies due to complete abolishment of synaptic exocytosis and, as a consequence, abolishment of neurotransmitter release from synaptic vesicles.

DFNB9 manifests in humans as two phenotypes, as a nonsyndromic bilateral loss of hearing before the acquiring of language and less frequently as a temperature-sensitive nonsyndromic auditory neuropathy. It was first discovered in an affected Lebanese family (Chaib et al. 1996) and has since been found in many parts of the world (see, e.g., Adato et al. 2000, Rodriguez-Ballesteros et al. 2003, Choi et al. 2009, Matsunaga et al. 2012).

Current treatment in humans with DFNB9 utilizes cochlear implants and hearing aids. In addition, for the temperature-sensitive form of DFNB9, prevention of fevers and other conditions that would cause the body temperature to rise are important. Applicants sought to use adeno-associated virus (AAV) as a means to restore expression of OTOF in the knock-out mice as a proof-of-concept for using AAV to delivery OTOF as a treatment for DFNB9. The mouse OTOF cDNA is 5979 base pairs in length whereas most AAVs cannot package more than approximately 4.8 kilobases of genome. As a result, a dual vector system was used to separately deliver the 5' portion of the cDNA and the 3' portion of the cDNA as separate AAV constructs such that the full-length cDNA could be reassembled in vivo once delivered.

Methods

Dual AAV Vector Constructs

Figure 1B:
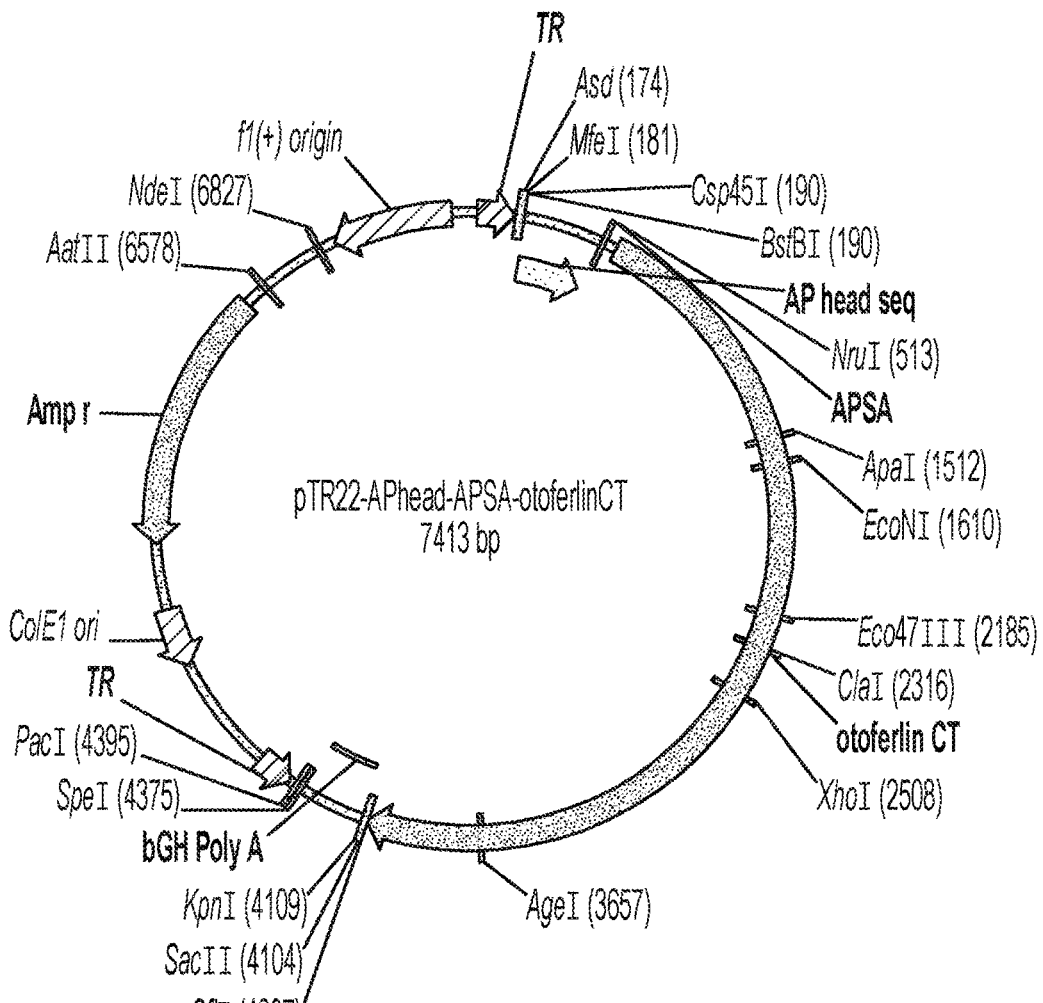
FIG. 1B is a map of a plasmid containing AAV2 inverted terminal repeats (TR) flanking a homologous sequence for recombination (APhead), a splice acceptor sequence (APSA), a 3' section of the mouse Otoferlin cDNA (Otoferlin CT), a bovine growth hormone polyadenylation signal (bGH PolyA).
Figure 2:
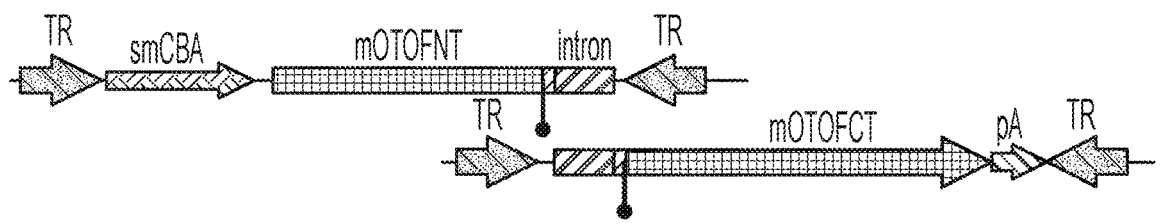
FIG. 2 is a schematic of the two expression cassettes in the plasmids in FIGS. 1A and 1B.

A mouse OTOF cDNA was split into two sections, a 5' and 3' section and inserted into two AAV ITR-containing plasmids. The sequence of each of the two cassettes in the plasmids is shown below and the maps of each construct are shown in FIGS. 1 and 2. Annotated versions of the cassettes are shown in FIGS. 3A and 3B. Each cassette contains a region of homology to promote homologous recombination between the 5' and 3' ends of the cDNA in vivo (see Ghosh et al., 2011). Once recombined in vivo, the full-length cDNA contains a splice donor/splice acceptor pair that causes splicing out of the region of homology. The vectors were packaged into AAV2 serotype particles using standard plasmid transfection methods as previously described (see Zolotukhin et al. Production and purification of serotype 1, 2, and 5 recombinant adeno-associated viral vectors. *Methods* 28 (2002) 158-167). The viral particles were purified by standard methods as previously described (see Zolotukhin et al. Production and purification of serotype 1, 2, and 5 recombinant adeno-associated viral vectors. *Methods* 28 (2002) 158-167). The viral particles carrying the 5' portion of the OTOF cDNA are also referred to herein as "AAV2-OTOF-NT." The viral particles carrying the 3' portion of the OTOF cDNA are also referred to herein as "AAV2-OTOF-CT."

```
pTR22-smCBA-otoferlinNT-APSD-APhead
                                           (SEQ ID NO: 1)
AGGGGGGGGGGGGGGGGGTTGGCCACTCCCTCTCTGCGCGCTCGCTCGCTCACTG

AGGCCGGGCGACCAAAGGTCGCCCGACGCCCGGGCTTTGCCCGGGCGGCCTCAGTG

AGCGAGCGAGCGCGCAGAGAGGGAGTGGCCAACTCCATCACTAGGGGTTCCTCAGA

TCTGGCGCGCCCAATTCGGTACCCTAGTTATTAATAGTAATCAATTACGGGGTCATT

AGTTCATAGCCCATATATGGAGTTCCGCGTTACATAACTTACGGTAAATGGCCCGCC

TGGCTGACCGCCCAACGACCCCCGCCCATTGACGTCAATAATGACGTATGTTCCCAT

AGTAACGCCAATAGGGACTTTCCATTGACGTCAATGGGTGGACTATTTACGGTAAA

CTGCCCACTTGGCAGTACATCAAGTGTATCATATGCCAAGTACGCCCCCTATTGACG

TCAATGACGGTAAATGGCCCGCCTGGCATTATGCCCAGTACATGACCTTATGGGACT

TTCCTACTTGGCAGTACATCTACGTATTAGTCATCGCTATTACCATGGTCGAGGTGA

GCCCCACGTTCTGCTTCACTCTCCCCATCTCCCCCCCTCCCCACCCCCAATTTTGTA

TTTATTTATTTTTTAATTATTTTGTGCAGCGATGGGGCGGGGGGGGGGGGGCG

CGCGCCAGGCGGGGCGGGGCGGGCGAGGGCGGGGCGGGGCGAGGCGGAGAGG

TGCGGCGGCAGCCAATCAGAGCGGCGCGCTCCGAAAGTTTCCTTTTATGGCGAGGC

GGCGGCGGCGGCGGCCCTATAAAAAGCGAAGCGCGCGGCGGGCGGGAGTCGCTGC

GACGCTGCCTTCGCCCCGTGCCCCGCTCCGCCGCCGCCTCGCGCCGCCCGCCCCGGC

TCTGACTGACCGCGTTACTCCCACAGGTGAGCGGGCGGGACGGCCCTTCTCCTCCGG

GCTGTAATTAGCGCTTGGTTTAATGACGGCTTGTTTCTTTTCTGTGGCTGCGTGAAAG

CCTTGAGGGGCTCCGGGAGCTAGAGCCTCTGCTAACCATGTTCATGCCTTCTTCTTTT
```

```
TCCTACAGCTCCTGGGCAACGTGCTGGTTATTGTGCTGTCTCATCATTTTGGCAAAG

AATTCTAGCGGCCGCCACCATGGCCCTGATTGTTCACCTCAAGACTGTCTCAGAGCT

CCGAGGCAAAGGTGACCGGATTGCCAAAGTCACTTTCCGAGGGCAGTCTTTCTACTC

CCGGGTCCTGGAGAACTGCGAGGGTGTGGCTGACTTTGATGAGACGTTCCGGTGGC

CAGTGGCCAGCAGCATCGACCGGAATGAAGTGTTGGAGATTCAGATTTTCAACTAC

AGCAAAGTCTTCAGCAACAAGCTGATAGGGACCTTCTGCATGGTGCTGCAGAAAGT

GGTGGAGGAGAATCGGGTAGAGGTGACCGACACGCTGATGGATGACAGCAATGCT

ATCATCAAGACCAGCCTGAGCATGGAGGTCCGGTATCAGGCCACAGATGGCACTGT

GGGCCCCTGGGATGATGGAGACTTCCTGGGAGATGAATCCCTCCAGGAGGAGAAGG

ACAGCCAGGAGACAGATGGGCTGCTACCTGGTTCCCGACCCAGCACCCGGATATCT

GGCGAGAAGAGCTTTCGCAGCAAAGGCAGAGAGAAGACCAAGGGAGGCAGAGATG

GCGAGCACAAAGCGGGAAGGAGTGTGTTCTCGGCCATGAAACTCGGCAAAACTCGG

TCCCACAAAGAGGAGCCCCAAAGACAAGATGAGCCAGCAGTGCTGGAGATGGAGG

ACCTGGACCACCTAGCCATTCAGCTGGGGGATGGGCTGGATCCTGACTCCGTGTCTC

TAGCCTCGGTCACCGCTCTCACCAGCAATGTCTCCAACAAACGGTCTAAGCCAGATA

TTAAGATGGAGCCCAGTGCTGGAAGGCCCATGGATTACCAGGTCAGCATCACAGTG

ATTGAGGCTCGGCAGCTGTGGGCTTGAACATGGACCCTGTGGTGTGTGTGGAGGT

GGGTGATGACAAGAAATACACGTCAATGAAGGAGTCCACAAACTGCCCTTACTACA

ACGAGTACTTTGTCTTCGACTTCCATGTCTCTCCTGATGTCATGTTTGACAAGATCAT

CAAGATCTCGGTTATCCATTCTAAGAACCTGCTTCGGAGCGGCACCCTGGTGGGTTC

CTTCAAAATGGATGTGGGGACTGTGTATTCCCAGCCTGAACACCAGTTCCATCACAA

ATGGGCCATCCTGTCAGACCCCGATGACATCTCTGCTGGGTTGAAGGGTTATGTAAA

GTGTGATGTCGCTGTGGTGGGCAAGGGAGACAACATCAAGACACCCCACAAGGCCA

ACGAGACGGATGAGGACGACATTGAAGGGAACTTGCTGCTCCCCGAGGGCGTGCCC

CCCGAACGGCAGTGGGCACGGTTCTATGTGAAAATTTACCGAGCAGAGGGACTGCC

CCGGATGAACACAAGCCTCATGGCCAACGTGAAGAAGGCGTTCATCGGTGAGAACA

AGGACCTCGTCGACCCCTATGTGCAAGTCTTCTTTGCTGGACAAAAGGGCAAAACA

TCAGTGCAGAAGAGCAGCTATGAGCCGCTATGGAATGAGCAGGTCGTCTTCACAGA

CTTGTTCCCCCCACTCTGCAAACGCATGAAGGTGCAGATCCGGGACTCTGACAAGGT

CAATGATGTGGCCATCGGCACCCACTTCATCGACCTGCGCAAGATTTCCAACGATGG

AGACAAAGGCTTCCTGCCTACCCTCGGTCCAGCCTGGGTGAACATGTACGGCTCCAC

GCGCAACTACACACTGCTGGACGAGCACCAGGACTTGAATGAAGGCCTGGGGGAG

GGTGTGTCCTTCCGGGCCCGCCTCATGTTGGGACTAGCTGTGGAGATCCTGGACACC

TCCAACCCAGAGCTCACCAGCTCCACGGAGGTGCAGGTGGAGCAGGCCACGCCTGT

CTCGGAGAGCTGCACAGGGAGAATGGAAGAATTTTTCTATTTGGAGCCTTCTTGGA

AGCCTCAATGATTGACCGGAAAAATGGGGACAAGCCAATTACCTTTGAGGTGACCA

TAGGAAACTACGGCAATGAAGTCGATGGTATGTCCCGGCCCCTGAGGCCTCGGCCC

CGGAAAGAGCCTGGGGATGAAGAAGAGGTAGACCTGATTCAGAACTCCAGTGACG

ATGAAGGTGACGAAGCCGGGGACCTGGCCTCGGTGTCCTCCACCCCACCTATGCGG

CCCCAGATCACGGACAGGAACTATTTCCACCTGCCCTACCTGGAGCGCAAGCCCTG

CATCTATATCAAGAGCTGGTGGCCTGACCAGAGGCGGCGCCTCTACAATGCCAACA
```

-continued

```
TCATGGATCACATTGCTGACAAGCTGGAAGAAGGCCTGAATGATGTACAGGAGATG

ATCAAAACGGAGAAGTCCTACCCGGAGCGCCGCCTGCGGGGTGTGCTAGAGGAACT

CAGCTGTGGCTGCCACCGCTTCCTCTCCCTCTCGGACAAGGACCAGGGCCGCTCGTC

CCGCACCAGGCTGGATCGAGAGCGTCTTAAGTCCTGTATGAGGGAGTTGGTAAGTA

TCAAGGTTACAAGACAGGTTTAAGGAGACCAATAGAAACTGGGCTTGTCGAGACAG

AGAAGACTCTTGCGTTTCTGAGCTAGCCCCCGGGTGCGCGGCGTCGGTGGTGCCGG

CGGGGGGCGCCAGGTCGCAGGCGGTGTAGGGCTCCAGGCAGGCGGCGAAGGCCAT

GACGTGCGCTATGAAGGTCTGCTCCTGCACGCCGTGAACCAGGTGCGCCTGCGGGC

CGCGCGCGAACACCGCCACGTCCTCGCCTGCGTGGGTCTCTTCGTCCAGGGGCACTG

CTGACTGCTGCCGATACTCGGGGCTCCCGCTCTCGCTCTCGGTAACATCCGGCCGGG

CGCCGTCCTTGAGCACATAGCCTGGACCGTTTCGTCGACTGTTAATTAAGCATGCTG

GGGAGAGATCTAGGAACCCCTAGTGATGGAGTTGGCCACTCCCTCTCTGCGCGCTC

GCTCGCTCACTGAGGCCGCCCGGGCAAAGCCCGGGCGTCGGGCGACCTTTGGTCGC

CCGGCCTCAGTGAGCGAGCGAGCGCGCAGAGAGGGAGTGGCCAACCCCCCCCCCCC

CCCCCCTGCAGCCCTGCATTAATGAATCGGCCAACGCGCGGGGAGAGGCGGTTTGC

GTATTGGGCGCTCTTCCGCTTCCTCGCTCACTGACTCGCTGCGCTCGGTCGTTCGGCT

GCGGCGAGCGGTATCAGCTCACTCAAAGGCGGTAATACGGTTATCCACAGAATCAG

GGGATAACGCAGGAAAGAACATGTGAGCAAAAGGCCAGCAAAAGGCCAGGAACCG

TAAAAAGGCCGCGTTGCTGGCGTTTTTCCATAGGCTCCGCCCCCCTGACGAGCATCA

CAAAAATCGACGCTCAAGTCAGAGGTGGCGAAACCCGACAGGACTATAAAGATAC

CAGGCGTTTCCCCCTGGAAGCTCCCTCGTGCGCTCTCCTGTTCCGACCCTGCCGCTTA

CCGGATACCTGTCCGCCTTTCTCCCTTCGGGAAGCGTGGCGCTTTCTCAATGCTCAC

GCTGTAGGTATCTCAGTTCGGTGTAGGTCGTTCGCTCCAAGCTGGGCTGTGTGCACG

AACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGC

AGAGCGAGGTATGTAGGCGGTGCTACAGAGTTCTTGAAGTGGTGGCCTAACTACGG

CTACACTAGAAGGACAGTATTTGGTATCTGCGCTCTGCTGAAGCCAGTTACCTTCGG

AAAAAGAGTTGGTAGCTCTTGATCCGGCAAACAAACCACCGCTGGTAGCGGTGGTT

TTTTTGTTTGCAAGCAGCAGATTACGCGCAGAAAAAAAGGATCTCAAGAAGATCCT

TTGATCTTTTCTACGGGGTCTGACGCTCAGTGGAACGAAAACTCACGTTAAGGGATT

TTGGTCATGAGATTATCAAAAAGGATCTTCACCTAGATCCTTTTAAATTAAAAATGA

AGTTTTAAATCAATCTAAAGTATATATGAGTAAACTTGGTCTGACAGTTACCAATGC

TTAATCAGTGAGGCACCTATCTCAGCGATCTGTCTATTTCGTTCATCCATAGTTGCCT

GACTCCCCGTCGTGTAGATAACTACGATACGGGAGGGCTTACCATCTGGCCCCAGT

GCTGCAATGATACCGCGAGACCCACGCTCACCGGCTCCAGATTTATCAGCAATAAA

CCAGCCAGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGGTA

TGGCTTCATTCAGCTCCGGTTCCCAACGATCAAGGCGAGTTACATGATCCCCCATGT

TGTGCAAAAAAGCGGTTAGCTCCTTCGGTCCTCCGATCGTTGTCAGAAGTAAGTTGG
```

-continued

```
CCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGCG

CCACATAGCAGAACTTTAAAAGTGCTCATCATTGGAAAACGTTCTTCGGGGCGAAA

ACTCTCAAGGATCTTACCGCTGTTGAGATCCAGTTCGATGTAACCCACTCGTGCACC

CAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTC

ATACTCTTCCTTTTTCAATATTATTGAAGCATTTATCAGGGTTATTGTCTCATGAGCG

GATACATATTTGAATGTATTTAGAAAAATAAACAAATAGGGGTTCCGCGCACATTTC

CCCGAAAAGTGCCACCTGACGTCTAAGAAACCATTATTATCATGACATTAACCTATA

AAAATAGGCGTATCACGAGGCCCTTTCGTCTCGCGCGTTTCGGTGATGACGGTGAA

AACCTCTGACACATGCAGCTCCCGGAGACGGTCACAGCTTGTCTGTAAGCGGATGC

CGGGAGCAGACAAGCCCGTCAGGGCGCGTCAGCGGGTGTTGGCGGGTGTCGGGGCT

GGCTTAACTATGCGGCATCAGAGCAGATTGTACTGAGAGTGCACCATATGCGGTGT

GAAATACCGCACAGATGCGTAAGGAGAAAATACCGCATCAGGAAATTGTAAACGTT

AATATTTTGTTAAAATTCGCGTTAAATTTTGTTAAATCAGCTCATTTTTTAACCAAT

AGGCCGAAATCGGCAAAATCCCTTATAAATCAAAAGAATAGACCGAGATAGGGTTG

AGTGTTGTTCCAGTTTGGAACAAGAGTCCACTATTAAAGAACGTGGACTCCAACGTC

AAAGGGCGAAAAACCGTCTATCAGGGCGATGGCCCACTACGTGAACCATCACCCTA

ATCAAGTTTTTTGGGGTCGAGGTGCCGTAAAGCACTAAATCGGAACCCTAAAGGGA

GCCCCCGATTTAGAGCTTGACGGGAAAGCCGGCGAACGTGGCGAGAAAGGAAGG

GAAGAAAGCGAAAGGAGCGGGCGCTAGGGCGCTGGCAAGTGTAGCGGTCACGCTG

CGCGTAACCACCACACCCGCCGCGCTTAATGCGCCGCTACAGGGCGCGTCGCGCCA

TTCGCCATTCAGGCTACGCAACTGTTGGGAAGGGCGATCGGTGCGGGCCTCTTCGCT

ATTACGCCAGGCTGC
``` pTR22-APhead-APSA-otoferlinCT
(SEQ ID NO: 2)

```
AGGGGGGGGGGGGGGGGGGTTGGCCACTCCCTCTCTGCGCGCTCGCTCGCTCACTG

AGGCCGGGCGACCAAAGGTCGCCCGACGCCCGGGCTTTGCCCGGGCGGCCTCAGTG

AGCGAGCGAGCGCGCAGAGAGGGAGTGGCCAACTCCATCACTAGGGGTTCCTCAGA

TCTGGCGCGCCCAATTGGCTTCGAATTCTAGCGGCCGCCCCCGGGTGCGCGGCGTCG

GTGGTGCCGGCGGGGGCGCCAGGTCGCAGGCGGTGTAGGGCTCCAGGCAGGCGG

CGAAGGCCATGACGTGCGCTATGAAGGTCTGCTCCTGCACGCCGTGAACCAGGTGC

GCCTGCGGGCCGCGCGCGAACACCGCCACGTCCTCGCCTGCGTGGGTCTCTTCGTCC

AGGGGCACTGCTGACTGCTGCCGATACTCGGGGCTCCCGCTCTCGCTCTCGGTAACA

TCCGGCCGGGCGCCGTCCTTGAGCACATAGCCTGGACCGTTTCCTTAAGCGACGCAT

GCTCGCGATAGGCACCTATTGGTCTTACTGACATCCACTTTGCCTTTCTCTCCACAGG

AGAGCATGGGACAGCAGGCCAAGAGCCTGAGGGCTCAGGTGAAGCGGCACACTGT

TCGGGACAAGCTGAGGTCATGCCAGAACTTTCTGCAGAAGCTACGCTTCCTGGCGG

ATGAGCCCCAGCACAGCATTCCTGATGTGTTCATTTGGATGATGAGCAACAACAAA

CGTATCGCCTATGCCCGCGTGCCTTCCAAAGACCTGCTCTTCTCCATCGTGGAGGAG

GAACTGGGCAAGGACTGCGCCAAAGTCAAGACCCTCTTCCTGAAGCTGCCAGGGAA
```

-continued

```
GAGGGGCTTCGGCTCGGCAGGCTGGACAGTACAGGCCAAGCTGGAGCTCTACCTGT

GGCTGGGCCTCAGCAAGCAGCGAAAGGACTTCCTGTGTGGTCTGCCCTGTGGCTTCG

AGGAGGTCAAGGCAGCCCAAGGCCTGGGCCTGCATTCCTTTCCGCCCATCAGCCTA

GTCTACACCAAGAAGCAAGCCTTCCAGCTCCGAGCACACATGTATCAGGCCCGAAG

CCTCTTTGCTGCTGACAGCAGTGGGCTCTCTGATCCCTTTGCCCGTGTCTTCTTCATC

AACCAGAGCCAATGCACTGAGGTTCTAAACGAGACACTGTGTCCCACCTGGGACCA

GATGCTGGTATTTGACAACCTGGAGCTGTACGGTGAAGCTCACGAGTTACGAGATG

ATCCCCCCATCATTGTCATTGAAATCTACGACCAGGACAGCATGGGCAAAGCCGAC

TTCATGGGCCGGACCTTCGCCAAGCCCCTGGTGAAGATGGCAGATGAAGCATACTG

CCCACCTCGCTTCCCGCCGCAGCTTGAGTACTACCAGATCTACCGAGGCAGTGCCAC

TGCCGGAGACCTACTGGCTGCCTTCGAGCTGCTGCAGATTGGGCCATCAGGGAAGG

CTGACCTGCCACCCATCAATGGCCCAGTGGACATGGACAGAGGGCCCATCATGCCT

GTGCCCGTGGGAATCCGGCCAGTGCTCAGCAAGTACCGAGTGGAGGTGCTGTTCTG

GGGCCTGAGGGACCTAAAGAGGGTGAACCTGGCCCAGGTGGACCGACCACGGGTG

GACATCGAGTGTGCAGGAAAGGGGGTACAATCCTCCCTGATTCACAATTATAAGAA

GAACCCCAACTTCAACACGCTGGTCAAGTGGTTTGAAGTGGACCTCCCGGAGAATG

AGCTCCTGCACCCACCCTTGAACATCCGAGTGGTAGATTGCCGGGCCTTTGGACGAT

ACACCCTGGTGGGTTCCCACGCAGTCAGCTCACTGAGGCGCTTCATCTACCGACCTC

CAGACCGCTCAGCCCCCAACTGGAACACCACAGGGGAGGTTGTAGTAAGCATGGAG

CCTGAGGAGCCAGTTAAGAAGCTGGAGACCATGGTGAAACTGGATGCGACTTCTGA

TGCTGTGGTCAAGGTGGATGTGGCTGAAGATGAGAAGGAAAGGAAGAAGAAGAAA

AAGAAAGGCCCGTCAGAGGAGCCAGAGGAGGAAGAGCCCGATGAGAGCATGCTGG

ATTGGTGGTCCAAGTACTTCGCCTCCATCGACACAATGAAGGAGCAACTTCGACAA

CATGAGACCTCTGGAACTGACTTGGAAGAGAAGGAAGAGATGGAAAGCGCTGAGG

GCCTGAAGGGACCAATGAAGAGCAAGGAGAAGTCCAGAGCTGCAAAGGAGGAGAA

AAAGAAGAAAAACCAGAGCCCTGGCCCTGGCCAGGGATCGGAGGCTCCTGAGAAG

AAGAAAGCCAAGATCGATGAGCTTAAGGTGTACCCCAAGGAGCTGGAATCGGAGTT

TGACAGCTTTGAGGACTGGCTGCACACCTTCAACCTGTTGAGGGGCAAGACGGGAG

ATGATGAGGATGGCTCCACAGAGGAGGAGCGCATAGTAGGCCGATTCAAGGGCTCC

CTCTGTGTGTACAAAGTGCCACTCCCAGAAGATGTATCTCGAGAAGCTGGCTATGAT

CCCACCTATGGAATGTTCCAGGGCATCCCAAGCAATGACCCCATCAATGTGCTGGTC

CGAATCTATGTGGTCCGGGCCACAGACCTGCACCCGGCCGACATCAATGGCAAAGC

TGACCCCTATATTGCCATCAAGTTAGGCAAGACCGACATCCGAGACAAGGAGAACT

ACATCTCCAAGCAGCTCAACCCTGTGTTTGGGAAGTCCTTTGACATTGAGGCCTCCT

TCCCCATGGAGTCCATGTTGACAGTGGCCGTGTACGACTGGGATCTGGTGGGCACTG

ATGACCTCATCGGAGAAACCAAGATTGACCTGGAAAACCGCTTCTACAGCAAGCAT

CGCGCCACCTGCGGCATCGCACAGACCTATTCCATACATGGCTACAATATCTGGAG

GGACCCCATGAAGCCCAGCCAGATCCTGACACGCCTCTGTAAAGAGGGCAAAGTGG

ACGGCCCCCACTTTGGTCCCCATGGGAGAGTGAGGGTTGCCAACCGTGTCTTCACGG

GGCCTTCAGAAATAGAGGATGAGAATGGTCAGAGGAAGCCCACAGATGAGCACGT
```

-continued
```
GGCACTGTCTGCTCTGAGACACTGGGAGGACATCCCCCGGGTGGGCTGCCGCCTTGT

GCCGGAACACGTGGAGACCAGGCCGCTGCTCAACCCTGACAAGCCAGGCATTGAGC

AGGGCCGCCTGGAGCTGTGGGTGGACATGTTCCCCATGGACATGCCAGCCCCTGGG

ACACCTCTGGATATATCCCCCAGGAAACCCAAGAAGTACGAGCTGCGGGTCATCGT

GTGGAACACAGACGAGGTGGTCCTGGAAGACGATGATTTCTTCACGGGAGAGAAGT

CCAGTGACATTTTTGTGAGGGGGTGGCTGAAGGGCCAGCAGGAGGACAAACAGGA

CACAGATGTCCACTATCACTCCCTCACGGGGGAGGGCAACTTCAACTGGAGATACC

TCTTCCCCTTCGACTACCTAGCGGCCGAAGAGAAGATCGTTATGTCCAAAAGGAG

TCTATGTTCTCCTGGGATGAGACGGAGTACAAGATCCCTGCGCGGCTCACCCTGCAG

ATCTGGGACGCTGACCACTTCTCGGCTGACGACTTCCTGGGGGCTATCGAGCTGGAC

CTGAACCGGTTCCCGAGGGGCGCTAAGACAGCCAAGCAGTGCACCATGGAGATGGC

CACCGGGGAGGTGGACGTACCCCTGGTTTCCATCTTTAAACAGAAACGTGTCAAAG

GCTGGTGGCCCCTCCTGGCCCGCAATGAGAATGATGAGTTTGAGCTCACAGGCAAA

GTGGAGGCGGAGCTACACCTACTCACGGCAGAGGAGGCAGAGAAGAACCCTGTGG

GCCTGGCTCGCAATGAACCTGATCCCCTAGAAAAACCCAACCGGCCTGACACGGCA

TTCGTCTGGTTCCTGAACCCACTCAAATCTATCAAGTACCTCATCTGCACCCGGTAC

AAGTGGCTGATCATCAAGATCGTGCTGGCGCTGCTGGGGCTGCTCATGCTGGCCCTC

TTCCTTTACAGCCTCCCAGGCTACATGGTCAAGAAGCTCCTAGGGGCCTGAGCGGCC

GCGGTACCAAGGGCGAATTCTGCAGTCGACTAGAGCTCGCTGATCAGCCTCGACTG

TGCCTTCTAGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCATCGCATTG

TCTGAGTAGGTGTCATTCTATTCTGGGGGGTGGGGTGGGGCAGGACAGCAAGGGGG

AGGATTGGGAAGACAATAGCAGGCATGCTGGGGAGAGATCTGAGGACTAGTCCGTC

GACTGTTAATTAAGCATGCTGGGGAGAGATCTAGGAACCCCTAGTGATGGAGTTGG

CCACTCCCTCTCTGCGCGCTCGCTCGCTCACTGAGGCCGCCCGGGCAAAGCCCGGGC

GTCGGGCGACCTTTGGTCGCCCGGCCTCAGTGAGCGAGCGAGCGCGCAGAGAGGGA

GTGGCCAACCCCCCCCCCCCCCCCCCTGCAGCCCTGCATTAATGAATCGGCCAACGC

GCGGGGAGAGGCGGTTTGCGTATTGGGCGCTCTTCCGCTTCCTCGCTCACTGACTCG

CTGCGCTCGGTCGTTCGGCTGCGGCGAGCGGTATCAGCTCACTCAAAGGCGGTAAT

ACGGTTATCCACAGAATCAGGGGATAACGCAGGAAAGAACATGTGAGCAAAAGGC

CAGCAAAAGGCCAGGAACCGTAAAAAGGCCGCGTTGCTGGCGTTTTTCCATAGGCT

CCGCCCCCCTGACGAGCATCACAAAAATCGACGCTCAAGTCAGAGGTGGCGAAACC

CGACAGGACTATAAAGATACCAGGCGTTTCCCCCTGGAAGCTCCCTCGTGCGCTCTC

CTGTTCCGACCCTGCCGCTTACCGGATACCTGTCCGCCTTTCTCCCTTCGGGAAGCGT

GGCGCTTTCTCAATGCTCACGCTGTAGGTATCTCAGTTCGGTGTAGGTCGTTCGCTC

CAAGCTGGGCTGTGTGCACGAACCCCCCGTTCAGCCCGACCGCTGCGCCTTATCCGG

TAACTATCGTCTTGAGTCCAACCCGGTAAGACACGACTTATCGCCACTGGCAGCAGC

CACTGGTAACAGGATTAGCAGAGCGAGGTATGTAGGCGGTGCTACAGAGTTCTTGA

AGTGGTGGCCTAACTACGGCTACACTAGAAGGACAGTATTTGGTATCTGCGCTCTGC

TGAAGCCAGTTACCTTCGGAAAAAGAGTTGGTAGCTCTTGATCCGGCAAACAAACC

ACCGCTGGTAGCGGTGGTTTTTTTGTTTGCAAGCAGCAGATTACGCGCAGAAAAAA
```

-continued

```
AGGATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAGAT
CCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATT
TCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCC
AGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATCGTGGTGT
CACGCTCGTCGTTTGGTATGGCTTCATTCAGCTCCGGTTCCCAACGATCAAGGCGAG
TTACATGATCCCCCATGTTGTGCAAAAAAGCGGTTAGCTCCTTCGGTCCTCCGATCG
TTGTCAGAAGTAAGTTGGCCGCAGTGTTATCACTCATGGTTATGGCAGCACTGCATA
ATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAAAC
GTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGG
GTGAGCAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGG
GGTTCCGCGCACATTTCCCCGAAAAGTGCCACCTGACGTCTAAGAAACCATTATTAT
CATGACATTAACCTATAAAAATAGGCGTATCACGAGGCCCTTTCGTCTCGCGCGTTT
CGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTT
GGCGGGTGTCGGGGCTGGCTTAACTATGCGGCATCAGAGCAGATTGTACTGAGAGT
GCACCATATGCGGTGTGAAATACCGCACAGATGCGTAAGGAGAAAATACCGCATCA
GGAAATTGTAAACGTTAATATTTTGTTAAAATTCGCGTTAAATTTTTGTTAAATCAG
CTCATTTTTTAACCAATAGGCCGAAATCGGCAAAATCCCTTATAAATCAAAAGAATA
GACCGAGATAGGGTTGAGTGTTGTTCCAGTTTGGAACAAGAGTCCACTATTAAAGA
ACGTGGACTCCAACGTCAAAGGGCGAAAAACCGTCTATCAGGGCGATGGCCCACTA
CGTGAACCATCACCCTAATCAAGTTTTTTGGGGTCGAGGTGCCGTAAAGCACTAAAT
CGGAACCCTAAAGGGAGCCCCCGATTTAGAGCTTGACGGGGAAAGCCGGCGAACGT
GGCGAGAAAGGAAGGGAAGAAAGCGAAAGGAGCGGGCGCTAGGGCGCTGGCAAG
TGTAGCGGTCACGCTGCGCGTAACCACCACACCCGCCGCGCTTAATGCGCCGCTAC
AGGGCGCGTCGCGCCATTCGCCATTCAGGCTACGCAACTGTTGGGAAGGGCGATCG
GTGCGGGCCTCTTCGCTATTACGCCAGGCTGC
```

Transfection of HEK 293 Cells

HEK 293 cells were grown on poly-lysine-coated coverslips in growth medium. 1 µl of each virus was used for each well as follows: Control cells without virus, cells with AAV2-OTOF n-terminal portion (AAV2-OTOF-NT), cells with AAV2-OTOF c-terminal portion (AAV2-OTOF-CT) and cells with both viruses (AAV2-OTOF-NT and AAV2-OTOF-CT). The cells were stained with anti-OTOF antibody and mounted on glass slides.

OTOF Knock-Out Mice

The OTOF knock-out mice used were generated in a previous study (see Roux et al. (2006) Otoferlin, defective in a human deafness form, is essential for exocytosis at the auditory ribbon synapse. Briefly, two fragments containing the genomic sequences 5' and 3' to exons 14 and 15 of Otof were amplified by PCR. The 5 kb BamHI-XhoI-BssHIII and 6 kb BssHIII-SfiI-BamHI-NaeI 129/SvPas fragments were inserted into pUC19 (New England BioLabs) previously modified by inserting a BamHI-XhoI-BssHIII-SfiI-NaeI-HindIII polylinker. A loxP-hygro-loxP (the gene conferring resistance to hygromycin under control of the phosphoglycerate kinase gene [Pgk-1] promoter) cassette was inserted into the BssHIII site. All constructs were sequenced, and the sequences obtained were compared with the 129/SvPas genomic sequence 282 CK35 ES cells resistant to hygromycin were screened for homologous recombination and monoinsertion events by Southern blot analysis. Two clones were injected into C57BL/6N blastocysts to create chimeric animals. Transmission of the mutant Otof allele was detected by PCR in agouti pups. Positive pups in the F1 progeny were crossed with Pgk-1-cre mice in a mixed C57BL/6-129/SvPas background. F2 animals carrying an allele in which the hygromycin selection cassette was deleted (Otof tm1Ugds allele) were selected by PCR, using primers 5'-CACTTGCTTTGTCT CATCTCC-3' (SEQ ID NO: 12) and 5'-GTCACTTCTTCTGGGTATTTC-3' (SEQ ID NO: 13), generating a 507 base pair PCR product. The heterozygous animals were interbred to generate $Otof^{-/-}$, $Otof^{+/-}$, and $Otof^{+/+}$ mice. The knockout mice were generated in C57BL/6-129/SvPas background as described above. Because this background strain is known to have some age-related hearing loss, the mice were backcrossed with FVB mice strain to the $10^{th}$ generation to obtain an FVB homogeneous genetic background with no known age-related hearing loss.

Delivery of AAV to Mice

OTOF knock-out mice (newborn and older than P10) were injected with 1 microliter of viral particles of each of the two AAV constructs using a round window membrane (RWM) injection as previously described (see Akil et al. (2012) Restoration of Hearing in the VGLUT3 Knockout Mouse Using Virally-Mediated Gene Therapy. Neuron. 75(2): 283-293 and Akil et al. (2015) Surgical Method for Virally Mediated Gene Delivery to the Mouse Inner Ear through the Round Window Membrane. J. Vis. Exp. (97), e52187, each of which is incorporated herein by reference). AAV2-OTOF-NT ($6.32 \times 10^{12}$ vg/ml) and AAV2-OTOF-CT ($4.5 \times 10^{12}$ vg/ml) were delivered through the RWM to P1-3 mice. AAV2-OTOF-NT ($1.43 \times 10^{13}$ vg/ml) and AAV2-OTOF-CT ($3.12 \times 10^{13}$ vg/ml) were delivered through the RWM to P≥12 mice. ABR tests were conducted 7 days after injection. Expression of OTOF protein in the mice was measured using anti-OTOF antibody to label cells in cochlear whole mounts. Reverse-transcriptase (RT)-PCR was used to screen for the presence of OTOF mRNA within the cochlear tissue of the mice. Wild-type mice were also injected using the same technique with AAV2-GFP to assess viral delivery to cochlea with AAV2 serotype. Cochlea were whole mounted and stained with anti-GFP antibody.

Auditory Brainstem Response (ABR) Testing

Hearing tests were performed as previously described (Akil et al. (2006) Progressive deafness and altered cochlear innervation in knockout mice lacking prosaposin. J. Neurosci. 26:13076-13088 and Akil et al. (2016), Mouse Auditory Brainstem Response Testing. Bio Protoc. 6(6), each of which is incorporated herein by reference) with the otoferlin knockout (OTOF KO) mice, rescued OTOF KO mice and wild-type (WT) littermates. Briefly, all auditory testing was performed in a sound-proof chamber. Before acoustic testing, mice were anesthetized by intraperitoneal injection of a mixture of ketamine hydrochloride (Ketaset, 100 mg/ml) and xylazine hydrochloride (xyla-ject, 10 mg/ml) and boosted with one-fifth the original dose as required. Body temperature was maintained with a heating pad and monitored with a rectal probe throughout recording.

The evoked acoustic brainstem response (ABR) thresholds were differentially recorded from the scalp of the mice. Responses were recorded using subdermal needle electrodes at the vertex, below the pinna of the left ear (reference), and below the contralateral ear (ground). The sound stimuli used included clicks (5 ms duration, 31 Hz) and tone pips at 8, 16, and 32 kHz (10 ms duration, cos 2 shaping, 21 Hz). Measurements were recorded using the TDT BioSig III system (Tucker Davis Technologies). For each stimulus, electroencephalographic (EEG) activity was recorded for 20 ms (at a sampling rate of 25 kHz) and filtered (0.3-3 kHz). Waveforms from 512 stimuli were averaged for click responses. Waveforms from 1000 stimuli were examined to identify frequency-specific tone-burst stimuli (8, 16, and 32 kHz). ABR waveforms were recorded in 5 dB sound pressure level (SPL) intervals down from the maximum amplitude. The threshold was defined as the lowest stimulus level at which response peaks for waves I-V were clearly and repetitively present upon visual inspection. These threshold judgments were confirmed by analysis of stored waveforms. The comparison of each group of animals was performed using one way ANOVA with Bonferroni's post hoc testing.

Results

Two different AAV plasmid constructs were generated to deliver the 5' half and the 3' half of the mouse OTOF cDNA to the inner ear of OTOF knock-out mice (OTOF N-terminal virus and OTOF C-terminal virus). The two constructs were packaged separately into AAV2 particles. The AAV2 particles were then pooled together and used to treat HEK 293 cells or were injected into the inner ear of OTOF knock-out mice.

Figure 4:
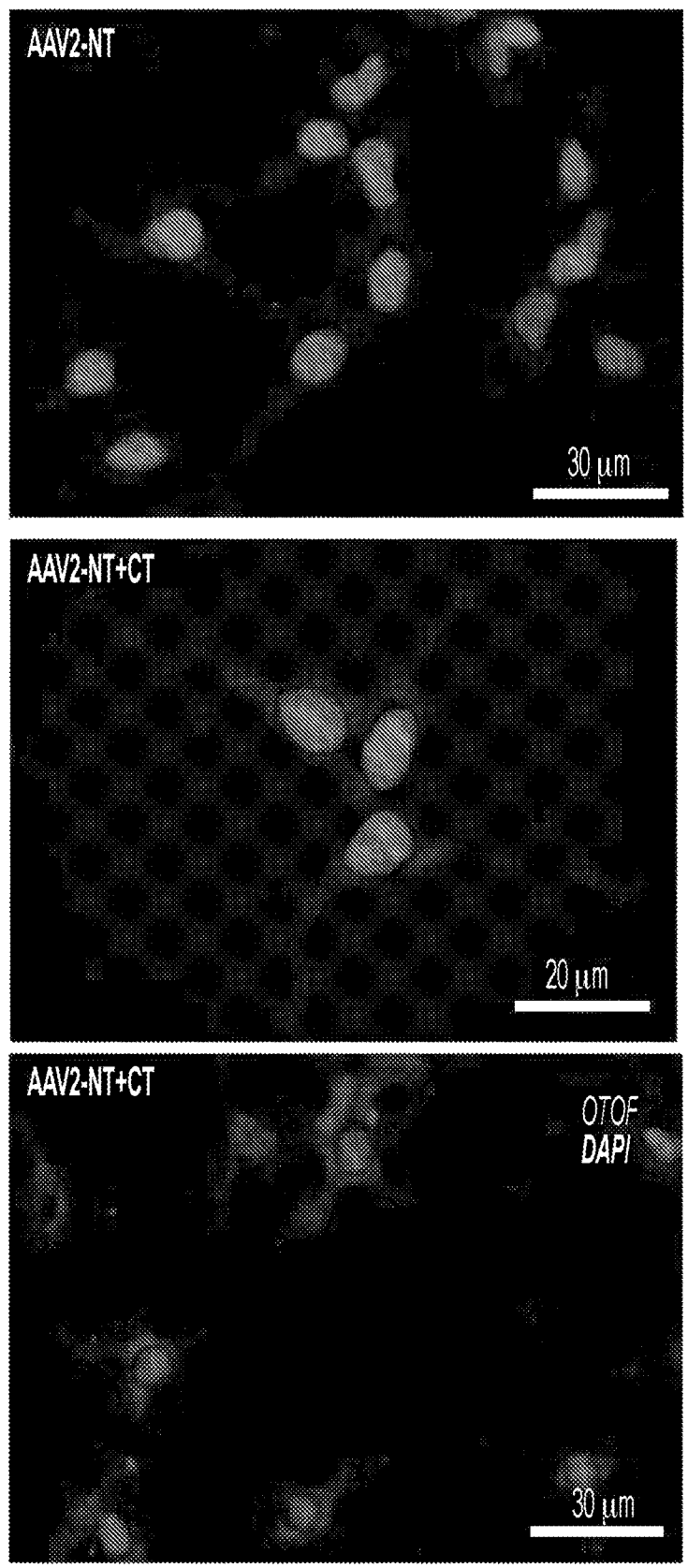
FIG. 4 is a series of photographs showing expression of OTOF protein in HEK 293 cells treated with AAV2-OTOF-NT (AAV-NT) or AAV2-OTOF-NT and AAV2-OTOF-CT (AAV2-NT+CT).

It was shown that HEK 293 cells only expressed Otoferlin protein when transfected with both viruses (FIG. 4). No expression of Otoferlin protein was observed in untreated cells, or in cells transfected with only the OTOF N-terminal or OTOF C-terminal virus.

Figure 5:
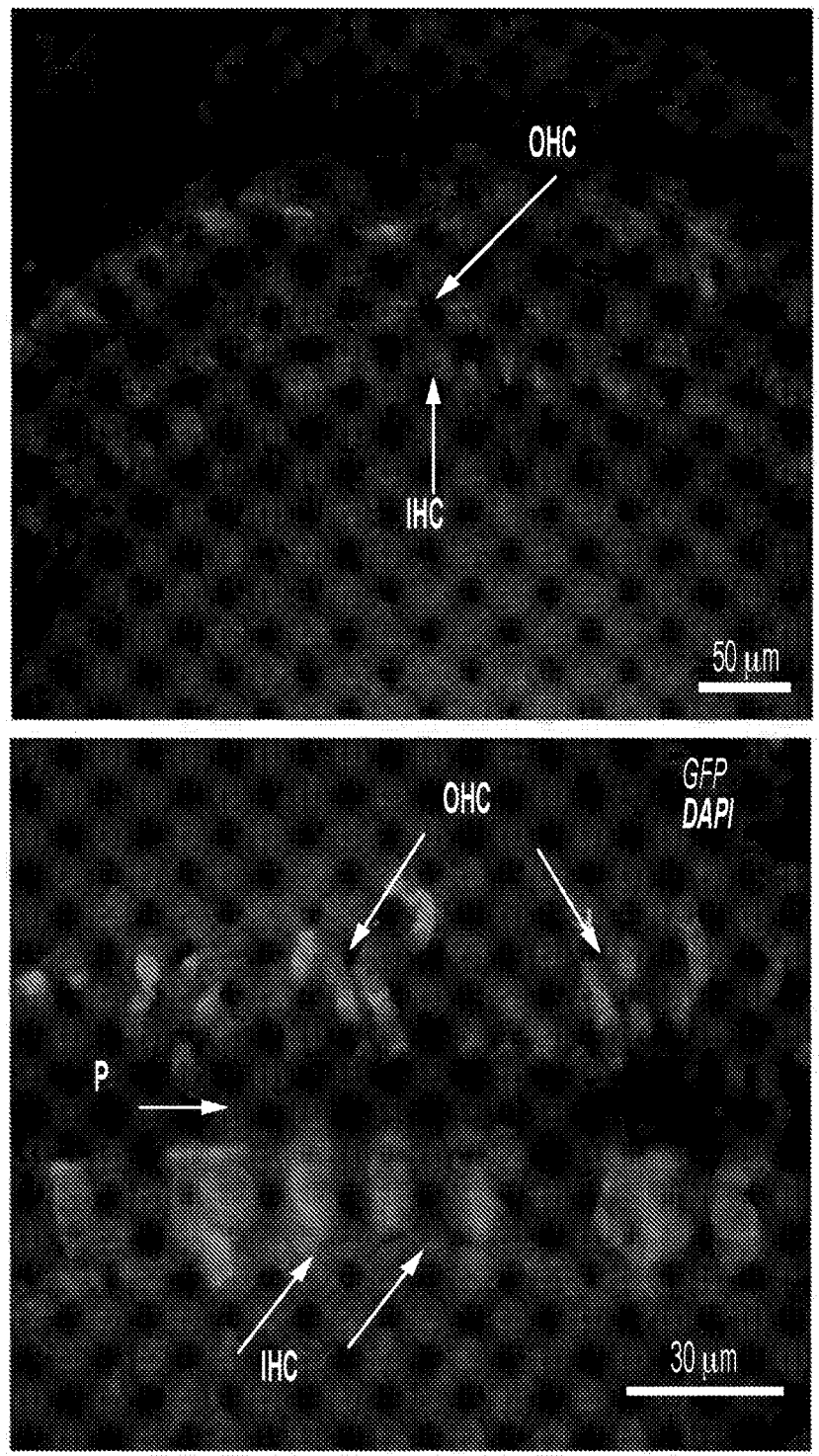
FIG. 5 is a series of photographs showing expression of GFP in the cochlea organ of *Corti* surface preparations from wild-type mice treated with AAV2-GFP.
Figure 6A:
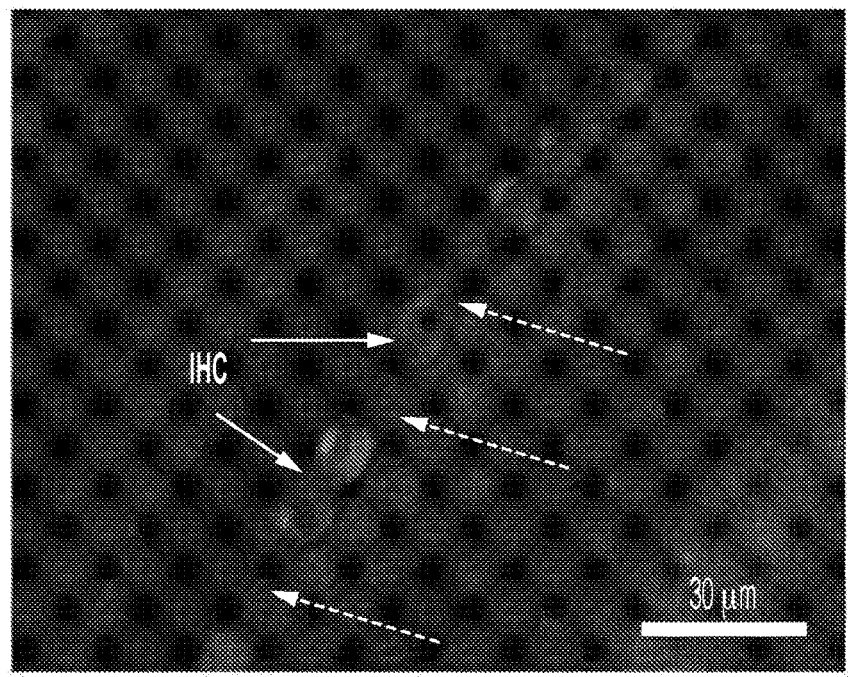
FIGS. 6A-D are a series of photographs and a graph showing OTOF expression in the cochlea of P1-P3 mice.
Figure 6B:
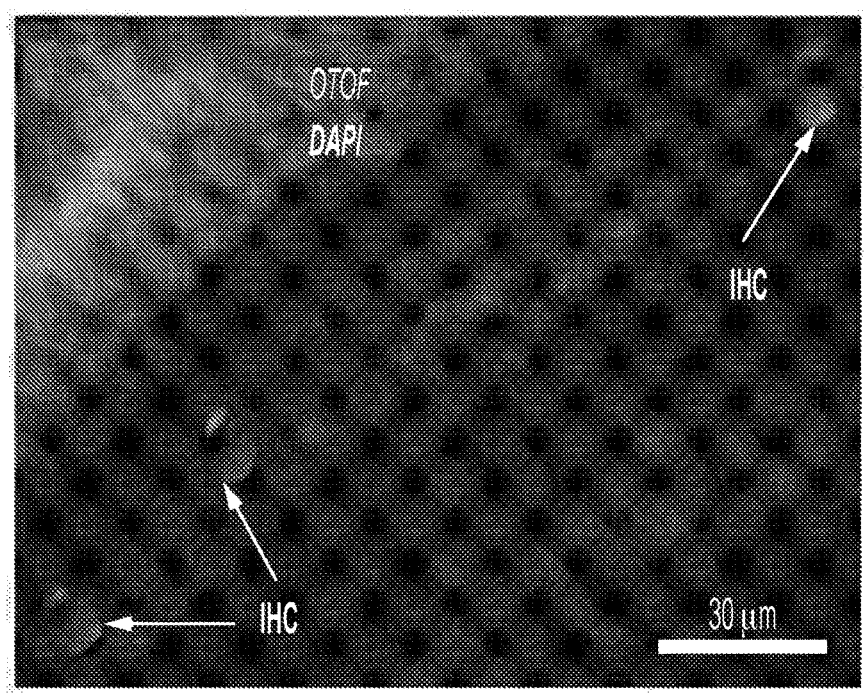
Figure 6C:
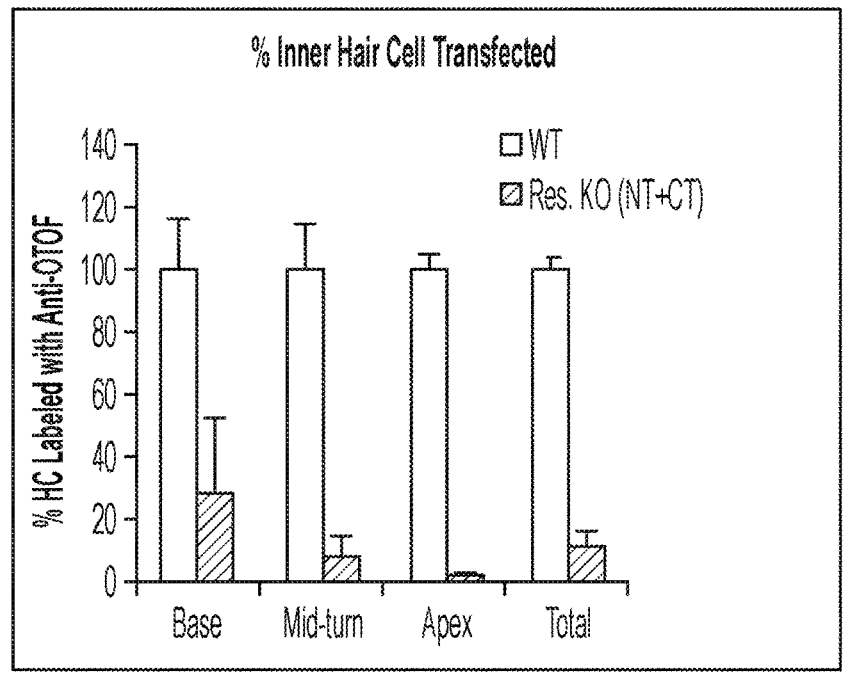
Figure 6D:
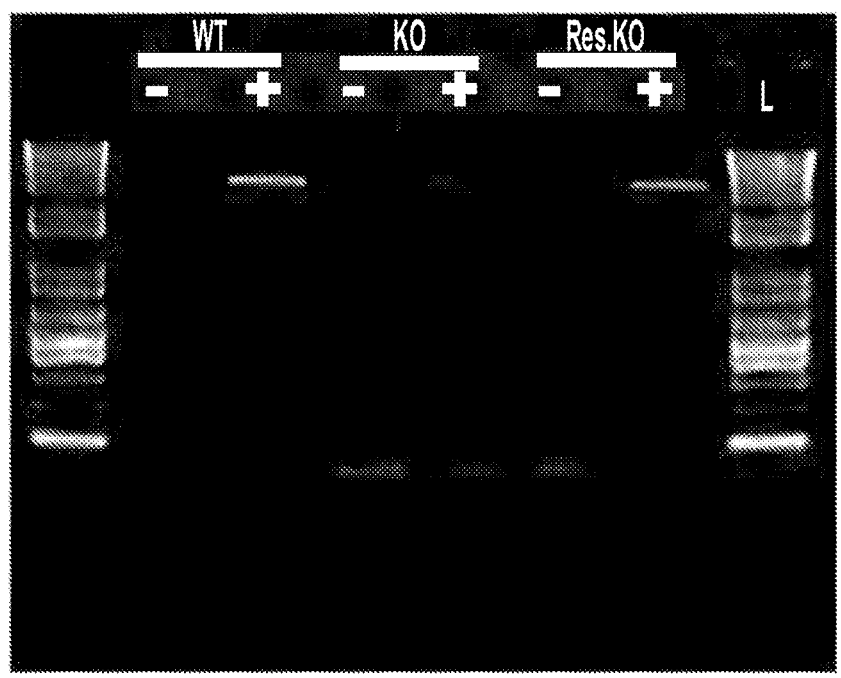
Figure 7A:
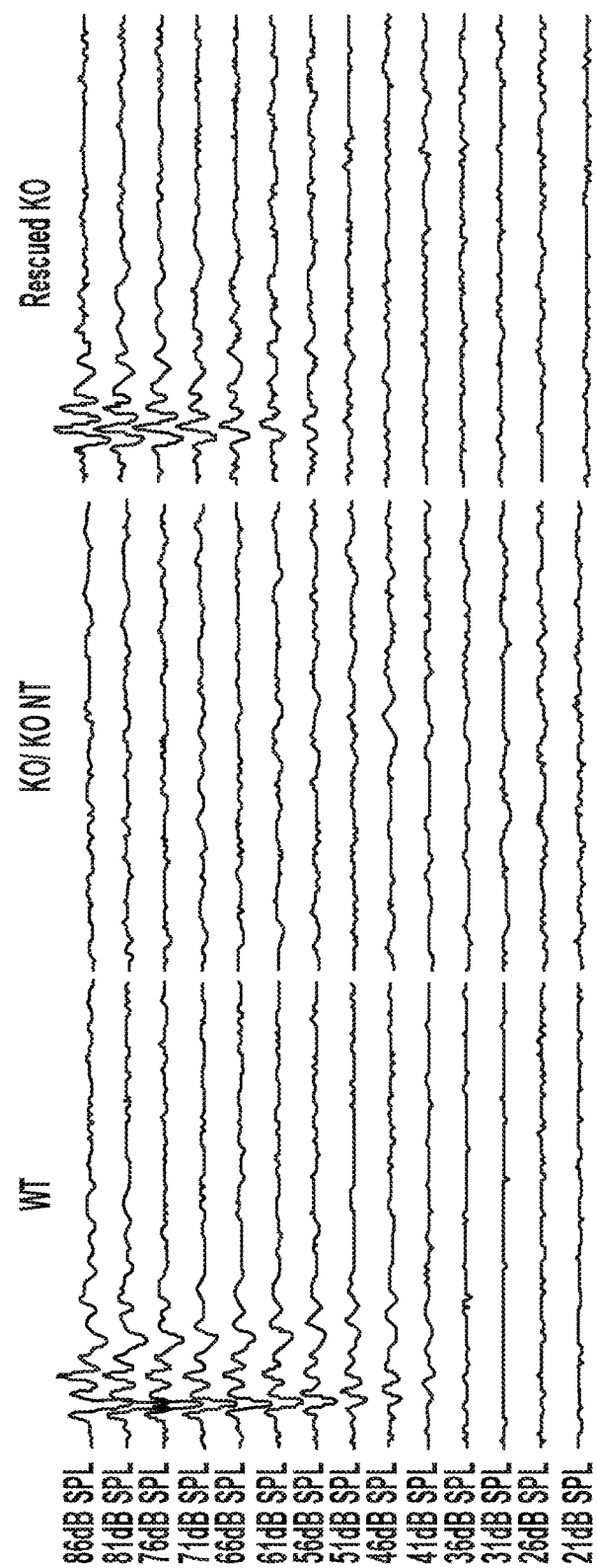
FIGS. 7A-D show a hearing assessment in mice.
Figure 7B:
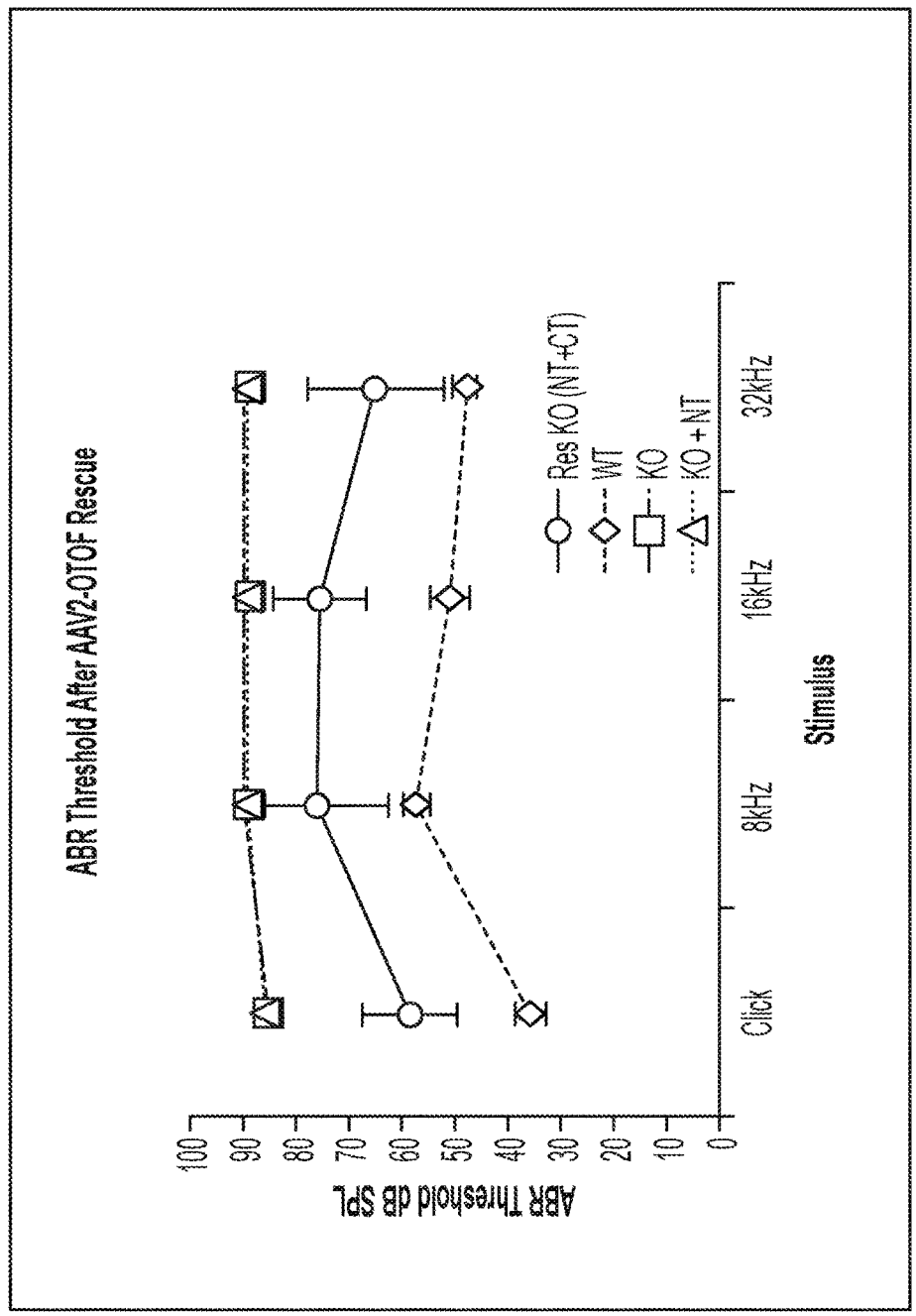
Figure 7C:
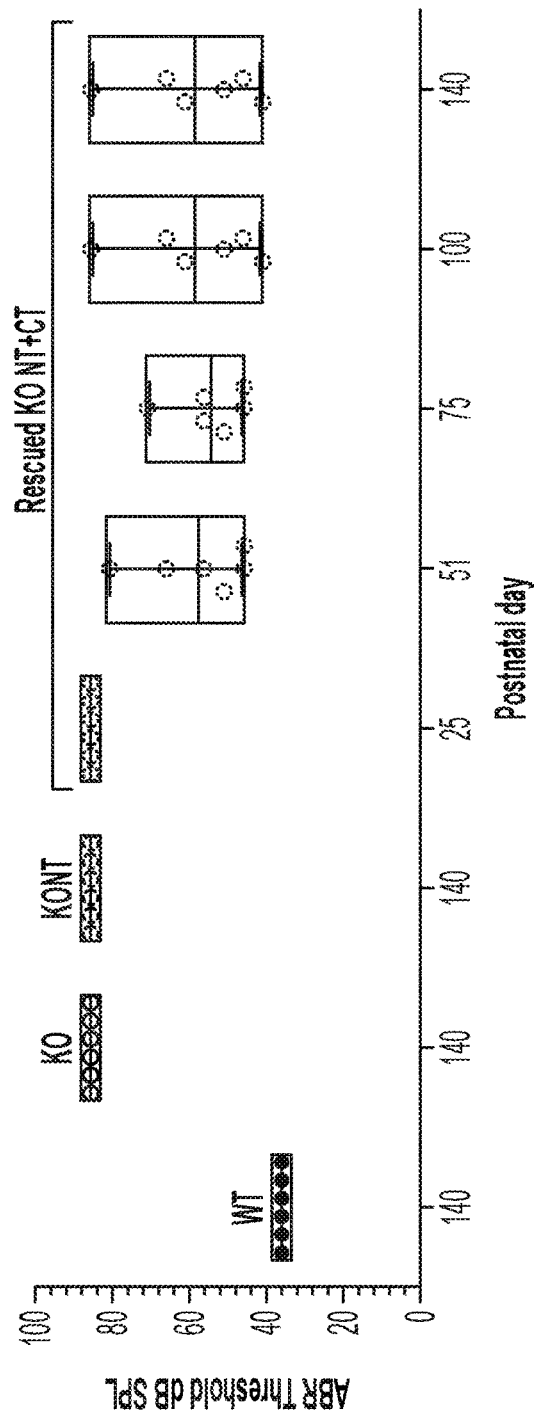
Figure 7D:
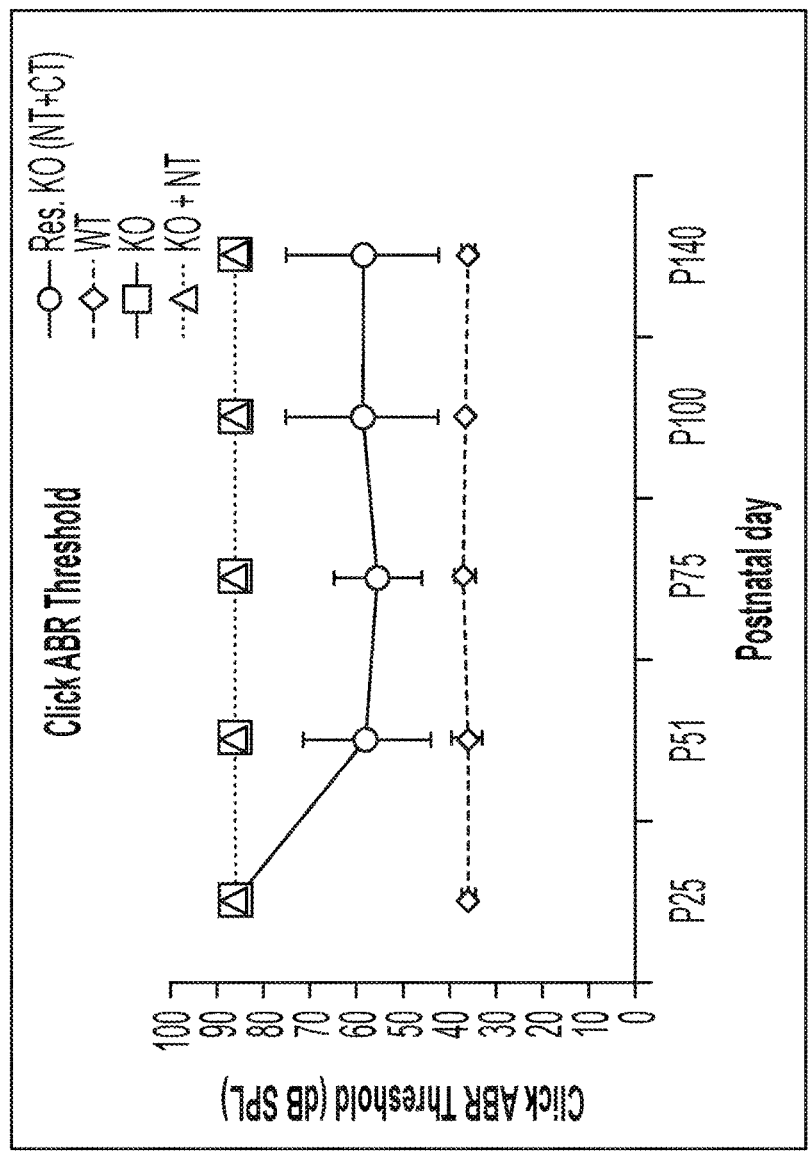

Next, the ability of AAV2 to transduce the mouse cochlea was assess using an AAV2-GFP reporter virus. It was shown that AAV2 transfects a number of cell types including inner hair cells (IHC), outer hair cells (OHC), pillar cells (P) and other supporting cells (SC) in the organ of Corti (FIG. 5). Thus, AAV2 can transduce mouse cochlea effectively.

Mice were then treated with the pooled OTOF N-terminal and C-terminal viruses and compared to various controls. Otoferlin protein was found to be expressed upon treatment with both viruses (FIG. 6). The largest number of transfected inner hair cells (IHCs) were observed in the base and fewer in the mid-turn and apex. IHCs counts demonstrated that ~11% of IHCs were labeled overall, with significant differences seen between the base (~29%), mid-turn (~8%), and apex (~2%). RT-PCR was used to show that OTOF mRNA was in whole cochlear extract and was the same size in both wild-type and OTOF knock-out mice treated with both viruses (FIG. 6). In contrast, the untreated OTOF knock-out mouse cochleae did not demonstrate OTOF mRNA expression. No products were detected when RT-PCR was performed in the absence of reverse transcriptase.

Next, hearing tests were performed to determine whether the Otoferlin expressed by the delivery of both the N- and C-terminal viruses was capable of rescuing hearing function. ABR waveforms from the wild-type and the OTOF knock-out mice treated with both viruses were similar, documenting hearing recovery in the rescued KO mice whereas untreated OTOF knock-out mice controls and the OTOF knock-out mice transfected with just OTOF N-terminal virus show no hearing recovery (FIG. 7). At P70, partial hearing recovery (improved ABR thresholds) was seen to clicks and at specific frequencies 8, 16 and 32 kHz in the OTOF knock-out mice treated with both viruses, while at 8 and 16 kHz the ABR thresholds appear to be slightly elevated, though still significantly better than untreated OTOF knock-out mice (FIG. 7). Remarkably, hearing was maintained in the OTOF knock-out mice treated with both viruses (KO NT+CT) for more than 4 months, although ABR thresholds were somewhat variable. Non-transfected KO controls and the KO transfected with OTOF NT remained deaf (FIG. 7).

Figure 8A:
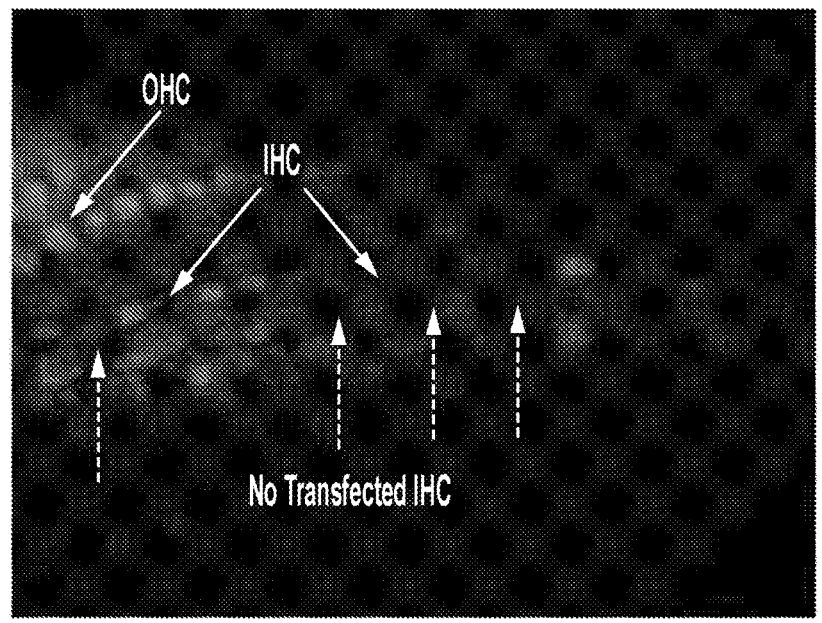
FIGS. 8A and B show Otoferlin protein expression in the OTOF rescued KO mice inner hair cells.
Figure 8B:
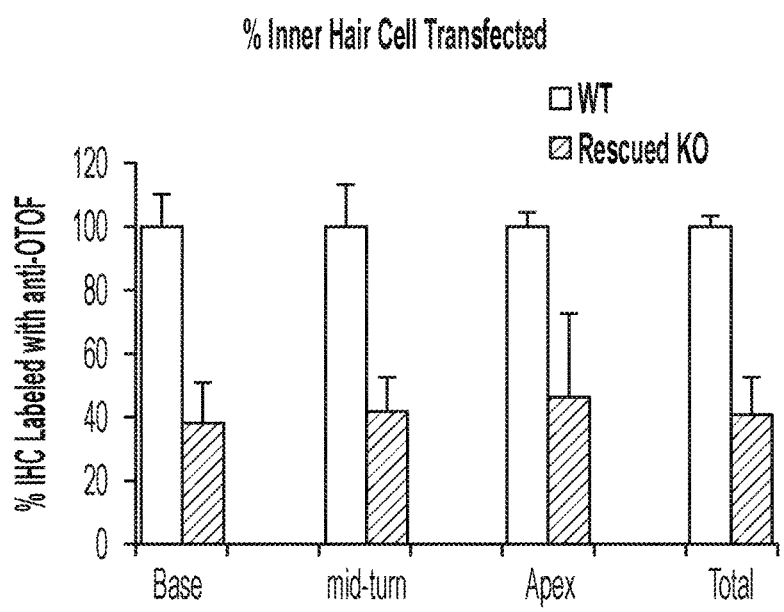
FIG. 8B shows the percent of inner hair cells expressing OTOF in wild-type mice (WT, n=5) and OTOF knock-out mice treated with AAV2-OTOF-NT and AAV2-OTOF-CT (Rescued KO, n=5). The left bar in each pair of bars is WT and the right bar in each pair of bars is Rescued KO.

Next, OTOF knock-out mice older than P12 treated with both viruses. The dually transfected IHCs expressed OTOF, with homogenous transfection rates seen in the base (not shown) and the apex (FIG. 8). IHCs counts demonstrated that ~41% of IHCs were labeled overall, with slight differences seen between the base (~38%), mid-turn (~42%), and apex (~47%).

Figure 9A:
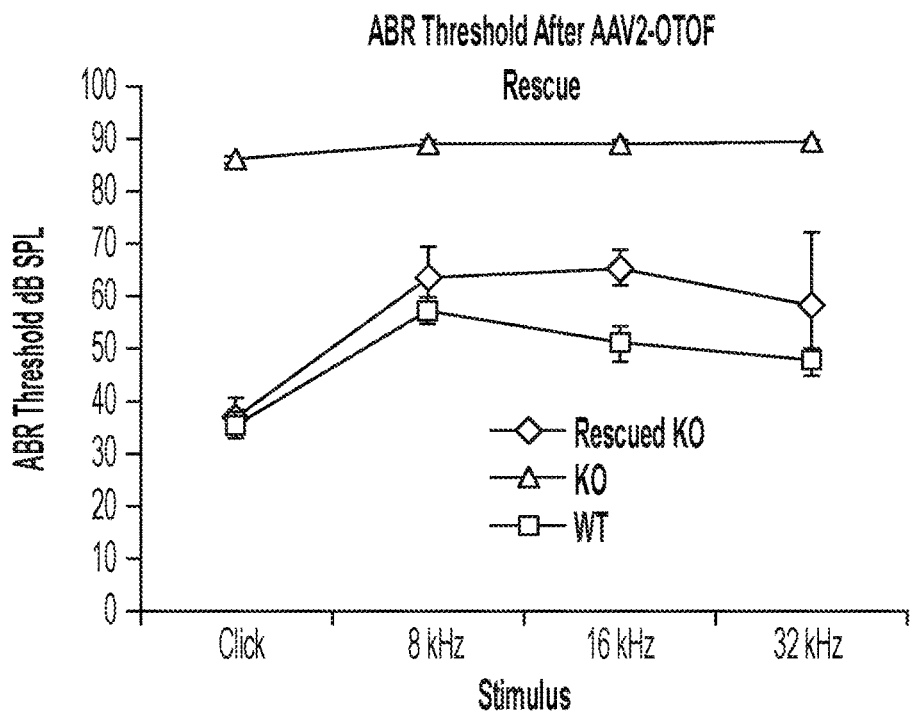
FIGS. 9A and 9B are a series of graphs showing hearing assessment.
Figure 9B:
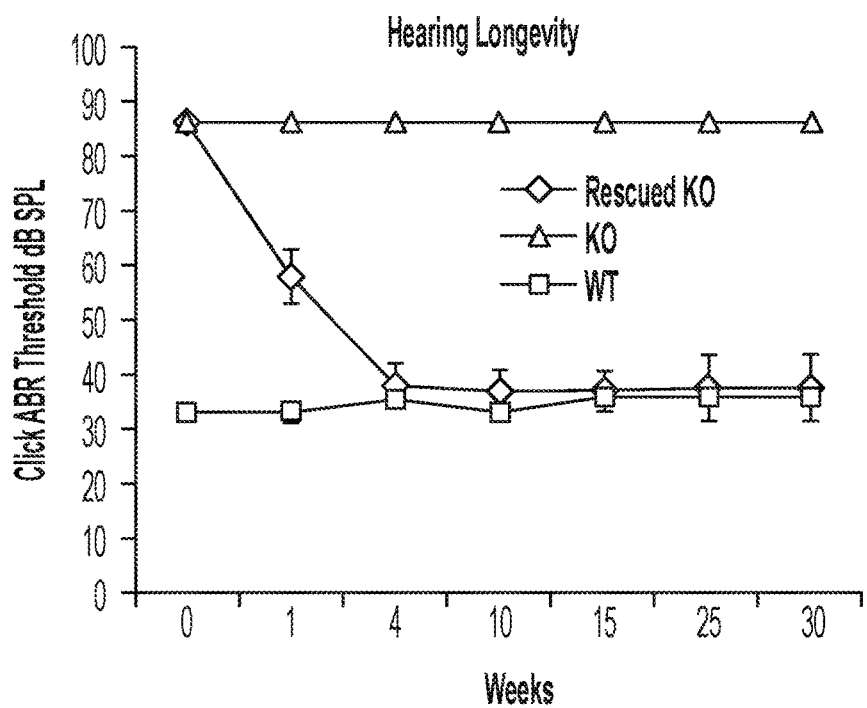
Figure 10:
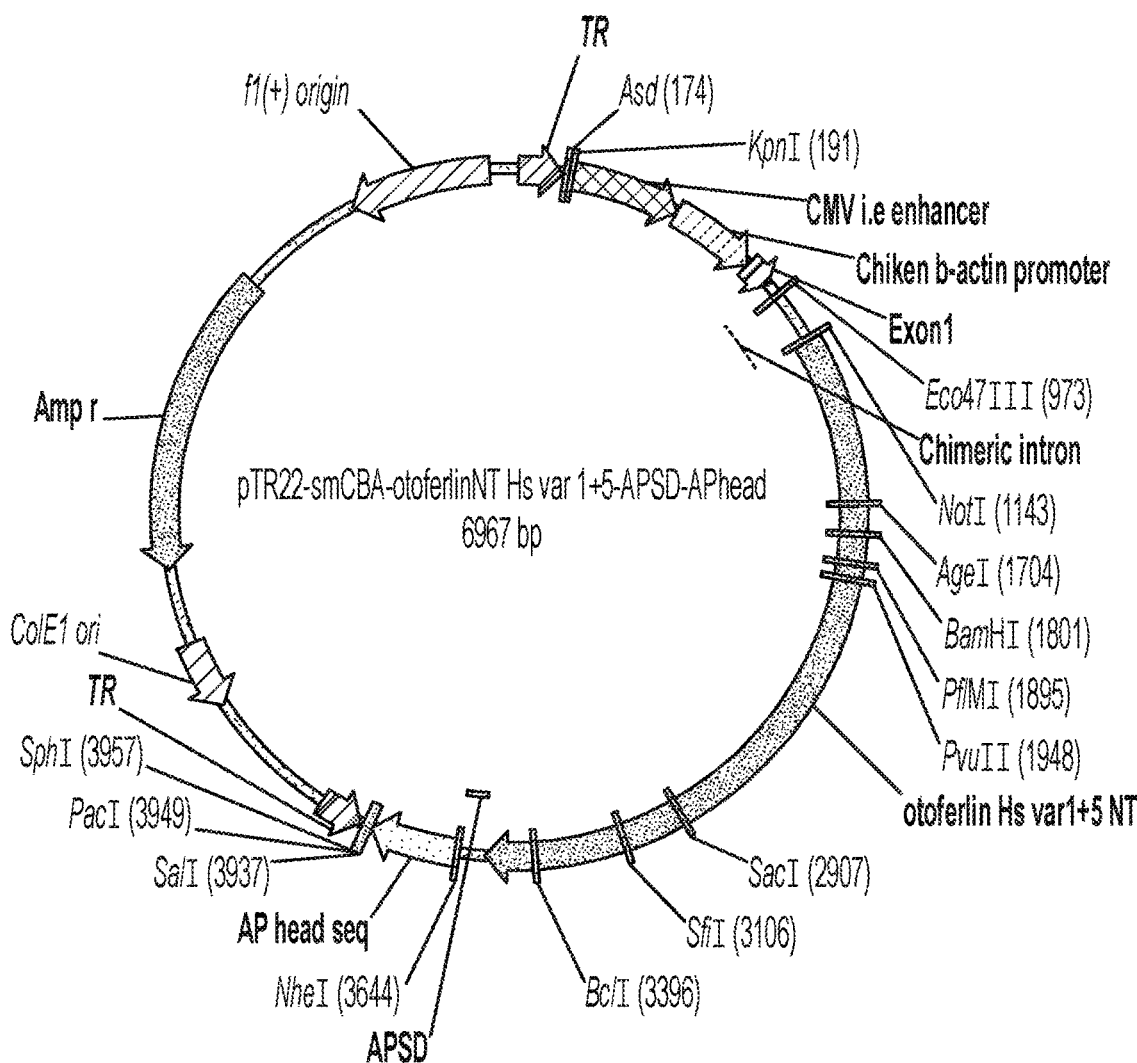
FIG. 10 is a map of a plasmid containing AAV2 inverted terminal repeats (TR) flanking a CMV enhancer, a chicken beta-actin promoter, a 5' section of a human Otoferlin cDNA (Otoferlin NT), a splice donor sequence (APSD), and a homologous sequence for recombination (APhead).
Figure 11:
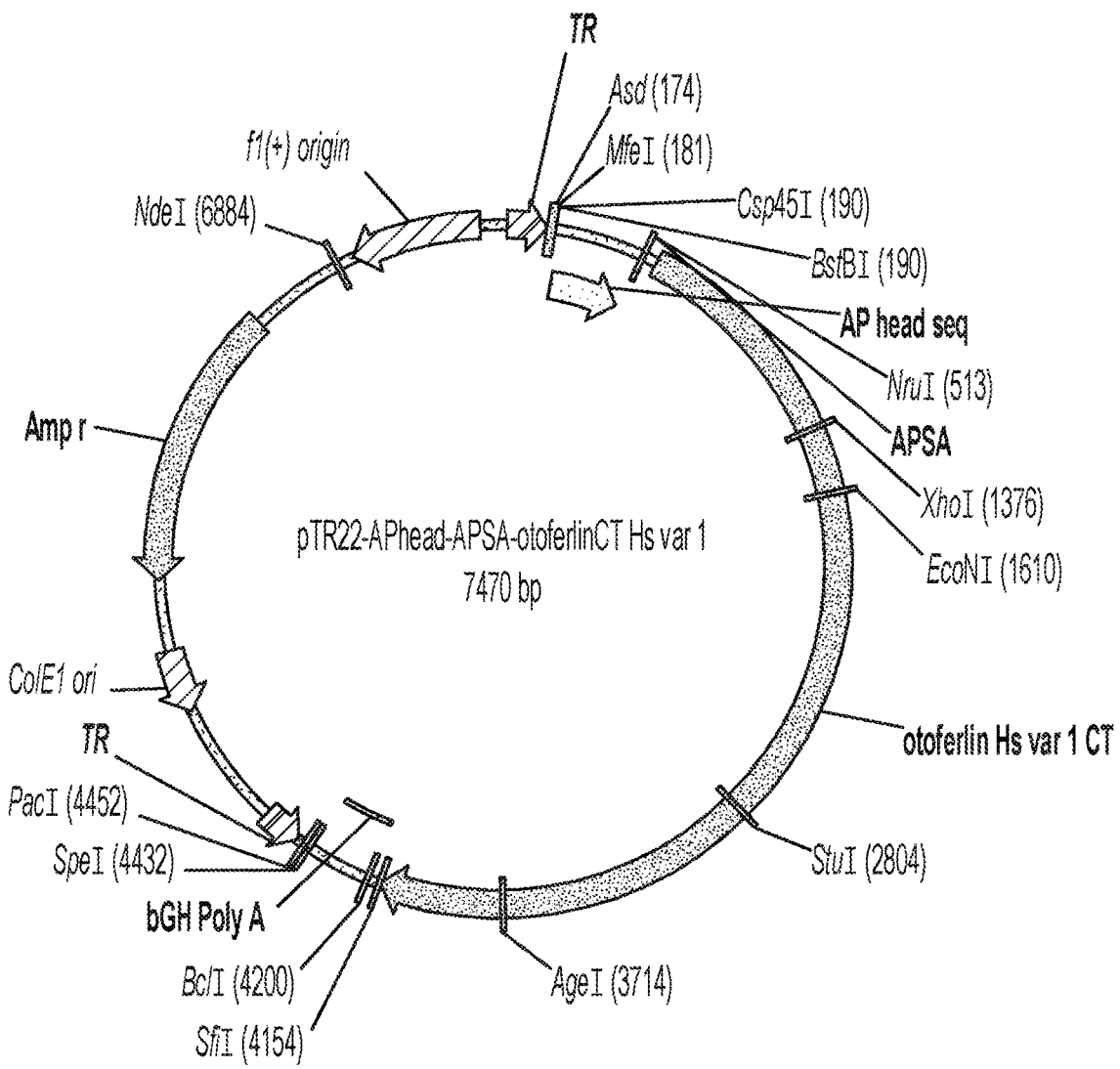
FIG. 11 is a map of a plasmid containing AAV2 inverted terminal repeats (TR) flanking a homologous sequence for recombination (APhead), a splice acceptor sequence (APSA), a 3' section of a human Otoferlin cDNA (Otoferlin CT) encoding isoform 1 of Otoferlin, a bovine growth hormone polyadenylation signal (bGH PolyA).
Figure 12:
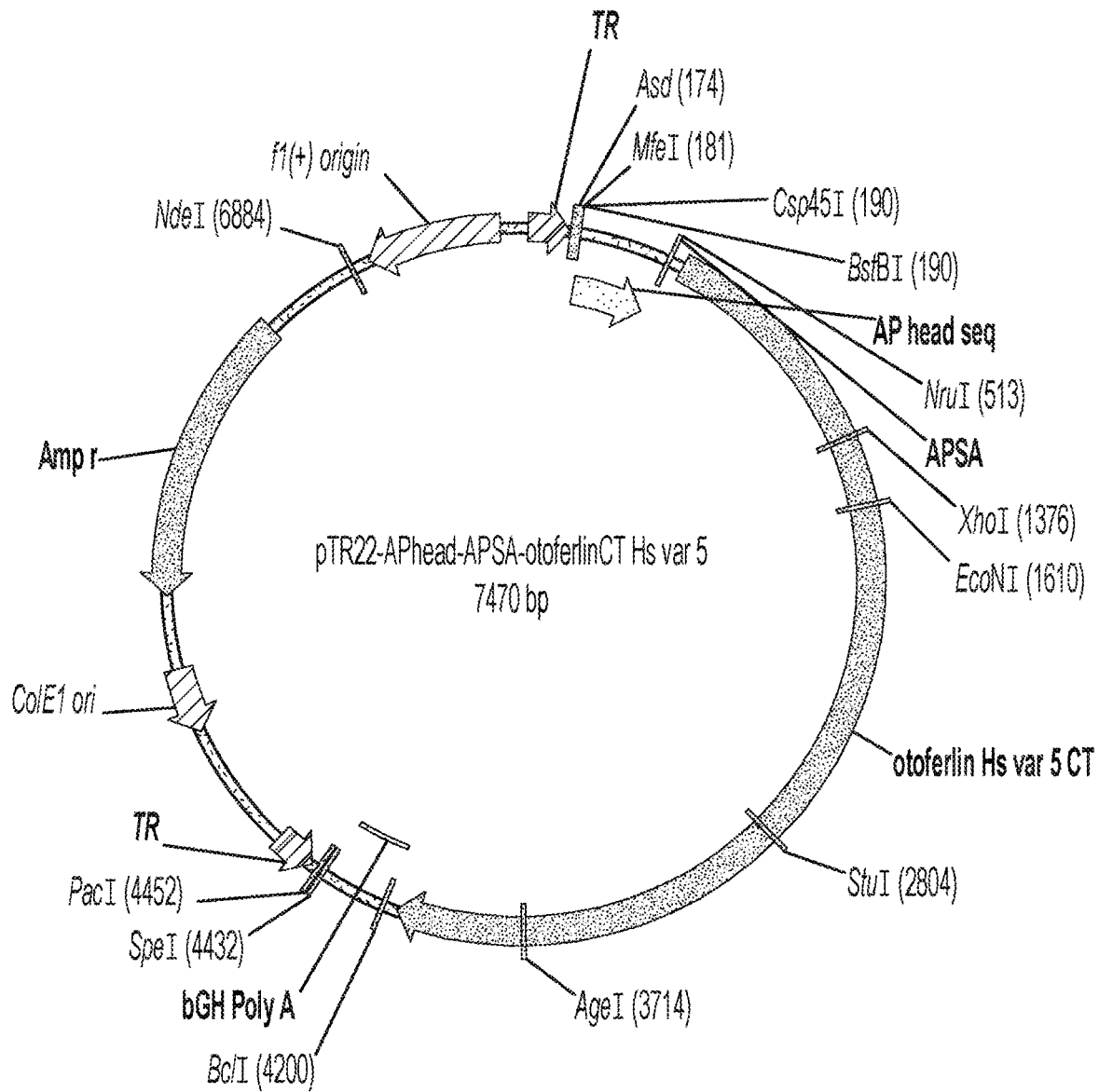
FIG. 12 is a map of a plasmid containing AAV2 inverted terminal repeats (TR) flanking a homologous sequence for recombination (APhead), a splice acceptor sequence (APSA), a 3' section of the mouse Otoferlin cDNA (Otoferlin CT) encoding isoform 5 of Otoferlin, a bovine growth hormone polyadenylation signal (bGH PolyA).

At P60 all OTOF knock-out mice treated with both viruses demonstrated normal ABR threshold to clicks stimulus while at specific frequencies 8, 16 and 32 kHz the ABR thresholds appeared to be slightly elevated, though still significantly better than untreated OTOF knock-out mice (FIG. 9). A time course of hearing recovery following injection of both viruses into OTOF knock-out mice at an age older than P12 showed that hearing was maintained in the treated mice for more than 30 weeks, and the ABR thresholds were restored to the WT levels (FIG. 9).

These results demonstrate that a use of more than one AAV construct to deliver different parts of an OTOF cDNA can result in a functional cDNA in vivo. These results also demonstrate that hearing loss can be treated by delivery of OTOF cDNA using an AAV delivery system.

Example 2: Human OTOF Dual Vector Constructs

Provided below are example dual vector sequences for expressing Human Otoferlin protein isoforms 1 and 5. The cDNAs encoding both isoforms 1 and 5 contain the same N-terminal sequence such that the same N-terminal vector may be used for expressing both isoforms. Vector maps and annotated sequences corresponding to the below sequences are shown in FIGS. 10-15.

```
pTR22-smCBA-otoferlinNT Hs var 1 + 5-APSD-APhead
                                               (SEQ ID NO: 14)
AGGGGGGGGGGGGGGGGGTTGGCCACTCCCTCTCTGCGCGCTCGCTCGCTCACTG

AGGCCGGGCGACCAAAGGTCGCCCGACGCCCGGGCTTTGCCCGGGCGGCCTCAGTG

AGCGAGCGAGCGCGCAGAGAGGGAGTGGCCAACTCCATCACTAGGGGTTCCTCAGA

TCTGGCGCGCCCAATTCGGTACCCTAGTTATTAATAGTAATCAATTACGGGTCATT

AGTTCATAGCCCATATATGGAGTTCCGCGTTACATAACTTACGGTAAATGGCCCGCC

TGGCTGACCGCCCAACGACCCCCGCCCATTGACGTCAATAATGACGTATGTTCCCAT

AGTAACGCCAATAGGGACTTTCCATTGACGTCAATGGGTGGACTATTTACGGTAAA

CTGCCCACTTGGCAGTACATCAAGTGTATCATATGCCAAGTACGCCCCCTATTGACG

TCAATGACGGTAAATGGCCCGCCTGGCATTATGCCCAGTACATGACCTTATGGGACT

TTCCTACTTGGCAGTACATCTACGTATTAGTCATCGCTATTACCATGGTCGAGGTGA

GCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGGCG

CGCGCCAGGCGGGGCGGGCGGGGCGAGGGGCGGGGCGGGGCGAGGCGGAGAGG

TGCGGCGGCAGCCAATCAGAGCGGCGCGCTCCGAAAGTTTCCTTTTATGGCGAGGC

GGCGGCGGCGGCGGCCCTATAAAAAGCGAAGCGCGCGGCGGGCGGGAGTCGCTGC

GACGCTGCCTTCGCCCCGTGCCCCGCTCCGCCGCCGCCTCGCGCCGCCCGCCCCGGC

TCTGACTGACCGCGTTACTCCCACAGGTGAGCGGGCGGGACGGCCCTTCTCCTCCGG

GCTGTAATTAGCGCTTGGTTTAATGACGGCTTGTTTCTTTTCTGTGGCTGCGTGAAAG

CCTTGAGGGGCTCCGGGAGCTAGAGCCTCTGCTAACCATGTTCATGCCTTCTTCTTTT

TCCTACAGCTCCTGGGCAACGTGCTGGTTATTGTGCTGTCTCATCATTTTGGCAAAG

AATTCTAGCGGCCGCCACCATGGCCTTGCTCATCCACCTCAAGACAGTCTCGGAGCT

GCGGGCAGGGCGACCGGATCGCCAAAGTGACTTTCCGAGGGCAATCCTTCTACT

CTCGGGTCCTGGAGAACTGTGAGGATGTGGCTGACTTTGATGAGACATTTCGGTGGC

CGGTGGCCAGCAGCATCGACAGAAATGAGATGCTGGAGATTCAGGTTTTCAACTAC

AGCAAAGTCTTCAGCAACAAGCTCATCGGGACCTTCCGCATGGTGCTGCAGAAGGT
```

-continued

```
GGTAGAGGAGAGCCATGTGGAGGTGACTGACACGCTGATTGATGACAACAATGCTA

TCATCAAGACCAGCCTGTGCGTGGAGGTCCGGTATCAGGCCACTGACGGCACAGTG

GGCTCCTGGGACGATGGGGACTTCCTGGGAGATGAGTCTCTTCAAGAGGAAGAGAA

GGACAGCCAAGAGACGGATGGACTGCTCCCAGGCTCCCGGCCCAGCTCCCGGCCCC

CAGGAGAGAAGAGCTTCCGGAGAGCCGGGAGGAGCGTGTTCTCCGCCATGAAGCTC

GGCAAAAACCGGTCTCACAAGGAGGAGCCCCAAAGACCAGATGAACCGGCGGTGC

TGGAGATGGAAGACCTTGACCATCTGGCCATTCGGCTAGGAGATGGACTGGATCCC

GACTCGGTGTCTCTAGCCTCAGTCACAGCTCTCACCACTAATGTCTCCAACAAGCGA

TCTAAGCCAGACATTAAGATGGAGCCAAGTGCTGGGCGGCCCATGGATTACCAGGT

CAGCATCACGGTGATCGAGGCCCGGCAGCTGGTGGGCTTGAACATGGACCCTGTGG

TGTGCGTGGAGGTGGGTGACGACAAGAAGTACACATCCATGAAGGAGTCCACTAAC

TGCCCCTATTACAACGAGTACTTCGTCTTCGACTTCCATGTCTCTCCGGATGTCATGT

TTGACAAGATCATCAAGATTTCGGTGATTCACTCCAAGAACCTGCTGCGCAGTGGCA

CCCTGGTGGGCTCCTTCAAAATGGACGTGGGAACCGTGTACTCGCAGCCAGAGCAC

CAGTTCCATCACAAGTGGGCCATCCTGTCTGACCCCGATGACATCTCCTCGGGGCTG

AAGGGCTACGTGAAGTGTGACGTTGCCGTGGTGGGCAAAGGGGACAACATCAAGA

CGCCCCACAAGGCCAATGAGACCGACGAAGATGACATTGAGGGGAACTTGCTGCTC

CCCGAGGGGGTGCCCCCCGAACGCCAGTGGGCCCGGTTCTATGTGAAAATTTACCG

AGCAGAGGGGCTGCCCCGTATGAACACAAGCCTCATGGCCAATGTAAAGAAGGCTT

TCATCGGTGAAAACAAGGACCTCGTGGACCCCTACGTGCAAGTCTTCTTTGCTGGCC

AGAAGGGCAAGACTTCAGTGCAGAAGAGCAGCTATGAGCCCCTGTGGAATGAGCA

GGTCGTCTTTACAGACCTCTTCCCCCCACTCTGCAAACGCATGAAGGTGCAGATCCG

AGACTCGGACAAGGTCAACGACGTGGCCATCGGCACCCACTTCATTGACCTGCGCA

AGATTTCTAATGACGGAGACAAAGGCTTCCTGCCCACACTGGGCCCAGCCTGGGTG

AACATGTACGGCTCCACACGTAACTACACGCTGCTGGATGAGCATCAGGACCTGAA

CGAGGGCCTGGGGGAGGGTGTGTCCTTCCGGGCCCGGCTCCTGCTGGGCCTGGCTG

TGGAGATCGTAGACACCTCCAACCCTGAGCTCACCAGCTCCACAGAGGTGCAGGTG

GAGCAGGCCACGCCCATCTCGGAGAGCTGTGCAGGTAAAATGGAAGAATTCTTTCT

CTTTGGAGCCTTCCTGGAGGCCTCAATGATCGACCGGAGAAACGGAGACAAGCCCA

TCACCTTTGAGGTCACCATAGGCAACTATGGGAACGAAGTTGATGGCCTGTCCCGG

CCCCAGCGGCCTCGGCCCCGGAAGGAGCCGGGGGATGAGGAAGAAGTAGACCTGA

TTCAGAACGCAAGTGATGACGAGGCCGGTGATGCCGGGGACCTGGCCTCAGTCTCC

TCCACTCCACCAATGCGGCCCCAGGTCACCGACAGGAACTACTTCCATCTGCCCTAC

CTGGAGCGAAAGCCCTGCATCTACATCAAGAGCTGGTGGCCGGACCAGCGCCGCCG

CCTCTACAATGCCAACATCATGGACCACATTGCCGACAAGCTGGAAGAAGGCCTGA

ACGACATACAGGAGATGATCAAAACGGAGAAGTCCTACCCTGAGCGTCGCCTGCGG

GGCGTCCTGGAGGAGCTGAGCTGTGGCTGCTGCCGCTTCCTCTCCCTCGCTGACAAG

GACCAGGGCCACTCATCCCGCACCAGGCTTGACCGGGAGCGCCTCAAGTCCTGCAT

GAGGGAGCTGGTAAGTATCAAGGTTACAAGACAGGTTTAAGGAGACCAATAGAAA

CTGGGCTTGTCGAGACAGAGAAGACTCTTGCGTTTCTGAGCTAGCCCCCGGGTGCGC

GGCGTCGGTGGTGCCGGCGGGGGGCGCCAGGTCGCAGGCGGTGTAGGGCTCCAGGC
```

-continued

```
AGGCGGCGAAGGCCATGACGTGCGCTATGAAGGTCTGCTCCTGCACGCCGTGAACC

AGGTGCGCCTGCGGGCCGCGCGCGAACACCGCCACGTCCTCGCCTGCGTGGGTCTC

TTCGTCCAGGGGCACTGCTGACTGCTGCCGATACTCGGGGCTCCCGCTCTCGCTCTC

GGTAACATCCGGCCGGGCGCCGTCCTTGAGCACATAGCCTGGACCGTTTCGTCGACT

GTTAATTAAGCATGCTGGGGAGAGATCTAGGAACCCCTAGTGATGGAGTTGGCCAC

TCCCTCTCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGG

CCAACCCCCCCCCCCCCCCCCTGCAGCCCTGCATTAATGAATCGGCCAACGCGCGG

GGAGAGGCGGTTTGCGTATTGGGCGCTCTTCCGCTTCCTCGCTCACTGACTCGCTGC

GCTCGGTCGTTCGGCTGCGGCAGCGGTATCAGCTCACTCAAAGGCGGTAATACGG

TTATCCACAGAATCAGGGGATAACGCAGGAAAGAACATGTGAGCAAAAGGCCAGC

AAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGT

TCCGACCCTGCCGCTTACCGGATACCTGTCCGCCTTTCTCCCTTCGGGAAGCGTGGC

GCTTTCTCAATGCTCACGCTGTAGGTATCTCAGTTCGGTGTAGGTCGTTCGCTCCAA

GCTGGGCTGTGTGCACGAACCCCCCGTTCAGCCCGACCGCTGCGCCTTATCCGGTAA

CTATCGTCTTGAGTCCAACCCGGTAAGACACGACTTATCGCCACTGGCAGCAGCCAC

TGGTAACAGGATTAGCAGAGCGAGGTATGTAGGCGGTGCTACAGAGTTCTTGAAGT

GGTGGCCTAACTACGGCTACACTAGAAGGACAGTATTTGGTATCTGCGCTCTGCTGA

AGCCAGTTACCTTCGGAAAAAGAGTTGGTAGCTCTTGATCCGGCAAACAAACCACC

GCTGGTAGCGGTGGTTTTTTTGTTTGCAAGCAGCAGATTACGCGCAGAAAAAAAGG

ATCTCAAGAAGATCCTTTGATCTTTTCTACGGGGTCTGACGCTCAGTGGAACGAAAA

CTCACGTTAAGGGATTTTGGTCATGAGATTATCAAAAAGGATCTTCACCTAGATCCT

TTTAAATTAAAAATGAAGTTTTAAATCAATCTAAAGTATATATGAGTAAACTTGGTC

TGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTT

ACCATCTGGCCCCAGTGCTGCAATGATACCGCGAGACCCACGCTCACCGGCTCCAG

ATTTATCAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGTAAGTAGT

TCGCCAGTTAATAGTTTGCGCAACGTTGTTGCCATTGCTACAGGCATCGTGGTGTCA

CGCTCGTCGTTTGGTATGGCTTCATTCAGCTCCGGTTCCCAACGATCAAGGCGAGTT

ACATGATCCCCCATGTTGTGCAAAAAAGCGGTTAGCTCCTTCGGTCCTCCGATCGTT

GTCAGAAGTAAGTTGGCCGCAGTGTTATCACTCATGGTTATGGCAGCACTGCATAAT

TCTCTTACTGTCATGCCATCCGTAAGATGCTTTTCTGTGACTGGTGAGTACTCAACCA

AGTCATTCTGAGAATAGTGTATGCGGCGACCGAGTTGCTCTTGCCCGGCGTCAATAC

GGGATAATACCGCGCCACATAGCAGAACTTTAAAAGTGCTCATCATTGGAAAACGT

TCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGT

GAGCAAAAACAGGAAGGCAAAATGCCGCAAAAAAGGGAATAAGGGCGACACGGA
```

```
AATGTTGAATACTCATACTCTTCCTTTTTCAATATTATTGAAGCATTTATCAGGGTTA

TTGTCTCATGAGCGGATACATATTTGAATGTATTTAGAAAAATAAACAAATAGGGG

TTCCGCGCACATTTCCCCGAAAAGTGCCACCTGACGTCTAAGAAACCATTATTATCA

TGACATTAACCTATAAAAATAGGCGTATCACGAGGCCCTTTCGTCTCGCGCGTTTCG

GTGATGACGGTGAAAACCTCTGACACATGCAGCTCCCGGAGACGGTCACAGCTTGT

CTGTAAGCGGATGCCGGGAGCAGACAAGCCCGTCAGGGCGCGTCAGCGGGTGTTGG

CGGGTGTCGGGGCTGGCTTAACTATGCGGCATCAGAGCAGATTGTACTGAGAGTGC

ACCATATGCGGTGTGAAATACCGCACAGATGCGTAAGGAGAAAATACCGCATCAGG

AAATTGTAAACGTTAATATTTTGTTAAAATTCGCGTTAAATTTTTGTTAAATCAGCTC

ATTTTTTAACCAATAGGCCGAAATCGGCAAAATCCCTTATAAATCAAAAGAATAGA

CCGAGATAGGGTTGAGTGTTGTTCCAGTTTGGAACAAGAGTCCACTATTAAAGAAC

GTGGACTCCAACGTCAAAGGGCGAAAAACCGTCTATCAGGGCGATGGCCCACTACG

TGAACCATCACCCTAATCAAGTTTTTTGGGGTCGAGGTGCCGTAAAGCACTAAATCG

GAACCCTAAAGGGAGCCCCCGATTTAGAGCTTGACGGGGAAAGCCGGCGAACGTG

GCGAGAAAGGAAGGGAAGAAAGCGAAAGGAGCGGGCGCTAGGGCGCTGGCAAGT

GTAGCGGTCACGCTGCGCGTAACCACCACACCCGCCGCGCTTAATGCGCCGCTACA

GGGCGCGTCGCGCCATTCGCCATTCAGGCTACGCAACTGTTGGGAAGGGCGATCGG

TGCGGGCCTCTTCGCTATTACGCCAGGCTGC
``` pTR22-APhead-APSA-otoferlinCT Hs var 1
(SEQ ID NO: 15)

```
AGGGGGGGGGGGGGGGGGTTGGCCACTCCCTCTCTGCGCGCTCGCTCGCTCACTG

AGGCCGGGCGACCAAAGGTCGCCCGACGCCCGGGCTTTGCCCGGGCGGCCTCAGTG

AGCGAGCGAGCGCGCAGAGAGGGAGTGGCCAACTCCATCACTAGGGGTTCCTCAGA

TCTGGCGCGCCCAATTGGCTTCGAATTCTAGCGGCCGCCCCCGGGTGCGCGGCGTCG

GTGGTGCCGGCGGGGGGCGCCAGGTCGCAGGCGGTGTAGGGCTCCAGGCAGGCGG

CGAAGGCCATGACGTGCGCTATGAAGGTCTGCTCCTGCACGCCGTGAACCAGGTGC

GCCTGCGGGCCGCGCGCGAACACCGCCACGTCCTCGCCTGCGTGGGTCTCTTCGTCC

AGGGGCACTGCTGACTGCTGCCGATACTCGGGGCTCCCGCTCTCGCTCTCGGTAACA

TCCGGCCGGGCGCCGTCCTTGAGCACATAGCCTGGACCGTTTCCTTAAGCGACGCAT

GCTCGCGATAGGCACCTATTGGTCTTACTGACATCCACTTTGCCTTTCTCTCCACAGG

AAAACATGGGGCAGCAGGCCAGGATGCTGCGGGCCCAGGTGAAGCGGCACACGGT

GCGGGACAAGCTGAGGCTGTGCCAGAACTTCCTGCAGAAGCTGCGCTTCCTGGCGG

ACGAGCCCCAGCACAGCATTCCCGACATCTTCATCTGGATGATGAGCAACAACAAG

CGTGTCGCCTATGCCCGTGTGCCCTCCAAGGACCTGCTCTTCTCCATCGTGGAGGAG

GAGACTGGCAAGGACTGCGCCAAGGTCAAGACGCTCTTCCTTAAGCTGCCAGGGAA

GCGGGGCTTCGGCTCGGCAGGCTGGACAGTGCAGGCCAAGGTGGAGCTGTACCTGT

GGCTGGGCCTCAGCAAACAGCGCAAGGAGTTCCTGTGCGGCCTGCCCTGTGGCTTC

CAGGAGGTCAAGGCAGCCCAGGGCCTGGGCCTGCATGCCTTCCCACCCGTCAGCCT

GGTCTACACCAAGAAGCAGGCGTTCCAGCTCCGAGCGCACATGTACCAGGCCCGCA

GCCTCTTTGCCGCCGACAGCAGCGGACTCTCAGACCCCTTTGCCCGCGTCTTCTTCA

TCAATCAGAGTCAGTGCACAGAGGTGCTGAATGAGACCCTGTGTCCCACCTGGGAC

CAGATGCTGGTGTTCGACAACCTGGAGCTCTATGGTGAAGCTCATGAGCTGAGGGA
```

-continued

```
CGATCCGCCCATCATTGTCATTGAAATCTATGACCAGGATTCCATGGGCAAAGCTGA

CTTCATGGGCCGGACCTTCGCCAAACCCCTGGTGAAGATGGCAGACGAGGCGTACT

GCCCACCCCGCTTCCCACCTCAGCTCGAGTACTACCAGATCTACCGTGGCAACGCCA

CAGCTGGAGACCTGCTGGCGGCCTTCGAGCTGCTGCAGATTGGACCAGCAGGGAAG

GCTGACCTGCCCCCCATCAATGGCCCGGTGGACGTGGACCGAGGTCCCATCATGCC

CGTGCCCATGGGCATCCGGCCCGTGCTCAGCAAGTACCGAGTGGAGGTGCTGTTCT

GGGGCCTACGGGACCTAAAGCGGGTGAACCTGGCCCAGGTGGACCGGCCACGGGT

GGACATCGAGTGTGCAGGGAAGGGGGTGCAGTCGTCCCTGATCCACAATTATAAGA

AGAACCCCAACTTCAACACCCTCGTCAAGTGGTTTGAAGTGGACCTCCCAGAGAAC

GAGCTGCTGCACCCGCCCTTGAACATCCGTGTGGTGGACTGCCGGGCCTTCGGTCGC

TACACACTGGTGGGCTCCCATGCCGTCAGCTCCCTGCGACGCTTCATCTACCGGCCC

CCAGACCGCTCGGCCCCCAGCTGGAACACCACGGTCAGGCTTCTCCGGCGCTGCCG

TGTGCTGTGCAATGGGGCTCCTCCTCTCACTCCACAGGGGAGGTTGTGGTGACTAT

GGAGCCAGAGGTACCCATCAAGAAACTGGAGACCATGGTGAAGCTGGACGCGACTT

CTGAAGCTGTTGTCAAGGTGGATGTGGCTGAGGAGGAGAAGGAGAAGAAGAAGAA

GAAGAAGGGCACTGCGGAGGAGCCAGAGGAGGAGGAGCCAGACGAGAGCATGCTG

GACTGGTGGTCCAAGTACTTTGCCTCCATTGACACCATGAAGGAGCAACTTCGACA

ACAAGAGCCCTCTGGAATTGACTTGGAGGAGAAGGAGGAAGTGGACAATACCGAG

GGCCTGAAGGGGTCAATGAAGGGCAAGGAGAAGGCAAGGGCTGCCAAAGAGGAGA

AGAAGAAGAAAACTCAGAGCTCTGGCTCTGGCCAGGGGTCCGAGGCCCCCGAGAA

GAAGAAACCCAAGATTGATGAGCTTAAGGTATACCCCAAAGAGCTGGAGTCCGAGT

TTGATAACTTTGAGGACTGGCTGCACACTTTCAACTTGCTTCGGGGCAAGACCGGGG

ATGATGAGGATGGCTCCACCGAGGAGGAGCGCATTGTGGGACGCTTCAAGGGCTCC

CTCTGCGTGTACAAAGTGCCACTCCCAGAGGACGTGTCCCGGGAAGCCGGCTACGA

CTCCACCTACGGCATGTTCCAGGGCATCCCGAGCAATGACCCCATCAATGTGCTGGT

CCGAGTCTATGTGGTCCGGGCCACGGACCTGCACCCTGCTGACATCAACGGCAAAG

CTGACCCCTACATCGCCATCCGGCTAGGCAAGACTGACATCCGCGACAAGGAGAAC

TACATCTCCAAGCAGCTCAACCCTGTCTTTGGGAAGTCCTTTGACATCGAGGCCTCC

TTCCCCATGGAATCCATGCTGACGGTGGCTGTGTATGACTGGGACCTGGTGGGCACT

GATGACCTCATTGGGGAAACCAAGATCGACCTGGAGAACCGCTTCTACAGCAAGCA

CCGCGCCACCTGCGGCATCGCCCAGACCTACTCCACACATGGCTACAATATCTGGCG

GGACCCCATGAAGCCCAGCCAGATCCTGACCCGCCTCTGCAAAGACGGCAAAGTGG

ACGGCCCCACTTTGGGCCCCCTGGGAGAGTGAAGGTGGCCAACCGCGTCTTCACT

GGGCCCTCTGAGATTGAGGACGAGAACGGTCAGAGGAAGCCCACAGACGAGCATG

TGGCGCTGTTGGCCCTGAGGCACTGGGAGGACATCCCCCGCGCAGGCTGCCGCCTG

GTGCCAGAGCATGTGGAGACGAGGCCGCTGCTCAACCCCGACAAGCCGGGCATCGA

GCAGGGCCGCCTGGAGCTGTGGGTGGACATGTTCCCCATGGACATGCCAGCCCCTG

GGACGCCTCTGGACATCTCACCTCGGAAGCCCAAGAAGTACGAGCTGCGGGTCATC

ATCTGGAACACAGATGAGGTGGTCTTGGAGGACGACGACTTCTTCACAGGGGAGAA

GTCCAGTGACATCTTCGTGAGGGGGTGGCTGAAGGGCCAGCAGGAGGACAAGCAG
```

```
-continued
GACACAGACGTCCACTACCACTCCCTCACTGGCGAGGGCAACTTCAACTGGCGCTA

CCTGTTCCCCTTCGACTACCTGGCGGCGGAGGAGAAGATCGTCATCTCCAAGAAGG

AGTCCATGTTCTCCTGGGACGAGACCGAGTACAAGATCCCCGCGCGGCTCACCCTG

CAGATCTGGGATGCGGACCACTTCTCCGCTGACGACTTCCTGGGGGCCATCGAGCTG

GACCTGAACCGGTTCCCGCGGGGCGCAAAGACAGCCAAGCAGTGCACCATGGAGAT

GGCCACCGGGGAGGTGGACGTGCCCCTCGTGTCCATCTTCAAGCAAAAGCGCGTCA

AAGGCTGGTGGCCCCTCCTGGCCCGCAATGAGAACGATGAGTTTGAGCTCACGGGC

AAGGTGGAGGCTGAGCTGCATTTACTGACAGCAGAGGAGGCAGAGAAGAACCCAG

TGGGCCTGGCCCGCAATGAACCTGACCCCCTAGAGAAACCCAACCGGCCCGACACG

AGCTTCATCTGGTTCCTGAACCCTCTCAAGTCGGCTCGCTACTTCTTGTGGCACACGT

ATCGCTGGCTGCTCCTCAAACTGTTGCTGCTCCTGCTGCTGCTCCTCCTCCTCGCCCT

GTTCCTCTACTCTGTGCCTGGCTACCTGGTCAAGAAAATCCTCGGGGCCTGAGCGGC

CGCGGTACCAAGGGCGAATTCTGCAGTCGACTAGAGCTCGCTGATCAGCCTCGACT

GTGCCTTCTAGTTGCCAGCCATCTGTTGTTTGCCCCTCCCCCGTGCCTTCCTTGACCC

TGGAAGGTGCCACTCCCACTGTCCTTTCCTAATAAAATGAGGAAATTGCATCGCATT

GTCTGAGTAGGTGTCATTCTATTCTGGGGGGTGGGGTGGGGCAGGACAGCAAGGGG

GAGGATTGGGAAGACAATAGCAGGCATGCTGGGGAGAGATCTGAGGACTAGTCCG

TCGACTGTTAATTAAGCATGCTGGGGAGAGATCTAGGAACCCCTAGTGATGGAGTT

GGCCACTCCCTCTCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCAGAGAGG

GAGTGGCCAACCCCCCCCCCCCCCCCCTGCAGCCCTGCATTAATGAATCGGCCAAC

GCGCGGGGAGAGGCGGTTTGCGTATTGGGCGCTCTTCCGCTTCCTCGCTCACTGACT

CGCTGCGCTCGGTCGTTCGGCTGCGGCGAGCGGTATCAGCTCACTCAAAGGCGGTA

ATACGGTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTC

TCCTGTTCCGACCCTGCCGCTTACCGGATACCTGTCCGCCTTTCTCCCTTCGGGAAGC

GTGGCGCTTTCTCAATGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGC

AGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTC

TGCTGAAGCCAGTTACCTTCGGAAAAAGAGTTGGTAGCTCTTGATCCGGCAAACAA

ACCACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGAAC

GAAAACTCACGTTAAGGGATTTTGGTCATGAGATTATCAAAAAGGATCTTCACCTA

GATCCTTTTAAATTAAAAATGAAGTTTTAAATCAATCTAAAGTATATATGAGTAAAC

TTGGTCTGACAGTTACCAATGCTTAATCAGTGAGGCACCTATCTCAGCGATCTGTCT

ATTTCGTTCATCCATAGTTGCCTGACTCCCCGTCGTGTAGATAACTACGATACGGGA

GGGCTTACCATCTGGCCCCAGTGCTGCAATGATACCGCGAGACCCACGCTCACCGG
```

-continued

```
CTCCAGATTTATCAGCAATAAACCAGCCAGCCGGAAGGGCCGAGCGCAGAAGTGGT

CCTGCAACTTTATCCGCCTCCATCCAGTCTATTAATTGTTGCCGGGAAGCTAGAGTA

AGTAGTTCGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACGATCAAGG

CGAGTTACATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGCAGCACTG

CATAATTCTCTTACTGTCATGCCATCCGTAAGATGCTTTTCTGTGACTGGTGAGTACT

CAACCAAGTCATTCTGAGAATAGTGTATGCGGCGACCGAGTTGCTCTTGCCCGGCGT

CAATACGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTTCG

ATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGAC

ACGGAAATGTTGAATACTCATACTCTTCCTTTTTCAATATTATTGAAGCATTTATCAG

GGTTATTGTCTCATGAGCGGATACATATTTGAATGTATTTAGAAAAATAAACAAATA

GGGGTTCCGCGCACATTTCCCCGAAAAGTGCCACCTGACGTCTAAGAAACCATTATT

ATCATGACATTAACCTATAAAAATAGGCGTATCACGAGGCCCTTTCGTCTCGCGCGT

TTCGGTGATGACGGTGAAAACCTCTGACACATGCAGCTCCCGGAGACGGTCACAGC

TTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGA

GTGCACCATATGCGGTGTGAAATACCGCACAGATGCGTAAGGAGAAAATACCGCAT

CAGGAAATTGTAAACGTTAATATTTTGTTAAAATTCGCGTTAAATTTTTGTTAAATC

AGCTCATTTTTTAACCAATAGGCCGAAATCGGCAAAATCCCTTATAAATCAAAAGA

ATAGACCGAGATAGGGTTGAGTGTTGTTCCAGTTTGGAACAAGAGTCCACTATTAA

AGAACGTGGACTCCAACGTCAAAGGGCGAAAAACCGTCTATCAGGGCGATGGCCCA

CTACGTGAACCATCACCCTAATCAAGTTTTTTGGGGTCGAGGTGCCGTAAAGCACTA

AATCGGAACCCTAAAGGGAGCCCCCGATTTAGAGCTTGACGGGGAAAGCCGGCGA

ACGTGGCGAGAAAGGAAGGGAAGAAAGCGAAAGGAGCGGGCGCTAGGGCGCTGG

CAAGTGTAGCGGTCACGCTGCGCGTAACCACCACACCCGCCGCGCTTAATGCGCCG

CTACAGGGCGCGTCGCGCCATTCGCCATTCAGGCTACGCAACTGTTGGGAAGGGCG

ATCGGTGCGGGCCTCTTCGCTATTACGCCAGGCTGC
``` pTR22-APhead-APSA-otoferlinCT Hs var 5
(SEQ ID NO: 16)

```
AGGGGGGGGGGGGGGGGGTTGGCCACTCCCTCTCTGCGCGCTCGCTCGCTCACTG

AGGCCGGGCGACCAAAGGTCGCCCGACGCCCGGGCTTTGCCCGGCGGCCTCAGTG

AGCGAGCGAGCGCGCAGAGAGGGAGTGGCCAACTCCATCACTAGGGGTTCCTCAGA

TCTGGCGCGCCCAATTGGCTTCGAATTCTAGCGGCCGCCCCCGGGTGCGCGGCGTCG

GTGGTGCCGGCGGGGGCGCCAGGTCGCAGGCGGTGTAGGGCTCCAGGCAGGCGG

CGAAGGCCATGACGTGCGCTATGAAGGTCTGCTCCTGCACGCCGTGAACCAGGTGC

GCCTGCGGGCCGCGCGCGAACACCGCCACGTCCTCGCCTGCGTGGGTCTCTTCGTCC

AGGGGCACTGCTGACTGCTGCCGATACTCGGGGCTCCCGCTCTCGCTCTCGGTAACA

TCCGGCCGGGCGCCGTCCTTGAGCACATAGCCTGGACCGTTTCCTTAAGCGACGCAT
```

```
                          -continued
GCTCGCGATAGGCACCTATTGGTCTTACTGACATCCACTTTGCCTTTCTCTCCACAGG

AAAACATGGGGCAGCAGGCCAGGATGCTGCGGGCCCAGGTGAAGCGGCACACGGT

GCGGGACAAGCTGAGGCTGTGCCAGAACTTCCTGCAGAAGCTGCGCTTCCTGGCGG

ACGAGCCCCAGCACAGCATTCCCGACATCTTCATCTGGATGATGAGCAACAACAAG

CGTGTCGCCTATGCCCGTGTGCCCTCCAAGGACCTGCTCTTCTCCATCGTGGAGGAG

GAGACTGGCAAGGACTGCGCCAAGGTCAAGACGCTCTTCCTTAAGCTGCCAGGGAA

GCGGGGCTTCGGCTCGGCAGGCTGGACAGTGCAGGCCAAGGTGGAGCTGTACCTGT

GGCTGGGCCTCAGCAAACAGCGCAAGGAGTTCCTGTGCGGCCTGCCCTGTGGCTTC

CAGGAGGTCAAGGCAGCCCAGGGCCTGGGCCTGCATGCCTTCCCACCCGTCAGCCT

GGTCTACACCAAGAAGCAGGCGTTCCAGCTCCGAGCGCACATGTACCAGGCCCGCA

GCCTCTTTGCCGCCGACAGCAGCGGACTCTCAGACCCCTTTGCCCGCGTCTTCTTCA

TCAATCAGAGTCAGTGCACAGAGGTGCTGAATGAGACCCTGTGTCCCACCTGGGAC

CAGATGCTGGTGTTCGACAACCTGGAGCTCTATGGTGAAGCTCATGAGCTGAGGGA

CGATCCGCCCATCATTGTCATTGAAATCTATGACCAGGATTCCATGGGCAAAGCTGA

CTTCATGGGCCGGACCTTCGCCAAACCCCTGGTGAAGATGGCAGACGAGGCGTACT

GCCCACCCCGCTTCCCACCTCAGCTCGAGTACTACCAGATCTACCGTGGCAACGCCA

CAGCTGGAGACCTGCTGGCGGCCTTCGAGCTGCTGCAGATTGGACCAGCAGGGAAG

GCTGACCTGCCCCCCATCAATGGCCCGGTGGACGTGGACCGAGGTCCCATCATGCC

CGTGCCCATGGGCATCCGGCCCGTGCTCAGCAAGTACCGAGTGGAGGTGCTGTTCT

GGGGCCTACGGGACCTAAAGCGGGTGAACCTGGCCCAGGTGGACCGGCCACGGGT

GGACATCGAGTGTGCAGGGAAGGGGGTGCAGTCGTCCCTGATCCACAATTATAAGA

AGAACCCCAACTTCAACACCCTCGTCAAGTGGTTTGAAGTGGACCTCCCAGAGAAC

GAGCTGCTGCACCCGCCCTTGAACATCCGTGTGGTGGACTGCCGGGCCTTCGGTCGC

TACACACTGGTGGGCTCCCATGCCGTCAGCTCCCTGCGACGCTTCATCTACCGGCCC

CCAGACCGCTCGGCCCCCAGCTGGAACACCACGGTCAGGCTTCTCCGGCGCTGCCG

TGTGCTGTGCAATGGGGGCTCCTCCTCTCACTCCACAGGGGAGGTTGTGGTGACTAT

GGAGCCAGAGGTACCCATCAAGAAACTGGAGACCATGGTGAAGCTGGACGCGACTT

CTGAAGCTGTTGTCAAGGTGGATGTGGCTGAGGAGGAGAAGGAGAAGAAGAAGAA

GAAGAAGGGCACTGCGGAGGAGCCAGAGGAGGAGGAGCCAGACGAGAGCATGCTG

GACTGGTGGTCCAAGTACTTTGCCTCCATTGACACCATGAAGGAGCAACTTCGACA

ACAAGAGCCCTCTGGAATTGACTTGGAGGAGAAGGAGGAAGTGGACAATACCGAG

GGCCTGAAGGGGTCAATGAAGGGCAAGGAGAAGGCAAGGGCTGCCAAAGAGGAGA

AGAAGAAGAAAACTCAGAGCTCTGGCTCTGGCCAGGGGTCCGAGGCCCCCGAGAA

GAAGAAACCCAAGATTGATGAGCTTAAGGTATACCCCAAAGAGCTGGAGTCCGAGT

TTGATAACTTTGAGGACTGGCTGCACACTTTCAACTTGCTTCGGGGCAAGACCGGGG

ATGATGAGGATGGCTCCACCGAGGAGGAGCGCATTGTGGGACGCTTCAAGGGCTCC

CTCTGCGTGTACAAAGTGCCACTCCCAGAGGACGTGTCCCGGGAAGCCGGCTACGA

CTCCACCTACGGCATGTTCCAGGGCATCCCGAGCAATGACCCCATCAATGTGCTGGT

CCGAGTCTATGTGGTCCGGGCCACGGACCTGCACCCTGCTGACATCAACGGCAAAG

CTGACCCCTACATCGCCATCCGGCTAGGCAAGACTGACATCCGCGACAAGGAGAAC

TACATCTCCAAGCAGCTCAACCCCTGTCTTTGGGAAGTCCTTTGACATCGAGGCCTCC
```

```
TTCCCCATGGAATCCATGCTGACGGTGGCTGTGTATGACTGGGACCTGGTGGGCACT

GATGACCTCATTGGGGAAACCAAGATCGACCTGGAGAACCGCTTCTACAGCAAGCA

CCGCGCCACCTGCGGCATCGCCCAGACCTACTCCACACATGGCTACAATATCTGGCG

GGACCCCATGAAGCCCAGCCAGATCCTGACCCGCCTCTGCAAAGACGGCAAAGTGG

ACGGCCCCACTTTGGGCCCCCTGGGAGAGTGAAGGTGGCCAACCGCGTCTTCACT

GGGCCCTCTGAGATTGAGGACGAGAACGGTCAGAGGAAGCCCACAGACGAGCATG

TGGCGCTGTTGGCCCTGAGGCACTGGGAGGACATCCCCCGCGCAGGCTGCCGCCTG

GTGCCAGAGCATGTGGAGACGAGGCCGCTGCTCAACCCCGACAAGCCGGGCATCGA

GCAGGGCCGCCTGGAGCTGTGGGTGGACATGTTCCCCATGGACATGCCAGCCCCTG

GGACGCCTCTGGACATCTCACCTCGGAAGCCCAAGAAGTACGAGCTGCGGGTCATC

ATCTGGAACACAGATGAGGTGGTCTTGGAGGACGACGACTTCTTCACAGGGGAGAA

GTCCAGTGACATCTTCGTGAGGGGGTGGCTGAAGGGCCAGCAGGAGGACAAGCAG

GACACAGACGTCCACTACCACTCCCTCACTGGCGAGGGCAACTTCAACTGGCGCTA

CCTGTTCCCCTTCGACTACCTGGCGGCGGAGGAGAAGATCGTCATCTCCAAGAAGG

AGTCCATGTTCTCCTGGGACGAGACCGAGTACAAGATCCCCGCGCGGCTCACCCTG

CAGATCTGGGATGCGGACCACTTCTCCGCTGACGACTTCCTGGGGGCCATCGAGCTG

GACCTGAACCGGTTCCCGCGGGGCGCAAAGACAGCCAAGCAGTGCACCATGGAGAT

GGCCACCGGGGAGGTGGACGTGCCCCTCGTGTCCATCTTCAAGCAAAAGCGCGTCA

AAGGCTGGTGGCCCCTCCTGGCCCGCAATGAGAACGATGAGTTTGAGCTCACGGGC

AAGGTGGAGGCTGAGCTGCATTTACTGACAGCAGAGGAGGCAGAGAAGAACCCAG

TGGGCCTGGCCCGCAATGAACCTGACCCCCTAGAGAAACCCAACCGGCCCGACACG

GCCTTCGTCTGGTTCCTCAACCCTCTCAAGTCCATCAAGTACCTCATCTGCACCCGGT

ACAAGTGGCTCATCATCAAGATCGTGCTGGCGCTGTTGGGGCTGCTCATGTTGGGGC

TCTTCCTCTACAGCCTCCCTGGCTACATGGTCAAAAAGCTCCTTGGGGCATGAGCGG

CCGCGGTACCAAGGGCGAATTCTGCAGTCGACTAGAGCTCGCTGATCAGCCTCGAC

TGTGCCTTCTAGTTGCCAGCCATCTGTTGTTTGCCCCTCCCCCGTGCCTTCCTTGACC

CTGGAAGGTGCCACTCCCACTGTCCTTTCCTAATAAAATGAGGAAATTGCATCGCAT

TGTCTGAGTAGGTGTCATTCTATTCTGGGGGGTGGGGTGGGCAGGACAGCAAGGG

GGAGGATTGGGAAGACAATAGCAGGCATGCTGGGGAGAGATCTGAGGACTAGTCC

GTCGACTGTTAATTAAGCATGCTGGGGAGAGATCTAGGAACCCCTAGTGATGGAGT

TGGCCACTCCCTCTCTGCGCGCTCGCTCGCTCACTGAGGCCGCCCGGGCAAAGCCCG

GGCGTCGGGCGACCTTTGGTCGCCCGGCCTCAGTGAGCGAGCGAGCGCGCAGAGAG

GGAGTGGCCAACCCCCCCCCCCCCCCCCTGCAGCCCTGCATTAATGAATCGGCCAA

CGCGCGGGGAGAGGCGGTTTGCGTATTGGGCGCTCTTCCGCTTCCTCGCTCACTGAC

TCGCTGCGCTCGGTCGTTCGGCTGCGGCGAGCGGTATCAGCTCACTCAAAGGCGGT

AATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAG

GCTCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGAAG
```

-continued

```
CGTGGCGCTTTCTCAATGCTCACGCTGTAGGTATCTCAGTTCGGTGTAGGTCGTTCG

CTCCAAGCTGGGCTGTGTGCACGAACCCCCCGTTCAGCCCGACCGCTGCGCCTTATC

CGGTAACTATCGTCTTGAGTCCAACCCGGTAAGACACGACTTATCGCCACTGGCAGC

AGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTC

TGCTGAAGCCAGTTACCTTCGGAAAAAGAGTTGGTAGCTCTTGATCCGGCAAACAA

ACCACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGAAC

GAAAACTCACGTTAAGGGATTTTGGTCATGAGATTATCAAAAAGGATCTTCACCTA

GATCCTTTTAAATTAAAAATGAAGTTTTAAATCAATCTAAAGTATATATGAGTAAAC

TTGGTCTGACAGTTACCAATGCTTAATCAGTGAGGCACCTATCTCAGCGATCTGTCT

ATTTCGTTCATCCATAGTTGCCTGACTCCCCGTCGTGTAGATAACTACGATACGGGA

GGGCTTACCATCTGGCCCCAGTGCTGCAATGATACCGCGAGACCCACGCTCACCGG

CTCCAGATTTATCAGCAATAAACCAGCCAGCCGGAAGGGCCGAGCGCAGAAGTGGT

CCTGCAACTTTATCCGCCTCCATCCAGTCTATTAATTGTTGCCGGGAAGCTAGAGTA

AGTAGTTCGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACGATCAAGG

CGAGTTACATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGCAGCACTG

CATAATTCTCTTACTGTCATGCCATCCGTAAGATGCTTTTCTGTGACTGGTGAGTACT

CAACCAAGTCATTCTGAGAATAGTGTATGCGGCGACCGAGTTGCTCTTGCCCGGCGT

CAATACGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTTCG

ATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGAC

ACGGAAATGTTGAATACTCATACTCTTCCTTTTTCAATATTATTGAAGCATTTATCAG

GGTTATTGTCTCATGAGCGGATACATATTTGAATGTATTTAGAAAAATAAACAAATA

GGGGTTCCGCGCACATTTCCCCGAAAAGTGCCACCTGACGTCTAAGAAACCATTATT

ATCATGACATTAACCTATAAAAATAGGCGTATCACGAGGCCCTTTCGTCTCGCGCGT

TTCGGTGATGACGGTGAAAACCTCTGACACATGCAGCTCCCGGAGACGGTCACAGC

TTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGA

GTGCACCATATGCGGTGTGAAATACCGCACAGATGCGTAAGGAGAAAATACCGCAT

CAGGAAATTGTAAACGTTAATATTTTGTTAAAATTCGCGTTAAATTTTTGTTAAATC

AGCTCATTTTTTAACCAATAGGCCGAAATCGGCAAAATCCCTTATAAATCAAAAGA

ATAGACCGAGATAGGGTTGAGTGTTGTTCCAGTTTGGAACAAGAGTCCACTATTAA

AGAACGTGGACTCCAACGTCAAAGGGCGAAAAACCGTCTATCAGGGCGATGGCCCA

CTACGTGAACCATCACCCTAATCAAGTTTTTTGGGGTCGAGGTGCCGTAAAGCACTA

AATCGGAACCCTAAAGGGAGCCCCCGATTTAGAGCTTGACGGGGAAAGCCGGCGA

ACGTGGCGAGAAAGGAAGGGAAGAAAGCGAAAGGAGCGGGCGCTAGGGCGCTGG

CAAGTGTAGCGGTCACGCTGCGCGTAACCACCACACCCGCCGCGCTTAATGCGCCG
```

-continued

CTACAGGGCGCGTCGCGCCATTCGCCATTCAGGCTACGCAACTGTTGGGAAGGGCG

ATCGGTGCGGGCCTCTTCGCTATTACGCCAGGCTGC

Example 3: Additional Human OTOF Dual Vector Constructs

Figure 16:
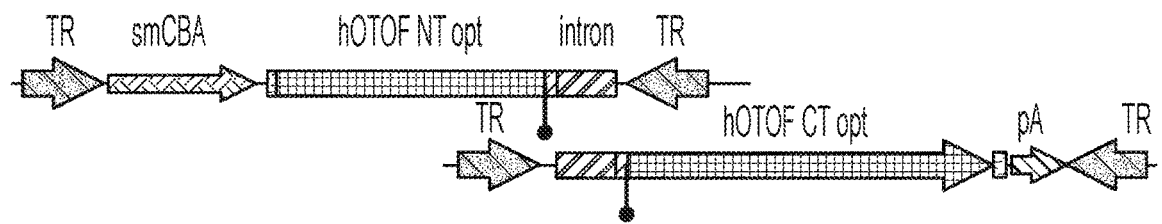
FIG. 16 is a schematic of the two expression cassettes encoding a myc-tagged human Otoferlin cDNA.

Provided below are example dual vectors for expressing human Otoferlin protein. These vectors contain polynucleotides that comprise (a) full-length Otoferlin cDNA ("hOtoferlin") that is codon optimized ("opt") for expression in human cells, (b) Otoferlin cDNA encoding isoform 1 ("V1") and isoform 5 ("V5") that is codon optimized for expression in human cells, and/or (c) sequences encoding myc tags (".myc"). A schematic of the two expression cassettes encoding a myc-tagged human Otoferlin cDNA is shown in FIG. 16. Annotated sequences corresponding to the below vectors are shown in FIGS. 17-21.

pTR-APhead-APSA-hOtoferlin V1-CTopt (SEQ ID NO: 17) (FIG. 17)
pTR-APhead-APSA-hOtoferlin V5-CTopt (SEQ ID NO: 18) (FIG. 18)
pTR-smCBA-hOtoferlinNTopt-APSD-APhead (SEQ ID NO: 19) (FIG. 19)
pTR22-APhead-APSA-hOtoferlinCT.myc (SEQ ID NO: 20) (FIG. 20)
pTR22-smCBA-myc.hOtoferlinNT-APSD-APhead (SEQ ID NO: 21) (FIG. 21)

In some aspects, provided herein are AAV nucleic acid vectors comprising a nucleotide sequence that is at least 80%, at least 85%, at least 90%, at least 95%, at least 98%, or at least 99% identical to the sequence as set forth in SEQ ID NO: 17, as shown in FIG. 17. In some embodiments, the AAV nucleic acid vector comprises a nucleotide sequence comprising the sequence set forth in SEQ ID NO: 17.

In some aspects, provided herein are AAV nucleic acid vectors comprising a nucleotide sequence that is at least 80%, at least 85%, at least 90%, at least 95%, at least 98%, or at least 99% identical to the sequence as set forth in SEQ ID NO: 18, as shown in FIG. 18. In some embodiments, the AAV nucleic acid vector comprises a nucleotide sequence comprising the sequence set forth in SEQ ID NO: 18.

In some aspects, the disclosure provides AAV nucleic acid vectors comprising a nucleotide sequence that is at least 80%, at least 85%, at least 90%, at least 95%, at least 98%, or at least 99% identical to the sequence as set forth in SEQ ID NO: 19, as shown in FIG. 19. In some embodiments, the AAV nucleic acid vector comprises a nucleotide sequence comprising the sequence set forth in SEQ ID NO: 19.

In some aspects, the disclosure provides AAV nucleic acid vectors comprising a nucleotide sequence that is at least 80%, at least 85%, at least 90%, at least 95%, at least 98%, or at least 99% identical to the sequence as set forth in SEQ ID NO: 20, as shown in FIG. 20. In some embodiments, the AAV nucleic acid vector comprises a nucleotide sequence comprising the sequence set forth in SEQ ID NO: 20.

In some aspects, the disclosure provides AAV nucleic acid vectors comprising a nucleotide sequence that is at least 80%, at least 85%, at least 90%, at least 95%, at least 98%, or at least 99% identical to the sequence as set forth in SEQ ID NO: 21, as shown in FIG. 21. In some embodiments, the AAV nucleic acid vector comprises a nucleotide sequence comprising the sequence set forth in SEQ ID NO: 21.

In some aspects, provided herein are one or more compositions comprising an rAAV particle comprising the recombinant AAV nucleic acid vector of any one of SEQ ID NOs: 17-21, or a variant thereof. In some aspects, provided herein are compositions comprising an rAAV particle comprising a recombinant AAV nucleic acid vector having at least 80%, at least 85%, at least 90%, at least 95%, at least 98%, or at least 99% identity to any one of SEQ ID NOs: 17-21.

Also provided herein are compositions comprising a first recombinant AAV nucleic acid vector comprising a nucleotide sequence having at least 90% identity to the sequence set forth in SEQ ID NO: 17, and a second recombinant AAV nucleic acid vector comprising a nucleotide sequence having at least 90% identity to the sequence set forth in SEQ ID NO: 19. Further provided herein are compositions comprising a first recombinant AAV nucleic acid vector comprising a nucleotide sequence having at least 95%, 98%, 99%, or 100% identity to the sequence set forth in SEQ ID NO: 17, and a second recombinant AAV nucleic acid vector comprising a nucleotide sequence having at least 95%, 98%, 99%, or 100% identity to the sequence set forth in SEQ ID NO: 19.

Also provided herein are compositions comprising a first recombinant AAV nucleic acid vector comprising a nucleotide sequence having at least 90% identity to the sequence set forth in SEQ ID NO: 18, and a second recombinant AAV nucleic acid vector comprising a nucleotide sequence having at least 90% identity to the sequence set forth in SEQ ID NO: 19. Further provided herein are compositions comprising a first recombinant AAV nucleic acid vector comprising a nucleotide sequence having at least 95%, 98%, 99%, or 100% identity to the sequence set forth in SEQ ID NO: 18, and a second recombinant AAV nucleic acid vector comprising a nucleotide sequence having at least 95%, 98%, 99%, or 100% identity to the sequence set forth in SEQ ID NO: 19.

Also provided herein are compositions comprising a first recombinant AAV nucleic acid vector comprising a nucleotide sequence having at least 90% identity to the sequence set forth in SEQ ID NO: 20, and a second recombinant AAV nucleic acid vector comprising a nucleotide sequence having at least 90% identity to the sequence set forth in SEQ ID NO: 21. Further provided herein are compositions comprising a first recombinant AAV nucleic acid vector comprising a nucleotide sequence having at least 95%, 98%, 99%, or 100% identity to the sequence set forth in SEQ ID NO: 20, and a second recombinant AAV nucleic acid vector comprising a nucleotide sequence having at least 95%, 98%, 99%, or 100% identity to the sequence set forth in SEQ ID NO: 21.

In various aspects, the above-described compositions are useful for restoring, completely or partially, hearing loss in a subject (e.g. a human subject).

Example 4: Analysis of ABR and Presynaptic Ribbons in Otof$^{-/-}$ Mice on P17 and P30

Figure 22A:
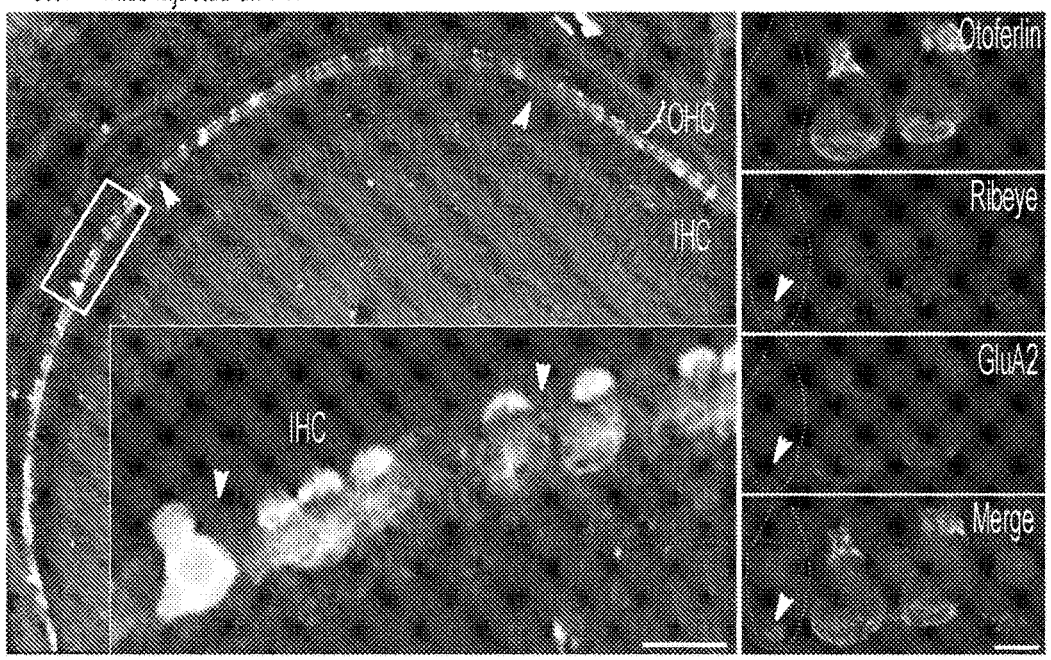
FIG. 22A shows the left organ of *Corti* following dual AAV delivery of the otoferlin cDNA to the left cochlea of Otof$^{-/-}$ mice on P80. Arrowheads indicate non-transduced IHCs. Right panel: the organ of *Corti* was co-immunostained for otoferlin, the ribbon protein ribeye, and GluA2.
Figure 22B:
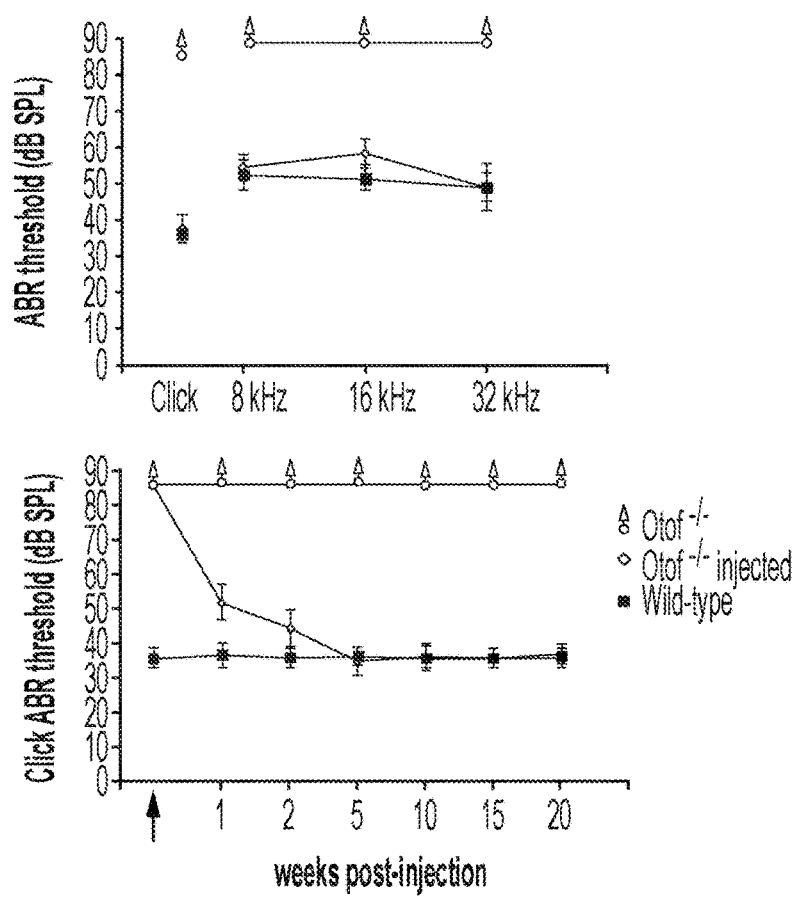
FIG. 22B shows that ABR thresholds of Otof$^{-/-}$ mice (n=5) and wild-type mice (n=5) in response to clicks or tone-burst stimuli at frequencies of 8, 16, and 32 kHz, four weeks after intracochlear injection of the recombinant vector pair in Otof$^{-/-}$ mice on P17; and the time course of hearing recovery in Otof$^{-/-}$ mice injected on P17 (arrow).
Figure 22C:
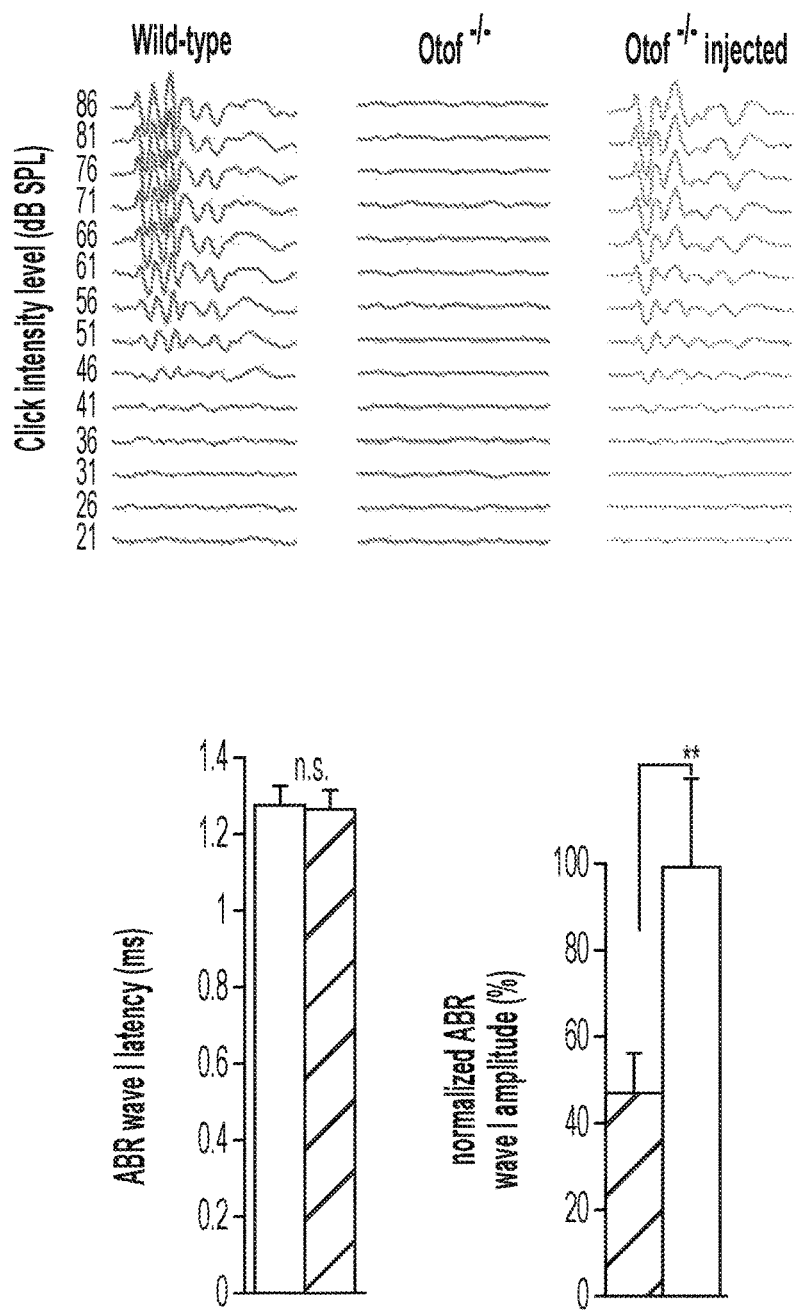
FIG. 22C shows ABR traces in P30 mice, illustrating that the waveforms of the treated Otof$^{-/-}$ mouse are similar to those of a wild-type mouse, whereas no identifiable ABR waves are visible for the untreated Otof$^{-/-}$ mouse; and a bar graph showing that the latency of ABR wave I in treated Otof$^{-/-}$ mice is similar to that in wild-type mice, whereas its amplitude is about half that in wild-type mice.
Figure 23A:
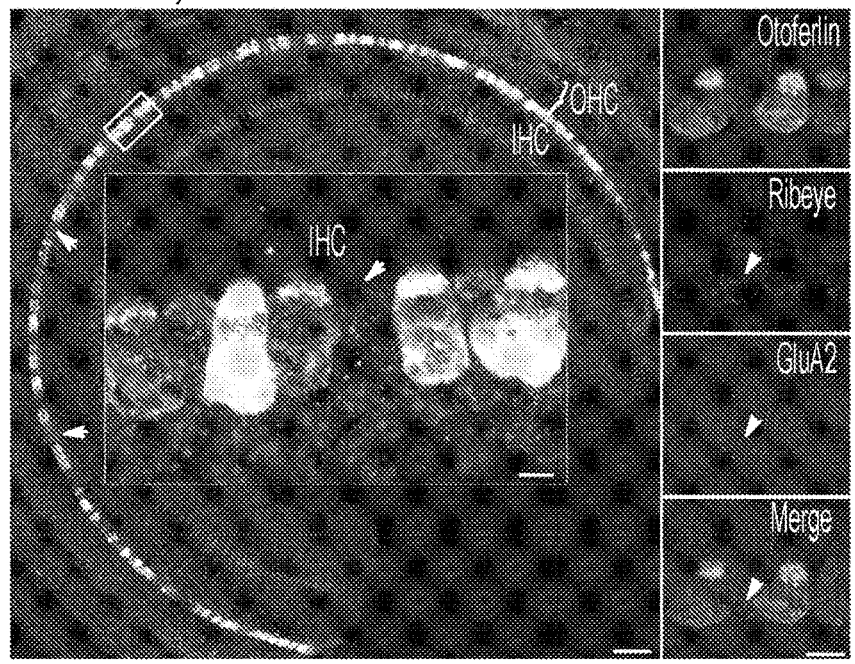
FIG. 23A shows the left sensory epithelium following dual AAV delivery of the otoferlin cDNA to the left cochlea of Otof$^{-/-}$ mice on P40. Arrowheads indicate non-transduced IHCs. Right panel: the organ of *Corti* was co-immunostained for otoferlin, the ribbon protein ribeye, and GluA2.

After injection of the dual AAV otoferlin vector pair into the cochleas of P17 or P30 Otof$^{-/-}$ mice, otoferlin was detected in IHCs throughout the treated cochlea. IHC transduction rates were similar in the two groups of mice (82±9%, n=5, and 85±7%, n=3 cochleas injected on P17 and P30, respectively), and significantly higher than those in mice receiving injections on P10 (64±6%, n=3; Mann-Whitney U test, p=0.01 and p=0.03, respectively) (FIGS. 22A and 23A). ABR recordings four weeks after injection showed hearing recovery in all the mice receiving injections on P17 (n=5), with ABR thresholds in response to clicks or tone-burst stimuli remarkably similar to those in wild-type mice (n=5) (Mann-Whitney U test, p>0.2 for all comparisons). Hearing thresholds in response to clicks remained unchanged for 20 weeks after gene therapy, demonstrating a sustained restoration of hearing in these mice despite mean ABR wave I amplitude at about half that in wild-type mice (47±10%) (FIGS. 22B and 22C).

Figure 23B:
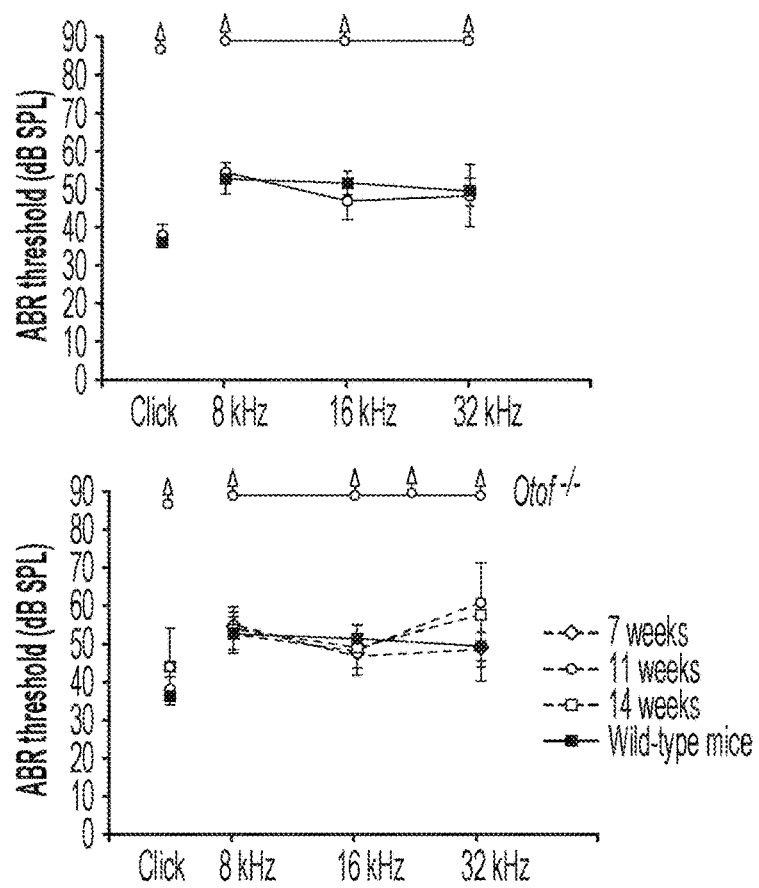
FIG. 23B shows that ABR thresholds of Otof$^{-/-}$ mice (n=3) and wild-type mice (n=3) in response to clicks and tone-burst stimuli at frequencies of 8, 16, and 32 kHz, three weeks after intracochlear injection of the recombinant vector pair in Otof$^{-/-}$ mice on P30; and the time course of hearing recovery in Otof$^{-/-}$ mice (n=3) injected on P30.
Figure 23C:
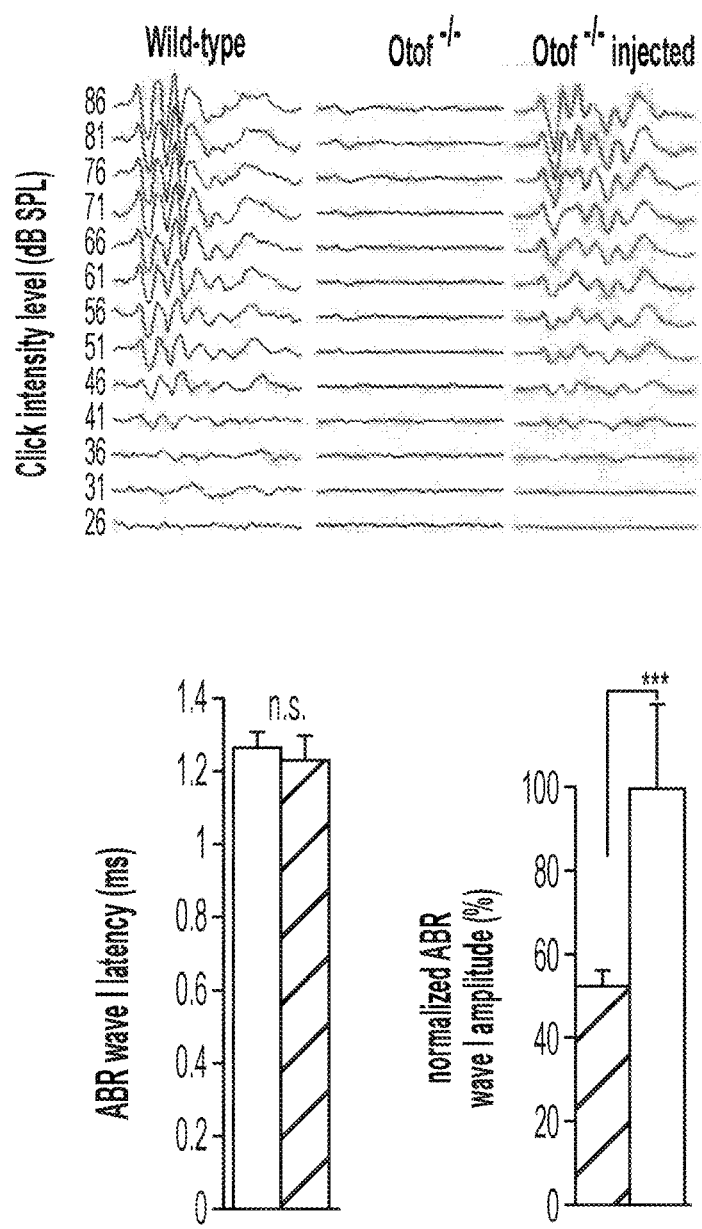
FIG. 23C shows ABR traces in P80 mice, illustrating that the waveforms of the treated Otof$^{-/-}$ mouse are similar to those of a wild-type mouse, whereas no identifiable ABR waves are visible for the untreated Otof$^{-/-}$ mouse; and a bar graph showing that the latency of ABR wave I in treated Otof$^{-/-}$ mice is similar to that in wild-type mice, whereas its amplitude is about half that in wild-type mice.

Likewise, $Otof^{-/-}$ mice receiving injections on P30 displayed a similar recovery of hearing as early as three weeks after the injection, with ABR thresholds persisting at the wild-type level for 14 weeks post-injection (n=3, Mann-Whitney U test, p>0.15 for all comparisons at all stages), despite mean ABR wave I amplitude at about half (55±10%) that in wild-type mice (FIGS. 23B and 23C).

The number of presynaptic auditory ribbons and postsynaptic glutamate receptors in the transduced IHCs of treated cochleas injected on P17 and on P30 were analyzed by immunofluorescence and 3D confocal microscopy imaging (FIGS. 22A and 23A, right panels). In P80 and P40 mice, tile scans of confocal images stitched into a large mosaic covering all the middle and apical cochlear turns shows that most IHCs express otoferlin, whereas other cell types, including outer hair cells (OHC), do not. Ribeye- and GluA2-immunoreactive synaptic active sites have a normal distribution in transduced IHCs producing otoferlin, but tend to form clusters (arrowheads) in non-transduced IHCs (indicated by dashed lines) (FIGS. 22A and 23A).

The numbers of ribbons per transduced IHC were not significantly different in the two groups of treated mice (10.2±0.3, mean±SD, n=87 cells from 3 mice treated on P17 and analyzed on P80, and 8.7±0.4, n=93 cells from 3 mice treated on P30 and analyzed on P40; Mann-Whitney U test, p=0.002). These numbers were both significantly higher than the numbers of ribbons in non-transduced IHCs of the same cochleas (6.3±0.4, n=117 cells, and 5.8±0.2, n=87 cells, for mice treated on P17 and on P30, respectively; Mann-Whitney test, p<0.001 for both comparisons), but they were still lower than those in wild-type mice analyzed on P70 (16±0.4, n=102 cells from 3 mice; Mann-Whitney U test, p<0.001 for both comparisons). The number of ribbons per IHC was already markedly reduced in untreated $Otof^{-/-}$ mice analyzed at P15 (8.2±0.2, n=111 cells from 3 mice) and remained unexpectedly stable in the non-transduced IHCs of treated mice at later stages.

These results demonstrate that a use of more than one AAV construct to deliver different parts of an OTOF cDNA increased the production of ribbons, rather than prevented their degeneration, in the IHCs of $Otof^{-/-}$ mice.

REFERENCES

1) Adato A1, Raskin L, Petit C, Bonne-Tamir B Deafness heterogeneity in a Druze isolate from the Middle East: novel OTOF and PDS mutations, low prevalence of GJB2 35delG mutation and indication for a new DFNB locus. Eur J Hum Genet. 2000 June; 8(6):437-42.
2) Allocca M, Doria M, Petrillo M, Colella P, Garcia-Hoyos M, Gibbs D, Kim S R, Maguire A, Rex T S, Di Vicino U, Cutillo L, Sparrow J R, Williams D S, Bennett J, Auricchio A. Serotype-dependent packaging of large genes in adeno-associated viral vectors results in effective gene delivery in mice. J Clin Invest. 2008 May; 118(5):1955-64.
3) Chaib, H., Place, C., Salem, N., Chardenoux, S., Vincent, C., Weissenbach, J., El-Zir, E., Loiselet, J., Petit, C. A gene responsible for a sensorineural nonsyndromic recessive deafness maps to chromosome 2p22-23. Hum. Molec. Genet. 1996 5: 155-158.
4) Choi, B. Y., Ahmed, Z. M., Riazuddin, S., Bhinder, M. A., Shahzad, M., Husnain, T., Riazuddin, S., Griffith, A. J., Friedman, T. B. Identities and frequencies of mutations of the otoferlin gene (OTOF) causing DFNB9 deafness in Pakistan. Clin. Genet. 2009 75: 237-243.
5) Dong B, Nakai H, Xiao W. Characterization of genome integrity for oversized recombinant AAV vector. Mol Ther. 2010 January; 18(1):87-92.
6) Ghosh A, Yue Y, Duan D. Efficient transgene reconstitution with hybrid dual AAV vectors carrying the minimized bridging sequences. Hum Gene Ther. 2011 January; 22(1):77-83.
7) Hirsch M L, Agbandje-McKenna M, Samulski R J. Little vector, big gene transduction: fragmented genome reassembly of adeno-associated virus. Mol Ther. 2010 January; 18(1):6-8.
8) Lai Y, Yue Y, Duan D. Evidence for the failure of adeno-associated virus serotype 5 to package a viral genome > or =8.2 kb. Mol Ther. 2010 January; 18(1):75-9.
9) Matsunaga T1, Mutai H, Kunishima S, Namba K, Morimoto N, Shinjo Y, Arimoto Y, Kataoka Y, Shintani T, Morita N, Sugiuchi T, Masuda S, Nakano A, Taiji H, Kaga K. A prevalent founder mutation and genotype-phenotype correlations of OTOF in Japanese patients with auditory neuropathy. Clin Genet. 2012 November; 82(5):425-32. doi: 10.1111/j.1399-0004.2012.01897.x. Epub 2012 Jun. 1.
10) Rodríguez-Ballesteros M, del Castillo F J, Martin Y, Moreno-Pelayo M A, Morera C, Prieto F, Marco J, Morant A, Gallo-Terán J, Morales-Angulo C, Navas C, Trinidad G, Tapia M C, Moreno F, del Castillo I. Auditory neuropathy in patients carrying mutations in the otoferlin gene (OTOF). Hum Mutat. 2003 December; 22(6):451-6.
11) Roux I, Safieddine S, Nouvian R, Grati M, Simmler M C, Bahloul A, Perfettini I, Le Gall M, Rostaing P, Hamard G, Triller A, Avan P, Moser T, Petit C. Otoferlin, defective in a human deafness form, is essential for exocytosis at the auditory ribbon synapse. Cell. 2006 Oct. 20; 127(2): 277-89.
12) Wu Z, Yang H, Colosi P. Effect of genome size on AAV vector packaging. Mol Ther. 2010 January; 18(1):80-6.
13) Yasunaga S, Grati M, Chardenoux S, Smith T N, Friedman T B, Lalwani A K, Wilcox E R, Petit C. Am J Hum Genet. OTOF encodes multiple long and short isoforms: genetic evidence that the long ones underlie recessive deafness DFNB9. 2000 September; 67(3):591-600. Epub 2000 Jul. 19.
14) Yasunaga S, Grati M, Cohen-Salmon M, El-Amraoui A, Mustapha M, Salem N, El-Zir E, Loiselet J, Petit C. A mutation in OTOF, encoding otoferlin, a FER-1-like protein, causes DFNB9, a nonsyndromic form of deafness. Nat Genet. 1999 April; 21(4):363-9.
15) Didier Dulon, Saaid Safieddine, Sherri M. Jones, Christine Petit. Otoferlin is Critical for a Highly Sensitive and Linear Calcium Dependent Exocytosis at Vestibular Hair Cell Ribbon Synapses. J Neurosci. 2009 August.

16) Zippora Brownstein, Yoni Bhonker and Karen B Avraham. High-throughput sequencing to decipher the genetic heterogeneity of deafness. Brownstein et al. Genome Biology 2012, 13:245
17) Rodríguez-Ballesteros et al. (2003) "Auditory neuropathy in patients carrying mutations in the otoferlin gene (OTOF)" Hum Mutat.; 22 (6):451-456.
18) Petersen M B, Willems P J: Non-syndromic, autosomal-recessive deafness. Clin Genet. 2006; 69 (5): 371-92.
19) Smith R, Gurrola J, Kelley P. OTOF-Related Deafness. In: Pagon R, Bird T, Dolan C, Stephens K, eds. Gene Reviews. Seattle: Internet; 2008
20) Roux I, Safieddine S, Nouvian R et al. Otoferlin, defective in a human deafness form, is essential for exocytosis at the auditory ribbon synapse. Cell 2006; 127:277-89
21) Kral A, O'Donoghue G M: Profound deafness in childhood. N Engl J Med. 2010; 363(15):1438-50. doi: 10.1056/NEJMra0911225.
22) Dyka F M, Boye S L, Chiodo V A, Hauswirth W W, Boye S E., Dual Adeno-Associated Virus Vectors Result in Efficient In Vitro and In Vivo Expression of an Oversized Gene MY07A, Hum Gene Ther Methods. 2014; 25 (2):166-77. doi: 10.1089/hgtb.2013.212.
23) Akil O, Seal R P, Burke K, Wang C, Alemi A, During M, Edwards R H, Lustig L R: Restoration of hearing in the VGLUT3 knockout mouse using virally mediated gene therapy. Neuron. 2012; 75 (2):283-93. doi: 10.1016/j.neuron.2012.05.019.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A recombinant AAV nucleic acid vector comprising a nucleotide sequence having at least 90% identity to any one of the sequences set forth in SEQ ID NOs: 17-21.

2. A composition comprising an rAAV particle comprising one or more of the recombinant AAV nucleic acid vector of claim 1.

3. The composition of claim 2, wherein the composition comprises a first recombinant AAV nucleic acid vector comprising a nucleotide sequence having at least 90% identity to the sequence set forth in SEQ ID NO: 17 or 18, and a second recombinant AAV nucleic acid vector comprising a nucleotide sequence having at least 90% identity to the sequence set forth in SEQ ID NO: 19.

4. The composition of claim 2, wherein the composition comprises a first recombinant AAV nucleic acid vector comprising a nucleotide sequence having at least 90% identity to the sequence set forth in SEQ ID NO: 20, and a second recombinant AAV nucleic acid vector comprising a nucleotide sequence having at least 90% identity to the sequence set forth in SEQ ID NO: 21.

5. A recombinant AAV nucleic acid vector comprising a nucleotide sequence that comprises any one of the sequences set forth in SEQ ID NOs: 17-21.

6. A recombinant AAV (rAAV) nucleic acid vector comprising a nucleotide sequence having at least 90% identity to the codon optimized portion of any one of the sequences set forth in SEQ ID NOs: 17-19, wherein the codon optimized portion comprises nucleotide positions 565-4152 of SEQ ID NO: 17 or SEQ ID NO: 18, or nucleotide positions 1153-3558 of SEQ ID NO: 19.

7. The rAAV nucleic acid vector of claim 6 comprising the nucleotide sequence of the codon optimized portion of any one of the sequences set forth in SEQ ID NOs: 17-19, wherein the codon optimized portion comprises nucleotide positions 565-4152 of SEQ ID NO: 17 or SEQ ID NO: 18, or nucleotide positions 1153-3558 of SEQ ID NO: 19.

* * * * *

SEQUENCE LISTING

<160> NUMBER OF SEQ ID NOS: 22

<210> SEQ ID NO 1
<211> LENGTH: 7009
<212> TYPE: DNA
<213> ORGANISM: Artificial sequence
<220> FEATURE:
<223> OTHER INFORMATION: pTR22-smCBA-otoferlinNT-APSD-APhead

<400> SEQUENCE: 1

```
agggggggg ggggggggt tggccactcc ctctctgcgc gctcgctcgc tcactgaggc      60
cgggcgacca aaggtcgccc gacgcccggg cttttgcccgg gcggcctcag tgagcgagcg    120
agcgcgcaga gaggagtgg ccaactccat cactaggggt tcctcagatc tggcgcgccc    180
aattcggtac cctagttatt aatagtaatc aattacgggg tcattagttc atagcccata    240
tatggagttc cgcgttacat aacttacggt aaatggcccg cctggctgac cgcccaacga    300 ccccccgccca ttgacgtcaa taatgacgta tgttcccata gtaacgccaa tagggacttt    360
ccattgacgt caatgggtgg actatttacg gtaaactgcc cacttggcag tacatcaagt    420
gtatcatatg ccaagtacgc cccctattga cgtcaatgac ggtaaatggc ccgcctggca    480
ttatgcccag tacatgacct tatgggactt tcctacttgg cagtacatct acgtattagt    540
catcgctatt accatggtcg aggtgagccc cacgttctgc ttcactctcc ccatctcccc    600 ccccctcccca ccccaattt tgtatttatt tattttttaa ttattttgtg cagcgatggg    660 ggcgggggg gggggggggc gcgcgccagg cggggcgggg cggggcgagg ggcggggcgg    720
ggcgaggcga agaggtgcgg cggcagccaa tcagagcggc gcgctccgaa agtttccttt    780
tatggcgagg cggcggcggc ggcggcccta taaaaagcga agcgcgcggc gggcgggagt    840
cgctgcgacg ctgccttcgc cccgtgcccc gctccgcgcc gcctcgcgc cgcccgcccc    900 ggctctgact gaccgcgtta ctcccacagg tgagcgggcg gacggccct tctcctccgg    960 gctgtaatta gcgcttggtt taatgacggc ttgtttcttt tctgtggctg cgtgaaagcc    1020 ttgagggggct ccgggagcta gagcctctgc taaccatgtt catgccttct tctttttcct    1080
acagctcctg ggcaacgtgc tggttattgt gctgtctcat catttggca aagaattcta    1140 gcggccgcca ccatggccct gattgttcac ctcaagactg tctcagagct ccgaggcaaa    1200
ggtgaccgga ttgccaaagt cactttccga gggcagtctt tctactcccg ggtcctggag    1260
aactgcgagg gtgtggctga cttttgatgag acgttccggt ggccagtggc cagcagcatc    1320
gaccggaatg aagtgttgga gattcagatt ttcaactaca gcaaagtctt cagcaacaag    1380
ctgataggga ccttctgcat ggtgctgcag aaagtggtgg aggagaatcg ggtagaggtg    1440
accgacacgc tgatggatga cagcaatgct atcatcaaga ccagcctgag catggaggtc    1500
```

-continued

```
cggtatcagg ccacagatgg cactgtgggc ccctgggatg atggagactt cctgggagat     1560
gaatccctcc aggaggagaa ggacagccag gagacagatg ggctgctacc tggttcccga     1620
cccagcaccc ggatatctgg cgagaagagc tttcgcagca aaggcagaga aagaccaag      1680 ggaggcagag atggcgagca caaagcggga aggagtgtgt tctcggccat gaaactcggc     1740
aaaactcggt cccacaaaga ggagcccaa agacaagatg agccagcagt gctggagatg      1800
gaggacctgg accacctagc cattcagctg ggggatgggc tggatcctga ctccgtgtct     1860
ctagcctcgg tcaccgctct caccagcaat gtctccaaca acggtctaa gccagatatt      1920 aagatggagc ccagtgctgg aaggcccatg gattaccagg tcagcatcac agtgattgag     1980
gctcggcagc tggtgggctt gaacatggac cctgtggtgt gtgtggaggt gggtgatgac     2040
aagaaataca cgtcaatgaa ggagtccaca aactgcccct actacaacga gtactttgtc     2100
ttcgacttcc atgtctctcc tgatgtcatg tttgacaaga tcatcaagat ctcggttatc     2160
cattctaaga acctgcttcg gagcggcacc ctggtgggtt ccttcaaaat ggatgtgggg     2220
actgtgtatt cccagcctga acaccagttc atcacaaat gggccatcct gtcagacccc      2280
gatgacatct tgctgggtt aagggttat gtaaagtgtg atgtcgctgt ggtgggcaag       2340
ggagacaaca tcaagacacc ccacaaggcc aacgagacgg atgaggacga cattgaaggg     2400
aacttgctgc tccccgaggg cgtgcccccc gaacggcagt gggcacggtt ctatgtgaaa     2460
atttaccgag cagagggact gccccggatg aacacaagcc tcatggccaa cgtgaagaag     2520
gcgttcatcg gtgagaacaa ggacctcgtc gaccccatg tgcaagtctt ctttgctgga      2580
caaaagggca aaacatcagt gcagaagagc agctatgagc cgctatggaa tgagcaggtc     2640
gtcttcacag acttgttccc cccactctgc aaacgcatga aggtgcagat ccgggactct     2700
gacaaggtca atgatgtggc catcggcacc cacttcatcg acctgcgcaa gatttccaac     2760
gatggagaca aaggcttcct gcctacccct ggtccagcct gggtgaacat gtacggctcc     2820
acgcgcaact acacactgct ggacgagcac caggacttga atgaaggcct gggggagggt     2880
gtgtccttcc gggcccgcct catgttggga ctagctgtgg agatcctgga cacctccaac     2940
ccagagctca ccagctccac ggaggtgcag gtggagcagg ccacgcctgt ctcggagagc     3000
tgcacaggga gaatggaaga attttttcta tttggagcct tcttggaagc ctcaatgatt     3060
gaccggaaaa atggggacaa gccaattacc tttgaggtga ccataggaaa ctacggcaat     3120
gaagtcgatg gtatgtcccg gcccctgagg cctcggcccc ggaaagagcc tggggatgaa     3180
gaagaggtag acctgattca gaactccagt gacgatgaag gtgacgaagc cggggacctg     3240
gcctcggtgt cctccacccc acctatgcgg ccccagatca cggacaggaa ctatttccac     3300
ctgccctacc tggagcgcaa gccctgcatc tatatcaaga gctggtggcc tgaccagagg     3360
cggcgcctct acaatgccaa catcatggat cacattgctg acaagctgga agaaggcctg     3420
aatgatgtac aggagatgat caaaacggag aagtcctacc ggagcgcccg cctgcgggt      3480 gtgctagagg aactcagctg tggctgccac cgcttcctct ccctctcgga caaggaccag     3540
ggccgctcgt cccgcaccag gctggatcga gagcgtctta agtcctgtat gagggagttg     3600
gtaagtatca aggttacaag acaggtttaa ggagaccaat agaaactggg cttgtcgaga     3660
cagagaagac tcttgcgttt ctgagctagc ccccgggtgc gcggcgtcgg tggtgccggc     3720 gggggggcgcc aggtcgcagg cggtgtaggg ctccaggcag gcggcgaagg ccatgacgtg    3780
cgctatgaag gtctgctcct gcacgccgtg aaccaggtgc gcctgcgggc cgcgcgcgaa     3840
caccgccacg tcctcgcctg cgtgggtctc ttcgtccagg ggcactgctg actgctgccg     3900
```

```
atactcgggg ctcccgctct cgctctcggt aacatccggc cgggcgccgt ccttgagcac    3960
atagcctgga ccgtttcgtc gactgttaat taagcatgct ggggagagat ctaggaaccc    4020
ctagtgatgg agttggccac tccctctctg cgcgctcgct cgctcactga ggccgcccgg    4080
gcaaagcccg ggcgtcgggc gacctttggt cgcccggcct cagtgagcga gcgagcgcgc    4140
agagagggag tggccaaccc cccccccccc cccctgcag ccctgcatta atgaatcggc    4200
caacgcgcgg ggagaggcgg tttgcgtatt gggcgctctt ccgcttcctc gctcactgac    4260
tcgctgcgct cggtcgttcg gctgcggcga gcggtatcag ctcactcaaa ggcggtaata    4320
cggttatcca cagaatcagg ggataacgca ggaaagaaca tgtgagcaaa aggccagcaa    4380
aaggccagga accgtaaaaa ggccgcgttg ctggcgtttt tccataggct ccgcccccct    4440
gacgagcatc acaaaaatcg acgctcaagt cagaggtggc gaaacccgac aggactataa    4500
agataccagg cgtttccccc tggaagctcc ctcgtgcgct ctcctgttcc gaccctgccg    4560
cttaccggat acctgtccgc ctttctccct tcgggaagcg tggcgctttc tcaatgctca    4620
cgctgtaggt atctcagttc ggtgtaggtc gttcgctcca agctgggctg tgtgcacgaa    4680
ccccccgttc agcccgaccg ctgcgcctta tccggtaact atcgtcttga gtccaacccg    4740
gtaagacacg acttatcgcc actggcagca gccactggta acaggattag cagagcgagg    4800
tatgtaggcg gtgctacaga gttcttgaag tggtggccta actacggcta cactagaagg    4860
acagtatttg gtatctgcgc tctgctgaag ccagttacct tcggaaaaag agttggtagc    4920
tcttgatccg gcaaacaaac caccgctggt agcggtggtt ttttggttg caagcagcag    4980 attacgcgca gaaaaaaagg atctcaagaa gatcctttga tcttttctac ggggtctgac    5040
gctcagtgga acgaaaactc acgttaaggg attttggtca tgagattatc aaaaaggatc    5100
ttcacctaga tccttttaaa ttaaaaatga agttttaaat caatctaaag tatatatgag    5160
taaacttggt ctgacagtta ccaatgctta atcagtgagg cacctatctc agcgatctgt    5220
ctatttcgtt catccatagt tgcctgactc cccgtcgtgt agataactac gatacgggag    5280
ggcttaccat ctggccccag tgctgcaatg ataccgcgag acccacgctc accggctcca    5340
gatttatcag caataaacca gccagccgga agggccgagc gcagaagtgg tcctgcaact    5400
ttatccgcct ccatccagtc tattaattgt tgccgggaag ctagagtaag tagttcgcca    5460
gttaatagtt tgcgcaacgt tgttgccatt gctacaggca tcgtggtgtc acgctcgtcg    5520
tttggtatgg cttcattcag ctccggttcc caacgatcaa ggcgagttac atgatccccc    5580
atgttgtgca aaaaagcggt tagctccttc ggtcctccga tcgttgtcag aagtaagttg    5640
gccgcagtgt tatcactcat ggttatggca gcactgcata attctcttac tgtcatgcca    5700
tccgtaagat gcttttctgt gactggtgag tactcaacca agtcattctg agaatagtgt    5760
atgcggcgac cgagttgctc ttgcccggcg tcaatacggg ataataccgc gccacatagc    5820
agaactttaa aagtgctcat cattggaaaa cgttcttcgg ggcgaaaact ctcaaggatc    5880
ttaccgctgt tgagatccag ttcgatgtaa cccactcgtg cacccaactg atcttcagca    5940
tcttttactt tcaccagcgt ttctgggtga gcaaaaacag gaaggcaaaa tgccgcaaaa    6000
aagggaataa gggcgacacg gaaatgttga atactcatac tcttcctttt tcaatattat    6060
tgaagcattt atcagggtta ttgtctcatg agcggataca tatttgaatg tatttagaaa    6120
aataaacaaa tagggggttcc gcgcacattt ccccgaaaag tgccacctga cgtctaagaa    6180
accattatta tcatgacatt aacctataaa aataggcgta tcacgaggcc ctttcgtctc    6240
```

| | | |
|---|---|---|
| gcgcgtttcg gtgatgacgg tgaaaacctc tgacacatgc agctcccgga gacggtcaca | 6300 | |
| gcttgtctgt aagcggatgc cgggagcaga caagcccgtc agggcgcgtc agcgggtgtt | 6360 | |
| ggcgggtgtc ggggctggct taactatgcg gcatcagagc agattgtact gagagtgcac | 6420 | |
| catatgcggt gtgaaatacc gcacagatgc gtaaggagaa ataccgcat caggaaattg | 6480 | |
| taaacgttaa tattttgtta aaattcgcgt taaattttg ttaaatcagc tcatttttta | 6540 | |
| accaataggc cgaaatcggc aaaatccctt ataaatcaaa agaatagacc gagatagggt | 6600 | |
| tgagtgttgt tccagtttgg aacaagagtc cactattaaa gaacgtggac tccaacgtca | 6660 | |
| aagggcgaaa aaccgtctat cagggcgatg gcccactacg tgaaccatca ccctaatcaa | 6720 | |
| gttttttggg gtcgaggtgc cgtaaagcac taaatcggaa ccctaaaggg agcccccgat | 6780 | |
| ttagagcttg acggggaaag ccggcgaacg tggcgagaaa ggaagggaag aaagcgaaag | 6840 | |
| gagcgggcgc tagggcgctg gcaagtgtag cggtcacgct gcgcgtaacc accacacccg | 6900 | |
| ccgcgcttaa tgcgccgcta cagggcgcgt cgcgccattc gccattcagg ctacgcaact | 6960 | |
| gttgggaagg gcgatcggtg cgggcctctt cgctattacg ccaggctgc | 7009 | |

<210> SEQ ID NO 2
<211> LENGTH: 7413
<212> TYPE: DNA
<213> ORGANISM: Artificial sequence
<220> FEATURE:
<223> OTHER INFORMATION: pTR22-APhead-APSA-otoferlinCT

<400> SEQUENCE: 2

| | | |
|---|---|---|
| agggggggggg gggggggggt tggccactcc ctctctgcgc gctcgctcgc tcactgaggc | 60 | |
| cgggcgacca aaggtcgccc gacgcccggg ctttgcccgg gcggcctcag tgagcgagcg | 120 | |
| agcgcgcaga gagggagtgg ccaactccat cactaggggg tcctcagatc tggcgcgccc | 180 | |
| aattggcttc gaattctagc ggccgccccc gggtgcgcgg cgtcggtggt gccggcgggg | 240 | |
| ggcgccaggt cgcaggcggt gtagggctcc aggcaggcgg cgaaggccat gacgtgcgct | 300 | |
| atgaaggtct gctcctgcac gccgtgaacc aggtgcgcct gcgggccgcg cgcgaacacc | 360 | |
| gccacgtcct cgcctgcgtg ggtctcttcg tccaggggca ctgctgactg ctgccgatac | 420 | |
| tcggggctcc cgctctcgct ctcggtaaca tccggccggg cgccgtcctt gagcacatag | 480 | |
| cctggaccgt ttccttaagc gacgcatgct cgcgataggc acctattggt cttactgaca | 540 | |
| tccactttgc ctttctctcc acaggagagc atgggacagc aggccaagag cctgagggct | 600 | |
| caggtgaagc ggcacactgt tcgggacaag ctgaggtcat gccagaactt tctgcagaag | 660 | |
| ctacgcttcc tggcggatga gccccagcac agcattcctg atgtgttcat ttggatgatg | 720 | |
| agcaacaaca aacgtatcgc ctatgcccgc gtgccttcca agacctgct cttctccatc | 780 | |
| gtggaggagg aactgggcaa ggactgcgcc aaagtcaaga ccctcttcct gaagctgcca | 840 | |
| gggaagaggg gcttcggctc ggcaggctgg acagtacagg ccaagctgga gctctacctg | 900 | |
| tggctgggcc tcagcaagca gcgaaaggac ttcctgtgtg gtctgcctg tggcttcgag | 960 | |
| gaggtcaagg cagcccaagg cctgggcctg cattcctttc cgcccatcag cctagtctac | 1020 | |
| accaagaagc aagccttcca gctccgagca cacatgtatc aggcccgaag cctctttgct | 1080 | |
| gctgacagca gtgggctctc tgatcccttt gccgtgtct tcttcatcaa ccagagccaa | 1140 | |
| tgcactgagg ttctaaacga gacactgtgt cccacctggg accagatgct ggtatttgac | 1200 | |
| aacctggagc tgtacggtga agctcacgag ttacgagatg atcccccccat cattgtcatt | 1260 | |
| gaaatctacg accaggacag catgggcaaa gccgacttca tgggccggac cttcgccaag | 1320 | |

```
ccctggtga agatggcaga tgaagcatac tgcccacctc gcttcccgcc gcagcttgag    1380
tactaccaga tctaccgagg cagtgccact gccggagacc tactggctgc cttcgagctg    1440
ctgcagattg ggccatcagg gaaggctgac ctgccaccca tcaatggccc agtggacatg    1500
gacagagggc ccatcatgcc tgtgcccgtg gaatccggc cagtgctcag caagtaccga    1560
gtggaggtgc tgttctgggg cctgagggac ctaaagaggg tgaacctggc ccaggtggac    1620
cgaccacggg tggacatcga gtgtgcagga aagggggtac aatcctccct gattcacaat    1680
tataagaaga accccaactt caacacgctg gtcaagtggt ttgaagtgga cctcccggag    1740
aatgagctcc tgcaccccac cttgaacatc cgagtggtag attgccgggc ctttggacga    1800
tacaccctgg tgggttccca cgcagtcagc tcactgaggc gcttcatcta ccgacctcca    1860
gaccgctcag cccccaactg gaacaccaca ggggaggttg tagtaagcat ggagcctgag    1920
gagccagtta agaagctgga gaccatggtg aaactggatg cgacttctga tgctgtggtc    1980
aaggtggatg tggctgaaga tgagaaggaa aggaagaaga agaaaaagaa aggcccgtca    2040
gaggagccag aggaggaaga gcccgatgag agcatgctgg attggtggtc caagtacttc    2100
gcctccatcg acacaatgaa ggagcaactt cgacaacatg agacctctgg aactgacttg    2160
gaagagaagg aagagatgga aagcgctgag ggcctgaagg accaatgaa gagcaaggag    2220 aagtccagag ctgcaaagga ggagaaaaag aagaaaaacc agagccctgg ccctggccag    2280
ggatcggagg ctcctgagaa gaagaaagcc aagatcgatg agcttaaggt gtaccccaag    2340
gagctggaat cggagtttga cagctttgag gactggctgc acaccttcaa cctgttgagg    2400
ggcaagacgg gagatgatga ggatggctcc acagaggagg agcgcatagt aggccgattc    2460
aagggctccc tctgtgtgta caagtgcca ctcccagaag atgtatctcg agaagctggc    2520
tatgatccca cctatggaat gttccagggc atcccaagca atgaccccat caatgtgctg    2580
gtccgaatct atgtggtccg ggccacagac ctgcacccgg ccgacatcaa tggcaaagct    2640 gaccccctata ttgccatcaa gttaggcaag accgacatcc gagacaagga gaactacatc    2700
tccaagcagc tcaaccctgt gtttgggaag tcctttgaca ttgaggcctc cttccccatg    2760
gagtccatgt tgacagtggc cgtgtacgac tgggatctgg tgggcactga tgacctcatc    2820
ggagaaacca agattgacct ggaaaaccgc ttctacagca gcatcgcgc cacctgcggc    2880 atcgcacaga cctattccat acatggctac aatatctgga gggaccccat gaagcccagc    2940
cagatcctga cacgcctctg taaagagggc aaagtggacg ccccactt tggtccccat    3000 gggagagtga gggttgccaa ccgtgtcttc acggggcctt cagaaataga ggatgagaat    3060
ggtcagagga agcccacaga tgagcacgtg gcactgtctg ctctgagaca ctgggaggac    3120
atcccccggg tgggctgccg ccttgtgccg gaacacgtgg agaccaggcc gctgctcaac    3180
cctgacaagc caggcattga gcagggccgc ctggagctgt gggtggacat gttccccatg    3240
gacatgccag cccctgggac acctctggat atatccccca ggaaacccaa gaagtacgag    3300
ctgcgggtca tcgtgtggaa cacagacgag gtggtcctgg aagacgatga tttcttcacg    3360
ggagagaagt ccagtgacat ttttgtgagg gggtggctga agggccagca ggaggacaaa    3420
caggacacag atgtccacta tcactccctc acggggagg gcaacttcaa ctggagatac    3480
ctcttcccct tcgactacct agcggccgaa gagaagatcg ttatgtccaa aaaggagtct    3540
atgttctcct gggatgagac ggagtacaag atccctgcgc ggctcaccct gcagatctgg    3600
gacgctgacc acttctcggc tgacgacttc ctggggcta tcgagctgga cctgaaccgg    3660
```

```
ttcccgaggg gcgctaagac agccaagcag tgcaccatgg agatggccac cggggaggtg     3720
gacgtacccc tggtttccat ctttaaacag aaacgtgtca aaggctggtg gccctcctg     3780 gcccgcaatg agaatgatga gtttgagctc acaggcaaag tggaggcgga gctacaccta     3840
ctcacggcag aggaggcaga gaagaaccct gtgggcctgg ctcgcaatga acctgatccc     3900
ctagaaaaac ccaaccggcc tgacacggca ttcgtctggt tcctgaaccc actcaaatct     3960
atcaagtacc tcatctgcac ccggtacaag tggctgatca tcaagatcgt gctgcgctg     4020 ctggggctgc tcatgctggc cctcttcctt tacagcctcc caggctacat ggtcaagaag     4080
ctcctagggg cctgagcggc cgcggtacca agggcgaatt ctgcagtcga ctagagctcg     4140
ctgatcagcc tcgactgtgc cttctagttg ccagccatct gttgtttgcc cctcccccgt     4200
gccttccttg accctggaag gtgccactcc cactgtcctt tcctaataaa atgaggaaat     4260
tgcatcgcat tgtctgagta ggtgtcattc tattctgggg ggtggggtgg ggcaggacag     4320
caagggggag gattgggaag acaatagcag gcatgctggg gagagatctg aggactagtc     4380
cgtcgactgt taattaagca tgctggggag agatctagga cccctagtg atggagttgg     4440 ccactccctc tctgcgcgct cgctcgctca ctgaggccgc ccgggcaaag cccgggcgtc     4500
gggcgacctt tggtcgcccg gcctcagtga gcgagcgagc gcgcagagag ggagtggcca     4560 acccccccc ccccccccct gcagccctgc attaatgaat cggccaacgc gcggggagag     4620
gcggtttgcg tattgggcgc tcttccgctt cctcgctcac tgactcgctg cgctcggtcg     4680
ttcggctgcg gcgagcggta tcagctcact caaaggcggt aatacggtta tccacagaat     4740
caggggataa cgcaggaaag aacatgtgag caaaaggcca gcaaaaggcc aggaaccgta     4800
aaaaggccgc gttgctggcg ttttccata ggctccgccc ccctgacgag catcacaaaa     4860
atcgacgctc aagtcagagg tggcgaaacc cgacaggact ataaagatac caggcgtttc     4920
cccctggaag ctccctcgtg cgctctcctg ttccgaccct gccgcttacc ggatacctgt     4980
ccgcctttct cccttcggga agcgtggcgc tttctcaatg ctcacgctgt aggtatctca     5040
gttcggtgta ggtcgttcgc tccaagctgg gctgtgtgca cgaaccccc gttcagcccg     5100 accgctgcgc cttatccggt aactatcgtc ttgagtccaa cccggtaaga cacgacttat     5160
cgccactggc agcagccact ggtaacagga ttagcagagc gaggtatgta ggcggtgcta     5220
cagagttctt gaagtggtgg cctaactacg gctacactag aaggacagta tttggtatct     5280
gcgctctgct gaagccagtt accttcggaa aaagagttgg tagctcttga tccggcaaac     5340
aaaccaccgc tggtagcggt ggtttttttg tttgcaagca gcagattacg cgcagaaaaa     5400
aaggatctca agaagatcct ttgatctttt ctacgggtc tgacgctcag tggaacgaaa     5460
actcacgtta agggattttg gtcatgagat tatcaaaaag gatcttcacc tagatccttt     5520
taaattaaaa atgaagtttt aaatcaatct aaagtatata tgagtaaact tggtctgaca     5580
gttaccaatg cttaatcagt gaggcaccta tctcagcgat ctgtctattt cgttcatcca     5640
tagttgcctg actccccgtc gtgtagataa ctacgatacg ggagggctta ccatctggcc     5700
ccagtgctgc aatgataccg cgagacccac gctcaccggc tccagattta tcagcaataa     5760
accagccagc cggaagggcc gagcgcagaa gtggtcctgc aactttatcc gcctccatcc     5820
agtctattaa ttgttgccgg gaagctagag taagtagttc gccagttaat agtttgcgca     5880
acgttgttgc cattgctaca ggcatcgtgg tgtcacgctc gtcgtttggt atggcttcat     5940
tcagctccgg ttcccaacga tcaaggcgag ttacatgatc cccatgttg tgcaaaaaag     6000 cggttagctc cttcggtcct ccgatcgttg tcagaagtaa gttggccgca gtgttatcac     6060
```

```
tcatggttat ggcagcactg cataattctc ttactgtcat gccatccgta agatgctttt   6120
ctgtgactgg tgagtactca accaagtcat tctgagaata gtgtatgcgg cgaccgagtt   6180
gctcttgccc ggcgtcaata cgggataata ccgcgccaca tagcagaact ttaaaagtgc   6240
tcatcattgg aaaacgttct cggggcgaaa actctcaag gatcttaccg ctgttgagat   6300
ccagttcgat gtaacccact cgtgcaccca actgatcttc agcatctttt actttcacca   6360
gcgtttctgg gtgagcaaaa acaggaaggc aaaatgccgc aaaaaaggga ataagggcga   6420
cacggaaatg ttgaatactc atactcttcc tttttcaata ttattgaagc atttatcagg   6480
gttattgtct catgagcgga tacatatttg aatgtattta aaaaataaa caaatagggg   6540 ttccgcgcac atttccccga aaagtgccac ctgacgtcta agaaaccatt attatcatga   6600
cattaaccta taaaaatagg cgtatcacga ggccctttcg tctcgcgcgt ttcggtgatg   6660
acggtgaaaa cctctgacac atgcagctcc cggagacggt cacagcttgt ctgtaagcgg   6720
atgccgggag cagacaagcc cgtcaggcg cgtcagcggg tgttggcggg tgtcggggct   6780
ggcttaacta tgcggcatca gagcagattg tactgagagt gcaccatatg cggtgtgaaa   6840
taccgcacag atgcgtaagg agaaaatacc gcatcaggaa attgtaaacg ttaatatttt   6900
gttaaaattc gcgttaaatt tttgttaaat cagctcattt tttaaccaat aggccgaaat   6960
cggcaaaatc ccttataaat caaaagaata accgagata gggttgagtg ttgttccagt   7020
ttggaacaag agtccactat taaagaacgt ggactccaac gtcaaagggc gaaaaccgt   7080 ctatcagggc gatggcccac tacgtgaacc atcaccctaa tcaagttttt tggggtcgag   7140
gtgccgtaaa gcactaaatc ggaaccctaa agggagcccc cgatttagag cttgacgggg   7200
aaagccggcg aacgtggcga gaaggaagg gaagaaagcg aaaggagcgg cgctagggc   7260 gctggcaagt gtagcggtca cgctgcgcgt aaccaccaca cccgccgcgc ttaatgcgcc   7320
gctacagggc gcgtcgcgcc attcgccatt caggctacgc aactgttggg aagggcgatc   7380
ggtgcgggcc tcttcgctat tacgccaggc tgc                                7413

<210> SEQ ID NO 3
<211> LENGTH: 287
<212> TYPE: DNA
<213> ORGANISM: Artificial sequence
<220> FEATURE:
<223> OTHER INFORMATION: Synthetic polynucleotide

<400> SEQUENCE: 3
ccccgggtgc gcggcgtcgg tggtgccggc gggggcgcc aggtcgcagg cggtgtaggg     60
ctccaggcag gcggcgaagg ccatgacgtg cgctatgaag gtctgctcct gcacgccgtg   120
aaccaggtgc gcctgcgggc gcgcgcgaa caccgccacg tcctcgcctg cgtgggtctc   180
ttcgtccagg ggcactgctg actgctgccg atactcgggg ctcccgctct cgctctcggt   240
aacatccggc cgggcgccgt ccttgagcac atagcctgga ccgtttc                 287

<210> SEQ ID NO 4
<211> LENGTH: 650
<212> TYPE: DNA
<213> ORGANISM: Artificial sequence
<220> FEATURE:
<223> OTHER INFORMATION: Synthetic polynucleotide

<400> SEQUENCE: 4
ggtaccctag ttattaatag taatcaatta cggggtcatt agttcatagc ccatatatgg    60
```

```
agttccgcgt tacataactt acggtaaatg gcccgcctgg ctgaccgccc aacgaccccc    120
gcccattgac gtcaataatg acgtatgttc ccatagtaac gccaataggg actttccatt    180
gacgtcaatg ggtggactat ttacggtaaa ctgcccactt ggcagtacat caagtgtatc    240
atatgccaag tacgccccct attgacgtca atgacggtaa atggcccgcc tggcattatg    300
cccagtacat gaccttatgg gactttccta cttggcagta catctacgta ttagtcatcg    360
ctattaccat ggtcgaggtg agccccacgt tctgcttcac tctccccatc tcccccccct    420
ccccaccccc aattttgtat ttatttattt tttaattatt ttgtgcagcg atggggggcgg    480 ggggggggggg gggcgcgcg ccaggcgggg cgggcgggg cgaggggcgg ggcggggcga    540
ggcggagagg tgcggcggca gccaatcaga gcggcgcgct ccgaaagttt ccttttatgg    600
cgaggcggcg gcggcggcgg ccctataaaa agcgaagcgc gcggcgggcg              650
```

<210> SEQ ID NO 5
<211> LENGTH: 1997
<212> TYPE: PRT
<213> ORGANISM: H. sapiens

<400> SEQUENCE: 5

```
Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
        195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
            260                 265                 270
```

-continued

Pro Val Val Cys Val Glu Val Gly Asp Asp Lys Lys Tyr Thr Ser Met
        275                 280             285

Lys Glu Ser Thr Asn Cys Pro Tyr Tyr Asn Glu Tyr Phe Val Phe Asp
    290             295             300

Phe His Val Ser Pro Asp Val Met Phe Asp Lys Ile Ile Lys Ile Ser
305             310             315                 320

Val Ile His Ser Lys Asn Leu Leu Arg Ser Gly Thr Leu Val Gly Ser
            325             330              335

Phe Lys Met Asp Val Gly Thr Val Tyr Ser Gln Pro Glu His Gln Phe
            340             345             350

His His Lys Trp Ala Ile Leu Ser Asp Pro Asp Asp Ile Ser Ser Gly
        355             360             365

Leu Lys Gly Tyr Val Lys Cys Asp Val Ala Val Gly Lys Gly Asp
    370             375             380

Asn Ile Lys Thr Pro His Lys Ala Asn Glu Thr Asp Glu Asp Ile
385             390             395             400

Glu Gly Asn Leu Leu Pro Glu Gly Val Pro Pro Glu Arg Gln Trp
            405             410             415

Ala Arg Phe Tyr Val Lys Ile Tyr Arg Ala Glu Gly Leu Pro Arg Met
        420             425             430

Asn Thr Ser Leu Met Ala Asn Val Lys Lys Ala Phe Ile Gly Glu Asn
        435             440             445

Lys Asp Leu Val Asp Pro Tyr Val Gln Val Phe Phe Ala Gly Gln Lys
    450             455             460

Gly Lys Thr Ser Val Gln Lys Ser Ser Tyr Glu Pro Leu Trp Asn Glu
465             470             475             480

Gln Val Val Phe Thr Asp Leu Phe Pro Pro Leu Cys Lys Arg Met Lys
            485             490             495

Val Gln Ile Arg Asp Ser Asp Lys Val Asn Asp Val Ala Ile Gly Thr
        500             505             510

His Phe Ile Asp Leu Arg Lys Ile Ser Asn Asp Gly Asp Lys Gly Phe
    515             520             525

Leu Pro Thr Leu Gly Pro Ala Trp Val Asn Met Tyr Gly Ser Thr Arg
    530             535             540

Asn Tyr Thr Leu Leu Asp Glu His Gln Asp Leu Asn Glu Gly Leu Gly
545             550             555             560

Glu Gly Val Ser Phe Arg Ala Arg Leu Leu Gly Leu Ala Val Glu
            565             570             575

Ile Val Asp Thr Ser Asn Pro Glu Leu Thr Ser Ser Thr Glu Val Gln
        580             585             590

Val Glu Gln Ala Thr Pro Ile Ser Glu Ser Cys Ala Gly Lys Met Glu
        595             600             605

Glu Phe Phe Leu Phe Gly Ala Phe Leu Glu Ala Ser Met Ile Asp Arg
    610             615             620

Arg Asn Gly Asp Lys Pro Ile Thr Phe Glu Val Thr Ile Gly Asn Tyr
625             630             635             640

Gly Asn Glu Val Asp Gly Leu Ser Arg Pro Gln Arg Pro Arg Pro Arg
            645             650             655

Lys Glu Pro Gly Asp Glu Glu Val Asp Leu Ile Gln Asn Ala Ser
            660             665             670

Asp Asp Glu Ala Gly Asp Ala Gly Asp Leu Ala Ser Val Ser Ser Thr
            675             680             685

Pro Pro Met Arg Pro Gln Val Thr Asp Arg Asn Tyr Phe His Leu Pro

```
              690             695             700
Tyr Leu Glu Arg Lys Pro Cys Ile Tyr Ile Lys Ser Trp Trp Pro Asp
705             710             715             720

Gln Arg Arg Arg Leu Tyr Asn Ala Asn Ile Met Asp His Ile Ala Asp
            725             730             735

Lys Leu Glu Glu Gly Leu Asn Asp Ile Gln Glu Met Ile Lys Thr Glu
            740             745             750

Lys Ser Tyr Pro Glu Arg Arg Leu Arg Gly Val Leu Glu Glu Leu Ser
            755             760             765

Cys Gly Cys Cys Arg Phe Leu Ser Leu Ala Asp Lys Asp Gln Gly His
            770             775             780

Ser Ser Arg Thr Arg Leu Asp Arg Glu Arg Leu Lys Ser Cys Met Arg
785             790             795             800

Glu Leu Glu Asn Met Gly Gln Gln Ala Arg Met Leu Arg Ala Gln Val
            805             810             815

Lys Arg His Thr Val Arg Asp Lys Leu Arg Leu Cys Gln Asn Phe Leu
            820             825             830

Gln Lys Leu Arg Phe Leu Ala Asp Glu Pro Gln His Ser Ile Pro Asp
            835             840             845

Ile Phe Ile Trp Met Met Ser Asn Asn Lys Arg Val Ala Tyr Ala Arg
850             855             860

Val Pro Ser Lys Asp Leu Leu Phe Ser Ile Val Glu Glu Thr Gly
865             870             875             880

Lys Asp Cys Ala Lys Val Lys Thr Leu Phe Leu Lys Leu Pro Gly Lys
            885             890             895

Arg Gly Phe Gly Ser Ala Gly Trp Thr Val Gln Ala Lys Val Glu Leu
            900             905             910

Tyr Leu Trp Leu Gly Leu Ser Lys Gln Arg Lys Glu Phe Leu Cys Gly
            915             920             925

Leu Pro Cys Gly Phe Gln Glu Val Lys Ala Ala Gln Gly Leu Gly Leu
            930             935             940

His Ala Phe Pro Pro Val Ser Leu Val Tyr Thr Lys Lys Gln Ala Phe
945             950             955             960

Gln Leu Arg Ala His Met Tyr Gln Ala Arg Ser Leu Phe Ala Ala Asp
            965             970             975

Ser Ser Gly Leu Ser Asp Pro Phe Ala Arg Val Phe Phe Ile Asn Gln
            980             985             990

Ser Gln Cys Thr Glu Val Leu Asn Glu Thr Leu Cys Pro Thr Trp Asp
            995             1000            1005

Gln Met Leu Val Phe Asp Asn Leu Glu Leu Tyr Gly Glu Ala His
    1010            1015            1020

Glu Leu Arg Asp Asp Pro Pro Ile Ile Val Ile Glu Ile Tyr Asp
    1025            1030            1035

Gln Asp Ser Met Gly Lys Ala Asp Phe Met Gly Arg Thr Phe Ala
    1040            1045            1050

Lys Pro Leu Val Lys Met Ala Asp Glu Ala Tyr Cys Pro Pro Arg
    1055            1060            1065

Phe Pro Pro Gln Leu Glu Tyr Tyr Gln Ile Tyr Arg Gly Asn Ala
    1070            1075            1080

Thr Ala Gly Asp Leu Leu Ala Ala Phe Glu Leu Leu Gln Ile Gly
    1085            1090            1095

Pro Ala Gly Lys Ala Asp Leu Pro Pro Ile Asn Gly Pro Val Asp
    1100            1105            1110
```

-continued

```
Val Asp Arg Gly Pro Ile Met Pro Val Pro Met Gly Ile Arg Pro
1115                1120                1125

Val Leu Ser Lys Tyr Arg Val Glu Val Leu Phe Trp Gly Leu Arg
1130                1135                1140

Asp Leu Lys Arg Val Asn Leu Ala Gln Val Asp Arg Pro Arg Val
1145                1150                1155

Asp Ile Glu Cys Ala Gly Lys Gly Val Gln Ser Ser Leu Ile His
1160                1165                1170

Asn Tyr Lys Lys Asn Pro Asn Phe Asn Thr Leu Val Lys Trp Phe
1175                1180                1185

Glu Val Asp Leu Pro Glu Asn Glu Leu Leu His Pro Pro Leu Asn
1190                1195                1200

Ile Arg Val Val Asp Cys Arg Ala Phe Gly Arg Tyr Thr Leu Val
1205                1210                1215

Gly Ser His Ala Val Ser Ser Leu Arg Arg Phe Ile Tyr Arg Pro
1220                1225                1230

Pro Asp Arg Ser Ala Pro Ser Trp Asn Thr Thr Val Arg Leu Leu
1235                1240                1245

Arg Arg Cys Arg Val Leu Cys Asn Gly Gly Ser Ser Ser His Ser
1250                1255                1260

Thr Gly Glu Val Val Thr Met Glu Pro Glu Val Pro Ile Lys
1265                1270                1275

Lys Leu Glu Thr Met Val Lys Leu Asp Ala Thr Ser Glu Ala Val
1280                1285                1290

Val Lys Val Asp Val Ala Glu Glu Lys Glu Lys Lys Lys
1295                1300                1305

Lys Lys Gly Thr Ala Glu Glu Pro Glu Glu Glu Pro Asp Glu
1310                1315                1320

Ser Met Leu Asp Trp Trp Ser Lys Tyr Phe Ala Ser Ile Asp Thr
1325                1330                1335

Met Lys Glu Gln Leu Arg Gln Gln Glu Pro Ser Gly Ile Asp Leu
1340                1345                1350

Glu Glu Lys Glu Glu Val Asp Asn Thr Glu Gly Leu Lys Gly Ser
1355                1360                1365

Met Lys Gly Lys Glu Lys Ala Arg Ala Ala Lys Glu Glu Lys Lys
1370                1375                1380

Lys Lys Thr Gln Ser Ser Gly Ser Gly Gln Gly Ser Glu Ala Pro
1385                1390                1395

Glu Lys Lys Lys Pro Lys Ile Asp Glu Leu Lys Val Tyr Pro Lys
1400                1405                1410

Glu Leu Glu Ser Glu Phe Asp Asn Phe Glu Asp Trp Leu His Thr
1415                1420                1425

Phe Asn Leu Leu Arg Gly Lys Thr Gly Asp Asp Glu Asp Gly Ser
1430                1435                1440

Thr Glu Glu Arg Ile Val Gly Arg Phe Lys Gly Ser Leu Cys
1445                1450                1455

Val Tyr Lys Val Pro Leu Pro Glu Asp Val Ser Arg Glu Ala Gly
1460                1465                1470

Tyr Asp Ser Thr Tyr Gly Met Phe Gln Gly Ile Pro Ser Asn Asp
1475                1480                1485

Pro Ile Asn Val Leu Val Arg Val Tyr Val Val Arg Ala Thr Asp
1490                1495                1500
```

```
Leu His Pro Ala Asp Ile Asn  Gly Lys Ala Asp Pro  Tyr Ile Ala
    1505                1510                 1515

Ile Arg Leu Gly Lys Thr Asp  Ile Arg Asp Lys Glu  Asn Tyr Ile
    1520                1525                 1530

Ser Lys Gln Leu Asn Pro Val  Phe Gly Lys Ser Phe  Asp Ile Glu
    1535                1540                 1545

Ala Ser Phe Pro Met Glu Ser  Met Leu Thr Val Ala  Val Tyr Asp
    1550                1555                 1560

Trp Asp Leu Val Gly Thr Asp  Asp Leu Ile Gly Glu  Thr Lys Ile
    1565                1570                 1575

Asp Leu Glu Asn Arg Phe Tyr  Ser Lys His Arg Ala  Thr Cys Gly
    1580                1585                 1590

Ile Ala Gln Thr Tyr Ser Thr  His Gly Tyr Asn Ile  Trp Arg Asp
    1595                1600                 1605

Pro Met Lys Pro Ser Gln Ile  Leu Thr Arg Leu Cys  Lys Asp Gly
    1610                1615                 1620

Lys Val Asp Gly Pro His Phe  Gly Pro Pro Gly Arg  Val Lys Val
    1625                1630                 1635

Ala Asn Arg Val Phe Thr Gly  Pro Ser Glu Ile Glu  Asp Glu Asn
    1640                1645                 1650

Gly Gln Arg Lys Pro Thr Asp  Glu His Val Ala Leu  Leu Ala Leu
    1655                1660                 1665

Arg His Trp Glu Asp Ile Pro  Arg Ala Gly Cys Arg  Leu Val Pro
    1670                1675                 1680

Glu His Val Glu Thr Arg Pro  Leu Leu Asn Pro Asp  Lys Pro Gly
    1685                1690                 1695

Ile Glu Gln Gly Arg Leu Glu  Leu Trp Val Asp Met  Phe Pro Met
    1700                1705                 1710

Asp Met Pro Ala Pro Gly Thr  Pro Leu Asp Ile Ser  Pro Arg Lys
    1715                1720                 1725

Pro Lys Lys Tyr Glu Leu Arg  Val Ile Ile Trp Asn  Thr Asp Glu
    1730                1735                 1740

Val Val Leu Glu Asp Asp Asp  Phe Phe Thr Gly Glu  Lys Ser Ser
    1745                1750                 1755

Asp Ile Phe Val Arg Gly Trp  Leu Lys Gly Gln Gln  Glu Asp Lys
    1760                1765                 1770

Gln Asp Thr Asp Val His Tyr  His Ser Leu Thr Gly  Glu Gly Asn
    1775                1780                 1785

Phe Asn Trp Arg Tyr Leu Phe  Pro Phe Asp Tyr Leu  Ala Ala Glu
    1790                1795                 1800

Glu Lys Ile Val Ile Ser Lys  Lys Glu Ser Met Phe  Ser Trp Asp
    1805                1810                 1815

Glu Thr Glu Tyr Lys Ile Pro  Ala Arg Leu Thr Leu  Gln Ile Trp
    1820                1825                 1830

Asp Ala Asp His Phe Ser Ala  Asp Asp Phe Leu Gly  Ala Ile Glu
    1835                1840                 1845

Leu Asp Leu Asn Arg Phe Pro  Arg Gly Ala Lys Thr  Ala Lys Gln
    1850                1855                 1860

Cys Thr Met Glu Met Ala Thr  Gly Glu Val Asp Val  Pro Leu Val
    1865                1870                 1875

Ser Ile Phe Lys Gln Lys Arg  Val Lys Gly Trp Trp  Pro Leu Leu
    1880                1885                 1890

Ala Arg Asn Glu Asn Asp Glu  Phe Glu Leu Thr Gly  Lys Val Glu
```

```
            1895                1900                1905
Ala Glu Leu His Leu Leu Thr Ala Glu Glu Ala Glu Lys Asn Pro
        1910                1915                1920

Val Gly Leu Ala Arg Asn Glu Pro Asp Pro Leu Glu Lys Pro Asn
    1925                1930                1935

Arg Pro Asp Thr Ser Phe Ile Trp Phe Leu Asn Pro Leu Lys Ser
    1940                1945                1950

Ala Arg Tyr Phe Leu Trp His Thr Tyr Arg Trp Leu Leu Leu Lys
    1955                1960                1965

Leu Leu Leu Leu Leu Leu Leu Leu Leu Leu Ala Leu Phe Leu
    1970                1975                1980

Tyr Ser Val Pro Gly Tyr Leu Val Lys Lys Ile Leu Gly Ala
    1985                1990                1995

<210> SEQ ID NO 6
<211> LENGTH: 1997
<212> TYPE: PRT
<213> ORGANISM: H. sapiens

<400> SEQUENCE: 6

Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Gly Glu Pro Gln
            180                 185                 190

Arg Pro Asp Glu Pro Ala Val Leu Glu Met Glu Asp Leu Asp His Leu
        195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
            260                 265                 270
```

```
Pro Val Val Cys Val Glu Val Gly Asp Asp Lys Lys Tyr Thr Ser Met
            275                 280                 285

Lys Glu Ser Thr Asn Cys Pro Tyr Tyr Asn Glu Tyr Phe Val Phe Asp
        290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Asp Ile Ser Ser Gly
        355                 360                 365

Leu Lys Gly Tyr Val Lys Cys Asp Val Ala Val Val Gly Lys Gly Asp
    370                 375                 380

Asn Ile Lys Thr Pro His Lys Ala Asn Glu Thr Asp Glu Asp Asp Ile
385                 390                 395                 400

Glu Gly Asn Leu Leu Pro Glu Gly Val Pro Pro Glu Arg Gln Trp
                405                 410                 415

Ala Arg Phe Tyr Val Lys Ile Tyr Arg Ala Glu Gly Leu Pro Arg Met
            420                 425                 430

Asn Thr Ser Leu Met Ala Asn Val Lys Lys Ala Phe Ile Gly Glu Asn
        435                 440                 445

Lys Asp Leu Val Asp Pro Tyr Val Gln Val Phe Phe Ala Gly Gln Lys
    450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
            500                 505                 510

His Phe Ile Asp Leu Arg Lys Ile Ser Asn Asp Gly Asp Lys Gly Phe
        515                 520                 525

Leu Pro Thr Leu Gly Pro Ala Trp Val Asn Met Tyr Gly Ser Thr Arg
    530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Leu Gly Leu Ala Val Glu
                565                 570                 575

Ile Val Asp Thr Ser Asn Pro Glu Leu Thr Ser Ser Thr Glu Val Gln
            580                 585                 590

Val Glu Gln Ala Thr Pro Ile Ser Glu Ser Cys Ala Gly Lys Met Glu
        595                 600                 605

Glu Phe Phe Leu Phe Gly Ala Phe Leu Glu Ala Ser Met Ile Asp Arg
    610                 615                 620

Arg Asn Gly Asp Lys Pro Ile Thr Phe Glu Val Thr Ile Gly Asn Tyr
625                 630                 635                 640

Gly Asn Glu Val Asp Gly Leu Ser Arg Pro Gln Arg Pro Arg Pro Arg
                645                 650                 655

Lys Glu Pro Gly Asp Glu Glu Val Asp Leu Ile Gln Asn Ala Ser
            660                 665                 670

Asp Asp Glu Ala Gly Asp Ala Gly Asp Leu Ala Ser Val Ser Ser Thr
        675                 680                 685

Pro Pro Met Arg Pro Gln Val Thr Asp Arg Asn Tyr Phe His Leu Pro
```

```
              690                 695                 700
Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                725                 730                 735

Lys Leu Glu Glu Gly Leu Asn Asp Ile Gln Glu Met Ile Lys Thr Glu
                740                 745                 750

Lys Ser Tyr Pro Glu Arg Arg Leu Arg Gly Val Leu Glu Glu Leu Ser
                755                 760                 765

Cys Gly Cys Cys Arg Phe Leu Ser Leu Ala Asp Lys Asp Gln Gly His
            770                 775                 780

Ser Ser Arg Thr Arg Leu Asp Arg Glu Arg Leu Lys Ser Cys Met Arg
785                 790                 795                 800

Glu Leu Glu Asn Met Gly Gln Gln Ala Arg Met Leu Arg Ala Gln Val
                805                 810                 815

Lys Arg His Thr Val Arg Asp Lys Leu Arg Leu Cys Gln Asn Phe Leu
                820                 825                 830

Gln Lys Leu Arg Phe Leu Ala Asp Glu Pro Gln His Ser Ile Pro Asp
                835                 840                 845

Ile Phe Ile Trp Met Met Ser Asn Asn Lys Arg Val Ala Tyr Ala Arg
850                 855                 860

Val Pro Ser Lys Asp Leu Leu Phe Ser Ile Val Glu Glu Thr Gly
865                 870                 875                 880

Lys Asp Cys Ala Lys Val Lys Thr Leu Phe Leu Lys Leu Pro Gly Lys
                885                 890                 895

Arg Gly Phe Gly Ser Ala Gly Trp Thr Val Gln Ala Lys Val Glu Leu
                900                 905                 910

Tyr Leu Trp Leu Gly Leu Ser Lys Gln Arg Lys Glu Phe Leu Cys Gly
                915                 920                 925

Leu Pro Cys Gly Phe Gln Glu Val Lys Ala Ala Gln Gly Leu Gly Leu
            930                 935                 940

His Ala Phe Pro Pro Val Ser Leu Val Tyr Thr Lys Lys Gln Ala Phe
945                 950                 955                 960

Gln Leu Arg Ala His Met Tyr Gln Ala Arg Ser Leu Phe Ala Ala Asp
                965                 970                 975

Ser Ser Gly Leu Ser Asp Pro Phe Ala Arg Val Phe Phe Ile Asn Gln
            980                 985                 990

Ser Gln Cys Thr Glu Val Leu Asn Glu Thr Leu Cys Pro Thr Trp Asp
            995                 1000                1005

Gln Met Leu Val Phe Asp Asn Leu Glu Leu Tyr Gly Glu Ala His
    1010                1015                1020

Glu Leu Arg Asp Asp Pro Pro Ile Ile Val Ile Glu Ile Tyr Asp
    1025                1030                1035

Gln Asp Ser Met Gly Lys Ala Asp Phe Met Gly Arg Thr Phe Ala
    1040                1045                1050

Lys Pro Leu Val Lys Met Ala Asp Glu Ala Tyr Cys Pro Pro Arg
    1055                1060                1065

Phe Pro Pro Gln Leu Glu Tyr Tyr Gln Ile Tyr Arg Gly Asn Ala
    1070                1075                1080

Thr Ala Gly Asp Leu Leu Ala Ala Phe Glu Leu Leu Gln Ile Gly
    1085                1090                1095

Pro Ala Gly Lys Ala Asp Leu Pro Pro Ile Asn Gly Pro Val Asp
    1100                1105                1110
```

```
Val Asp Arg Gly Pro Ile Met Pro Val Pro Met Gly Ile Arg Pro
1115                 1120                1125

Val Leu Ser Lys Tyr Arg Val Glu Val Leu Phe Trp Gly Leu Arg
1130                 1135                1140

Asp Leu Lys Arg Val Asn Leu Ala Gln Val Asp Arg Pro Arg Val
1145                 1150                1155

Asp Ile Glu Cys Ala Gly Lys Gly Val Gln Ser Ser Leu Ile His
1160                 1165                1170

Asn Tyr Lys Lys Asn Pro Asn Phe Asn Thr Leu Val Lys Trp Phe
1175                 1180                1185

Glu Val Asp Leu Pro Glu Asn Glu Leu Leu His Pro Pro Leu Asn
1190                 1195                1200

Ile Arg Val Val Asp Cys Arg Ala Phe Gly Arg Tyr Thr Leu Val
1205                 1210                1215

Gly Ser His Ala Val Ser Ser Leu Arg Arg Phe Ile Tyr Arg Pro
1220                 1225                1230

Pro Asp Arg Ser Ala Pro Ser Trp Asn Thr Thr Val Arg Leu Leu
1235                 1240                1245

Arg Arg Cys Arg Val Leu Cys Asn Gly Gly Ser Ser Ser His Ser
1250                 1255                1260

Thr Gly Glu Val Val Thr Met Glu Pro Glu Val Pro Ile Lys
1265                 1270                1275

Lys Leu Glu Thr Met Val Lys Leu Asp Ala Thr Ser Glu Ala Val
1280                 1285                1290

Val Lys Val Asp Val Ala Glu Glu Lys Glu Lys Lys Lys
1295                 1300                1305

Lys Lys Gly Thr Ala Glu Glu Pro Glu Glu Glu Pro Asp Glu
1310                 1315                1320

Ser Met Leu Asp Trp Trp Ser Lys Tyr Phe Ala Ser Ile Asp Thr
1325                 1330                1335

Met Lys Glu Gln Leu Arg Gln Gln Glu Pro Ser Gly Ile Asp Leu
1340                 1345                1350

Glu Glu Lys Glu Glu Val Asp Asn Thr Glu Gly Leu Lys Gly Ser
1355                 1360                1365

Met Lys Gly Lys Glu Lys Ala Arg Ala Ala Lys Glu Glu Lys Lys
1370                 1375                1380

Lys Lys Thr Gln Ser Ser Gly Ser Gly Gln Gly Ser Glu Ala Pro
1385                 1390                1395

Glu Lys Lys Lys Pro Lys Ile Asp Glu Leu Lys Val Tyr Pro Lys
1400                 1405                1410

Glu Leu Glu Ser Glu Phe Asp Asn Phe Glu Asp Trp Leu His Thr
1415                 1420                1425

Phe Asn Leu Leu Arg Gly Lys Thr Gly Asp Asp Glu Asp Gly Ser
1430                 1435                1440

Thr Glu Glu Glu Arg Ile Val Gly Arg Phe Lys Gly Ser Leu Cys
1445                 1450                1455

Val Tyr Lys Val Pro Leu Pro Glu Asp Val Ser Arg Glu Ala Gly
1460                 1465                1470

Tyr Asp Ser Thr Tyr Gly Met Phe Gln Gly Ile Pro Ser Asn Asp
1475                 1480                1485

Pro Ile Asn Val Leu Val Arg Val Tyr Val Val Arg Ala Thr Asp
1490                 1495                1500
```

```
Leu His Pro Ala Asp Ile Asn Gly Lys Ala Asp Pro Tyr Ile Ala
    1505                1510                1515

Ile Arg Leu Gly Lys Thr Asp Ile Arg Asp Lys Glu Asn Tyr Ile
    1520                1525                1530

Ser Lys Gln Leu Asn Pro Val Phe Gly Lys Ser Phe Asp Ile Glu
    1535                1540                1545

Ala Ser Phe Pro Met Glu Ser Met Leu Thr Val Ala Val Tyr Asp
    1550                1555                1560

Trp Asp Leu Val Gly Thr Asp Asp Leu Ile Gly Glu Thr Lys Ile
    1565                1570                1575

Asp Leu Glu Asn Arg Phe Tyr Ser Lys His Arg Ala Thr Cys Gly
    1580                1585                1590

Ile Ala Gln Thr Tyr Ser Thr His Gly Tyr Asn Ile Trp Arg Asp
    1595                1600                1605

Pro Met Lys Pro Ser Gln Ile Leu Thr Arg Leu Cys Lys Asp Gly
    1610                1615                1620

Lys Val Asp Gly Pro His Phe Gly Pro Pro Gly Arg Val Lys Val
    1625                1630                1635

Ala Asn Arg Val Phe Thr Gly Pro Ser Glu Ile Glu Asp Glu Asn
    1640                1645                1650

Gly Gln Arg Lys Pro Thr Asp Glu His Val Ala Leu Leu Ala Leu
    1655                1660                1665

Arg His Trp Glu Asp Ile Pro Arg Ala Gly Cys Arg Leu Val Pro
    1670                1675                1680

Glu His Val Glu Thr Arg Pro Leu Leu Asn Pro Asp Lys Pro Gly
    1685                1690                1695

Ile Glu Gln Gly Arg Leu Glu Leu Trp Val Asp Met Phe Pro Met
    1700                1705                1710

Asp Met Pro Ala Pro Gly Thr Pro Leu Asp Ile Ser Pro Arg Lys
    1715                1720                1725

Pro Lys Lys Tyr Glu Leu Arg Val Ile Ile Trp Asn Thr Asp Glu
    1730                1735                1740

Val Val Leu Glu Asp Asp Asp Phe Phe Thr Gly Glu Lys Ser Ser
    1745                1750                1755

Asp Ile Phe Val Arg Gly Trp Leu Lys Gly Gln Gln Glu Asp Lys
    1760                1765                1770

Gln Asp Thr Asp Val His Tyr His Ser Leu Thr Gly Glu Gly Asn
    1775                1780                1785

Phe Asn Trp Arg Tyr Leu Phe Pro Phe Asp Tyr Leu Ala Ala Glu
    1790                1795                1800

Glu Lys Ile Val Ile Ser Lys Lys Glu Ser Met Phe Ser Trp Asp
    1805                1810                1815

Glu Thr Glu Tyr Lys Ile Pro Ala Arg Leu Thr Leu Gln Ile Trp
    1820                1825                1830

Asp Ala Asp His Phe Ser Ala Asp Asp Phe Leu Gly Ala Ile Glu
    1835                1840                1845

Leu Asp Leu Asn Arg Phe Pro Arg Gly Ala Lys Thr Ala Lys Gln
    1850                1855                1860

Cys Thr Met Glu Met Ala Thr Gly Glu Val Asp Val Pro Leu Val
    1865                1870                1875

Ser Ile Phe Lys Gln Lys Arg Val Lys Gly Trp Trp Pro Leu Leu
    1880                1885                1890

Ala Arg Asn Glu Asn Asp Glu Phe Glu Leu Thr Gly Lys Val Glu
```

```
                       1895                1900                1905
Ala  Glu  Leu  His  Leu  Leu  Thr  Ala  Glu  Glu  Ala  Glu  Lys  Asn  Pro
                 1910                1915                1920

Val  Gly  Leu  Ala  Arg  Asn  Glu  Pro  Asp  Pro  Leu  Glu  Lys  Pro  Asn
     1925                1930                1935

Arg  Pro  Asp  Thr  Ala  Phe  Val  Trp  Phe  Leu  Asn  Pro  Leu  Lys  Ser
     1940                1945                1950

Ile  Lys  Tyr  Leu  Ile  Cys  Thr  Arg  Tyr  Lys  Trp  Leu  Ile  Ile  Lys
     1955                1960                1965

Ile  Val  Leu  Ala  Leu  Leu  Gly  Leu  Leu  Met  Leu  Gly  Leu  Phe  Leu
     1970                1975                1980

Tyr  Ser  Leu  Pro  Gly  Tyr  Met  Val  Lys  Lys  Leu  Leu  Gly  Ala
     1985                1990                1995

<210> SEQ ID NO 7
<211> LENGTH: 84
<212> TYPE: DNA
<213> ORGANISM: Artificial sequence
<220> FEATURE:
<223> OTHER INFORMATION: Synthetic polynucleotide

<400> SEQUENCE: 7
gtaagtatca aggttacaag acaggtttaa ggagaccaat agaaactggg cttgtcgaga    60
cagagaagac tcttgcgttt ctga                                           84

<210> SEQ ID NO 8
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 8
taggcaccta ttggtcttac tgacatccac tttgcctttc tctccacag               49

<210> SEQ ID NO 9
<211> LENGTH: 1992
<212> TYPE: PRT
<213> ORGANISM: M. musculus

<400> SEQUENCE: 9

Met  Ala  Leu  Ile  Val  His  Leu  Lys  Thr  Val  Ser  Glu  Leu  Arg  Gly  Lys
1                   5                   10                  15

Gly  Asp  Arg  Ile  Ala  Lys  Val  Thr  Phe  Arg  Gly  Gln  Ser  Phe  Tyr  Ser
                20                  25                  30

Arg  Val  Leu  Glu  Asn  Cys  Glu  Gly  Val  Ala  Asp  Phe  Asp  Glu  Thr  Phe
            35                  40                  45

Arg  Trp  Pro  Val  Ala  Ser  Ser  Ile  Asp  Arg  Asn  Glu  Val  Leu  Glu  Ile
    50                  55                  60

Gln  Ile  Phe  Asn  Tyr  Ser  Lys  Val  Phe  Ser  Asn  Lys  Leu  Ile  Gly  Thr
65                  70                  75                  80

Phe  Cys  Met  Val  Leu  Gln  Lys  Val  Val  Glu  Glu  Asn  Arg  Val  Glu  Val
                85                  90                  95

Thr  Asp  Thr  Leu  Met  Asp  Ser  Asn  Ala  Ile  Ile  Lys  Thr  Ser  Leu
            100                 105                 110

Ser  Met  Glu  Val  Arg  Tyr  Gln  Ala  Thr  Asp  Gly  Thr  Val  Gly  Pro  Trp
            115                 120                 125

Asp  Asp  Gly  Asp  Phe  Leu  Gly  Asp  Glu  Ser  Leu  Gln  Glu  Glu  Lys  Asp
```

-continued

```
               130                 135                 140
Ser Gln Glu Thr Asp Gly Leu Leu Pro Gly Ser Arg Pro Ser Thr Arg
145                 150                 155                 160

Ile Ser Gly Glu Lys Ser Phe Arg Ser Lys Gly Arg Glu Lys Thr Lys
                165                 170                 175

Gly Gly Arg Asp Gly Glu His Lys Ala Gly Arg Ser Val Phe Ser Ala
                180                 185                 190

Met Lys Leu Gly Lys Thr Arg Ser His Lys Glu Glu Pro Gln Arg Gln
                195                 200                 205

Asp Glu Pro Ala Val Leu Glu Met Glu Asp Leu Asp His Leu Ala Ile
210                 215                 220

Gln Leu Gly Asp Gly Leu Asp Pro Asp Ser Val Ser Leu Ala Ser Val
225                 230                 235                 240

Thr Ala Leu Thr Ser Asn Val Ser Asn Lys Arg Ser Lys Pro Asp Ile
                245                 250                 255

Lys Met Glu Pro Ser Ala Gly Arg Pro Met Asp Tyr Gln Val Ser Ile
                260                 265                 270

Thr Val Ile Glu Ala Arg Gln Leu Val Gly Leu Asn Met Asp Pro Val
                275                 280                 285

Val Cys Val Glu Val Gly Asp Asp Lys Lys Tyr Thr Ser Met Lys Glu
                290                 295                 300

Ser Thr Asn Cys Pro Tyr Tyr Asn Glu Tyr Phe Val Phe Asp Phe His
305                 310                 315                 320

Val Ser Pro Asp Val Met Phe Asp Lys Ile Ile Lys Ile Ser Val Ile
                325                 330                 335

His Ser Lys Asn Leu Leu Arg Ser Gly Thr Leu Val Gly Ser Phe Lys
                340                 345                 350

Met Asp Val Gly Thr Val Tyr Ser Gln Pro Glu His Gln Phe His His
                355                 360                 365

Lys Trp Ala Ile Leu Ser Asp Pro Asp Asp Ile Ser Ala Gly Leu Lys
370                 375                 380

Gly Tyr Val Lys Cys Asp Val Ala Val Val Gly Lys Gly Asp Asn Ile
385                 390                 395                 400

Lys Thr Pro His Lys Ala Asn Glu Thr Asp Glu Asp Ile Glu Gly
                405                 410                 415

Asn Leu Leu Leu Pro Glu Gly Val Pro Pro Glu Arg Gln Trp Ala Arg
                420                 425                 430

Phe Tyr Val Lys Ile Tyr Arg Ala Glu Gly Leu Pro Arg Met Asn Thr
                435                 440                 445

Ser Leu Met Ala Asn Val Lys Lys Ala Phe Ile Gly Glu Asn Lys Asp
450                 455                 460

Leu Val Asp Pro Tyr Val Gln Val Phe Phe Ala Gly Gln Lys Gly Lys
465                 470                 475                 480

Thr Ser Val Gln Lys Ser Ser Tyr Glu Pro Leu Trp Asn Glu Gln Val
                485                 490                 495

Val Phe Thr Asp Leu Phe Pro Pro Leu Cys Lys Arg Met Lys Val Gln
                500                 505                 510

Ile Arg Asp Ser Asp Lys Val Asn Asp Val Ala Ile Gly Thr His Phe
                515                 520                 525

Ile Asp Leu Arg Lys Ile Ser Asn Asp Gly Asp Lys Gly Phe Leu Pro
530                 535                 540

Thr Leu Gly Pro Ala Trp Val Asn Met Tyr Gly Ser Thr Arg Asn Tyr
545                 550                 555                 560
```

-continued

```
Thr Leu Leu Asp Glu His Gln Asp Leu Asn Glu Gly Leu Gly Glu Gly
            565                 570                 575

Val Ser Phe Arg Ala Arg Leu Met Leu Gly Leu Ala Val Glu Ile Leu
        580                 585                 590

Asp Thr Ser Asn Pro Glu Leu Thr Ser Thr Glu Val Gln Val Glu
    595                 600                 605

Gln Ala Thr Pro Val Ser Glu Ser Cys Thr Gly Arg Met Glu Glu Phe
610                 615                 620

Phe Leu Phe Gly Ala Phe Leu Glu Ala Ser Met Ile Asp Arg Lys Asn
625                 630                 635                 640

Gly Asp Lys Pro Ile Thr Phe Glu Val Thr Ile Gly Asn Tyr Gly Asn
                645                 650                 655

Glu Val Asp Gly Met Ser Arg Pro Leu Arg Pro Arg Pro Arg Lys Glu
            660                 665                 670

Pro Gly Asp Glu Glu Val Asp Leu Ile Gln Asn Ser Ser Asp Asp
        675                 680                 685

Glu Gly Asp Glu Ala Gly Asp Leu Ala Ser Val Ser Ser Thr Pro Pro
    690                 695                 700

Met Arg Pro Gln Ile Thr Asp Arg Asn Tyr Phe His Leu Pro Tyr Leu
705                 710                 715                 720

Glu Arg Lys Pro Cys Ile Tyr Ile Lys Ser Trp Trp Pro Asp Gln Arg
                725                 730                 735

Arg Arg Leu Tyr Asn Ala Asn Ile Met Asp His Ile Ala Asp Lys Leu
            740                 745                 750

Glu Glu Gly Leu Asn Asp Val Gln Met Ile Lys Thr Glu Lys Ser
        755                 760                 765

Tyr Pro Glu Arg Arg Leu Arg Gly Val Leu Glu Glu Leu Ser Cys Gly
    770                 775                 780

Cys His Arg Phe Leu Ser Leu Ser Asp Lys Asp Gln Gly Arg Ser Ser
785                 790                 795                 800

Arg Thr Arg Leu Asp Arg Glu Arg Leu Lys Ser Cys Met Arg Glu Leu
                805                 810                 815

Glu Ser Met Gly Gln Gln Ala Lys Ser Leu Arg Ala Gln Val Lys Arg
            820                 825                 830

His Thr Val Arg Asp Lys Leu Arg Ser Cys Gln Asn Phe Leu Gln Lys
        835                 840                 845

Leu Arg Phe Leu Ala Asp Glu Pro Gln His Ser Ile Pro Asp Val Phe
    850                 855                 860

Ile Trp Met Met Ser Asn Asn Lys Arg Ile Ala Tyr Ala Arg Val Pro
865                 870                 875                 880

Ser Lys Asp Leu Leu Phe Ser Ile Val Glu Glu Leu Gly Lys Asp
                885                 890                 895

Cys Ala Lys Val Lys Thr Leu Phe Leu Lys Leu Pro Gly Lys Arg Gly
            900                 905                 910

Phe Gly Ser Ala Gly Trp Thr Val Gln Ala Lys Leu Glu Leu Tyr Leu
        915                 920                 925

Trp Leu Gly Leu Ser Lys Gln Arg Lys Asp Phe Leu Cys Gly Leu Pro
    930                 935                 940

Cys Gly Phe Glu Glu Val Lys Ala Ala Gln Gly Leu Gly Leu His Ser
945                 950                 955                 960

Phe Pro Pro Ile Ser Leu Val Tyr Thr Lys Lys Gln Ala Phe Gln Leu
                965                 970                 975
```

```
Arg Ala His Met Tyr Gln Ala Arg Ser Leu Phe Ala Ala Asp Ser Ser
            980                 985                 990
Gly Leu Ser Asp Pro Phe Ala Arg Val Phe Phe Ile Asn Gln Ser Gln
        995                 1000                1005
Cys Thr Glu Val Leu Asn Glu Thr Leu Cys Pro Thr Trp Asp Gln
    1010                1015                1020
Met Leu Val Phe Asp Asn Leu Glu Leu Tyr Gly Glu Ala His Glu
    1025                1030                1035
Leu Arg Asp Asp Pro Pro Ile Ile Val Glu Ile Tyr Asp Gln
    1040                1045                1050
Asp Ser Met Gly Lys Ala Asp Phe Met Gly Arg Thr Phe Ala Lys
    1055                1060                1065
Pro Leu Val Lys Met Ala Asp Glu Ala Tyr Cys Pro Pro Arg Phe
    1070                1075                1080
Pro Pro Gln Leu Glu Tyr Tyr Gln Ile Tyr Arg Gly Ser Ala Thr
    1085                1090                1095
Ala Gly Asp Leu Leu Ala Ala Phe Glu Leu Leu Gln Ile Gly Pro
    1100                1105                1110
Ser Gly Lys Ala Asp Leu Pro Pro Ile Asn Gly Pro Val Asp Met
    1115                1120                1125
Asp Arg Gly Pro Ile Met Pro Val Pro Val Gly Ile Arg Pro Val
    1130                1135                1140
Leu Ser Lys Tyr Arg Val Glu Val Leu Phe Trp Gly Leu Arg Asp
    1145                1150                1155
Leu Lys Arg Val Asn Leu Ala Gln Val Asp Arg Pro Arg Val Asp
    1160                1165                1170
Ile Glu Cys Ala Gly Lys Gly Val Gln Ser Ser Leu Ile His Asn
    1175                1180                1185
Tyr Lys Lys Asn Pro Asn Phe Asn Thr Leu Val Lys Trp Phe Glu
    1190                1195                1200
Val Asp Leu Pro Glu Asn Glu Leu Leu His Pro Pro Leu Asn Ile
    1205                1210                1215
Arg Val Val Asp Cys Arg Ala Phe Gly Arg Tyr Thr Leu Val Gly
    1220                1225                1230
Ser His Ala Val Ser Ser Leu Arg Arg Phe Ile Tyr Arg Pro Pro
    1235                1240                1245
Asp Arg Ser Ala Pro Asn Trp Asn Thr Thr Gly Glu Val Val Val
    1250                1255                1260
Ser Met Glu Pro Glu Glu Pro Val Lys Lys Leu Glu Thr Met Val
    1265                1270                1275
Lys Leu Asp Ala Thr Ser Asp Ala Val Val Lys Val Asp Val Ala
    1280                1285                1290
Glu Asp Glu Lys Glu Arg Lys Lys Lys Lys Lys Gly Pro Ser
    1295                1300                1305
Glu Glu Pro Glu Glu Glu Pro Asp Glu Ser Met Leu Asp Trp
    1310                1315                1320
Trp Ser Lys Tyr Phe Ala Ser Ile Asp Thr Met Lys Glu Gln Leu
    1325                1330                1335
Arg Gln His Glu Thr Ser Gly Thr Asp Leu Glu Glu Lys Glu Glu
    1340                1345                1350
Met Glu Ser Ala Glu Gly Leu Lys Gly Pro Met Lys Ser Lys Glu
    1355                1360                1365
Lys Ser Arg Ala Ala Lys Glu Glu Lys Lys Lys Lys Asn Gln Ser
```

-continued

```
              1370                1375                1380
Pro Gly  Pro Gly Gln Gly Ser  Glu Ala Pro Glu Lys  Lys Lys Ala
    1385                1390                1395

Lys Ile  Asp Glu Leu Lys Val  Tyr Pro Lys Glu Leu  Glu Ser Glu
    1400                1405                1410

Phe Asp  Ser Phe Glu Asp Trp  Leu His Thr Phe Asn  Leu Leu Arg
    1415                1420                1425

Gly Lys  Thr Gly Asp Asp Glu  Asp Gly Ser Thr Glu  Glu Glu Arg
    1430                1435                1440

Ile Val  Gly Arg Phe Lys Gly  Ser Leu Cys Val Tyr  Lys Val Pro
    1445                1450                1455

Leu Pro  Glu Asp Val Ser Arg  Glu Ala Gly Tyr Asp  Pro Thr Tyr
    1460                1465                1470

Gly Met  Phe Gln Gly Ile Pro  Ser Asn Asp Pro Ile  Asn Val Leu
    1475                1480                1485

Val Arg  Ile Tyr Val Val Arg  Ala Thr Asp Leu His  Pro Ala Asp
    1490                1495                1500

Ile Asn  Gly Lys Ala Asp Pro  Tyr Ile Ala Ile Lys  Leu Gly Lys
    1505                1510                1515

Thr Asp  Ile Arg Asp Lys Glu  Asn Tyr Ile Ser Lys  Gln Leu Asn
    1520                1525                1530

Pro Val  Phe Gly Lys Ser Phe  Asp Ile Glu Ala Ser  Phe Pro Met
    1535                1540                1545

Glu Ser  Met Leu Thr Val Ala  Val Tyr Asp Trp Asp  Leu Val Gly
    1550                1555                1560

Thr Asp  Asp Leu Ile Gly Glu  Thr Lys Ile Asp Leu  Glu Asn Arg
    1565                1570                1575

Phe Tyr  Ser Lys His Arg Ala  Thr Cys Gly Ile Ala  Gln Thr Tyr
    1580                1585                1590

Ser Ile  His Gly Tyr Asn Ile  Trp Arg Asp Pro Met  Lys Pro Ser
    1595                1600                1605

Gln Ile  Leu Thr Arg Leu Cys  Lys Glu Gly Lys Val  Asp Gly Pro
    1610                1615                1620

His Phe  Gly Pro His Gly Arg  Val Arg Val Ala Asn  Arg Val Phe
    1625                1630                1635

Thr Gly  Pro Ser Glu Ile Glu  Asp Glu Asn Gly Gln  Arg Lys Pro
    1640                1645                1650

Thr Asp  Glu His Val Ala Leu  Ser Ala Leu Arg His  Trp Glu Asp
    1655                1660                1665

Ile Pro  Arg Val Gly Cys Arg  Leu Val Pro Glu His  Val Glu Thr
    1670                1675                1680

Arg Pro  Leu Leu Asn Pro Asp  Lys Pro Gly Ile Glu  Gln Gly Arg
    1685                1690                1695

Leu Glu  Leu Trp Val Asp Met  Phe Pro Met Asp Met  Pro Ala Pro
    1700                1705                1710

Gly Thr  Pro Leu Asp Ile Ser  Pro Arg Lys Pro Lys  Lys Tyr Glu
    1715                1720                1725

Leu Arg  Val Ile Val Trp Asn  Thr Asp Glu Val Val  Leu Glu Asp
    1730                1735                1740

Asp Asp  Phe Phe Thr Gly Glu  Lys Ser Ser Asp Ile  Phe Val Arg
    1745                1750                1755

Gly Trp  Leu Lys Gly Gln Gln  Glu Asp Lys Gln Asp  Thr Asp Val
    1760                1765                1770
```

His Tyr His Ser Leu Thr Gly Glu Gly Asn Phe Asn Trp Arg Tyr
    1775                1780                1785

Leu Phe Pro Phe Asp Tyr Leu Ala Ala Glu Glu Lys Ile Val Met
    1790                1795                1800

Ser Lys Lys Glu Ser Met Phe Ser Trp Asp Glu Thr Glu Tyr Lys
    1805                1810                1815

Ile Pro Ala Arg Leu Thr Leu Gln Ile Trp Ala Asp His Phe
    1820                1825                1830

Ser Ala Asp Asp Phe Leu Gly Ala Ile Glu Leu Asp Leu Asn Arg
    1835                1840                1845

Phe Pro Arg Gly Ala Lys Thr Ala Lys Gln Cys Thr Met Glu Met
    1850                1855                1860

Ala Thr Gly Glu Val Asp Val Pro Leu Val Ser Ile Phe Lys Gln
    1865                1870                1875

Lys Arg Val Lys Gly Trp Trp Pro Leu Leu Ala Arg Asn Glu Asn
    1880                1885                1890

Asp Glu Phe Glu Leu Thr Gly Lys Val Glu Ala Glu Leu His Leu
    1895                1900                1905

Leu Thr Ala Glu Glu Ala Glu Lys Asn Pro Val Gly Leu Ala Arg
    1910                1915                1920

Asn Glu Pro Asp Pro Leu Glu Lys Pro Asn Arg Pro Asp Thr Ala
    1925                1930                1935

Phe Val Trp Phe Leu Asn Pro Leu Lys Ser Ile Lys Tyr Leu Ile
    1940                1945                1950

Cys Thr Arg Tyr Lys Trp Leu Ile Ile Lys Ile Val Leu Ala Leu
    1955                1960                1965

Leu Gly Leu Leu Met Leu Ala Leu Phe Leu Tyr Ser Leu Pro Gly
    1970                1975                1980

Tyr Met Val Lys Lys Leu Leu Gly Ala
    1985                1990

<210> SEQ ID NO 10
<211> LENGTH: 143
<212> TYPE: DNA
<213> ORGANISM: Artificial sequence
<220> FEATURE:
<223> OTHER INFORMATION: Synthetic polynucleotide

<400> SEQUENCE: 10
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg    120
gccaactcca tcactagggg ttc                                            143

<210> SEQ ID NO 11
<211> LENGTH: 143
<212> TYPE: DNA
<213> ORGANISM: Artificial sequence
<220> FEATURE:
<223> OTHER INFORMATION: Synthetic polynucleotide

<400> SEQUENCE: 11
acccctagtg atggagttgg ccactccctc tctgcgcgct cgctcgctca ctgaggccgc    60
ccgggcaaag cccgggcgtc gggcgacctt tggtcgcccg gcctcagtga gcgagcgagc    120
gcgcagagag ggagtggcca acc                                            143

```
<210> SEQ ID NO 12
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 12
cacttgcttt gtctcatctc c                                              21

<210> SEQ ID NO 13
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 13
gtcacttctt ctgggtattt c                                              21

<210> SEQ ID NO 14
<211> LENGTH: 6967
<212> TYPE: DNA
<213> ORGANISM: Artificial sequence
<220> FEATURE:
<223> OTHER INFORMATION: pTR22-smCBA-otoferlinNT Hs var 1 5-APSD-APhead

<400> SEQUENCE: 14 agggggggg  gggggggggt  tggccactcc  ctctctgcgc  gctcgctcgc  tcactgaggc    60
cgggcgacca  aaggtcgccc  gacgcccggg  ctttgcccgg  gcggcctcag  tgagcgagcg   120
agcgcgcaga  gagggagtgg  ccaactccat  cactaggggt  tcctcagatc  tggcgcgccc   180
aattcggtac  cctagttatt  aatagtaatc  aattacgggg  tcattagttc  atagcccata   240
tatggagttc  cgcgttacat  aacttacggt  aaatggcccg  cctggctgac  cgcccaacga   300
cccccgccca  ttgacgtcaa  taatgacgta  tgttcccata  gtaacgccaa  tagggacttt   360
ccattgacgt  caatgggtgg  actatttacg  gtaaactgcc  cacttggcag  tacatcaagt   420
gtatcatatg  ccaagtacgc  ccctattga  cgtcaatgac  ggtaaatggc  ccgcctggca   480
ttatgcccag  tacatgacct  tatgggactt  tcctacttgg  cagtacatct  acgtattagt   540
catcgctatt  accatggtcg  aggtgagccc  cacgttctgc  ttcactctcc  ccatctcccc   600 cccctccca  cccccaattt  tgtatttatt  tatttttaa  ttattttgtg  cagcgatggg   660
ggcggggggg  gggggggggc  gcgcgccagg  cggggcgggg  cggggcgagg  ggcggggcgg   720 ggcgaggcg  agaggtgcgg  cggcagccaa  tcagagcggc  gcgctccgaa  agtttccttt   780
tatggcgagg  cggcggcggc  ggcggcccta  taaaagcga  agcgcgcggc  gggcgggagt   840
cgctgcgacg  ctgccttcgc  cccgtgcccc  gctccgccgc  cgcctcgcgc  cgcccgcccc   900
ggctctgact  gaccgcgtta  ctcccacagg  tgagcgggcg  ggacggccct  tctcctccgg   960
gctgtaatta  gcgcttggtt  taatgacggc  ttgtttcttt  tctgtggctg  cgtgaaagcc  1020 ttgagggct  ccgggagcta  gagcctctgc  taaccatgtt  catgccttct  tctttttcct  1080
acagctcctg  ggcaacgtgc  tggttattgt  gctgtctcat  cattttggca  aagaattcta  1140
gcggccgcca  ccatgccctt  gctcatccac  ctcaagacag  tctcggagct  gcggggcagg  1200
ggcgaccgga  tcgccaaagt  gactttccga  gggcaatcct  tctactctcg  ggtcctggag  1260
aactgtgagg  atgtggctga  ctttgatgag  acatttcggt  ggccggtggc  cagcagcatc  1320
gacagaaatg  agatgctgga  gattcaggtt  ttcaactaca  gcaaagtctt  cagcaacaag  1380
```

```
ctcatcggga ccttccgcat ggtgctgcag aaggtggtag aggagagcca tgtggaggtg    1440
actgacacgc tgattgatga caacaatgct atcatcaaga ccagcctgtg cgtggaggtc    1500
cggtatcagg ccactgacgg cacagtgggc tcctgggacg atggggactt cctgggagat    1560
gagtctcttc aagaggaaga gaaggacagc caagagacgg atggactgct cccaggctcc    1620
cggcccagct cccggccccc aggagagaag agcttccgga gagccgggag gagcgtgttc    1680
tccgccatga agctcggcaa aaaccggtct cacaaggagg agccccaaag accagatgaa    1740
ccggcggtgc tggagatgga agaccttgac catctggcca ttcggctagg agatggactg    1800
gatcccgact cggtgtctct agcctcagtc acagctctca ccactaatgt ctccaacaag    1860
cgatctaagc cagacattaa gatggagcca agtgctgggc ggcccatgga ttaccaggtc    1920
agcatcacgg tgatcgaggc ccggcagctg gtgggcttga acatggaccc tgtggtgtgc    1980
gtggaggtgg gtgacgacaa gaagtacaca tccatgaagg agtccactaa ctgcccctat    2040
tacaacgagt acttcgtctt cgacttccat gtctctccgg atgtcatgtt tgacaagatc    2100
atcaagattt cggtgattca ctccaagaac ctgctgcgca gtggcaccct ggtgggctcc    2160
ttcaaaatgg acgtgggaac cgtgtactcg cagccagagc accagttcca tcacaagtgg    2220
gccatcctgt ctgaccccga tgacatctcc tcggggctga agggctacgt gaagtgtgac    2280
gttgccgtgg tgggcaaagg ggacaacatc aagacgcccc acaaggccaa tgagaccgac    2340
gaagatgaca tttgagggga acttgctgct ccccgagggg tgcccccgga cgccagtgg    2400 gcccggttct atgtgaaaat ttaccgagca gaggggctgc ccgtatgaa cacaagcctc    2460 atggccaatg taaagaaggc tttcatcggt gaaaacaagg acctcgtgga ccctacgtg    2520 caagtcttct ttgctggcca gaagggcaag acttcagtgc agaagagcag ctatgagccc    2580
ctgtggaatg agcaggtcgt cttttacagac ctcttccccc cactctgcaa acgcatgaag    2640
gtgcagatcc gagactcgga caaggtcaac gacgtggcca tcggcaccca cttcattgac    2700
ctgcgcaaga tttctaatga cggagacaaa ggcttcctgc ccacactggg cccagcctgg    2760
gtgaacatgt acggctccac acgtaactac acgctgctgg atgagcatca ggacctgaac    2820
gagggcctgg ggagggtgt gtccttccgg gcccggctcc tgctgggcct ggctgtggag    2880
atcgtagaca cctccaaccc tgagctcacc agctccacag aggtgcaggt ggagcaggcc    2940
acgcccatct cggagagctg tgcaggtaaa atggaagaat tctttctctt tggagccttc    3000
ctggaggcct caatgatcga ccggagaaac ggagacaagc ccatcacctt tgaggtcacc    3060
ataggcaact atgggaacga agttgatggc ctgtcccggc cccagcggcc tcggccccgg    3120
aaggagccgg gggatgagga agaagtagac ctgattcaga acgcaagtga tgacgaggcc    3180
ggtgatgccg ggaccctggc ctcagtctcc tccactccac caatgcggcc ccaggtcacc    3240
gacaggaact acttccatct gccctacctg gagcgaaagc cctgcatcta catcaagagc    3300
tggtggccgg accagcgccg ccgcctctac aatgccaaca tcatggacca cattgccgac    3360
aagctggaag aaggcctgaa cgacatacag gagatgatca aaacggagaa gtcctaccct    3420
gagcgtcgcc tgcggggcgt cctggaggag ctgagctgtg gctgctgccg cttcctctcc    3480
ctcgctgaca aggaccaggg ccactcatcc cgcaccagcc ttgaccggga cgcctcaag    3540 tcctgcatga gggagctggt aagtatcaag gttacaagac aggtttaagg agaccaatag    3600
aaactgggct tgtcgagaca gagaagactc ttgcgtttct gagctagccc ccgggtgcgc    3660
ggcgtcggtg gtgccggcgg ggggcgccag gtcgcaggcg gtgtagggct ccaggcaggc    3720
ggcgaaggcc atgacgtgcg ctatgaaggt ctgctcctgc acgccgtgaa ccaggtgcgc    3780
```

```
ctgcgggccg cgcgcgaaca ccgccacgtc ctcgcctgcg tgggtctctt cgtccagggg      3840
cactgctgac tgctgccgat actcggggct cccgctctcg ctctcggtaa catccggccg      3900
ggcgccgtcc ttgagcacat agcctggacc gtttcgtcga ctgttaatta agcatgctgg      3960
ggagagatct aggaaccccct agtgatggag ttggccactc cctctctgcg cgctcgctcg     4020
ctcactgagg ccgcccgggc aaagcccggg cgtcgggcga cctttggtcg cccggcctca      4080
gtgagcgagc gagcgcgcag agagggagtg gccaaccccc ccccccccc cctgcagcc        4140 ctgcattaat gaatcggcca acgcgcgggg agaggcggtt tgcgtattgg gcgctcttcc      4200
gcttcctcgc tcactgactc gctgcgctcg gtcgttcggc tgcggcgagc ggtatcagct      4260
cactcaaagg cggtaatacg gttatccaca gaatcagggg ataacgcagg aaagaacatg      4320
tgagcaaaag gccagcaaaa ggccaggaac cgtaaaaagg ccgcgttgct ggcgtttttc      4380
cataggctcc gccccctga cgagcatcac aaaaatcgac gctcaagtca gaggtggcga       4440
aacccgacag gactataaag ataccaggcg tttccccctg gaagctccct cgtgcgctct      4500
cctgttccga ccctgccgct taccggatac ctgtccgcct ttctcccttc gggaagcgtg      4560
gcgctttctc aatgctcacg ctgtaggtat ctcagttcgg tgtaggtcgt tcgctccaag      4620
ctgggctgtg tgcacgaacc ccccgttcag cccgaccgct gcgccttatc cggtaactat      4680
cgtcttgagt ccaacccggt aagacacgac ttatcgccac tggcagcagc cactggtaac      4740
aggattagca gagcgaggta tgtaggcggt gctacagagt tcttgaagtg gtggcctaac      4800
tacggctaca ctagaaggac agtatttggt atctgcgctc tgctgaagcc agttaccttc      4860
ggaaaaagag ttggtagctc ttgatccggc aaacaaacca ccgctggtag cggtggtttt      4920
tttgtttgca agcagcagat tacgcgcaga aaaaaaggat ctcaagaaga tcctttgatc      4980
ttttctacgg ggtctgacgc tcagtggaac gaaaactcac gttaagggat tttggtcatg      5040
agattatcaa aaaggatctt cacctagatc cttttaaatt aaaaatgaag ttttaaatca      5100
atctaaagta tatatgagta aacttggtct gacagttacc aatgcttaat cagtgaggca      5160
cctatctcag cgatctgtct atttcgttca tccatagttg cctgactccc cgtcgtgtag      5220
ataactacga tacgggaggg cttaccatct ggccccagtg ctgcaatgat accgcgagac      5280
ccacgctcac cggctccaga tttatcagca ataaaccagc cagccggaag ggccgagcgc      5340
agaagtggtc ctgcaacttt atccgcctcc atccagtcta ttaattgttg ccgggaagct      5400
agagtaagta gttcgccagt taatagtttg cgcaacgttg ttgccattgc tacaggcatc      5460
gtggtgtcac gctcgtcgtt tggtatggct tcattcagct ccggttccca acgatcaagg      5520
cgagttacat gatcccccat gttgtgcaaa aaagcggtta gctccttcgg tcctccgatc      5580
gttgtcagaa gtaagttggc cgcagtgtta tcactcatgg ttatggcagc actgcataat      5640
tctcttactg tcatgccatc cgtaagatgc ttttctgtga ctggtgagta ctcaaccaag      5700
tcattctgag aatagtgtat gcggcgaccg agttgctctt gcccggcgtc aatacgggat      5760
aataccgcgc cacatagcag aactttaaaa gtgctcatca ttggaaaacg ttcttcgggg      5820
cgaaaactct caaggatctt accgctgttg agatccagtt cgatgtaacc cactcgtgca      5880
cccaactgat cttcagcatc ttttactttc accagcgttt ctgggtgagc aaaaacagga      5940
aggcaaaatg ccgcaaaaaa gggaataagg gcgacacgga aatgttgaat actcatactc      6000 ttccttttc aatattattg aagcatttat cagggttatt gtctcatgag cggatacata       6060
tttgaatgta tttagaaaaa taaacaaata ggggttccgc gcacatttcc ccgaaaagtg      6120
```

```
ccacctgacg tctaagaaac cattattatc atgacattaa cctataaaaa taggcgtatc    6180
acgaggccct ttcgtctcgc gcgtttcggt gatgacggtg aaaacctctg acacatgcag    6240
ctcccggaga cggtcacagc ttgtctgtaa gcggatgccg ggagcagaca agcccgtcag    6300
ggcgcgtcag cgggtgttgg cgggtgtcgg ggctggctta actatgcggc atcagagcag    6360
attgtactga gagtgcacca tatgcggtgt gaaataccgc acagatgcgt aaggagaaaa    6420
taccgcatca ggaaattgta aacgttaata ttttgttaaa attcgcgtta aattttgtt     6480 aaatcagctc attttttaac caataggccg aaatcggcaa aatcccttat aaatcaaaag    6540
aatagaccga gatagggttg agtgttgttc cagtttggaa caagagtcca ctattaaaga    6600
acgtggactc caacgtcaaa gggcgaaaaa ccgtctatca gggcgatggc ccactacgtg    6660
aaccatcacc ctaatcaagt tttttggggt cgaggtgccg taaagcacta aatcggaacc    6720
ctaaagggag cccccgattt agagcttgac ggggaaagcc ggcgaacgtg gcgagaaagg    6780
aagggaagaa agcgaaagga gcgggcgcta gggcgctggc aagtgtagcg gtcacgctgc    6840
gcgtaaccac cacacccgcc gcgcttaatg cgccgctaca gggcgcgtcg cgccattcgc    6900
cattcaggct acgcaactgt tgggaagggc gatcggtgcg ggcctcttcg ctattacgcc    6960
aggctgc                                                              6967

<210> SEQ ID NO 15
<211> LENGTH: 7475
<212> TYPE: DNA
<213> ORGANISM: Artificial sequence
<220> FEATURE:
<223> OTHER INFORMATION: pTR22-APhead-APSA-otoferlinCT Hs var 1

<400> SEQUENCE: 15 agggggggggg gggggggggt tggccactcc ctctctgcgc gctcgctcgc tcactgaggc     60
cgggcgacca aggtcgccc gacgcccggg ctttgcccgg gcggcctcag tgagcgagcg    120
agcgcgcaga gagggagtgg ccaactccat cactaggggt tcctcagatc tggcgcgccc    180
aattggcttc gaattctagc ggccgccccc gggtgcgcgg cgtcggtggt gccggcgggg    240
ggcgccaggt cgcaggcggt gtagggctcc aggcaggcgg cgaaggccat gacgtgcgct    300
atgaaggtct gctcctgcac gccgtgaacc aggtgcgcct gcgggccgcg cgcgaacacc    360
gccacgtcct cgcctgcgtg ggtctcttcg tccaggggca ctgctgactg ctgccgatac    420
tcggggctcc cgctctcgct ctcggtaaca tccggccggg cgccgtcctt gagcacatag    480
cctggaccgt ttccttaagc gacgcatgct cgcgataggc acctattggt cttactgaca    540
tccactttgc ctttctctcc acaggaaaac atggggcagc aggccaggat gctgcgggcc    600
caggtgaagc ggcacacggt gcgggacaag ctgaggctgt gccagaactt cctgcagaag    660
ctgcgcttcc tggcggacga gccccagcac agcattcccg acatcttcat ctggatgatg    720
agcaacaaca agcgtgtcgc ctatgcccgt gtgccctcca aggacctgct cttctccatc    780
gtggaggagg agactggcaa ggactgcgcc aagtcaaga cgctcttcct taagctgcca    840
gggaagcggg gcttcggctc ggcaggctgg acagtgcagg ccaaggtgga gctgtacctg    900
tggctgggcc tcagcaaaca gcgcaaggag ttcctgtgcg gcctgcctg tggcttccag    960 gaggtcaagg cagcccaggg cctgggcctg catgccttcc cacccgtcag cctggtctac   1020
accaagaagc aggcgttcca gctccgagcg cacatgtacc aggcccgcag cctctttgcc   1080
gccgacagca gcggactctc agacccctt gccccgcgtct tcttcacaat cagagtcagt   1140
gcacagaggt gctgaatgag accctgtgtc ccacctggga ccagatgctg gtgttcgaca   1200
```

```
acctggagct ctatggtgaa gctcatgagc tgagggacga tccgcccatc attgtcattg   1260
aaatctatga ccaggattcc atgggcaaag ctgacttcat gggccgtgac cttcgccaaa   1320
cccctggtga agatggcaga cgaggcgtac tgcccacccc gcttcccacc tcagctcgag   1380
tactaccaga tctaccgtgg caacgccaca gctggagacc tgctggcggc cttcgagctg   1440
ctgcagattg gaccagcagg gaaggctgac ctgcccccca tcaatggccc ggtggacgtg   1500
gaccgaggtc ccatcatgcc cgtgcccatg ggcatccggc ccgtgctcag caagtaccga   1560
gtggaggtgc tgttctgggg cctacgggac ctaaagcggg tgaacctggc ccaggtggac   1620
cggccacggg tggacatcga gtgtgcaggg aaggggtgc agtcgtccct gatccacaat   1680
tataagaaga accccaactt caacaccctc gtcaagtggt ttgaagtgga cctcccagag   1740
aacgagctgc tgcacccgcc cttgaacatc cgtgtggtgg actgccgggc cttcggtcgc   1800
tacacactgg tgggctccca tgccgtcagc tccctgcgac gcttcatcta ccggccccca   1860
gaccgctcgg cccccagctg gaacaccacg gtcaggcttc tccggcgctg ccgtgtgctg   1920
tgcaatgggg gctcctcctc tcactccaca ggggaggttg tggtgactat ggagccagag   1980
gtacccatca agaaactgga gaccatggtg aagctggacg cgacttctga agctgttgtc   2040
aaggtggatg tggctgagga ggagaaggag aagaagaaga agaagaaggg cactgcggag   2100
gagccagagg aggaggagcc agacgagagc atgctggact ggtggtccaa gtactttgcc   2160
tccattgaca ccatgaagga gcaacttcga caacaagagc cctctggaat tgacttggag   2220
gagaaggagg aagtggacaa taccgagggc ctgaaggggt caatgaaggg caaggagaag   2280
gcaagggctg ccaaagagga gaagaagaag aaaactcaga gctctggctc tggccagggg   2340
tccgaggccc ccgagaagaa gaaacccaag attgatgagc ttaaggtata ccccaaagag   2400
ctggagtccg agtttgataa cttttgagga ctggctgcaca ctttcaactt gcttcggggc   2460
aagaccgggg atgatgagga tggctccacc gaggaggagc gcattgtggg acgcttcaag   2520
ggctccctct gcgtgtacaa agtgccactc ccagaggacg tgtcccggga agccggctac   2580
gactccacct acggcatgtt ccagggcatc ccgagcaatg accccatcaa tgtgctggtc   2640
cgagtctatg tggtccgggc cacggacctg caccctgctg acatcaacgg caaagctgac   2700
ccctacatcg ccatccggct aggcaagact gacatccgcg acaaggagaa ctacatctcc   2760
aagcagctca accctgtctt tgggaagtcc tttgacatcg aggcctcctt ccccatggaa   2820
tccatgctga cggtggctgt gtatgactgg gacctggtgg gcactgatga cctcattggg   2880
gaaaccaaga tcgacctgga gaaccgcttc tacagcaagc accgcgccac ctgcggcatc   2940
gcccagacct actccacaca tggctacaat atctggcggg accccatgaa gcccagccag   3000
atcctgaccc gcctctgcaa agacggcaaa gtggacggcc ccactttggg gccccctggg   3060
agagtgaagg tggccaaccg cgtcttcact gggccctctg agattgagga cgagaacggt   3120
cagaggaagc ccacagacga gcatgtggcg ctgttggccc tgaggcactg gaggacatc   3180 ccccgcgcag gctgccgcct ggtgccagag catgtggaga cgaggccgct gctcaacccc   3240
gacaagccgg catcgagca gggccgcctg gagctgtggg tggacatgtt ccccatggac   3300
atgccagccc ctgggacgcc tctggacatc tcacctcgga gcccaagaa gtacgagctg   3360 cgggtcatca tctggaacac agatgaggtg gtcttggagg acgacgactt cttcacaggg   3420
gagaagtcca gtgacatctt cgtgagggg tggctgaagg ccagcagga ggacaagcag   3480 gacacagacg tccactacca ctccctcact ggcgagggca acttcaactg gcgctacctg   3540
```

```
ttccccttcg actacctggc ggcggaggag aagatcgtca tctccaagaa ggagtccatg    3600
ttctcctggg acgagaccga gtacaagatc cccgcgcggc tcaccctgca gatctgggat    3660
gcggaccact tctccgctga cgacttcctg ggggccatcg agctggacct gaaccggttc    3720
ccgcggggcg caaagacagc caagcagtgc accatggaga tggccaccgg ggaggtggac    3780
gtgcccctcg tgtccatctt caagcaaaag cgcgtcaaag gctggtggcc cctcctggcc    3840
cgcaatgaga cgatgagtt tgagctcacg ggcaaggtgg aggctgagct gcatttactg    3900
acagcagagg aggcagagaa gaacccagtg ggcctggccc gcaatgaacc tgaccccta    3960 gagaaaccca accggcccga cacgagcttc atctggttcc tgaaccctct caagtcggct    4020
cgctacttct tgtggcacac gtatcgctgg ctgctcctca aactgttgct gctcctgctg    4080
ctgctcctcc tcctcgccct gttcctctac tctgtgcctg gctacctggt caagaaaatc    4140
ctcggggcct gaacggccgc tatgctagct tggtaccaag gcggatcct gcatagagct    4200 cgctgatcag cctcgactgt gccttctagt tgccagccat ctgttgtttg ccctcccccc    4260
gtgccttcct tgaccctgga aggtgccact cccactgtcc tttcctaata aaatgaggaa    4320
attgcatcgc attgtctgag taggtgtcat tctattctgg ggggtggggt gggcaggac    4380 agcaaggggg aggattggga agacaatagc aggcatgctg gggagagatc tgaggactag    4440
tccgtcgact gttaattaag catgctgggg agagatctag gaaccctag tgatggagtt    4500 ggccactccc tctctgcgcg ctcgctcgct cactgaggcc gcccgggcaa agcccgggcg    4560
tcgggcgacc tttggtcgcc cggcctcagt gagcgagcga gcgcgcagag agggagtggc    4620
caaccccccc cccccccccc ctgcagccct gcattaatga atcggccaac gcgcggggag    4680
aggcggtttg cgtattgggc gctcttccgc ttcctcgctc actgactcgc tgcgctcgt    4740 cgttcggctg cggcgagcgg tatcagctca ctcaaaggcg gtaatacggt tatccacaga    4800
atcaggggat aacgcaggaa agaacatgtg agcaaaaggc cagcaaaagg ccaggaaccg    4860
taaaaaggcc gcgttgctgg cgttttttcca taggctccgc ccccctgacg agcatcacaa    4920
aaatcgacgc tcaagtcaga ggtggcgaaa cccgacagga ctataaagat accaggcgtt    4980
tccccctgga agctccctcg tgcgctctcc tgttccgacc ctgccgctta ccggatacct    5040
gtccgccttt ctcccttcgg gaagcgtggc gctttctcaa tgctcacgct gtaggtatct    5100
cagttcggtg taggtcgttc gctccaagct gggctgtgtg cacgaacccc ccgttcagcc    5160
cgaccgctgc gccttatccg gtaactatcg tcttgagtcc aacccggtaa gacacgactt    5220
atcgccactg gcagcagcca ctggtaacag gattagcaga gcgaggtatg taggcggtgc    5280
tacagagttc ttgaagtggt ggcctaacta cggctacact agaaggacag tatttggtat    5340
ctgcgctctg ctgaagccag ttaccttcgg aaaaagagtt ggtagctctt gatccggcaa    5400
acaaaccacc gctggtagcg tggttttttt tgtttgcaag cagcagatta cgcgcagaaa    5460
aaaaggatct caagaagatc ctttgatctt ttctacgggg tctgacgctc agtggaacga    5520
aaactcacgt taagggattt tggtcatgag attatcaaaa aggatcttca cctagatcct    5580
tttaaattaa aaatgaagtt ttaaatcaat ctaaagtata tatgagtaaa cttggtctga    5640
cagttaccaa tgcttaatca gtgaggcacc tatctcagcg atctgtctat ttcgttcatc    5700
catagttgcc tgactccccg tcgtgtagat aactacgata cgggagggct taccatctgg    5760
ccccagtgct gcaatgatac cgcgagaccc acgctcaccg gctccagatt tatcagcaat    5820
aaaccagcca gccggaaggg ccgagcgcag aagtggtcct gcaactttat ccgcctccat    5880
ccagtctatt aattgttgcc gggaagctag agtaagtagt tcgccagtta atagtttgcg    5940
```

| | |
|---|---|
| caacgttgtt gccattgcta caggcatcgt ggtgtcacgc tcgtcgtttg gtatggcttc | 6000 |
| attcagctcc ggttcccaac gatcaaggcg agttacatga tcccccatgt tgtgcaaaaa | 6060 |
| agcggttagc tccttcggtc ctccgatcgt tgtcagaagt aagttggccg cagtgttatc | 6120 |
| actcatggtt atggcagcac tgcataattc tcttactgtc atgccatccg taagatgctt | 6180 |
| ttctgtgact ggtgagtact caaccaagtc attctgagaa tagtgtatgc ggcgaccgag | 6240 |
| ttgctcttgc ccggcgtcaa tacgggataa taccgcgcca catagcagaa ctttaaaagt | 6300 |
| gctcatcatt ggaaaacgtt cttcgggggcg aaaactctca aggatcttac cgctgttgag | 6360 |
| atccagttcg atgtaaccca ctcgtgcacc caactgatct tcagcatctt ttactttcac | 6420 |
| cagcgtttct gggtgagcaa aacaggaag gcaaatgcc gcaaaaaagg gaataagggc | 6480 |
| gacacggaaa tgttgaatac tcatactctt ccttttcaa tattattgaa gcatttatca | 6540 |
| gggttattgt ctcatgagcg gatacatatt tgaatgtatt tagaaaaata aacaaatagg | 6600 |
| ggttccgcgc acatttcccc gaaaagtgcc acctgacgtc taagaaacca ttattatcat | 6660 |
| gacattaacc tataaaaata ggcgtatcac gaggccctt cgtctcgcgc gtttcggtga | 6720 |
| tgacggtgaa aacctctgac acatgcagct cccggagacg gtcacagctt gtctgtaagc | 6780 |
| ggatgccggg agcagacaag cccgtcaggg cgcgtcagcg ggtgttggcg ggtgtcgggg | 6840 |
| ctggcttaac tatgcggcat cagagcagat tgtactgaga gtgcaccata tgcggtgtga | 6900 |
| aataccgcac agatgcgtaa ggagaaaata ccgcatcagg aaattgtaaa cgttaatatt | 6960 |
| ttgttaaaat tcgcgttaaa ttttttgttaa atcagctcat tttttaacca ataggccgaa | 7020 |
| atcggcaaaa tcccttataa atcaaagaa tagaccgaga taggttgag tgttgttcca | 7080 |
| gtttggaaca agagtccact attaagaac gtggactcca acgtcaaagg gcgaaaaacc | 7140 |
| gtctatcagg gcgatggccc actacgtgaa ccatcaccct aatcaagttt tttggggtcg | 7200 |
| aggtgccgta aagcactaaa tcggaaccct aaagggagcc cccgatttag agcttgacgg | 7260 |
| ggaaagccgg cgaacgtggc gagaaaggaa gggaagaaag cgaaaggagc gggcgctagg | 7320 |
| gcgctggcaa gtgtagcggt cacgctgcgc gtaaccacca cacccgccgc gcttaatgcg | 7380 |
| ccgctacagg gcgcgtcgcg ccattcgcca ttcaggctac gcaactgttg gaagggcga | 7440 |
| tcggtgcggg cctcttcgct attacgccag gctgc | 7475 |

<210> SEQ ID NO 16
<211> LENGTH: 7475
<212> TYPE: DNA
<213> ORGANISM: Artificial sequence
<220> FEATURE:
<223> OTHER INFORMATION: pTR22-APhead-APSA-otoferlinCT Hs var 5

<400> SEQUENCE: 16

| | |
|---|---|
| aggggggggg gggggggggt tggccactcc ctctctgcgc gctcgctcgc tcactgaggc | 60 |
| cgggcgacca aggtcgccc gacgcccggg ctttgcccgg gcggcctcag tgagcgagcg | 120 |
| agcgcgcaga gagggagtgg ccaactccat cactagggt tcctcagatc tggcgcgccc | 180 |
| aattggcttc gaattctagc ggccgccccc gggtgcgcgg cgtcggtggt gccggcgggg | 240 |
| ggcgccaggt cgcaggcggt gtagggctcc aggcaggcg cgaaggccat gacgtgcgct | 300 |
| atgaaggtct gctcctgcac gccgtgaacc aggtgcgcct gcgggccgcg cgcgaacacc | 360 |
| gccacgtcct cgcctgcgtg ggtctcttcg tccagggggca ctgctgactg ctgccgatac | 420 |
| tcggggctcc cgctctcgct ctcggtaaca tccggccggg cgccgtcctt gagcacatag | 480 |

```
cctggaccgt ttccttaagc gacgcatgct cgcgataggc acctattggt cttactgaca      540
tccactttgc ctttctctcc acaggaaaac atggggcagc aggccaggat gctgcgggcc      600
caggtgaagc ggcacacggt gcgggacaag ctgaggctgt gccagaactt cctgcagaag      660
ctgcgcttcc tggcggacga gccccagcac agcattcccg acatcttcat ctggatgatg      720
agcaacaaca agcgtgtcgc ctatgcccgt gtgccctcca aggacctgct cttctccatc      780
gtggaggagg agactggcaa ggactgcgcc aaggtcaaga cgctcttcct taagctgcca      840
gggaagcggg gcttcggctc ggcaggctgg acagtgcagg ccaaggtgga gctgtacctg      900
tggctgggcc tcagcaaaca cgcaaggag ttcctgtgcg gcctgccctg tggcttccag       960
gaggtcaagg cagcccaggg cctgggcctg catgccttcc cacccgtcag cctggtctac     1020
accaagaagc aggcgttcca gctccgagcg cacatgtacc aggcccgcag cctctttgcc     1080
gccgacagca gcggactctc agacccctt gcccgcgtct tcttcatcaa tcagagtcag      1140
tgcacagagg tgctgaatga gaccctgtgt ccccacctggg accagatgct ggtgttcgac    1200
aacctggagc tctatggtga agctcatgag ctgagggacg atccgcccat cattgtcatt     1260
gaaatctatg accaggattc catgggcaaa gctgacttca tgggccggac cttcgccaaa    1320
cccctggtga agatggcaga cgaggcgtac tgcccacccc gcttcccacc tcagctcgag    1380
tactaccaga tctaccgtgg caacgccaca gctggagacc tgctggcggc cttcgagctg    1440
ctgcagattg accagcagg gaaggctgac ctgccccca tcaatggccc ggtggacgtg       1500
gaccgaggtc ccatcatgcc cgtgcccatg gcatccggc ccgtgctcag caagtaccga     1560
gtggaggtgc tgttctgggg cctacgggac ctaaagcggg tgaacctggc ccaggtggac    1620
cggccacggg tggacatcga gtgtgcaggg aaggggtgc agtcgtccct gatccacaat     1680
tataagaaga ccccaacttt caacaccctc gtcaagtggt ttgaagtgga cctcccagag    1740
aacgagctgc tgcacccgcc cttgaacatc cgtgtggtgg actgccgggc cttcggtcgc    1800
tacacactgg tgggctccca tgccgtcagc tccctgcgac gcttcatcta ccggccccca    1860
gaccgctcgg cccccagctg gaacaccacg gtcaggcttc tccggcgctg ccgtgtgctg    1920
tgcaatgggg gctcctcctc tcactccaca ggggaggttg tggtgactat ggagccagag    1980
gtacccatca agaaactgga gaccatggtg aagctggacg cgacttctga agctgttgtc    2040
aaggtggatg tggctgagga ggagaaggag aagaagaaga agaagaaggg cactgcggag    2100
gagccagagg aggaggagcc agacgagagc atgctggact ggtggtccaa gtactttgcc    2160
tccattgaca ccatgaagga gcaacttcga caacaagagc cctctggaat tgacttggag    2220
gagaaggagg aagtggacaa taccgagggc ctgaaggggt caatgaaggg caaggagaag    2280
gcaagggctg ccaaagagga gaagaagaag aaaactcaga gctctggctc tggccagggg   2340
tccgaggccc ccgagaagaa gaaacccaag attgatgagc ttaaggtata ccccaaagag    2400
ctggagtccg agtttgataa ctttgaggac tggctgcaca cttttcaactt gcttcggggc   2460 aagaccgggg atgatgagga tggctccacc gaggaggagc gcattgtggg acgcttcaag    2520 ggctcccctct gcgtgtacaa agtgccactc ccagaggacg tgtcccggga agccggctac    2580
gactccacct acggcatgtt ccagggcatc ccgagcaatg accccatcaa tgtgctggtc    2640
cgagtctatg tggtccgggc cacggacctg caccctgctg acatcaacgg caaagctgac    2700
ccctacatcg ccatccggct aggcaagact gacatccgcg acaaggagaa ctacatctcc    2760
aagcagctca accctgtctt tgggaagtcc tttgacatcg aggcctcctt ccccatggaa    2820
tccatgctga cggtggctgt gtatgactgg gacctggtgg gcactgatga cctcattggg    2880
```

-continued

```
gaaaccaaga tcgacctgga gaaccgcttc tacagcaagc accgcgccac ctgcggcatc    2940
gcccagacct actccacaca tggctacaat atctggcggg acccatgaa gcccagccag     3000 atcctgaccc gcctctgcaa agacggcaaa gtggacggcc cccactttgg gcccctggg    3060 agagtgaagg tggccaaccg cgtcttcact gggccctctg agattgagga cgagaacggt    3120
cagaggaagc ccacagacga gcatgtggcg ctgttggccc tgaggcactg ggaggacatc    3180
ccccgcgcag gctgccgcct ggtgccagag catgtggaga cgaggccgct gctcaaccc     3240 gacaagccgg gcatcgagca gggccgcctg gagctgtggg tggacatgtt ccccatggac    3300
atgccagccc ctgggacgcc tctggacatc tcacctcgga agcccaagaa gtacgagctg    3360
cgggtcatca tctggaacac agatgaggtg gtcttggagg acgacgactt cttcacaggg    3420
gagaagtcca gtgacatctt cgtgaggggg tggctgaagg ccagcagga ggacaagcag    3480 gacacagacg tccactacca ctccctcact ggcgagggca acttcaactg cgctacctg     3540 ttcccttcg actacctggc ggcggaggag aagatcgtca tctccaagaa ggagtccatg    3600
ttctcctggg acgagaccga gtacaagatc cccgcgcggc tcaccctgca gatctgggat    3660
gcggaccact tctccgctga cgacttcctg ggggccatcg agctggacct gaaccggttc    3720
ccgcggggcg caaagacagc caagcagtgc accatggaga tggccaccgg ggaggtggac    3780
gtgcccctcg tgtccatctt caagcaaaag cgcgtcaaag gctggtggcc cctcctggcc    3840
cgcaatgaga acgatgagtt tgagctcacg ggcaaggtgg aggctgagct gcatttactg    3900
acagcagagg aggcagagaa gaacccagtg ggcctggccc gcaatgaacc tgaccccta    3960 gagaaaccca accggcccga cacggccttc gtctggttcc tcaaccctct caagtccatc    4020
aagtacctca tctgcacccg gtacaagtgg ctcatcatca agatcgtgct ggcgctgttg    4080
gggctgctca tgttggggct cttcctctac agcctccctg gctacatggt caaaaagctc    4140 cttgggcat gaacgccgc tatgctagct tggtaccaag gcggatcct gcatagagct     4200 cgctgatcag cctcgactgt gccttctagt tgccagccat ctgttgtttg cccctccccc    4260
gtgccttcct tgaccctgga aggtgccact cccactgtcc tttcctaata aatgaggaa     4320 attgcatcgc attgtctgag taggtgtcat tctattctgg ggggtggggt ggggcaggac    4380
agcaaggggg aggattggga agacaatagc aggcatgctg gggagagatc tgaggactag    4440
tccgtcgact gttaattaag catgctgggg agagatctag gaacccctag tgatggagtt    4500
ggccactccc tctctgcgcg ctcgctcgct cactgaggcc gcccgggcaa gcccgggcg    4560 tcgggcgacc tttggtcgcc cggcctcagt gagcgagcga gcgcgcagag agggagtggc    4620
caaccccccc cccccccccc ctgcagccct gcattaatga atcggccaac gcgcggggag    4680
aggcggtttg cgtattgggc gctcttccgc ttcctcgctc actgactcgc tgcgctcggt    4740
cgttcggctg cggcgagcgg tatcagctca ctcaaaggcg gtaatacggt tatccacaga    4800 atcagggat aacgcaggaa agaacatgtg agcaaaggc cagcaaaagg ccaggaaccg     4860
taaaaaggcc gcgttgctgg cgttttccca taggctccgc cccctgacg agcatcacaa    4920 aaatcgacgc tcaagtcaga ggtggcgaaa cccgacagga ctataaagat accaggcgtt    4980
tccccctgga agctccctcg tgcgctctcc tgttccgacc ctgccgctta ccggatacct    5040
gtccgccttt ctcccttcgg gaagcgtggc gctttctcaa tgctcacgct gtaggtatct    5100
cagttcggtg taggtcgttc gctccaagct gggctgtgtg cacgaacccc ccgttcagcc    5160
cgaccgctgc gccttatccg gtaactatcg tcttgagtcc aacccggtaa gacacgactt    5220
```

```
atcgccactg gcagcagcca ctggtaacag gattagcaga gcgaggtatg taggcggtgc   5280
tacagagttc ttgaagtggt ggcctaacta cggctacact agaaggacag tatttggtat   5340
ctgcgctctg ctgaagccag ttaccttcgg aaaaagagtt ggtagctctt gatccggcaa   5400
acaaaccacc gctggtagcg gtggtttttt tgtttgcaag cagcagatta cgcgcagaaa   5460
aaaaggatct caagaagatc ctttgatctt ttctacgggg tctgacgctc agtggaacga   5520
aaactcacgt taagggattt tggtcatgag attatcaaaa aggatcttca cctagatcct   5580
tttaaattaa aaatgaagtt ttaaatcaat ctaaagtata tatgagtaaa cttggtctga   5640
cagttaccaa tgcttaatca gtgaggcacc tatctcagcg atctgtctat ttcgttcatc   5700
catagttgcc tgactccccg tcgtgtagat aactacgata cgggagggct taccatctgg   5760
ccccagtgct gcaatgatac cgcgagaccc acgctcaccg gctccagatt tatcagcaat   5820
aaaccagcca gccggaaggg ccgagcgcag aagtggtcct gcaactttat ccgcctccat   5880
ccagtctatt aattgttgcc gggaagctag agtaagtagt tcgccagtta atagtttgcg   5940
caacgttgtt gccattgcta caggcatcgt ggtgtcacgc tcgtcgtttg gtatggcttc   6000
attcagctcc ggttcccaac gatcaaggcg agttacatga tcccccatgt tgtgcaaaaa   6060
agcggttagc tccttcggtc ctccgatcgt tgtcagaagt aagttggccg cagtgttatc   6120
actcatggtt atggcagcac tgcataattc tcttactgtc atgccatccg taagatgctt   6180
ttctgtgact ggtgagtact caaccaagtc attctgagaa tagtgtatgc ggcgaccgag   6240
ttgctcttgc ccggcgtcaa tacgggataa taccgcgcca catagcagaa ctttaaaagt   6300
gctcatcatt ggaaaacgtt cttcggggcg aaaactctca aggatcttac cgctgttgag   6360
atccagttcg atgtaaccca ctcgtgcacc caactgatct tcagcatctt ttactttcac   6420
cagcgtttct gggtgagcaa aaacaggaag gcaaaatgcc gcaaaaaagg gaataagggc   6480
gacacggaaa tgttgaatac tcatactctt cctttttcaa tattattgaa gcatttatca   6540
gggttattgt ctcatgagcg gatacatatt tgaatgtatt tagaaaaata aacaaatagg   6600
ggttccgcgc acatttcccc gaaaagtgcc acctgacgtc taagaaacca ttattatcat   6660
gacattaacc tataaaaata ggcgtatcac gaggccctt cgtctcgcgc gtttcggtga   6720
tgacggtgaa aacctctgac acatgcagct cccggagacg gtcacagctt gtctgtaagc   6780
ggatgccggg agcagacaag cccgtcaggg cgcgtcagcg ggtgttggcg ggtgtcgggg   6840
ctggcttaac tatgcggcat cagagcagat tgtactgaga gtgcaccata tgcggtgtga   6900
aataccgcac agatgcgtaa ggagaaaata ccgcatcagg aaattgtaaa cgttaatatt   6960
ttgttaaaat tcgcgttaaa ttttgttaa atcagctcat tttttaacca ataggccgaa   7020
atcggcaaaa tcccttataa atcaaaagaa tagaccgaga tagggttgag tgttgttcca   7080
gtttggaaca agagtccact attaaagaac gtggactcca acgtcaaagg gcgaaaaacc   7140
gtctatcagg gcgatggccc actacgtgaa ccatcaccct aatcaagttt ttggggtcg   7200 aggtgccgta aagcactaaa tcggaaccct aaagggagcc cccgatttag agcttgacgg   7260
ggaaagccgg cgaacgtggc gagaaaggaa gggaagaaag cgaaaggagc gggcgctagg   7320
gcgctggcaa gtgtagcggt cacgctgcgc gtaaccacca cccgccgcg gcttaatgcg   7380 ccgctacagg gcgcgtcgcg ccattcgcca ttcaggctac gcaactgttg ggaagggcga   7440
tcggtgcggg cctcttcgct attacgccag gctgc                             7475

<210> SEQ ID NO 17
<211> LENGTH: 7475
```

<212> TYPE: DNA
<213> ORGANISM: Artificial Sequence
<220> FEATURE:
<223> OTHER INFORMATION: Synthetic Polynucleotide

<400> SEQUENCE: 17

```
agggggggggg gggggggggt tggccactcc ctctctgcgc gctcgctcgc tcactgaggc      60
cgggcgacca aggtcgccc  gacgcccggg ctttgcccgg gcggcctcag tgagcgagcg     120
agcgcgcaga gagggagtgg ccaactccat cactaggggt tcctcagatc tggcgcgccc     180
aattggcttc gaattctagc ggccgccccc gggtgcgcgg cgtcggtggt gccggcgggg     240
ggcgccaggt cgcaggcggt gtagggctcc aggcaggcgg cgaaggccat gacgtgcgct     300
atgaaggtct gctcctgcac gccgtgaacc aggtgcgcct gcgggccgcg cgcgaacacc     360
gccacgtcct cgcctgcgtg ggtctcttcg tccaggggca ctgctgactg ctgccgatac     420
tcggggctcc cgctctcgct ctcggtaaca tccggccggg cgccgtcctt gagcacatag     480
cctggaccgt ttccttaagc gacgcatgct cgcgataggc acctattggt cttactgaca     540
tccactttgc ctttctctcc acaggaaaat atgggacagc aggcaaggat gctgcgcgcc     600
caggtgaaga ggcacaccgt gagagacaag ctgcggctgt gccagaactt cctgcagaag     660
ctgcgctttc tggccgatga gccacagcac agcatccccg acatcttcat ctggatgatg     720
tccaacaata agagagtggc ctacgcccgg gtgccctcta aggatctgct gtttagcatc     780
gtggaggagg agacaggcaa ggactgtgcc aaggtgaaga ccctgttcct gaagctgcct     840
ggcaagagag gctttggcag cgccggatgg accgtgcagg caaaggtgga gctgtatctg     900
tggctgggcc tgtctaagca gcggaaggag ttcctgtgcg gcctgccctg tggctttcag     960
gaggtgaagg cagcacaggg actgggactg cacgccttcc ccccgtgag cctggtgtac     1020
accaagaagc aggcctttca gctgagggcc catatgtacc aggccaggtc tctgttcgcc     1080
gccgatagct ccggactgag cgacccttt gccagggtgt tctttatcaa tcagagccag     1140
tgcacagagg tgctgaacga gaccctgtgc ccaacatggg atcagatgct ggtgttcgac     1200
aacctggagc tgtacggaga ggcacacgag ctgagggacg atccacccat catcgtgatc     1260
gagatctatg atcaggactc catgggcaag gccgatttca tgggcaggac ctttgccaag     1320
cccctggtga agatggccga cgaggcctac tgccctccaa gattccccc  tcagctcgag     1380
tactatcaga tctataggg  aaatgcaacc gccgagacc  tgctggccgc ctttgagctg     1440
ctgcagatcg gccccgccgg aaaggcagac ctgccaccca tcaacggccc agtggatgtg     1500
gacagaggcc ccatcatgcc tgtgccaatg ggcatcagac cagtgctgtc caagtacagg     1560
gtggaggtgc tgttctgggg actgcgcgac ctgaagaggg tgaatctggc ccaggtggat     1620
aggcccagag tggacatcga gtgcgccgga aagggcgtgc agtctagcct gatccacaac     1680
tataagaaga acccaaattt caacaccctg gtgaagtggt ttgaggtgga tctgcccgag     1740
aatgagctgc tgcaccctcc actgaacatc cgggtggtgg actgtagagc cttcggcagg     1800
tacaccctgg tgggcagcca cgccgtgagc agcctgagga ggttcatcta caggccccct     1860
gacaggtccg ccccttcttg gaataccaca gtgagactgc tgcggcgctg cagggtgctg     1920
tgcaacggag gcagctcctc tcactctacc ggcgaggtgg tggtgacaat ggagcctgag     1980
gtacccatca agaagctgga gaccatggtg aagctggatg ccacaagcga ggcagtggtg     2040
aaggtggacg tggcagagga ggagaaggag aagaagaaga agaagaaggg aaccgccgag     2100
gagcctgagg aagaggagcc agatgagagc atgctggact ggtggtccaa gtacttcgcc     2160
```

```
tctatcgaca caatgaagga gcagctgaga cagcaggagc ctagcggcat cgatctggag    2220
gagaaggagg aggtggacaa taccgagggc ctgaagggct ccatgaaggg caaggagaag    2280
gcaagggcag caaaggaaga gaagaagaag aagacccaga gcagcggctc tggacagggc    2340
agcgaggcac cagagaagaa gaagcctaag atcgatgagc tgaaggtgta cccaaaggag    2400
ctggagtccg agttcgataa ttttgaggac tggctgcaca ccttcaacct gctgcgcggc    2460
aagacaggcg acgatgagga cggcagcacc gaggaggaga gaatcgtggg ccggtttaag    2520
ggctccctgt gcgtgtacaa ggtgccactg cctgaggacg tgagcaggga ggccggatac    2580
gactctacct atggcatgtt ccagggcatc ccctctaatg atcctatcaa cgtgctggtg    2640
cgcgtgtatg tggtgagggc cacagatctg caccccgccg acatcaacgg caaggccgac    2700
ccttacatcg ccatccgcct gggcaagacc gatatcaggg acaaggagaa ttatatctcc    2760
aagcagctga accccgtgtt cggcaagtct tttgacatcg aggccagctt ccctatggag    2820
tccatgctga ccgtggccgt gtacgattgg gacctggtgg gcaccgacga tctgatcggc    2880
gagacaaaga tcgatctgga gaatcgcttt tattctaagc acagggcaac ctgcggaatc    2940
gcacagacct acagcacaca cggctataac atctggcgcg accccatgaa gcctagccag    3000
atcctgacaa ggctgtgcaa ggatggcaag gtggacggac cacacttcgg accacccggc    3060
agagtgaagg tggccaatcg ggtgtttaca ggcccttccg agatcgagga tgagaacggc    3120
cagcgcaagc caaccgacga gcacgtggcc ctgctggccc tgaggcactg gaggatatc    3180 ccaagggccg gatgtaggct ggtgcctgag cacgtggaga ccagaccact gctgaatcca    3240
gacaagccag gaatcgagca gggcaggctg gagctgtggg tggatatgtt cccaatggac    3300
atgccagccc caggaacacc cctggatatc tcccctagaa agccaaagaa gtacgagctg    3360
agagtgatca tctggaacac agacgaggtg gtgctggagg acgatgactt ctttaccggc    3420
gagaagtcta gcgatatctt tgtgcgcgga tggctgaagg acagcagga ggacaagcag    3480 gatacagacg tgcactacca ctccctgacc ggcgagggca atttcaactg gagatacctg    3540
ttcccttttg attatctggc cgccgaggag aagatcgtga tctctaagaa ggagagcatg    3600
ttttcctggg acgagacaga gtataagatc ccagccagac tgaccctgca gatctgggat    3660
gccgaccact tcagcgccga tgactttctg ggcgccatcg agctggacct gaaccggttc    3720
ccaagaggcg ccaagaccgc caagcagtgc acaatggaga tggcaaccgg agaggtggac    3780
gtgcctctgg tgtctatctt caagcagaag agggtgaagg gctggtggcc actgctggcc    3840
agaaacgaga tgatgagtt tgagctgaca ggcaaggtgg aggcagagct gcacctgctg    3900
accgccgagg aggcagagaa gaacccagtg ggcctggcca ggaatgagcc cgaccctctg    3960
gagaagccaa acaggcccga caccagcttc atctggtttc tgaatcctct gaagtccgcc    4020
cggtacttcc tgtggcacac ctatcgctgg ctgctgctga agctgttatt actgttatta    4080
ctgctgctgc tgctggccct gtttctgtac agcgtgcccg gctatctggt gaagaagatc    4140
ctgggcgcct gaacggccgc tatgctagct tggtaccaag gcggatcct gcatagagct    4200 cgctgatcag cctcgactgt gccttctagt tgccagccat ctgttgtttg cccctccccc    4260
gtgccttcct tgaccctgga aggtgccact cccactgtcc tttcctaata aaatgaggaa    4320
attgcatcgc attgtctgag taggtgtcat tctattctgg ggggtggggt ggggcaggac    4380
agcaaggggg aggattggga agacaatagc aggcatgctg gggagagatc tgaggactag    4440
tccgtcgact gttaattaag catgctgggg agagatctag gaacccctag tgatggagtt    4500
ggccactccc tctctgcgcg ctcgctcgct cactgaggcc gcccgggcaa agcccgggcg    4560
```

```
tcgggcgacc tttggtcgcc cggcctcagt gagcgagcga gcgcgcagag agggagtggc    4620
caaccccccc cccccccccc ctgcagccct gcattaatga atcggccaac gcgcggggag    4680
aggcggtttg cgtattgggc gctcttccgc ttcctcgctc actgactcgc tgcgctcggt    4740
cgttcggctg cggcgagcgg tatcagctca ctcaaaggcg gtaatacggt tatccacaga    4800
atcaggggat aacgcaggaa agaacatgtg agcaaaaggc cagcaaaagg ccaggaaccg    4860
taaaaaggcc gcgttgctgg cgttttccca taggctccgc cccctgacg agcatcacaa    4920 aaatcgacgc tcaagtcaga ggtggcgaaa cccgacagga ctataaagat accaggcgtt    4980
tccccctgga agctccctcg tgcgctctcc tgttccgacc ctgccgctta ccggatacct    5040
gtccgccttt ctcccttcgg gaagcgtggc gctttctcaa tgctcacgct gtaggtatct    5100
cagttcggtg taggtcgttc gctccaagct gggctgtgtg cacgaacccc cgttcagcc    5160 cgaccgctgc gccttatccg gtaactatcg tcttgagtcc aacccggtaa gacacgactt    5220
atcgccactg gcagcagcca ctggtaacag gattagcaga gcgaggtatg taggcggtgc    5280
tacagagttc ttgaagtggt ggcctaacta cggctacact agaaggacag tatttggtat    5340
ctgcgctctg ctgaagccag ttaccttcgg aaaaagagtt ggtagctctt gatccggcaa    5400
acaaaccacc gctggtagcg gtggtttttt tgtttgcaag cagcagatta cgcgcagaaa    5460
aaaaggatct caagaagatc ctttgatctt ttctacgggg tctgacgctc agtggaacga    5520
aaactcacgt taagggattt tggtcatgag attatcaaaa aggatcttca cctagatcct    5580
tttaaattaa aaatgaagtt ttaaatcaat ctaaagtata tatgagtaaa cttggtctga    5640
cagttaccaa tgcttaatca gtgaggcacc tatctcagcg atctgtctat ttcgttcatc    5700
catagttgcc tgactccccg tcgtgtagat aactacgata cgggagggct taccatctgg    5760
ccccagtgct gcaatgatac cgcgagaccc acgctcaccg gctccagatt tatcagcaat    5820
aaaccagcca gccggaaggg ccgagcgcag aagtggtcct gcaactttat ccgcctccat    5880
ccagtctatt aattgttgcc gggaagctag agtaagtagt tcgccagtta atagtttgcg    5940
caacgttgtt gccattgcta caggcatcgt ggtgtcacgc tcgtcgtttg gtatggcttc    6000
attcagctcc ggttcccaac gatcaaggcg agttacatga tcccccatgt tgtgcaaaaa    6060
agcggttagc tccttcggtc ctccgatcgt tgtcagaagt aagttggccg cagtgttatc    6120
actcatggtt atggcagcac tgcataattc tcttactgtc atgccatccg taagatgctt    6180
ttctgtgact ggtgagtact caaccaagtc attctgagaa tagtgtatgc ggcgaccgag    6240
ttgctcttgc ccggcgtcaa tacgggataa taccgcgcca catagcagaa ctttaaaagt    6300
gctcatcatt ggaaaacgtt cttcggggcg aaaactctca aggatcttac cgctgttgag    6360
atccagttcg atgtaaccca ctcgtgcacc caactgatct tcagcatctt ttactttcac    6420
cagcgtttct gggtgagcaa aaacaggaag gcaaaatgcc gcaaaaaagg gaataagggc    6480
gacacggaaa tgttgaatac tcatactctt ccttttcaa tattattgaa gcatttatca    6540
gggttattgt ctcatgagcg gatacatatt tgaatgtatt tagaaaaata aacaaatagg    6600
ggttccgcgc acatttcccc gaaaagtgcc acctgacgtc taagaaacca ttattatcat    6660
gacattaacc tataaaaata ggcgtatcac gaggcccttt cgtctcgcgc gtttcggtga    6720
tgacggtgaa aacctctgac acatgcagct cccggagacg gtcacagctt gtctgtaagc    6780
ggatgccggg agcagacaag cccgtcaggg cgcgtcagcg ggtgttggcg ggtgtcgggg    6840
ctggcttaac tatgcggcat cagagcagat tgtactgaga gtgcaccata tgcggtgtga    6900
```

| | |
|---|---|
| aataccgcac agatgcgtaa ggagaaaata ccgcatcagg aaattgtaaa cgttaatatt | 6960 |
| ttgttaaaat tcgcgttaaa tttttgttaa atcagctcat tttttaacca ataggccgaa | 7020 |
| atcggcaaaa tcccttataa atcaaaagaa tagaccgaga tagggttgag tgttgttcca | 7080 |
| gtttggaaca agagtccact attaaagaac gtggactcca acgtcaaagg gcgaaaaacc | 7140 |
| gtctatcagg gcgatggccc actacgtgaa ccatcaccct aatcaagttt tttggggtcg | 7200 |
| aggtgccgta agcactaaa tcggaaccct aaagggagcc cccgatttag agcttgacgg | 7260 |
| ggaaagccgg cgaacgtggc gagaaaggaa gggaagaaag cgaaaggagc gggcgctagg | 7320 |
| gcgctggcaa gtgtagcggt cacgctgcgc gtaaccacca cccgccgc gcttaatgcg | 7380 |
| ccgctacagg gcgcgtcgcg ccattcgcca ttcaggctac gcaactgttg ggaagggcga | 7440 |
| tcggtgcggg cctcttcgct attacgccag gctgc | 7475 |

<210> SEQ ID NO 18
<211> LENGTH: 7475
<212> TYPE: DNA
<213> ORGANISM: Artificial Sequence
<220> FEATURE:
<223> OTHER INFORMATION: Synthetic Polynucleotide

<400> SEQUENCE: 18

| | |
|---|---|
| agggggggggg ggggggggggt tggccactcc ctctctgcgc gctcgctcgc tcactgaggc | 60 |
| cgggcgacca aaggtcgccc gacgcccggg ctttgcccgg gcggcctcag tgagcgagcg | 120 |
| agcgcgcaga gagggagtgg ccaactccat cactaggggt tcctcagatc tggcgcgccc | 180 |
| aattggcttc gaattctagc ggccgccccc gggtgcgcgg cgtcggtggt gccggcgggg | 240 |
| ggcgccaggt cgcaggcggt gtagggctcc aggcaggcgg cgaaggccat gacgtgcgct | 300 |
| atgaaggtct gctcctgcac gccgtgaacc aggtgcgcct gcgggccgcg cgcgaacacc | 360 |
| gccacgtcct cgcctgcgtg ggtctcttcg tccagggca ctgctgactg ctgccgatac | 420 |
| tcggggctcc cgctctcgct ctcggtaaca tccggccggg cgccgtcctt gagcacatag | 480 |
| cctggaccgt ttccttaagc gacgcatgct cgcgataggc acctattggt cttactgaca | 540 |
| tccactttgc ctttctctcc acaggaaaat atgggacagc aggcaaggat gctgcgcgcc | 600 |
| caggtgaaga ggcacaccgt gagagacaag ctgcggctgt gccagaactt cctgcagaag | 660 |
| ctgcgctttc tggccgatga gccacagcac agcatccccg acatcttcat ctggatgatg | 720 |
| tccaacaata agagagtggc ctacgcccgg gtgccctcta aggatctgct gtttagcatc | 780 |
| gtggaggagg agacaggcaa ggactgtgcc aaggtgaaga ccctgttcct gaagctgcct | 840 |
| ggcaagagag gctttggcag cgccggatgg accgtgcagg caaaggtgga gctgtatctg | 900 |
| tggctgggcc tgtctaagca gcggaaggag ttcctgtgcg gcctgccctg ggctttcag | 960 |
| gaggtgaagg cagcacaggg actgggactg cacgccttcc cccccgtgag cctggtgtac | 1020 |
| accaagaagc aggcctttca gctgagggcc catatgtacc aggccaggtc tctgttcgcc | 1080 |
| gccgatagct ccggactgag cgaccctttt gccagggtgt tctttatcaa tcagagccag | 1140 |
| tgcacagagg tgctgaacga gaccctgtgc ccaacatggg atcagatgct ggtgttcgac | 1200 |
| aacctggagc tgtacggaga ggcacacgag ctgagggacg atccacccat catcgtgatc | 1260 |
| gagatctatg atcaggactc catgggcaag gccgatttca tgggcaggac ctttgccaag | 1320 |
| cccctggtga agatggccga cgaggcctac tgccctccaa gattcccccc tcagctcgag | 1380 |
| tactatcaga tctatagggg aaatgcaacc gccgagacc tgctgccgc ctttgagctg | 1440 |
| ctgcagatcg gccccgccgg aaaggcagac ctgccaccca tcaacggccc agtggatgtg | 1500 |

-continued

```
gacagaggcc ccatcatgcc tgtgccaatg ggcatcagac cagtgctgtc caagtacagg    1560
gtggaggtgc tgttctgggg actgcgcgac ctgaagaggg tgaatctggc ccaggtggat    1620
aggcccagag tggacatcga gtgcgccgga aagggcgtgc agtctagcct gatccacaac    1680
tataagaaga acccaaattt caacaccctg gtgaagtggt tgaggtgga tctgcccgag     1740
aatgagctgc tgcaccctcc actgaacatc cgggtggtgg actgtagagc cttcggcagg    1800
tacaccctgg tgggcagcca cgccgtgagc agcctgagga ggttcatcta caggcccct    1860
gacaggtccg cccctttcttg aataccaca gtgagactgc tgcggcgctg cagggtgctg    1920
tgcaacggag gcagctcctc tcactctacc ggcgaggtgg tggtgacaat ggagcctgag    1980
gtacccatca agaagctgga gaccatggtg aagctggatg ccacaagcga ggcagtggtg    2040
aaggtggacg tggcagagga ggagaaggag aagaagaaga agaagaaggg aaccgccgag    2100
gagcctgagg aagaggagcc agatgagagc atgctggact ggtggtccaa gtacttcgcc    2160
tctatcgaca caatgaagga gcagctgaga cagcaggagc ctagcggcat cgatctggag    2220
gagaaggagg aggtggacaa taccgagggc ctgaagggct ccatgaaggg caaggagaag    2280
gcaagggcag caaaggaaga gaagaagaag aagacccaga gcagcggctc tggacagggc    2340
agcgaggcac cagagaagaa gaagcctaag atcgatgagc tgaaggtgta cccaaaggag    2400
ctggagtccg agttcgataa ttttgaggac tggctgcaca ccttcaacct gctgcgcggc    2460
aagacaggcg acgatgagga cggcagcacc gaggaggaga gaatcgtggg ccggtttaag    2520
ggctccctgt gcgtgtacaa ggtgccactg cctgaggacg tgagcaggga ggccggatac    2580
gactctacct atggcatgtt ccagggcatc ccctctaatg atcctatcaa cgtgctggtg    2640
cgcgtgtatg tggtgagggc cacagatctg caccccgccg acatcaacgg caaggccgac    2700
ccttacatcg ccatccgcct gggcaagacc gatatcagga caaggagaa ttatatctcc    2760
aagcagctga accccgtgtt cggcaagtct tttgacatcg aggccagctt ccctatggag    2820
tccatgctga ccgtggccgt gtacgattgg gacctggtgg gcaccgacga tctgatcggc    2880
gagacaaaga tcgatctgga gaatcgcttt tattctaagc acagggcaac ctgcggaatc    2940
gcacagacct acagcacaca cggctataac atctggcgcg accccatgaa gcctagccag    3000
atcctgacaa ggctgtgcaa ggatggcaag gtggacggac cacacttcgg accacccggc    3060
agagtgaagg tggccaatcg ggtgtttaca ggcccttccg agatcgagga tgagaacggc    3120
cagcgcaagc caaccgacga gcacgtggcc ctgctggccc tgaggcactg ggaggatatc    3180
ccaagggccg gatgtaggct ggtgcctgag cacgtggaga ccagaccact gctgaatcca    3240
gacaagccag gaatcgagca gggcaggctg gagctgtggg tggatatgtt cccaatggac    3300
atgccagccc caggaacacc cctggatatc tcccctagaa agccaaagaa gtacgagctg    3360
agagtgatca tctggaacac agacgaggtg gtgctggagg acgatgactt ctttaccggc    3420
gagaagtcta gcgatatctt tgtgcgcgga tggctgaagg acagcagga ggacaagcag     3480
gatacagacg tgcactacca ctccctgacc ggcgagggca attttcaactg gagataccctg  3540
ttcccttttg attatctggc cgccgaggag aagatcgtga tctctaagaa ggagagcatg    3600
ttttcctggg acgagacaga gtataagatc ccagccagac tgaccctgca gatctgggat    3660
gccgaccact tcagcgccga tgactttctg ggcgccatcg agctggacct gaaccggttc    3720
ccaagaggcg ccaagaccgc caagcagtgc acaatggaga tggcaaccgg agaggtggac    3780
gtgcctctgg tgtctatctt caagcagaag cgggtgaagg gatggtggcc actgctggcc    3840
```

```
aggaacgaga atgatgagtt tgagctgaca ggcaaggtgg aggcagagct gcacctgctg    3900
accgccgagg aggcagagaa gaacccagtg ggcctggcca ggaatgagcc cgaccctctg    3960
gagaagccaa acaggcccga tacagccttc gtgtggtttc tgaatcctct gaagagcatc    4020
aagtacctga tctgtaccag gtataagtgg ctgatcatca agatcgtgct ggccctgctg    4080
ggactgctga tgctgggcct gtttctgtac tccctgcccg gctatatggt gaagaagctg    4140
ctgggcgcct gaacgccgcc tatgctagct tggtaccaag gcggatcct gcatagagct     4200
cgctgatcag cctcgactgt gccttctagt tgccagccat ctgttgtttg cccctccccc    4260
gtgccttcct tgaccctgga aggtgccact cccactgtcc tttcctaata aaatgaggaa    4320
attgcatcgc attgtctgag taggtgtcat tctattctgg ggggtggggt ggggcaggac    4380
agcaaggggg aggattggga agacaatagc aggcatgctg gggagagatc tgaggactag    4440
tccgtcgact gttaattaag catgctgggg agagatctag gaaccctag tgatggagtt     4500
ggccactccc tctctgcgcg ctcgctcgct cactgaggcc gcccgggcaa agcccgggcg    4560
tcgggcgacc tttggtcgcc cggcctcagt gagcgagcga gcgcgcagag agggagtggc    4620
caaccccccc cccccccccc ctgcagccct gcattaatga atcggccaac gcgcggggag    4680
aggcggtttg cgtattgggc gctcttccgc ttcctcgctc actgactcgc tgcgctcggt    4740
cgttcggctg cggcgagcgg tatcagctca ctcaaaggcg gtaatacggt tatccacaga    4800
atcaggggat aacgcaggaa agaacatgtg agcaaaaggc cagcaaaagg ccaggaaccg    4860
taaaaaggcc gcgttgctgg cgttttttcca taggctccgc cccctgacg agcatcacaa    4920
aaatcgacgc tcaagtcaga ggtggcgaaa cccgacagga ctataaagat accaggcgtt    4980
tccccctgga agctccctcg tgcgctctcc tgttccgacc ctgccgctta ccggatacct    5040
gtccgccttt ctcccttcgg gaagcgtggc gctttctcaa tgctcacgct gtaggtatct    5100
cagttcggtg taggtcgttc gctccaagct gggctgtgtg cacgaacccc ccgttcagcc    5160
cgaccgctgc gccttatccg gtaactatcg tcttgagtcc aacccggtaa gacacgactt    5220
atcgccactg gcagcagcca ctggtaacag gattagcaga gcgaggtatg taggcggtgc    5280
tacagagttc ttgaagtggt ggcctaacta cggctacact agaaggacag tatttggtat    5340
ctgcgctctg ctgaagccag ttaccttcgg aaaaagagtt ggtagctctt gatccggcaa    5400
acaaaccacc gctggtagcg gtggtttttt tgtttgcaag cagcagatta cgcgcagaaa    5460
aaaaggatct caagaagatc ctttgatctt ttctacgggg tctgacgctc agtggaacga    5520
aaactcacgt taagggattt tggtcatgag attatcaaaa aggatcttca cctagatcct    5580
tttaaattaa aaatgaagtt ttaaatcaat ctaaagtata tatgagtaaa cttggtctga    5640
cagttaccaa tgcttaatca gtgaggcacc tatctcagcg atctgtctat ttcgttcatc    5700
catagttgcc tgactccccg tcgtgtagat aactacgata cgggagggct taccatctgg    5760
ccccagtgct gcaatgatac cgcgagaccc acgctcaccg gctccagatt tatcagcaat    5820
aaaccagcca gccggaaggg ccgagcgcag aagtggtcct gcaactttat ccgcctccat    5880
ccagtctatt aattgttgcc gggaagctag agtaagtagt tcgccagtta atagtttgcg    5940
caacgttgtt gccattgcta caggcatcgt ggtgtcacgc tcgtcgtttg gtatggcttc    6000
attcagctcc ggttcccaac gatcaaggcg agttacatga tcccccatgt tgtgcaaaaa    6060
agcggttagc tccttcggtc ctccgatcgt tgtcagaagt aagttggccg cagtgttatc    6120
actcatggtt atggcagcac tgcataattc tcttactgtc atgccatccg taagatgctt    6180
ttctgtgact ggtgagtact caaccaagtc attctgagaa tagtgtatgc ggcgaccgag    6240
```

```
ttgctcttgc ccggcgtcaa tacgggataa taccgcgcca catagcagaa ctttaaaagt    6300
gctcatcatt ggaaaacgtt cttcggggcg aaaactctca aggatcttac cgctgttgag    6360
atccagttcg atgtaaccca ctcgtgcacc caactgatct tcagcatctt ttactttcac    6420
cagcgtttct gggtgagcaa aaacaggaag gcaaaatgcc gcaaaaaagg gaataagggc    6480
gacacggaaa tgttgaatac tcatactctt ccttttcaa tattattgaa gcatttatca     6540
gggttattgt ctcatgagcg gatacatatt tgaatgtatt tagaaaaata aacaaatagg    6600
ggttccgcgc acatttcccc gaaaagtgcc acctgacgtc taagaaacca ttattatcat    6660
gacattaacc tataaaaata ggcgtatcac gaggccctt cgtctcgcgc gtttcggtga     6720
tgacggtgaa aacctctgac acatgcagct cccggagacg gtcacagctt gtctgtaagc    6780
ggatgccggg agcagacaag cccgtcaggg cgcgtcagcg ggtgttggcg ggtgtcgggg    6840
ctggcttaac tatgcggcat cagagcagat tgtactgaga gtgcaccata tgcggtgtga    6900
aataccgcac agatgcgtaa ggagaaaata ccgcatcagg aaattgtaaa cgttaatatt    6960
ttgttaaaat tcgcgttaaa tttttgttaa atcagctcat tttttaacca ataggccgaa    7020
atcggcaaaa tcccttataa atcaaaagaa tagaccgaga tagggttgag tgttgttcca    7080
gtttggaaca agagtccact attaaagaac gtggactcca acgtcaaagg gcgaaaaacc    7140
gtctatcagg gcgatggccc actacgtgaa ccatcaccct aatcaagttt ttggggtcg     7200 aggtgccgta aagcactaaa tcggaaccct aaagggagcc ccgatttag agcttgacgg     7260 ggaaagccgg cgaacgtggc gagaaaggaa gggaagaaag cgaaaggagc gggcgctagg    7320
gcgctggcaa gtgtagcggt cacgctgcgc gtaaccacca caccgccgc gcttaatgcg     7380 ccgctacagg gcgcgtcgcg ccattcgcca ttcaggctac gcaactgttg ggaagggcga    7440
tcggtgcggg cctcttcgct attacgccag gctgc                               7475
```

<210> SEQ ID NO 19
<211> LENGTH: 6967
<212> TYPE: DNA
<213> ORGANISM: Artificial Sequence
<220> FEATURE:
<223> OTHER INFORMATION: Synthetic Polynucleotide

<400> SEQUENCE: 19

```
aggggggggg ggggggggt tggccactcc ctctctgcgc gctcgctcgc tcactgaggc      60
cgggcgacca aagtcgccc gacgcccggg ctttgcccgg gcggcctcag tgagcgagcg     120
agcgcgcaga gagggagtgg ccaactccat cactaggggg tcctcagatc tggcgcgccc    180
aattcggtac cctagttatt aatagtaatc aattacgggg tcattagttc atagcccata    240
tatggagttc cgcgttacat aacttacggt aaatggcccg cctggctgac cgcccaacga    300
cccccgccca ttgacgtcaa taatgacgta tgttcccata gtaacgccaa tagggacttt    360
ccattgacgt caatgggtgg actatttacg gtaaactgcc cacttggcag tacatcaagt    420
gtatcatatg ccaagtacgc cccctattga cgtcaatgac ggtaaatggc ccgcctggca    480
ttatgcccag tacatgacct tatgggactt tcctacttgg cagtacatct acgtattagt    540
catcgctatt accatggtcg aggtgagccc cacgttctgc ttcactctcc ccatctcccc    600
cccctcccca cccccaattt tgtatttatt tattttttaa ttattttgtg cagcgatggg    660 ggcgggggg ggggggggc gcgcgccagg cggggcgggg cggggcgagg gcggggcgg     720 ggcgaggcgg agaggtgcgg cggcagccaa tcagagcggc gcgctccgaa agtttccttt    780
```

```
tatggcgagg cggcggcggc ggcggcccta taaaaagcga agcgcgcggc gggcgggagt    840
cgctgcgacg ctgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagcta gagcctctgc taaccatgtt catgccttct tcttttttcct  1080 acagctcctg ggcaacgtgc tggttattgt gctgtctcat cattttggca aagaattcta   1140
gcggccgcca ccatggcact gctgatccac ctgaaaaccg tctccgaact gagaggcaga   1200
ggggacagaa tcgctaaagt caccttccgg ggacagagct tttacagcag ggtgctggag   1260
aactgcgagg acgtggccga ctttgacgag acattcaggt ggcccgtggc cagctccatc   1320
gatcgcaatg agatgctgga gatccaggtg tttaactata gcaaggtgtt ctccaataag   1380
ctgatcggca ccttccggat ggtgctgcag aaggtggtgg aggagtccca cgtggaggtg   1440
accgacacac tgatcgacga taacaatgcc atcatcaaga catccctgtg cgtggaggtg   1500
cgctaccagg ccaccgatgg cacagtgggc tcttgggacg atggcgactt cctgggcgat   1560
gagtccctgc aggaggagga gaaggactct caggagacag atggcctgct gcctggctcc   1620
cggccatcta gccgcccccc tggcgagaag tcttttagga gagccggcag gtccgtgttc   1680
tctgccatga agctgggcaa gaacaggagc cacaaggagg agcctcagag gcccgacgag   1740
ccagccgtgc tggagatgga ggacctggat cacctggcca tcagactggg cgatggcctg   1800
gaccctgata gcgtgtccct ggcctccgtg accgccctga ccacaaacgt gtctaataag   1860
cggagcaagc cagacatcaa gatggagcca tctgccggca ggcccatgga ttaccaggtg   1920
agcatcacag tgatcgaggc cagacagctg gtgggcctga acatggaccc cgtggtgtgc   1980
gtggaagtgg cgacgataa gaagtacacc tccatgaagg agtctacaaa ctgtccatac   2040
tacaacgagt acttcgtgtt tgatttccac gtgagccccg acgtgatgtt cgataagatc   2100
atcaagatca gcgtgatcca ctccaagaat ctgctgcggt ctggcacccct ggtgggaagc   2160 tttaagatgg acgtgggcac agtgtactct cagcctgagc accagttcca ccacaagtgg   2220
gccatcctga gcgatccaga cgatatctcc tctggcctga agggctatgt gaagtgcgac   2280
gtggcagtgg tgggcaaggg cgataacatc aagaccccac acaaggccaa tgagacagac   2340
gaggacgata tcgagggaaa cctgctgctg ccagagggag tgccacccga gaggcagtgg   2400
gccaggttct acgtgaagat ctatagggca gagggcctgc ctaggatgaa caccagcctg   2460
atggccaatg tgaagaaggc cttcatcggc gagaacaagg acctggtgga tccctacgtg   2520
caggtgttct tgccggcca gaagggcaag acctccgtgc agaagagctc ctatgagcct   2580
ctgtggaatg agcaggtggt gtttacagac ctgttccctc cactgtgcaa gaggatgaag   2640
gtgcagatca gagactctga taaggtgaac gacgtggcca tcggcaccca ctttatcgat   2700
ctgaggaaga tcagcaatga cggcgataag ggcttcctgc ccaccctggg ccccgcctgg   2760
gtgaacatgt acggcagcac cagaaattat acactgctgg acgagcacca ggatctgaac   2820
gagggcctgg cgagggcgt gagctttaga gccaggctgc tgctgggcct ggccgtggag   2880
atcgtggaca cctccaatcc cgagctgacc tctagcacag aggtgcaggt ggagcaggcc   2940
acacctatct ctgagagctg tgccggcaag atggaggagt ctttctgtt tggcgccttc   3000 ctggaggcct ccatgatcga ccggcgcaac ggcgataagc ctatcacctt cgaggtgaca   3060 atcgcaact acggcaatga ggtggacggc ctgtctcggc cccagcgccc aaggcccaga   3120
aaggagcctg gcgacgagga ggaggtggat ctgatccaga acgccagcga cgatgaggca   3180
```

```
ggcgacgcag gcgatctggc ctccgtgtcc tctaccccc  ctatgcggcc acaggtgaca   3240
gaccgcaatt actttcacct gccttatctg gagcgcaagc catgcatcta catcaagtct   3300
tggtggcccg atcagaggag acggctgtat aacgccaata tcatggacca catcgccgat   3360
aagctggagg agggcctgaa tgacatccag gagatgatca agaccgagaa gtcctatcca   3420
gagcgcaggc tgagggcgt  gctggaggag ctgagctgtg gctgctgtag attcctgtcc   3480
ctggccgaca aggatcaggg gcactcatca cggacacggc tggaccggga gcggctgaaa   3540
tcatgtatgc gggagctggt aagtatcaag gttacaagac aggtttaagg agaccaatag   3600
aaactgggct tgtcgagaca gagaagactc ttgcgtttct gagctagccc ccgggtgcgc   3660
ggcgtcggtg gtgccggcgg ggggcgccag gtcgcaggcg gtgtagggct ccaggcaggc   3720
ggcgaaggcc atgacgtgcg ctatgaaggt ctgctcctgc acgccgtgaa ccaggtgcgc   3780
ctgcgggccg cgcgcgaaca ccgccacgtc ctcgcctgcg tgggtctctt cgtccagggg   3840
cactgctgac tgctgccgat actcgggct  cccgctctcg ctctcggtaa catccggccg   3900
ggcgccgtcc ttgagcacat agcctggacc gtttcgtcga ctgttaatta agcatgctgg   3960
ggagagatct aggaacccct agtgatggag ttggccactc cctctctgcg cgctcgctcg   4020
ctcactgagg ccgcccgggc aaagcccggg cgtcgggcga cctttggtcg cccggcctca   4080
gtgagcgagc gagcgcgcag agagggagtg gccaacccc  ccccccccc  ccctgcagcc   4140 ctgcattaat gaatcggcca acgcgcgggg agaggcggtt tgcgtattgg gcgctcttcc   4200
gcttcctcgc tcactgactc gctgcgctcg gtcgttcggc tgcggcgagc ggtatcagct   4260
cactcaaagg cggtaatacg gttatccaca gaatcagggg ataacgcagg aaagaacatg   4320
tgagcaaaag gccagcaaaa ggccaggaac cgtaaaaagg ccgcgttgct ggcgtttttc   4380
cataggctcc gccccctga  cgagcatcac aaaaatcgac gctcaagtca gaggtggcga   4440
aacccgacag gactataaag ataccaggcg tttccccctg gaagctccct cgtgcgctct   4500
cctgttccga ccctgccgct taccggatac ctgtccgcct ttctcccttc gggaagcgtg   4560
gcgctttctc aatgctcacg ctgtaggtat ctcagttcgg tgtaggtcgt tcgctccaag   4620
ctgggctgtg tgcacgaacc ccccgttcag cccgaccgct gcgccttatc cggtaactat   4680
cgtcttgagt ccaacccggt aagacacgac ttatcgccac tggcagcagc cactggtaac   4740
aggattagca gagcgaggta tgtaggcggt gctacagagt tcttgaagtg gtggcctaac   4800
tacggctaca ctagaaggac agtatttggt atctgcgctc tgctgaagcc agttaccttc   4860
ggaaaaagag ttggtagctc ttgatccggc aaacaaacca ccgctggtag cggtggtttt   4920
tttgtttgca agcagcagat tacgcgcaga aaaaaggat  ctcaagaaga tcctttgatc   4980
ttttctacgg ggtctgacgc tcagtggaac gaaaactcac gttaagggat tttggtcatg   5040
agattatcaa aaaggatctt cacctagatc cttttaaatt aaaaatgaag ttttaaatca   5100
atctaaagta tatatgagta aacttggtct gacagttacc aatgcttaat cagtgaggca   5160
cctatctcag cgatctgtct atttcgttca tccatagttg cctgactccc cgtcgtgtag   5220
ataactacga tacgggaggg cttaccatct ggccccagtg ctgcaatgat accgcgagac   5280
ccacgctcac cggctccaga tttatcagca ataaccagc  cagccggaag ggccgagcgc   5340
agaagtggtc ctgcaacttt atccgcctcc atccagtcta ttaattgttg ccgggaagct   5400
agagtaagta gttcgccagt taatagtttg cgcaacgttg ttgccattgc tacaggcatc   5460
gtggtgtcac gctcgtcgtt tggtatggct tcattcagct ccggttccca acgatcaagg   5520
```

```
cgagttacat gatcccccat gttgtgcaaa aaagcggtta gctccttcgg tcctccgatc   5580
gttgtcagaa gtaagttggc cgcagtgtta tcactcatgg ttatggcagc actgcataat   5640
tctcttactg tcatgccatc cgtaagatgc ttttctgtga ctggtgagta ctcaaccaag   5700
tcattctgag aatagtgtat gcggcgaccg agttgctctt gcccggcgtc aatacgggat   5760
aataccgcgc cacatagcag aactttaaaa gtgctcatca ttggaaaacg ttcttcgggg   5820
cgaaaactct caaggatctt accgctgttg agatccagtt cgatgtaacc cactcgtgca   5880
cccaactgat cttcagcatc ttttactttc accagcgttt ctgggtgagc aaaaacagga   5940
aggcaaaatg ccgcaaaaaa gggaataagg gcgacacgga aatgttgaat actcatactc   6000
ttcctttttc aatattattg aagcatttat cagggttatt gtctcatgag cggatacata   6060
tttgaatgta tttagaaaaa taaacaaata ggggttccgc gcacatttcc ccgaaaagtg   6120
ccacctgacg tctaagaaac cattattatc atgacattaa cctataaaaa taggcgtatc   6180
acgaggccct ttcgtctcgc gcgtttcggt gatgacggtg aaaacctctg acacatgcag   6240
ctcccggaga cggtcacagc ttgtctgtaa gcggatgccg ggagcagaca agcccgtcag   6300
ggcgcgtcag cgggtgttgg cgggtgtcgg gctggcttaa ctatgcggc atcagagcag   6360 attgtactga gagtgcacca tatgcggtgt gaaataccgc acagatgcgt aaggagaaaa   6420
taccgcatca ggaaattgta acgttaata ttttgttaaa attcgcgtta aattttttgtt   6480 aaatcagctc attttttaac cataggccg aaatcggcaa atcccttat aaatcaaaag   6540 aatagaccga gatagggttg agtgttgttc cagtttggaa caagagtcca ctattaaaga   6600
acgtggactc caacgtcaaa gggcgaaaaa ccgtctatca gggcgatggc ccactacgtg   6660
aaccatcacc ctaatcaagt tttttggggt cgaggtgccg taaagcacta atcggaacc   6720 ctaaagggag cccccgattt agagcttgac ggggaaagcc ggcgaacgtg gcgagaaagg   6780
aagggaagaa agcgaaagga gcgggcgcta gggcgctggc aagtgtagcg gtcacgctgc   6840
gcgtaaccac cacacccgcc gcgcttaatg cgccgctaca gggcgcgtcg cgccattcgc   6900
cattcaggct acgcaactgt tgggaagggc gatcggtgcg ggcctcttcg ctattacgcc   6960
aggctgc                                                             6967
```

<210> SEQ ID NO 20
<211> LENGTH: 7520
<212> TYPE: DNA
<213> ORGANISM: Artificial Sequence
<220> FEATURE:
<223> OTHER INFORMATION: Synthetic Polynucleotide

<400> SEQUENCE: 20

```
agggggggggg ggggggggggt tggccactcc ctctctgcgc gctcgctcgc tcactgaggc     60
cgggcgacca aaggtcgccc gacgcccggg ctttgcccgg gcggcctcag tgagcgagcg    120
agcgcgcaga gagggagtgg ccaactccat cactaggggt tcctcagatc tggcgcgccc    180
aattggcttc gaattctagc ggccgccccc gggtgcgcgg cgtcggtggt gccgcgggg    240 ggcgccaggt cgcaggcggt gtagggctcc aggcaggcgg cgaaggccat gacgtgcgct    300
atgaaggtct gctcctgcac gccgtgaacc aggtgcgcct gcgggccgcg cgcgaacacc    360
gccacgtcct cgcctgcgtg ggtctcttcg tccagggggca ctgctgactg ctgccgatac    420
tcggggctcc cgctctcgct ctcggtaaca tccggccggg cgccgtcctt gagcacatag    480
cctggaccgt ttccttaagc gacgcatgct cgcgataggc acctattggt cttactgaca    540
tccactttgc ctttctctcc acaggaaaac atggggcagc aggccaggat gctgcgggcc    600
```

```
caggtgaagc ggcacacggt gcgggacaag ctgaggctgt gccagaactt cctgcagaag    660
ctgcgcttcc tggcggacga gccccagcac agcattcccg acatcttcat ctggatgatg    720
agcaacaaca agcgtgtcgc ctatgcccgt gtgccctcca aggacctgct cttctccatc    780
gtggaggagg agactggcaa ggactgcgcc aaggtcaaga cgctcttcct taagctgcca    840
gggaagcggg gcttcggctc ggcaggctgg acagtgcagg ccaaggtgga gctgtacctg    900
tggctgggcc tcagcaaaca gcgcaaggag ttcctgtgcg gcctgccctg tggcttccag    960
gaggtcaagg cagcccaggg cctgggcctg catgccttcc cacccgtcag cctggtctac   1020
accaagaagc aggcgttcca gctccgagcg cacatgtacc aggcccgcag cctctttgcc   1080
gccgacagca gcggactctc agacccctt  gcccgcgtct tcttcatcaa tcagagtcag   1140
tgcacagagg tgctgaatga gaccctgtgt cccacctggg accagatgct ggtgttcgac   1200
aacctggagc tctatggtga agctcatgag ctgagggacg atccgcccat cattgtcatt   1260
gaaatctatg accaggattc catgggcaaa gctgacttca tgggccggac cttcgccaaa   1320
cccctggtga agatggcaga cgaggcgtac tgcccacccc gcttcccacc tcagctcgag   1380
tactaccaga tctaccgtgg caacgccaca gctggagacc tgctggcggc cttcgagctg   1440
ctgcagattg accagcagg  gaaggctgac ctgcccccca tcaatggccc ggtggacgtg   1500
gaccgaggtc ccatcatgcc cgtgcccatg ggcatccggc ccgtgctcag caagtaccga   1560
gtggaggtgc tgttctgggg cctacgggac ctaaagcggg tgaacctggc ccaggtggac   1620
cggccacggg tggacatcga gtgtgcaggg aagggggtgc agtcgtccct gatccacaat   1680
tataagaaga ccccaacttc caacaccctc gtcaagtggt ttgaagtgga cctcccagag   1740
aacgagctgc tgcacccgcc cttgaacatc cgtgtggtgg actgccgggc cttcggtcgc   1800
tacacactgg tgggctccca tgccgtcagc tccctgcgac gcttcatcta ccggccccca   1860
gaccgctcgg cccccagctg gaacaccacg gtcaggcttc tccggcgctg ccgtgtgctg   1920
tgcaatgggg gctcctcctc tcactccaca ggggaggttg tggtgactat ggagccagag   1980
gtacccatca gaaactgga  gaccatggtg aagctggacg cgacttctga agctgttgtc   2040
aaggtggatg tggctgagga ggagaaggag aagaagaaga agaagaaggg cactgcggag   2100
gagccagagg aggaggagcc agacgagagc atgctggact ggtggtccaa gtactttgcc   2160
tccattgaca ccatgaagga gcaacttcga caacaagagc cctctggaat tgacttggag   2220
gagaaggagg aagtggacaa taccgagggc ctgaaggggt caatgaaggg caaggagaag   2280
gcaagggctg ccaaagagga gaagaagaag aaaactcaga gctctggctc tggccagggg   2340
tccgaggccc ccgagaagaa gaaacccaag attgatgagc ttaaggtata ccccaaagag   2400 ctggagtccag agtttgataa ctttgaggac tggctgcaca cttttcaactt gcttcggggc   2460 aagaccgggg atgatgagga tggctccacc gaggaggagc gcattgtggg acgcttcaag   2520
ggctccctct gcgtgtacaa agtgccactc ccagaggacg tgtcccggga agccggctac   2580
gactccacct acggcatgtt ccagggcatc ccgagcaatg accccatcaa tgtgctggtc   2640
cgagtctatg tggtccgggc cacggacctg caccctgctg acatcaacgg caaagctgac   2700
ccctacatcg ccatccggct aggcaagact gacatccgcg acaaggagaa ctacatctcc   2760
aagcagctca accctgtctt tgggaagtcc tttgacatcg aggcctcctt ccccatggaa   2820
tccatgctga cggtggctgt gtatgactgg gacctggtgg gcactgatga cctcattggg   2880
gaaaccaaga tcgacctgga gaaccgcttc tacagcaagc accgcgccac ctgcggcatc   2940
```

```
gcccagacct actccacaca tggctacaat atctggcggg accccatgaa gcccagccag    3000
atcctgaccc gcctctgcaa agacggcaaa gtggacggcc ccactttgg gcccctggg     3060 agagtgaagg tggccaaccg cgtcttcact gggccctctg agattgagga cgagaacggt    3120
cagaggaagc ccacagacga gcatgtggcg ctgttggccc tgaggcactg gaggacatc     3180 ccccgcgcag gctgccgcct ggtgccagag catgtggaga cgaggccgct gctcaacccc    3240
gacaagccgg gcatcgagca gggccgcctg gagctgtggg tggacatgtt ccccatggac    3300
atgccagccc ctgggacgcc tctggacatc tcacctcgga agcccaagaa gtacgagctg    3360
cgggtcatca tctggaacac agatgaggtg gtcttggagg acgacgactt cttcacaggg    3420
gagaagtcca gtgacatctt cgtgaggggg tggctgaagg gccagcagga ggacaagcag    3480
gacacagacg tccactacca ctccctcact ggcgagggca acttcaactg gcgctacctg    3540
ttccccttcg actacctggc ggcggaggag aagatcgtca tctccaagaa ggagtccatg    3600
ttctcctggg acgagaccga gtacaagatc cccgcgcggc tcaccctgca gatctgggat    3660
gcggaccact tctccgctga cgacttcctg ggggccatcg agctggacct gaaccggttc    3720
ccgcggggcg caaagacagc caagcagtgc accatggaga tggccaccgg ggaggtggac    3780 gtgccctcg tgtccatctt caagcaaaag cgcgtcaaag ctggtggcc cctcctggcc      3840 cgcaatgaga acgatgagtt tgagctcacg ggcaaggtgg aggctgagct gcatttactg    3900
acagcagagg aggcagagaa gaacccagtg ggcctggccc gcaatgaacc tgacccccta    3960
gagaaaccca accggcccga cacggccttc gtctggttcc tcaaccctct caagtccatc    4020
aagtacctca tctgcacccg gtacaagtgg ctcatcatca agatcgtgct ggcgctgttg    4080
gggctgctca tgttggggct cttcctctac agcctccctg gctacatggt caaaaagctc    4140 cttgggcag gaggtggcgg atcagagcag aaactcatct ctgaagagga tctgtgaacg     4200
gccgctatgc tagcttggta ccaagggcgg atcctgcata gagctcgctg atcagcctcg    4260
actgtgcctt ctagttgcca gccatctgtt gtttgcccct cccccgtgcc ttccttgacc    4320
ctggaaggtg ccactcccac tgtcctttcc taataaaatg aggaaattgc atcgcattgt    4380
ctgagtaggt gtcattctat tctgggggt ggggtgggc aggacagcaa gggggaggat     4440
tgggaagaca atagcaggca tgctggggag agatctgagg actagtccgt cgactgttaa    4500
ttaagcatgc tggggagaga tctaggaacc cctagtgatg gagttggcca ctccctctct    4560
gcgcgctcgc tcgctcactg aggccgcccg ggcaaagccc gggcgtcggg cgacctttgg    4620
tcgcccggcc tcagtgagcg agcgagcgcg cagagaggga gtggccaacc ccccccccc    4680 ccccctgca gccctgcatt aatgaatcgg ccaacgcgcg gggagaggcg gtttgcgtat    4740
tgggcgctct tccgcttcct cgctcactga ctcgctgcgc tcggtcgttc ggctgcggcg    4800
agcggtatca gctcactcaa aggcggtaat acggttatcc acagaatcag ggataacgc     4860 aggaaagaac atgtgagcaa aaggccagca aaaggccagg aaccgtaaaa aggccgcgtt    4920
gctggcgttt ttccataggc tccgcccccc tgacgagcat cacaaaaatc gacgctcaag    4980
tcagaggtgg cgaaacccga caggactata aagataccag gcgtttcccc ctggaagctc    5040
cctcgtgcgc tctcctgttc cgaccctgcc gcttaccgga tacctgtccg cctttctccc    5100
ttcgggaagc gtggcgcttt ctcaatgctc acgctgtagg tatctcagtt cggtgtaggt    5160
cgttcgctcc aagctgggct gtgtgcacga accccccgtt cagcccgacc gctgcgcctt    5220
atccggtaac tatcgtcttg agtccaaccc ggtaagacac gacttatcgc cactggcagc    5280
agccactggt aacaggatta gcagagcgag gtatgtaggc ggtgctacag agttcttgaa    5340
```

-continued

```
gtggtggcct aactacggct acactagaag gacagtattt ggtatctgcg ctctgctgaa      5400
gccagttacc ttcggaaaaa gagttggtag ctcttgatcc ggcaaacaaa ccaccgctgg      5460
tagcggtggt ttttttgttt gcaagcagca gattacgcgc agaaaaaaag gatctcaaga      5520
agatcctttg atcttttcta cggggtctga cgctcagtgg aacgaaaact cacgttaagg      5580
gattttggtc atgagattat caaaaaggat cttcacctag atccttttaa attaaaaatg      5640
aagttttaaa tcaatctaaa gtatatatga gtaaacttgg tctgacagtt accaatgctt      5700
aatcagtgag gcacctatct cagcgatctg tctatttcgt tcatccatag ttgcctgact      5760
ccccgtcgtg tagataacta cgatacggga gggcttacca tctggcccca gtgctgcaat      5820
gataccgcga gacccacgct caccggctcc agatttatca gcaataaacc agccagccgg      5880
aagggccgag cgcagaagtg gtcctgcaac tttatccgcc tccatccagt ctattaattg      5940
ttgccgggaa gctagagtaa gtagttcgcc agttaatagt ttgcgcaacg ttgttgccat      6000
tgctacaggc atcgtggtgt cacgctcgtc gtttggtatg gcttcattca gctccggttc      6060
ccaacgatca aggcgagtta catgatcccc catgttgtgc aaaaaagcgg ttagctcctt      6120
cggtcctccg atcgttgtca gaagtaagtt ggccgcagtg ttatcactca tggttatggc      6180
agcactgcat aattctctta ctgtcatgcc atccgtaaga tgcttttctg tgactggtga      6240
gtactcaacc aagtcattct gagaatagtg tatgcggcga ccgagttgct cttgcccggc      6300
gtcaatacgg gataataccg cgccacatag cagaacttta aaagtgctca tcattggaaa      6360
acgttcttcg gggcgaaaac tctcaaggat cttaccgctg ttgagatcca gttcgatgta      6420
acccactcgt gcacccaact gatcttcagc atcttttact ttcaccagcg tttctgggtg      6480
agcaaaaaca ggaaggcaaa atgccgcaaa aagggaata agggcgacac ggaaatgttg      6540
aatactcata ctcttccttt ttcaatatta ttgaagcatt tatcagggtt attgtctcat      6600
gagcggatac atatttgaat gtatttagaa aaataaacaa ataggggttc cgcgcacatt      6660
tccccgaaaa gtgccacctg acgtctaaga accattatt atcatgacat taacctataa      6720
aaataggcgt atcacgaggc cctttcgtct cgcgcgtttc ggtgatgacg gtgaaaacct      6780
ctgacacatg cagctcccgg agacggtcac agcttgtctg taagcggatg ccggagcag       6840
acaagcccgt cagggcgcgt cagcgggtgt tggcgggtgt cggggctggc ttaactatgc      6900
ggcatcagag cagattgtac tgagagtgca ccatatgcgg tgtgaaatac cgcacagatg      6960
cgtaaggaga aaataccgca tcaggaaatt gtaaacgtta atattttgtt aaaattcgcg      7020
ttaaattttt gttaaatcag ctcatttttt aaccataagg ccgaaatcgg caaaatccct      7080
tataaatcaa agaatagac cgagataggg ttgagtgttg ttccagtttg gaacaagagt       7140
ccactattaa agaacgtgga ctccaacgtc aaagggcgaa aaaccgtcta tcagggcgat      7200
ggcccactac gtgaaccatc accctaatca agttttttgg ggtcgaggtg ccgtaaagca      7260
ctaaatcgga accctaaagg gagccccga tttagagctt gacggggaaa gccggcgaac       7320
gtggcgagaa aggaagggaa gaaagcgaaa ggagcgggcg ctagggcgct ggcaagtgta      7380
gcggtcacgc tgcgcgtaac caccacaccc gccgcgctta atgcgccgct acagggcgcg      7440
tcgcgccatt cgccattcag gctacgcaac tgttgggaag ggcgatcggt gcgggcctct      7500
tcgctattac gccaggctgc                                                  7520
```

<210> SEQ ID NO 21
<211> LENGTH: 7012
<212> TYPE: DNA

<213> ORGANISM: Artificial Sequence
<220> FEATURE:
<223> OTHER INFORMATION: Synthetic Polynucleotide

<400> SEQUENCE: 21

```
agggggggggg gggggggggt tggccactcc ctctctgcgc gctcgctcgc tcactgaggc    60
cgggcgacca aaggtcgccc gacgcccggg ctttgcccgg gcggcctcag tgagcgagcg   120
agcgcgcaga gagggagtgg ccaactccat cactagggggt tcctcagatc tggcgcgccc   180
aattcggtac cctagttatt aatagtaatc aattacgggg tcattagttc atagcccata   240
tatggagttc cgcgttacat aacttacggt aaatggcccg cctggctgac cgcccaacga   300
ccccccgccca ttgacgtcaa taatgacgta tgttcccata gtaacgccaa tagggacttt   360
ccattgacgt caatgggtgg actatttacg gtaaactgcc cacttggcag tacatcaagt   420
gtatcatatg ccaagtacgc cccctattga cgtcaatgac ggtaaatggc ccgcctggca   480
ttatgcccag tacatgacct tatgggactt tcctacttgg cagtacatct acgtattagt   540
catcgctatt accatggtcg aggtgagccc cacgttctgc ttcactctcc ccatctcccc   600
cccctcccca cccccaattt tgtatttatt tattttttaa ttattttgtg cagcgatggg   660
ggcggggggg ggggggggc gcgcgccagg cgggcgggg cggggcgagg ggcggggcgg   720
ggcgaggcgg agaggtgcgg cggcagccaa tcagagcggc gcgctccgaa agtttccttt   780
tatggcgagg cggcggcggc ggcggcccta aaaaagcga agcgcgcggc gggcgggagt   840
cgctgcgacg ctgccttcgc cccgtgcccc gctccgccgc cgcctcgcgc cgcccgcccc   900
ggctctgact gaccgcgtta ctcccacagg tgagcgggcg ggacggccct ctcctccgg   960
gctgtaatta gcgcttggtt taatgacggc ttgtttcttt tctgtggctg cgtgaaagcc  1020
ttgaggggct ccgggagcta gagcctctgc taaccatgtt catgccttct tctttttcct  1080
acagctcctg ggcaacgtgc tggttattgt gctgtctcat cattttggca aagaattcta  1140
gcggccgcca ccatggagca gaaactcatc tctgaagagg atctgggagg tggcggatca  1200
gccttgctca tccacctcaa gacagtctcg gagctgcggg gcaggggcga ccggatcgcc  1260
aaagtgactt tccgagggca atccttctac tctcgggtcc tggagaactg tgaggatgtg  1320
gctgactttg atgagacatt tcggtggccg gtggccagca gcatcgacag aaatgagatg  1380
ctggagattc aggttttcaa ctacagcaaa gtcttcagca acaagctcat cgggaccttc  1440
cgcatggtgc tgcagaaggt ggtagaggag agccatgtgg aggtgactga cacgctgatt  1500
gatgacaaca atgctatcat caagaccagc ctgtgcgtgg aggtccggta tcaggccact  1560
gacggcacag tgggctcctg gacgatggg gacttcctgg gagatgagtc tcttcaagag  1620
gaagagaagg acagccaaga gacgcgatgga ctgctcccag gctcccggcc cagctcccgg  1680
cccccaggag agaagagctt ccggagagcc gggaggagcg tgttctccgc catgaagctc  1740
ggcaaaaacc ggtctcacaa ggaggagccc caaagaccag atgaaccggc ggtgctggag  1800
atggaagacc ttgaccatct ggccattcgg ctaggagatg gactggatcc cgactcggtg  1860
tctctagcct cagtcacagc tctcaccact aatgtctcca acaagcgatc taagccagac  1920
attaagatgg agccaagtgc tgggcggccc atggattacc aggtcagcat cacggtgatc  1980
gaggcccggc agctggtggg cttgaacatg gaccctgtgg tgtgcgtgga ggtgggtgac  2040
gacaagaagt acacatccat gaaggagtcc actaactgcc cctattacaa cgagtacttc  2100
gtcttcgact ccatgtctc tccggatgtc atgtttgaca agatcatcaa gatttcggtg  2160
attcactcca gaacctgct gcgcagtggc accctggtgg gctccttcaa aatggacgtg  2220
```

```
ggaaccgtgt actcgcagcc agagcaccag ttccatcaca agtgggccat cctgtctgac    2280
cccgatgaca tctcctcggg gctgaagggc tacgtgaagt gtgacgttgc cgtggtgggc    2340 aaagggaca acatcaagac gccccacaag gccaatgaga ccgacgaaga tgacattgag     2400
gggaacttgc tgctccccga gggggtgccc ccgaacgcc agtgggcccg gttctatgtg     2460
aaaatttacc gagcagaggg gctgccccgt atgaacacaa gcctcatggc caatgtaaag    2520
aaggctttca tcggtgaaaa caaggacctc gtgacccct acgtgcaagt cttctttgct    2580
ggccagaagg gcaagacttc agtgcagaag agcagctatg agcccctgtg aatgagcag    2640 gtcgtcttta cagacctctt ccccccactc tgcaaacgca tgaaggtgca gatccgagac    2700
tcggacaagg tcaacgacgt ggccatcggc acccacttca ttgacctgcg caagatttct    2760
aatgacggag acaaaggctt cctgcccaca ctgggcccag cctgggtgaa catgtacggc    2820
tccacacgta actacacgct gctggatgag catcaggacc tgaacgaggg cctggggag    2880 ggtgtgtcct tccgggcccg gctcctgctg ggcctggctg tggagatcgt agacacctcc    2940
aaccctgagc tcaccagctc cacagaggtg caggtggagc aggccacgcc catctcggag    3000
agctgtgcag gtaaaatgga agaattcttt ctctttggag ccttcctgga ggcctcaatg    3060
atcgaccgga gaaacggaga caagcccatc acctttgagg tcaccatagg caactatggg    3120
aacgaagttg atggcctgtc ccggcccag cggcctcggc cccggaagga gccgggggat    3180
gaggaagaag tagacctgat tcagaacgca agtgatgacg aggccggtga tgccggggac    3240
ctggcctcag tctcctccac tccaccaatg cggccccagg tcaccgacag gaactacttc    3300
catctgccct acctggagcg aaagccctgc atctacatca agagctggtg gccggaccag    3360
cgccgccgcc tctacaatgc caacatcatg gaccacattg ccgacaagct ggaagaaggc    3420
ctgaacgaca tacaggagat gatcaaaacg gagaagtcct accctgagcg tcgcctgcgg    3480
ggcgtcctgg aggagctgag ctgtggctgc tgccgcttcc tctccctcgc tgacaaggac    3540
cagggccact catcccgcac caggcttgac cgggagcgcc tcaagtcctg catgagggag    3600
ctggtaagta tcaaggttac aagacaggtt aaggagacc aatagaaact gggcttgtcg    3660
agacagagaa gactcttgcg tttctgagct agccccggg tgcgcggcgt cggtggtgcc    3720 ggcgggggc gccaggtcgc aggcggtgta gggctccagg caggcggcga aggccatgac    3780
gtgcgctatg aaggtctgct cctgcacgcc gtgaaccagg tgcgcctgcg ggccgcgcgc    3840
gaacaccgcc acgtcctcgc ctgcgtgggt ctcttcgtcc aggggcactg ctgactgctg    3900
ccgatactcg gggctcccgc tctcgctctc ggtaacatcc ggccgggcgc cgtccttgag    3960
cacatagcct ggaccgtttc gtcgactgtt aattaagcat gctggggaga gatctaggaa    4020
cccctagtga tggagttggc cactccctct ctgcgcgctc gctcgctcac tgaggccgcc    4080
cgggcaaagc ccgggcgtcg ggcgaccttt ggtcgcccgg cctcagtgag cgagcgagcg    4140
cgcagagagg gagtggccaa cccccccccc ccccccctg cagccctgca ttaatgaatc    4200
ggccaacgcg cggggagagg cggtttgcgt attgggcgct cttccgcttc ctcgctcact    4260
gactcgctgc gctcggtcgt tcggctgcgg cgagcggtat cagctcactc aaaggcggta    4320
atacggttat ccacagaatc aggggataac gcaggaaaga acatgtgagc aaaaggccag    4380
caaaaggcca ggaaccgtaa aaaggccgcg ttgctggcgt ttttccatag gctccgcccc    4440
cctgacgagc atcacaaaaa tcgacgctca agtcagaggt ggcgaaaccc gacaggacta    4500
taaagatacc aggcgtttcc ccctggaagc tccctcgtgc gctctcctgt tccgaccctg    4560
```

```
ccgcttaccg gatacctgtc cgcctttctc ccttcgggaa gcgtggcgct ttctcaatgc    4620
tcacgctgta ggtatctcag ttcggtgtag gtcgttcgct ccaagctggg ctgtgtgcac    4680
gaaccccccg ttcagcccga ccgctgcgcc ttatccggta actatcgtct tgagtccaac    4740
ccggtaagac acgacttatc gccactggca gcagccactg gtaacaggat tagcagagcg    4800
aggtatgtag gcggtgctac agagttcttg aagtggtggc ctaactacgg ctacactaga    4860
aggacagtat ttggtatctg cgctctgctg aagccagtta ccttcggaaa aagagttggt    4920
agctcttgat ccggcaaaca aaccaccgct ggtagcggtg gtttttttgt ttgcaagcag    4980
cagattacgc gcagaaaaaa aggatctcaa gaagatcctt tgatcttttc tacggggtct    5040
gacgctcagt ggaacgaaaa ctcacgttaa gggattttgg tcatgagatt atcaaaaagg    5100
atcttcacct agatcctttt aaattaaaaa tgaagtttta atcaatcta aagtatatat     5160 gagtaaactt ggtctgacag ttaccaatgc ttaatcagtg aggcacctat ctcagcgatc    5220
tgtctatttc gttcatccat agttgcctga ctccccgtcg tgtagataac tacgatacgg    5280
gagggcttac catctggccc cagtgctgca atgataccgc gagacccacg ctcaccggct    5340
ccagatttat cagcaataaa ccagccagcc ggaagggccg agcgcagaag tggtcctgca    5400
actttatccg cctccatcca gtctattaat tgttgccggg aagctagagt aagtagttcg    5460
ccagttaata gtttgcgcaa cgttgttgcc attgctacag gcatcgtggt gtcacgctcg    5520
tcgtttggta tggcttcatt cagctccggt tcccaacgat caaggcgagt tacatgatcc    5580
cccatgttgt gcaaaaaagc ggttagctcc ttcggtcctc cgatcgttgt cagaagtaag    5640
ttggccgcag tgttatcact catggttatg gcagcactgc ataattctct tactgtcatg    5700
ccatccgtaa gatgcttttc tgtgactggt gagtactcaa ccaagtcatt ctgagaatag    5760
tgtatgcggc gaccgagttg ctcttgcccg gcgtcaatac gggataatac cgcgccacat    5820
agcagaactt taaaagtgct catcattgga aaacgttctt cggggcgaaa actctcaagg    5880
atcttaccgc tgttgagatc cagttcgatg taacccactc gtgcacccaa ctgatcttca    5940
gcatctttta ctttcaccag cgtttctggg tgagcaaaaa caggaaggca aaatgccgca    6000
aaaaagggaa taagggcgac acggaaatgt tgaatactca tactcttcct ttttcaatat    6060
tattgaagca tttatcaggg ttattgtctc atgagcggat acatatttga atgtatttag    6120
aaaaataaac aaataggggt tccgcgcaca tttccccgaa aagtgccacc tgacgtctaa    6180
gaaaccatta ttatcatgac attaacctat aaaaataggc gtatcacgag gccctttcgt    6240
ctcgcgcgtt tcggtgatga cggtgaaaac ctctgacaca tgcagctccc ggagacggtc    6300
acagcttgtc tgtaagcgga tgccgggagc agacaagccc gtcagggcgc gtcagcgggt    6360
gttggcgggt gtcggggctg gcttaactat gcggcatcag agcagattgt actgagagtg    6420
caccatatgc ggtgtgaaat accgcacaga tgcgtaagga gaaaataccg catcaggaaa    6480
ttgtaaacgt taatattttg ttaaaattcg cgttaaattt ttgttaaatc agctcatttt    6540
ttaaccaata ggccgaaatc ggcaaaatcc cttataaatc aaaagaatag accgagatag    6600
ggttgagtgt tgttccagtt tggaacaaga gtccactatt aaagaacgtg gactccaacg    6660
tcaaagggcg aaaaaccgtc tatcaggcg atggcccact acgtgaacca tcaccctaat    6720
caagtttttt ggggtcgagg tgccgtaaag cactaaatcg gaaccctaaa gggagccccc    6780
gatttagagc ttgacgggga aagccggcga acgtggcgag aaaggaaggg aagaaagcga    6840
aaggagcggg cgctagggcg ctggcaagtg tagcggtcac gctgcgcgta accaccacac    6900
ccgccgcgct taatgcgccg ctacagggcg cgtcgcgcca ttcgccattc aggctacgca    6960
```

```
actgttggga agggcgatcg gtgcgggcct cttcgctatt acgccaggct gc         7012
```

<210> SEQ ID NO 22
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 22

Glu Gln Lys Leu Ile Ser Glu Glu Asp Leu
1               5                   10